US009822357B2

(12) United States Patent
Vogl et al.

(10) Patent No.: US 9,822,357 B2
(45) Date of Patent: Nov. 21, 2017

(54) BIDIRECTIONAL PROMOTER

(71) Applicants: Technische Universität Graz, Graz (AT); ACIB GmbH, Graz (AT)

(72) Inventors: Thomas Vogl, Graz (AT); Thomas Kickenweiz, Graz (AT); Lukas Sturmberger, Graz (AT); Anton Glieder, Gleisdorf (AT)

(73) Assignee: TECHNISCHE UNIVERSITAT GRAZ, Graz (AT)

( * ) Notice: Subject to any disclaimer, the term of this patent is extended or adjusted under 35 U.S.C. 154(b) by 0 days.

(21) Appl. No.: 14/325,111

(22) Filed: Jul. 7, 2014

(65) Prior Publication Data
US 2015/0011407 A1 Jan. 8, 2015

(30) Foreign Application Priority Data

Jul. 5, 2013 (EP) .................................... 13175416

(51) Int. Cl.
C12N 15/10 (2006.01)
C12N 15/81 (2006.01)
C12N 15/85 (2006.01)
C12Q 1/68 (2006.01)

(52) U.S. Cl.
CPC ....... *C12N 15/1086* (2013.01); *C12N 15/815* (2013.01); *C12N 15/85* (2013.01); *C12Q 1/6897* (2013.01); *C12N 15/1051* (2013.01)

(58) Field of Classification Search
None
See application file for complete search history.

(56) References Cited

U.S. PATENT DOCUMENTS 6,630,324 B1 * 10/2003 Barski .................. C12N 9/0004
435/320.1
7,557,203 B2 * 7/2009 Linemann .......... C12N 15/8216
435/320.1

OTHER PUBLICATIONS

CMV Vector, Clontech, 2009, Catalog No. 631630.*
Stadlymayr et al., Journal of Biotechnology, 2010, vol. 150 pp. 519-529.*
FLD1 Promoter, Genbank AF066054.1—downloaded from: http://www.ncbi.nlm.nih.gov/nucleotide/3599998?report=genbank&log$=nuclalign&blast_rank=4&RID=TFTZVR1H01R.*
Anonymous, "GeneArt Type IIs Assembly kits", Thermo Fisher Scientific Inc., 2015 [obtained from 222.lifetechnologies.com, 2013, XP002733017, URL: http://www.lifetechnologies.com/content/dam/LifeTech/migration/files/(cloning/pdfs.par.0677.file.dat/C0115274%20final.pdf].
Engler C et al., PLOS One, vol. 4(5):e5553, pp. 1-9, 2009.
Trinklein, Nathan D et al., Genome Research, 14(1):62-66, 2004.
Wiberg F C et al., Biotechnology and Bioengineering, 94(2):396-405, 2006.
Amendola et al.(2005). Coordinate dual-gene transgenesis by lentiviral vectors carrying synthetic bidirectional promoters. Nature Biotechnology, 23(1):108-116.
Andrianaki et al. (2010). Dual transgene expression by foamy virus vectors carrying an endogenous bidirectional promoter. Gene Therapy, 17(3):380-388.
Baron et al. (1995). Co-regulation of two gene activities by tetracycline via a bidirectional promoter. Nucleic Acids Research, 23(17):3605-3606.
Bernhardt, R. (2006). Cytochromes P450 as versatile biocatalysts. Journal of Biotechnology, 124(1):128-145.
Chen et al. (2012). Generation of diploid Pichia pastoris strains by mating and their application for recombinant protein production. Microbial Cell Factories, 11(1):91.
Crook et al. (2011). Re-engineering multicloning sites for function and convenience. Nucleic Acids Research, 39(14), e92.
Delic et al. (2013). Repressible promoters—A novel tool to generate conditional mutants in Pichia pastoris. Microbial Cell Factories, 12(1):6.
Egner et al. (1981). Excision of transposon Tn5 is dependent on the inverted repeats but not on the transposase function of Tn5. Proceedings of the National Academy of Sciences of the United States of America, 78(1):459-463.
Foster et al. (1981). Three Tn10-associated excision events: relationship to transposition and role of direct and inverted repeats. Cell, 23(1):215-227.
Fux et al (2003). Bidirectional expression units enable streptogramin-adjustable gene expression in mammalian cells. Biotechnol Bioeng, 83:618-625.
Geier et al. (2012). Production of human cytochrome P450 2D6 drug metabolites with recombinant microbes—a comparative study. Biotechnology Journal, 7:1-13.
Gibson et al. (2009). Enzymatic assembly of DNA molecules up to several hundred kilobases. Nat Methods, 6(5):343-345.
Gudiminchi et al. (2013). Screening for cytochrome P450 expression in Pichia pastoris whole cells by P450-carbon monoxide complex determination. Biotechnology Journal, 8(1):146-152.
Guerfal et al. (2010). The HAC1 gene from Pichia pastoris: characterization and effect of its overexpression on the production of secreted, surface displayed and membrane proteins. Microb. Cell Fact., 9:49-60.

(Continued)

*Primary Examiner* — Mindy G Brown
(74) *Attorney, Agent, or Firm* — Loza & Loza, LLP; Michael F. Fedrick

(57) ABSTRACT

The invention refers to a library of bidirectional expression cassettes or expression vectors comprising a repertoire of bidirectional promoter sequences, each expression cassette comprising a promoter sequence operably linked to a first gene in one direction, and operably linked to an oppositely oriented second gene in the other direction which is different from the first gene, and bidirectional *Pichia pastoris* or CHO cells promoter sequences. The invention further refers to a method of screening or selecting a bidirectional promoter suitable for expressing at least two GOI in a host cell and a kit comprising a) an expression cassette consisting of the first and second genes and a stuffer sequence separating them, which stuffer sequence comprises a recognition site for a type IIS restriction enzyme at both ends;
b) the type IIS restriction enzyme;
c) and a repertoire of promoter, preferably a promoter library including bidirectional promoters.

9 Claims, 82 Drawing Sheets

(56) References Cited

OTHER PUBLICATIONS

Hartner et al. (2006). Regulation of methanol utilisation pathway genes in yeasts. Microb. Cell Fact., 5(39):39-59.

Hartner et al. (2008). Promoter library designed for fine-tuned gene expression in Pichia pastoris. Nucleic Acids Res, 36(12):e76.

Ishida et al. (2006). The UGA3-GLT1 intergenic region constitutes a promoter whose bidirectional nature is determined by chromatin organization in *Saccharomyces cerevisiae*. Molecular Microbiology, 59(6):1790-1806.

Li et al. (2008). Construction and characterization of bidirectional expression vectors in *Saccharomyces cerevisiae*. FEMS Yeast Research, 8(1):6-9.

Lohr et al. (1995). Transcriptional regulation in the yeast GAL gene family: a complex genetic network. FASEB Journal : official publication of the Federation of American Societies for Experimental Biology, 9(9):777-787.

Mead et al. (1991). A universal method for the direct cloning of PCR amplified nucleic acid. Bio/technology (Nature Publishing Company), 9(7):657-663.

Miller et al. (1998). Assessment of aryl hydrocarbon receptor complex interactions using pBEVY plasmids: expressionvectors with bi-directional promoters for use in *Saccharomyces cerevisiae*. Nucleic Acids Research, 26(15):3577-3583.

Näätsaari et al. (2012). Deletion of the Pichia pastoris KU70 homologue facilitates platform strain generation for gene expression and synthetic biology. PLoS One, 7(6), e39720.

Neil et al (2009). Widespread bidirectional promoters are the major source of cryptic transcripts in yeast. Nature, 457(7232), 1038-1042.

Partow et al. (2010). Characterization of different promoters for designing a new expression vector in *Saccharomyces cerevisiae*. Yeast (Chichester, England), 27(11):955-964.

Polson et al. (2011). A bidirectional promoter reporter vector for the analysis of the p53/WDR79 dual regulatory element. Plasmid, 66(3):169-179.

Prielhofer et al. (2013). Induction without methanol: novel regulated promoters enable high-level expression in Pichia pastoris. Microbial cell factories, 12(1):5.

Rao et al. (2010). Efficient vectors for expression cloning of large numbers of PCR fragments in P . pastoris. Yeast, 27:285-292.

Sammarco et al. (2005). A series of bidirectional tetracycline-inducible promoters provides coordinated protein expression. Analytical Biochemistry, 346(2):210-216.

St John et al. (1981). The organization and transcription of the galactose gene cluster of *Saccharomyces*. Journal of Molecular Biology, 152(2):285-315.

Staley et al. (2012). Analysis of the 5' untranslated region (5'UTR) of the alcohol oxidase 1 (AOX1) gene in recombinant protein expression in Pichia pastoris. Gene, 496(2):118-127.

Vogl et al. (2013). Regulation of Pichia pastoris promoters and its consequences for protein production. New Biotechnology, 30(4):385-404.

Weber et al. (2002). Versatile macrolide-responsive mammalian expression vectors for multiregulated multigene metabolic engineering. Biotechnol Bioeng, 80:691-705.

Xie et al. (2001). Bidirectionalization of polar promoters in plants. Nature Biotechnology, 19(7):677-679.

Xu et al. (2009). Bidirectional promoters generate pervasive transcription in yeast. Nature, 457(7232):1033-1037.

\* cited by examiner

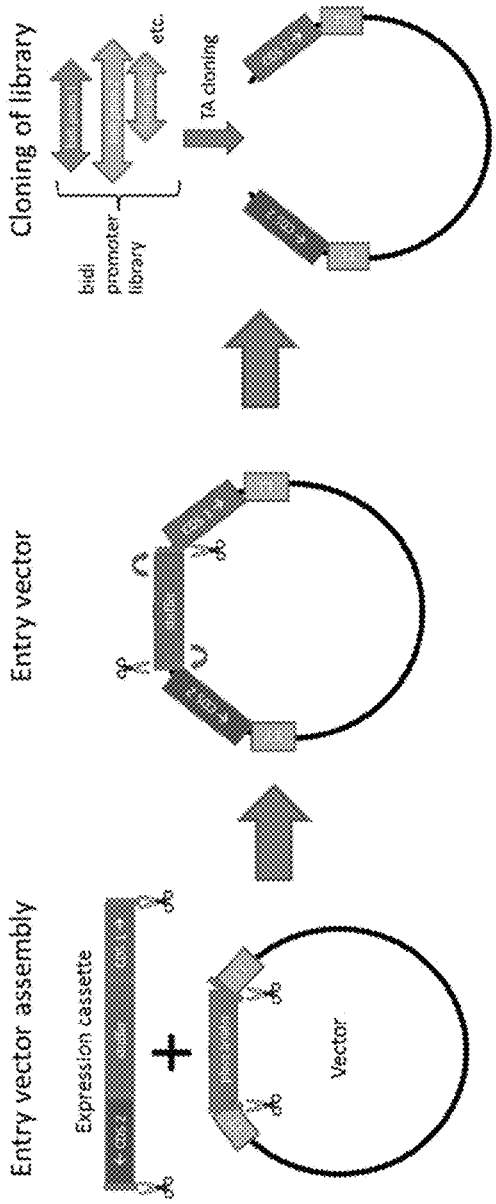
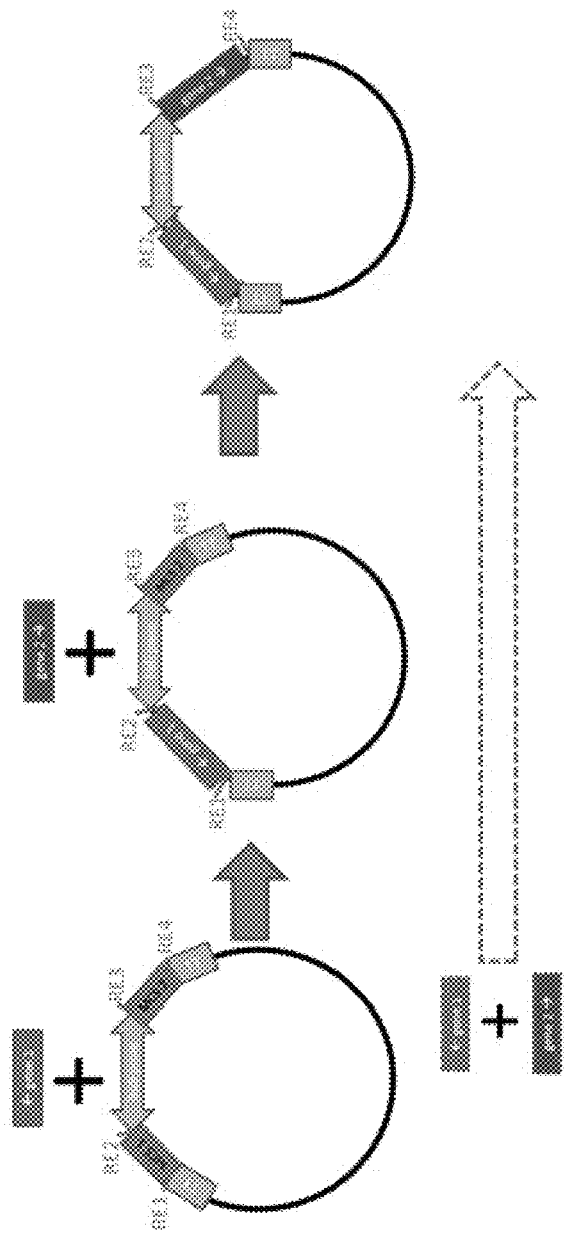
Figure 2A
Figure 2B

Figure 3

| EcoRI | BsaI (SEQ ID NO: 496) | BmrI (SEQ ID NO: 498) |
|---|---|---|
| 5'-GAATTC-3'<br>3'-CTTAAG-5' | 5'-GGTCTCNNNNN-3<br>3'-CCAGAGNNNNN-5<br>(SEQ ID NO: 497) | 5'-ACTGGGNNNNN-3<br>3'-TGACCCNNNNN-5<br>(SEQ ID NO: 499) |
| EcoRV<br>5'-GATATC-3'<br>3'-CTATAG-5' | MlyI (SEQ ID NO: 500)<br>5'-GAGTCNNNNN-3'<br>3'-CTCAGNNNNN-5'<br>(SEQ ID NO: 501) | |

Figure 25

SEQ ID NO: 1 (pAOX1bidi; ←pCBP1|pAOX1→)

gttggtattgtgaaatagacgcagatcgggaacactgaaaaataacagttattattcgagatctaacatccaaagacgaaag
gttgaatgaaaccttttgccatccgacatccacaggtccattctcacacataagtgccaaacgcaacaggaggggatacact
agcagcagaccgttgcaaacgcaggacctccactcctcttctcctcaacacccacttttgccatcgaaaaaccagcccagtt
attgggcttgattggagctcgctcattccaattccttctattaggctactaacaccatgactttattagcctgtctatcctggcccccc
tggcgaggttcatgtttgtttatttccgaatgcaacaagctccgcattacacccgaacatcactccagatgagggctttctgagtg
tggggtcaaatagtttcatgttccccaaatggcccaaaactgacagtttaaacgctgtcttggaacctaatatgacaaaagcgt
gatctcatccaagatgaactaagtttggttcgttgaaatgctaacggccagttggtcaaaaagaaacttccaaaagtcggcat
accgtttgtcttgtttggtattgattgacgaatgctcaaaaataatctcattaatgcttagcgcagtctctctatcgcttctgaacccc
ggtgcacctgtgccgaaacgcaaatggggaaacacccgcttttggatgattatgcattgtctccacattgtatgcttccaagatt
ctggtgggaatactgctgatagcctaacgttcatgatcaaaatttaactgttctaaccccctacttgacagcaatatataaacaga
aggaagctgccctgtcttaaacctttttttatcatcattattagcttactttcataattgcgactggttccaattgacaagcttttgatttt
aacgacttttaacgacaacttgagaagatcaaaaaacaactaattattcgaaacg SEQ ID NO: 2 (pFLD1bidi; ←pCRT10|pFLD1→)

gaattagtgagataacagagttgggtaactagagagaataatagacgtatgcatgattactacacaacggatgtcgcactctt
tccttagttaaaactatcatccaatcacaagatgcgggctggaaagacttgctcccgaaggataatcttctgcttctatctcccttc
ctcatatggtttcgcagggctcatgccccttcttccttcgaactgcccgatgaggaagtccttagcctatcaaagaattcgggac
catcatcgattttagagccttacctgatcgcaatcaggatttcactactcatataaatacatcgctcaaagctccaactttgcttgtt
catacaattcttgatattcaca SEQ ID NO: 3 (pDAS1,2; ←pDAS2|pDAS1→)

ttttgatgtttgatagtttgataagagtgaactttagtgtttagaggggttataatttgttgtaactggttttggtcttaagttaaaacgaa
cttgttatattaaacacaacggtcactcaggatacaagaataggaaagaaaaactttaaactggggacatgttgtctttatata
atttggcggttaaccccttaatgcccgtttccgtctcttcatgataacaaagctgcccatctatgactgaatgtggagaagtatcgg
aacaacccttcactaaggatatctaggctaaactcattcgcgccttagatttctccaaggtatcggttaagtttcctctttcgtactg
gctaacgatggtgttgctcaacaaagggatggaacggcagctaaagggagtgcatggaatgactttaattggctgagaaag
tgttctatttgtccgaatttcttttttctattatctgttcgtttgggcggatctctccagtgggggtaaatggaagatttctgttcatgggg
taaggaagctgaaatccttcgtttcttataggggcaagtatactaaatctcggaacattgaatggggtttactttcattggctacag

Figure 25 (continued)

aaattattaagtttgttatggggtgaagttaccagtaattttcatttttcacttcaacttttggggtatttctgtggggtagcatagcttg
acaggtaatatgatgtactatgggataggcaagtcttgtgtttcagataccgccaaacgttaaataggaccctcttggtgacttg
ctaacttagaaagtcatgcccaggtgttacgtaatcttacttggtatgactttttgagtaacggacttgctagagtccttaccagact
tccagtttagcaaaccacagattgatctgtcctctggcatatctcaaaccaatcaacacccgtaaccctttcatgaaacaactct
agaatgcgtcttatcaacaggattgcccaaaacagtaattggggcggtggaatctacatgggagttccatcgttgtctcggttttt
ctccctataagctactctggagacgaagtaactaacaccctcaaatatcattatgtcctggtcagggttcaagaaagccgtca
atagagctggaacgcaggtccttatgaagacaaaccatcttgatgagagtctggatgaagagtttgatttccaggagaagaa
cttccggattatccaacaatttactcaagagctctacaatcgactttcaagcttattggaaaatcatcatagttgtctaaaggctaa
tctagccgttgctaccactttgaactcatattatggaacctccactacggatggatttgaaggaaaatatctggagatcgtcaac
aggataaaagacgatgtgttacccaattcagtggaaccgttcaattatacaatattgcaaccgttagagactcttaaacagtac
aatgaagagtttgacttgttaataaaaaaacgttatagaaagaaattggactacgatatgctccaatccaaattgtcaaaattg
accaccgaaaaagaacaattggaatttgacaagaggaacaactcactagattctcaaacggagcgtcacctagagtcagtt
tccaagtcaattacagaaagtttggaaacagaagaggagtatctacaattgaattccaaacttaaagtcgagctgtccgaatt
catgtcgctaaggctttcttacttggaccccattttgaaagtttcattaaagttcagtcaaaaattttcatggacatttatgacacatt
aaagagcggactaccttatgttgattctctatccaaagaggattatcagtccaagatcttggactctagaatagataacattctgt
cgaaaatggaagcgctgaaccttcaagcttacattgatgattagagcaatgatataaacaacaattgagtgacaggtctactt
gttctcaaaaggccataaccatctgtttgcatctcttatcaccacaccatcctcctcatctggccttcaattgtggggaacaacta
gcatcccaacaccagactaactccacccagatgaaaccagttgtcgcttaccagtcaatgaatgttgagctaacgttccttga
aactcgaatgatcccagccttgctgcgtatcatccctccgctattccgccgcttgctccaaccatgtttccgccttttcgaacaag
ttcaaatacctatcttggcaggacttttcctcctgccttttttagcctcaggtctcggttagcctctaggcaaattctggtcttcatacc
tatatcaacttttcatcagatagcctttgggttcaaaaaagaactaaagcaggatgcctgatatataaatcccagatgatctgctt
ttgaaactattttcagtatcttgattcgtttacttacaaacaactattgttgattttatctggagaataatcgaacaaa SEQ ID NO: 4 (pDAS2NEFbidi; ←pDAS2|pNEF→)

ttttgatgtttgatagtttgataagagtgaactttagtgtttagaggggttataatttgttgtaactggttttggtcttaagttaaaacgaa
cttgttatattaaacacaacggtcactcaggatacaagaataggaaagaaaaactttaaactggggacatgttgtctttatata
atttggcggttaacccttaatgcccgtttccgtctcttcatgataacaaagctgcccatctatgactgaatgtggagaagtatcgg
aacaacccttcactaaggatatctaggctaaactcattcgcgccttagatttctccaaggtatcggttaagtttcctctttcgtactg
gctaacgatggtgttgctcaacaaagggatggaacggcagctaaagggagtgcatggaatgactttaattggctgagaaag
tgttctatttgtccgaatttctttttctattatctgttcgtttgggcggatctctccagtgggggtaaatggaagatttctgttcatgggg

Figure 25 (continued)

taaggaagctgaaatccttcgtttcttataggggcaagtatactaaatctcggaacattgaatggggtttactttcattggctacag
aaattattaagtttgttatggggtgaagttaccagtaattttcattttttcacttcaacttttggggtatttctgtggggtagcatagcttg
acaggtaatatgatgtactatgggataggcaagtcttgtgtttcagataccgccaaacgttaaataggaccctcttggtgacttg
ctaacttagaaagtcatgcccaggtgttacgtaatcttacttggtatgacttttgagtaacggacttgctagagtccttaccagact
tccagtttagcaaaccacagattgatctgtcctctggcatatctcaaaccaatcaacacccgtaaccctttcatgaaacaactct
agaatgcgtcttatcaacaggattgcccaaaacagtaattggggcggtggaatctacatgggagttccatcgttgtctcggtttt
ctccctataagctactctggagacgaagtaactaacaccctcaaatatcatt SEQ ID NO: 5 (pDAS1w/oNEF; pDAS1short→)

agcaatgatataaacaacaattgagtgacaggtctactttgttctcaaaaggccataaccatctgtttgcatctcttatcaccaca
ccatcctcctcatctggccttcaattgtggggaacaactagcatcccaacaccagactaactccacccagatgaaaccagttg
tcgcttaccagtcaatgaatgttgagctaacgttccttgaaactcgaatgatcccagccttgctgcgtatcatccctccgctattcc
gccgcttgctccaaccatgtttccgccttttttcgaacaagttcaaataccctatctttggcaggacttttcctcctgccttttttagcctca
ggtctcggttagcctctaggcaaattctggtcttcatacctatatcaacttttcatcagatagcctttgggttcaaaaaagaactaa
agcaggatgcctgatatataaatcccagatgatctgcttttgaaactattttcagtatcttgattcgtttacttacaaacaactattgtt
gattttatctggagaataatcgaacaaa SEQ ID NO: 6 (pFBA1bidi; ←pPGBB|pFBA1→)

ttctctattgaacggcttgaaatttggaaaccagatgaaaaataaaaggaatggaagaagaatgagaaaaggataattaat
ctttggtttagctaaattcttcattgcactttgaccttaaaggggctgatttaaggttatgccggggaagaagaaatagcgcgatg
agcaaagtcgatgcctaaaggagtggttttgctacctcatttaagaagagaataggacgtgcatccagcgatgcgtgctagg
acaaagaaccgcacttggcgggtacaaacctgacgtcattcctgatattattgacatttgagctgaccaattaaggtgcccat
ccacaatagccacctggatagcggaatgcacccccattgagttgatcaaactaccatttgcttatacctcaagttaatgttgaa
ctaccattcttcacatgctcctcctagatcccctgtcccctttctccccctctttcatcctttaatttgcatttcttgacggtcttctatccct
agaaagtttggaacgcctgctatatggttaggacacgactgactagctataaaattttcagaccagactctttctcttcttaacgc
aaatttaacaggcagacaacaacataggaaagaatcaccatataggttggactcttacagacgtccttggccgttgaccatg
gtggtacagttgtccaagttctacaagtttgtctgaagaatgaagttattggtcttgggtgcagctttccatctgttcgatttattcggc
taagagtttaccattgtgtgctcgtatggggaagggtgcaaggatcagtaatacagtcgaacctggagtatctaccatagtggg
gatacaatgtagtttatctgttatctcgattgttcctaattaaggttttctttgatcctcttctagtccacacctcctagatgacattcgag
ctgcctggattggatgcctaggtttattgcctagttcaatacaattcgtgcgggctacagtagaaggcccttacataatccggaa

Figure 25 (continued)

agcatggtcccccaccaaattgagagcttttcagccttcactggtggtatcattttcgggagataataaggtttcgattgggaatt
cccaccagagaacactatagagggaccaagctgatgctagcctgacatccccaaagcacacttcgtaattgaaaaccgtta
cctctagcacactgtccagactaccccgtcaaaaaaacgctcttttctcgactaattgagtcttcaactcatcccgtccttgcc
gaattacttgaattcatttcacacctccgttgcttacgtactctcaccggtctccggtgtacatggatccgctattgccagatattct
catacaacaatcaccagatcaaggtcgtgaacggaccaatggcatccagagcaatcctgaacagatagggggtccgggct
gtataaagtgaaataacgtgacttgaaccagcaactatgtcccagttgtgctacacttaacacgcgattaccccggagctcac
caggcctcttcccctctcattggaaccctcctagcgcttcgaaataatggctgcgtactatttaactggtgccagttcccgctga
caatatccttttcttctcccttagttccccacatatcaattgaacatattttttacaca SEQ ID NO: 7 (pFBA2bidi; ← PP7435_Chr1-0638 protein motif:KOG:SNF2 family DNA-dependent ATPase|pFBA2→)

aaattaatccataagataaggcaaatgtgcttaagtaattgaaaacagtgttgtgattatataagcatggtatttgaatagaact
actggggttaacttatctagtaggatggaagttgagggagatcaagatgcttaaagaaaaggattggccaatatgaaagcca
taattagcaatacttatttaatcagataattgtggggcattgtgacttgacttttaccaggacttcaaacctcaaccatttaaacagt
tatagaagacgtaccgtcacttttgcttttaatgtgatctaaatgtgatcacatgaactcaaactaaaatgatatcttttactggaca
aaaatgttatcctgcaaacagaaagctttcttctattctaagaagaacatttacattggtgggaaacctgaaaacagaaaataa
atactccccagtgacccctatgagcaggattttttgcatccctattgtaggcctttcaaactcacacctaatatttcccgccactcaca
ctatcaatgatcacttcccagttctcttcttcccctattcgtaccatgcaacccttacacgccttttccatttcggttcggatgcgactt
ccagtctgtggggtacgtagcctattctcttagccggtatttaaacatacaaattcacccaaattctaccttgataaggtaattgatt
aatttcataaat SEQ ID NO: 8 (pADH2bidi; ←pADH2|pGEF1→)

tttcgtaaagtaaataagataaaagctagtagctgatggaagaaggaaaaaagaatttgggagcaggacaggggtatttat
agtgaggtgaattgtgaatattagagattggggaggggtggaccaattgttggtgtgatcattgggggtgcgctatattcgcacc
agatgcgggttgacgtctacaataggcagggtgaaaggaattgggcacgaattcgcaccccggagagcgctcacccccgt
tttcaaacagcggggggagcacaaaatgttgaaaactacacagatcttttcggacaccggtcgctttatgtagtcgacatgca
gattctcccaaatggaaaacgagattggacaatttgtggagttggaaagggggtgggaatcaacgaaattagcagattcat
gggcaattggcaggactgggcagaagggggtgagaattgcaatcgaatggaacaggcactcccgttgcgaaatcaaaaaa
gtctcgctatctgaactgattttttttaagcagcaacttacggtcaatacatctccgatggaggaattttcacccctcgctaactag
atgggccccttctaagaaatttgggtttaaggttgggcagtcagtcagtgcaccaatgctaactgccatttgtccaaagagggg

Figure 25 (continued)

tgcaaggatgagggaccgttgagaataagatttggggtgttaatcggtgatactgatttgtcaaagagtggggaggactgctg
ggcattgttcacccccctagttgttagagttcgatagccggccgaatcaccccctcttcttacataatcattgtcactatgtgggg
tctctacagtctcaccctgcgatccgggacgacgccgcgaaattaggggggcaagtctcctccgggcatgcaatattggtaac
aggatcaattgatgcgagaaaagttggaggggggtgtaaaattcaagcccacaaagtcacacccttatgcctgtagaggggc
aatcggagagcagccatggggtgtttcactcgcacttgggtggtaaaaaggaagaaacggtttaccaccatccggcatcca
ctctggtcgtgcaatttggcgagatcgcgcatccacacctagtctcctattccatccaaaatttgcttacctaatatgatctttattga
ttctaccttcccctaagagtcctctagtaccgtcagaaaacgctgcg SEQ ID NO: 9 (pFGH1bidi; ←pFGH1|putative secreted protein→)
tagaaagatggaatgaacgctacagcgaggaagagcaattgctatatataaccccagagtattgcttaggctaagttgtcaa
gattgggtaaacaattcgagaatcaaagattaagtaagaagtgttatgttgtaggcttgaagcttcacgcaaggaagactggg
agaagtagttgattcctgtggtgattgtcctgaaatgactgtgagcgggtccgcctagagtgttggatcccttcagtgtttccact
aatgggtctacattgcgtcccagatcgatagaccaggagatcaattaaaccctacgcaaactatagggcatgaatcaaga
gtatcaattggcatactcggatcattttctaccgtttcataccaagagaagatggcaaaatgggacttctgcgttatcatgagttg
gctccatcggaattttccacacttcaggttttcagatgtattacccttttgagccattcacaatgatatcttggtatttcaaacagttgt
agcttttactataaaagtcacaccgatcacaacgtttcatcaatgaagat SEQ ID NO: 10 (pFDH1bidi; ←pFDH1|p[ubiquitin carboxyl-terminal hydrolase 5/13] →)
tgtttaagtgggtgatgttggaggtatttgaggtaaaataggtttatagtttgataactagcggagaaaagaaggagagtctcat
ctggaggagaaataaacttacttaaatagttttcggccatttaactgggttacgacatcattacgtgtaggtcagcacactgaat
agaattagactaagtataagcacagggagttgggggtagccctcgaaaatcaggacatctggggtaaattttcccctaaaatg
cgcaccaactgcagtacaatatggcgtttggaggagcaacatcccgacaagatttgggatttctgtagcctttgccataaact
ggacaggagtttccacacccgtttcagccggtccctttattggttcttcggaaggctagagtaacggcccaatgtgaagagag
gaacattgtttcgttacgttccgaaacctagaatggtgttttgggaagggactactaagatgatgctgtgtagaagtttgagccgt
agagtcccacttagagaacatcatcgaactatttaattagaagctggttccgcaccca SEQ ID NO: 11 (pDAK1bidi; ←pDAK1|pSST2→)
ttaaagtgtataaattcctttgtttcctgttataaaagaagaagcaacaagcaaaggatcgggaaaggagtcgaaggttgagc
aagcgggttctttatatagtgagccattatgacatattagacatccttaccccctcgattagagagctcaaacagccgactagcta
gccgctctagtatgacccacgcgaaaatgagccgagcgatgccctctatggaacgtattggaataggaaatggtaagcttta

Figure 25 (continued)

atgggctggggggaagggaattgtccttctggtgtgatttttttttggcattggcgctaccagatgtctctttcgtaagggttcaac
ctcggaggccgatctttgtggtttatgtttacacatcgtatttttcaggactaagaaaatcactggatggcagatgtcggtctggag
acttgaaacgggcttacttagtagctttgaaacttatcagataatccgaatgtgttgcatattgttgcatggtcacttttccacaactt
tgaaacgctaatctttgatctgaaacaaacatgctttgcctataaaccatgtatcaccccctacttctttctccctcacagcatcagc
agatgaca SEQ ID NO: 12 (pFBP1bidi; ←p[hypothetical protein]|pFBP1→)
tgctcaaacgagtggagagggaaatcgattcagcagttaaatcaatgctggaaaatattcgagattacctaatcggatctgga
acttacttcgacctgacattttcttgcctggggagccacgatcgattatgtaatcaagaatatggacagagggaaacagattta
gctgtcaaaagcccaagagaagctaccgatcaatggatgcggatagataaagaaaagccttttttttttcattagccatccgag
ttgtccaatcaaatgtctgcctgctacgctggagaggaatcacgcgtgtttaacattcggattgtcgcctaaaataagcctattac
ctacacagtaaaacccgggggggtgcttggtatcaatgaccccgggattttatccaccagttttttcttctggcaagagtgcatt
gcatccccgtacaaatagtagcaacctccacaagaggaatccctatgagcgagaagtccatagtaataccccgcggaa
aagagatatttttgtttccgtgttgcccttgaacttcagtttcccccatcagtttatatagtagccgggttcccaatctctagcccttcttt
cctcctatttcattcctctcttcttacgttatcttacattagc SEQ ID NO: 13 (pPEX8bidi; ←pPEX8|p[60S ribosomal protein L18]→)
taacaggcacctgaagataggtaaaaaaaaattgcttcgtcttgttgatctgaggacgcagaggctatttatacgggtcggctc
tttgaagtgggggttggttgaccccccagccttatcgaatcctaagttcacatgtagttcgcgcaagtattacataagcaagaattc
agctgatatctgaggaggaatcaatcgcatggattcgtacttcactttagtgtaaaaagacaaatagataagaaaacactggt
taatgtcttccctgatacccaaaggattccaccaggttccacgatgtaaggcgttcacagtgttgctgatattgctcccaatttttgc
atcacttttttgacctcaagtatgtgtttatccttagctacgaccccctttatcagtcagtggagacaatactggaggatattgatctac
caattgagctttcagaacgaatcagaggtc SEQ ID NO: 14 (pPEX5bidi; ←pPEX5|p[ATP-dependent RNA helicase DDX23/PRP28]→)
tacgattagttagatggttgggttgagaatagttggatgtgttcaacaaacggagggggatttcgccacctttaaatacccttgcc
aaaactgattgaattgatctgaccccctatcgctaacgtaaaaaaaaaatgcggaggagatgaccagagacggatcggac
cgaaacagatgaatggaagagggaaggagagctaaacaaagtttaaaaggttgctagcacggtaaattctacagcaaca
aaaaaagagagctgatagcacagactatcataaatccacaagtgttgaatggtggagctcaatttcctctgctgacaatctc
tgttgtgtagggaatgtgagcagcgagcatgtgacactttaggctacgctatcccagttgcgaaaaatgtgaggagaagaac

Figure 25 (continued)

cgaaggcagaggtagtaaaccggtggtagtgtacaaaaccaattgaaaagttctttaaagttatcgttttgctagaccgtttgg
tttgga SEQ ID NO: 15 (pGAPbidi; ←p[hypothetical protein (protein motif:KOG:DNA helicase PIF1/RRM]|pGAP→)

tcttctcataaaaaaggtcaatctgctagttaaaatatatgctgtaaacggattatggtacatcccttaaatgcagcgttaaagac
cttcttattgggcagtatgaatggtacttcaaggtgattctgtcgagtaaggcttgaaagagtagtcgttagatttaagtaataata
gagcagagcgaatactaaacacgaaacgcgcgagcataaaatgacaatataaccatattaggaagcaaggagatatata
ccaaaaacgaagacctggtcggatctgatcagatcacattctttcactctacaaaatgaccagagtacgaaatatacgcata
cattcgattcaagttttttaaagccttacatcgtatgtctggcaaaatcagagaatgcctcgtgaaagaaaaagactgaatccat
taacttgcatgccaactcaatcccgactgtcaatcattcatccttgcgtcttttgaacatctatgcttccacaagtcaattcttgattta
gtatacacataaccaaatttggatcaagtttgaagtaaaactttaacttcagctccttacatttgcactaagatctctgctactctgg
tcccaagtgaaccaccttttggacccttattgaccggaccttaacttgccaaacctaaacgcttaatgcctcagacgttttaatgc
ctctcaacacctccaaggttgctttcttgagcatgcctactaggaactttaacgaactgtggggttgcagacagtttcaggcgtgt
cccgaccaatatggcctactagactctctgaaaaatcacagttttccagtagttccgatcaaattaccatcgaaatggtcccata
aacggacatttgacatccgttcctgaattatagtcttccaccgtggatcatggtgttccttttttcccaaagaatatcagcatccctt
aactacgttaggtcagtgatgacaatggaccaaattgttgcaaggttttctttttctttcatcggcacatttcagcctcacatgcga
ctattatcgatcaatgaaatccatcaagattgaaatcttaaaattgcccctttcacttgacaggatcctttttgtagaaatgtcttgg
tgtcctcgtccaatcaggtagccatctctgaaatatctggctccgttgcaactccgaacgacctgctggcaacgtaaaattctcc
ggggtaaaacttaaatgtggagtaatggaaccagaaacgtctcttcccttctctctccttccaccgcccgttaccgtccctagga
aattttactctgctggagagcttcttctacggccccttgcagcaatgctcttcccagcattacgttgcgggtaaaacggaggtcg
tgtacccgacctagcagcccagggatggaaaagtcccggccgtcgctggcaataatagcgggcggacgcatgtcatgag
attattggaaaccaccagaatcgaatataaaaggcgaacacctttcccaattttggtttctcctgacccaaagactttaaatttaa
tttatttgtccctatttcaatcaattgaacaactatcaaaacaca SEQ ID NO: 16 (pGPM1bidi; ←pGPM1|pNSP1→)

tgtttgtttgtgtaattgaaagttgttactgacaaaatagaggcacttaagctaggggggcagaagtatccttatatatggaggttgt
gcccactaggaatagtgaaatccgtctgagtcctgtccgggattcgcggcatggatgtacgattcccggggtaacgccagaa
gcatgagagggagccagggtatggtgtgcgcgcagcagggcaagagtcaatcgaaaactgagaactgaaagctcagac

Figure 25 (continued)

tgacggatgtgatgagatgaggtcgagaaaacaggatgcctgatggcacttaaaggtcgtgtagcactggttcttttgtttccct cctcccaaaaaatctggcaaaatcgtaacctaaacagaaaaataacggacactactaataacccaaggtattgata SEQ ID NO: 17 (pPGI1bidi; ←pPGI1|pGPI2 →)

tttatcaattggttggagttgaattattccggaagaatggaaaggttgggactcgaatagatttaaatttaagcaacctaggagg tttaaatagacaaggggatgggacgtcagattgtctgcaatcgcttatatatttattgcctgacggaataagggctacctggaatt tcttttctgcgaacgggcaagtgtggtgcgcggcgaaaagacttccacaaagtataaggtgggcggaactttgcgtggtggg tgggcgagaaaggcgtccgagctcggtgggggaggatatcctgaaaggtagacagctgaccgaatgccgggtgttactg caatcacagacatccgacatctagtaacacaggtgacctattacgtcaaagcaacgtttctaagttctgatgtagtatcttccaa gtcttgaagcttctgcctgtatgcagtttcgtcttgatgcctagactgctgaatttcagccaactcttgcatttctttcaacagcttcact tgcaaccctttagtgattttatcttggagtaatgatctttagggaagacgaatcctttcccttcctgttccatctgcgttgacagttgtt taacatcatcaagaatgtctatttcggtcaatagtttgtcctggtagttgattccaggacggatggtttcgatgttatcagccatttgg ttacaacttctcgaatagtagaaggtaagagataattacacgatggccttcttgtatggggaaaaaagtattacctcagcaatt gaattttgttctcaaatttggggaaaggccagccaaagacattcggttcccatcctgaccatcgattactaatctccagagaaa gtgctttcgagtagccctctagaaacgttgtcacttttgcgccgagtccactcaa SEQ ID NO: 18 (pPFK1bidi; ←PFK1|p[hypothetical protein]→)

ctgtaattcgatttgagtctaacaagcaaacaaaatactaatttatgattgttctccttagcagttcaagacggaaccaattgcaa tcaatgttatgctttgttgaatcgattaaactctgtatgaataatgtttgatttatagcaagagaagaaagatcttctccctggctgca tcgctcttttttatggatttgacaccttcgagactaagaaaatcaccttacgataatagctcatcgccggagcagagaaattcag gaacaaattcgggcctaactggtgcgtttaaagcataatatatgcttgcgattatctagttttttattaattgctcaagagcagctga atcttttccaaaatcgatgattttcaacgttctaaaagctaaaagttgtagttcactctgtcagcctcgatcttagtacgtgagacg gtgtcccgagcggttcccagacgaccatttcaaggctaatgaaaaagcgcgctgacttcgcgtatggtctatcagttaccatttt cgtacgtctctttcatcacctttcactttggtgcctagtaactagatcttcgaaccactgaagacagcacagtcggattaatttgtcc tcaaagtatcatatctgaattactggtcttcaattgagtactttgatacattcagaaggtag SEQ ID NO: 19 (pTKL1bidi; ←p[hypothetical protein]|pTKL1→)

gaattccgagggtggctcaacaactattcacgtgacttggacgttggaagttgaggtggttggtggatgttgcacggagtatcat ttgtaagcatgaaatcagtctaaaaaacttgcagaatagcagagcggttcggaaattcattcaaaaccacctcctcagattgg atctgccctactctgtttagctctgggagattttctcggtcgtgttctttcgctggtctacccacgctataggaatcgctgtgaacgct

Figure 25 (continued)

accttcttcccaacttctcggtgactattataagccattcccactttgttttcaagcaccaacaacccaccccaccttatctactcc
atcttgggtgtccccgcgcctgttgcaaagtccgaaccatagaaccccgacctttgtcccactaaccctcagacacccctcg
gaagtcagggagaaaccactccgaagtacattaatcatccctcgtattctcgacggtgcccatttctttataaaagggagac
acaggttgcttcactaactctagacttgtattctacatccactctacaca SEQ ID NO: 20 (pPXR1bidi; ←pPXR1|p[putative secreted protein]→)
Cttagattttttttttgcttggtgggattccttcgttttgtgcgattactctgaaatctagaaaatttgaaatctatccagctgcttcattg
acatctctccagccttttatattgttcacccttctccacatcgatatcgcctatgaatcttgaatagcctctggaaaaagaggttac
aagactaagatacctcctttcgagtcgtgcaccaatcccccgcgttatcgttaagctgccttcagttgtctctcccccagctcta
agctacttgtaggaattacgcaatccttgttgagtttgaacccttctggttggggtattttcaagttaaagttacgtcatttccattgg
aaagaacagggattccctctttttctcttttggcaggtctgtttgaatcactttcctccgcgagcccctagacaacctccttcatag
cctttatcactactgttttgacactccagaa SEQ ID NO: 21 (pSOD1mitoBIDI; ←p[hypothetical protein]|pSODmito1→)
ggtcgaaccaatcaaggaggaagggacagcaactaaaaaaagattggcttatctatgcaaaatgatgatatgttttaatca
acgtgaagagaacgacagagataaaaagcgactcaatgttgtgtatagaaaatgcttgtggggctagggatttgaagaaaa
gtaggagactaataacctggttgaggagatatgcgatatgatgatctgttaatatggtaaaagaaaagaatttcccgatttggat
atggagcgatttggtgcaacttttatatatgacatactcttgatgtgtacaacttcaagtatccgcagtgaagttaactacctgaag
aatgaaagccagcgcagtagagtaaacaagcgacaaaaagactaatattatgaaagactatgtagatatgaattaaaatc
ccgaaacaaaccatcaggaaaacgttacaaatccttcagtcagttattccccggtcgggaaaacgagtatagtatgagcag
gctaatccagtactttggcaagcctcatcctgtgcaacgaaagaactaaatactataacccaatggctcaattgattcaaaac
ctccttactcgtcctatttaacttctgtaaccattacaattccaacgtaagaaccaactaaagttgctcctaaaatcattaaaacta
ccgggagttggatggccagttcccgatttggaaatagagacatcagaaaagtgccttcatctaagaatggtgatagaaatag
ccataaggtgtagtagataaacagaactgtggtcactataagccacatacagttaaccaactagaatttgccttaatcttttccg
agtccgagacggctcttgcacgtgatctttaaacatagcagtttgctgattgttgcttctaagctacactcccttctcttttatcttga
accagagagcggaatcatctacttaccttgacctaaattaac SEQ ID NO: 22 (pMSR1c3bidi; ←pMSR1c3|p[Protein PYRAB00100]→)
ctgaaaaaaactacgtttggaaaaacgtgggaaggaacttatgaaacgcaaactcgttggtcttttctgggatttggcggaag
ctaaggtatttatatattttcatttccgttctacggtatttgaaatttagtaaccgttctgacgtgctattagttgatgtcacgtgtaatggt

Figure 25 (continued)

gaaattttcatgttttttcttcctacaaagcgtttcttttttgcagagctcatcacaaaaacagcaattgccgagatccgaccccaa
aagccagagccttgaatcgcgacattattcccgagtcttaggtaataatgtgggttgagacatgtcgttttttaaactttctcaaat
cctgggcttagaagtggagttgacagaaatcacggcgcaactgcactaaaa SEQ ID NO: 23 (pGLR1bidi; ←p[3-methyl-2-oxobutanoate
hydroxymethyltransferase]|pGLR1→)
agttaattttcaagcagttgagagaaaaaaatgcgagagatgcaccgttatttacccgaatatagtttgttcgcggacatctctc
atgctaatcttgctccaaagatcaaagtcccgagaactcggctcagattttcccatgtgctttcggtaagatggtttactgccaac
tttaagtttgcccactatcgattattggaataaagttttgagattattctgattcgaatcgacagggaaaggaatacgttgactcac
tcagtaccttaaactctgtaagcgccgtagacatactagcaagtacactactagacctagccacagcacgaaccaagaggc
gagcctctcagctctgttcaaactttataccccccaataagactacaag SEQ ID NO: 24 pSODcytoSODmitobidi; ←superoxide dismutase, Fe-Mn family|Cu/Zn
superoxide dismutase→)
ggcactggatgatgttcaaatcttattctcgtctgaacgatcgaaaaatttgtcttgtgggcttctgagtggaattttcttaggcgca
cggaaatacagaggtgaatggtttctcttggggagatacttttttcgcgtgctcctccgtgcggaacttccttctgagcttctacctc
tcagattagtctaatcgcatcaggaataagactgagaatgcttttaaggagaggcttgagattggctaattgcgttccgaagtac
tctttcaaaaggagttataccccctctcaactacgattctctaaagaattatcgtaggcatgctcaggcgcctcaaccccatcagtt
tgacgccactagatgggaccaacaaccagttactaatgagcaaggagtaatactcccatccgactcaattgcaaacattctg
agacaaccaactctggtcatagaacggcaaatggaaatgatgaatatattttttaggatttgagcaggcgaaccgatatgttatc
atggatcctacaggaagtattttgggttacatgctagaaagggatctgggcatcaccaaagctatattgagacagatctaccgt
ttgcatcgaccttttacagtggatgtaatggatactgcaggaaatgtattaatgacaatcaagaggccgtttagtttcatcaattcg
cacatcaaagctatattaccccctttcaggaacagcgacccagacgaacatgtaattggagaatccgttcaaagctggcatc
cttggagacgaagatacaatctatttacagcacaaattggcgaaaaggacactgtctacgatcagttcgggtacattgacgc
accgtttctttcctttgagtttcctgtactttcagaatctaggcaaacgctaggtgctgtctctagaaacttcgtgggctttgcaagag
agcttttcacagatacaggagtttacatcatccgtatggggcctgaatcttttgtagggctagaagggaactacgggaacaatg
tggcccaacatgcccttacgctggaccaaagggctgtattattagccaatgccgtttcaattgactttgattacttttctaggcactc
gtcacacagtggtggcttcatgggtttgaggaatagacagggtctcgtcaactcagctcctgccaccaaaccaatcattgatc
aacgagcacacttttgtccacgtgagatcgctttcgcttgcagaaagagcaatgcatgaaaacggcaaacgcaaaacgag
caaaaaaacgagtaaataactacaatttcaccaccaacagggtcaaagagcttttgagacactataaaaggggccctttcc

Figure 25 (continued)

ccccaggttccttgaaatcctcattcaattatgttttttactcataatttgactcaattggcatcttcttcttgttcatatacagtaattgat
atgacgcttagtcattattagtgttctcgactagcagtggcgaaaaaagggggagttattttctagaaccgaccgcaaactata
aaagaaagctgcccctcatataccttcgaattctttattttctgtgtttcttccctatttaacatctacacaaaa SEQ ID NO: 25 (pTFIID+pTBP (=pNatbidi1); ←p[Transcription initiation factor TFIID subunit 10]|p[TATA-box-binding protein]→)

gtttctgcttctagaagaatgtgatgtgatgagtgccaaactagtatcgtagatggaagagtcgcgaaaagttatggttaggag
caccagtatatctaatcttgcaagtgagaagaagtcaagcagaagagggatagtgttcgatagccacttgggcccattaacc
agctaaagggccctagagatttactttgtatagatgatattttctatgcttcggggactgtgtagaccacctattgttcaagtgcag
tattaagtgagcaccttgtgaaaaatttccttatggggtataatcagtaattgaagtgcgcgccttgacttatcgcatagctttcca
ctgttagtcagttaaccacaggaaaaagtgatggaaagctaccgtaaaaacttccgctcgtcaaattgggtttctctaacatca
actaacgttataggaagctgaatttcccactcaattctattagactcacctattatgaagatgcagtcaagacgtagcaatgatt
acccggatataaataagaaaactatataagcagcgcgatttcccttctcatctacatttgagttttcttagggggtaactaattgcat
aagcctgagaatcattaaattgcattctctttctcttccttctcccttcaaagtcacaca SEQ ID NO: 26 (pPFK+pRGD3(=Natbidi4); ←pPFK(6-phosphofructo-2-kinase 1)|pRGD3[TATA-binding protein-associated factor MOT1]→)

gttgtcaattaaagaggtgatatattcagaagaaaggggcctgttgcttaaactaactttggatgcacgaggctactccgggat
ggcatgtcgcggatttgaaaaagacagatcgcgaattcactgtcactatcaagatggattgatcagataacgtgacacgaaa
gagaactggtaaaggagagggtgagcaatgacagcagacaacagcaatcaagggagcaatcaaccggggtaacaaa
ggaaaagttgagtggttatgaattttcaggaaataaatcgtgtctgctatttaatatatagctattgatctgtataatattgcgtatgc
aactttccttctcgaataaaatgcgtaattgtaagctgctcattgggttcaattaaatattaattgcccgtcactgtgggctcccaga
tcaagaaacagcagcaaaagaccacgagtaccaatggaaatcttggttctagttccgattcgtacagatgataaaccaaca
atcaatttccaacgaaagatgtaagttgtggatttgcttgatgacttgggacgcaataaatacccagttgttgtacatctaacatct
cggccatcgacacgtccgtttatctcgtgcactaccgatttccacccctaagtaaacccttttttcctctcgattatgtaaacagctt
catttttccttaccttctgttgggctatggttcctggctgttaagtttcatccaaccgta SEQ ID NO: 27 (p[two ribosomal proteins] (=Natbidi5); ←p(40S ribosomal protein S16)|p(60S ribosomal protein L13)→)

Figure 25 (continued)

tgttactcttacaaagaacaagttttttgttagcaattttttcacaatccgagagagagcgtgagcgatcaggtagtgtgtcgcac
aataagagttaacgttttcagaggtttgactgggagggtgaaacagttagtgtgtagccattgactgttagtgcacgacttgaaa
taactgtttgcaaagaaatctaaatctcgaatttgtgactgctgtaactgaactaggaaggccagacctgtaaatacacgcgat
ttatctcccaaaactagagcgatcacgtgcattataagactaaattgctttgtgaaaaatagtccacctggggaaccgagcatc
gtccgcccatctccaaagaagacccgcgcatactctcccgccagcacttttcccttcagattttggttacgaagcccctgctcga
aatctttctcgatctgtgccttcactcaccttttacaaattttcaccaagttaaaaaaagcttccaggttaactacaacaatcaaag SEQ ID NO: 28 (p[RNA Pol subunit]|+pTFB2 (=Natbidi6); ←p[DNA-directed RNA polymerase II subunit B]|pTFB2→)

tgcttacttttgtttccaaaaaaccacccctttctgtgctgataactaaaagcacttggagagaaatcaaatcaaaagtttcagaa
aaaaaaaatgctaactacaaacagcttacaaattttcttggaaaatgtttacataagcttcgatactcagatgtctctacaaaaa
atctgatcctagagatagagatcttttggcacatttcagggacaggaac SEQ ID NO: 29 (p[ribosomal protein]+pSER3(=Natbidi7); ←p[60S ribosomal protein L15]|pSER3→)

tgtaaatgataattgataacttgtttagaagtttgtatgaggagaagaaagcttgaggatttttttcttagactccacgacgcactg
aaaattttatggaacgcgcgaaattgttttcagaaagtttgcgtggtgttacccgactgtgtttatttcagagagttaccctgaattct
ggatttggaatcagacgatttatccgtgctcatctgacgcgcgaattttatttggcacatggagtctcaacatccatcggcctttgg
cctaaattattcaagggagagtactgatagtcacgtgacgtttcaccatgtagtaagtctttttttttttcagagtgactctttcacag
ataacagcataactatatagacttcacagaggtctgtcatctctagatacctgcacacaaacttaaaca SEQ ID NO: 30 (pFTR1+p FET3 (=Natbidi8); ←pFTR1|FET3→)

tttgaaaagaactacaacgaccactgaacgttgagtggcactgctattggaaggaagttcgagaaatgacttgaaggcgag
atttgtggaaggaaggatcgagtttatatagctctgaaactttctccctaaaacacataagccaataaaactttaagaaactag
cttctatattgtaaatttaagattattatctactggtgcatgaacatgcacgcattgcatcaaaaatagcattttagtaacaaattatc
gaattttaaacagtggtgcgaaatgatattaattatcagatcatctctgggctgtgcacattaacgaccccaaaagtcaagta
cagtcgtgtggttcgtgggctttcgtaccaaatggaaaaatcacgtacaagtatgcccagagctaagctaatcggatggcaa
gtagaaagtggatgggtttcacagaacaataaagaatgagtgacggatattattggctggcaggcattaaagatgcataattt
aagctttctgttttctactttggaattgtcacaaatttgaactgtggatgttattgaaacacagacccgtataaatacctcttgagag
aaatttgaaagtgaagctatttcagtgaattaatcactcgccatacacgaggtagataattcacgtagacgaatttcttttgatcc

Figure 25 (continued)

attttattcagggtggacagtcagaagtgttcgttcacctgatatgttctagatgcagctcgaaacgctgtaaaaaaaaagtcc
caaaagtcacgtgcataaaggtgtagttcaatttaatggagataacataacatctatgactcctttcatgaatccatctcaaaaa
cacaaactttgctagaatatctggtggcaccgatttttcatcatttcacgagtttatatagcatatgcgccaacagaacgttgcctg
acacaatgttaaggcttttaaattttgcttgtgtagtaaaaagttagtagtgtgttactcgatatcatatttctatcagaagtggaatat
tctaatctctcctctaccttigttacaatccgtttcgaacagaaaaaagaatttatg SEQ ID NO: 31 (pCYC3+pPDA1(=Natbidi9); ←pCYC3|pPDA1→)
tttttattggtgcttttttgaggttttttttttgagtttctctaactgaggcggattccctggaaggatagcgacggagcaaataggagg
agacagcaggaggtgctggttgcaaactagagtaaattcatgctaccaactgagtcgcgaatcgacagggattgctcaatat
tatgcagtctatcttaattctggagaagcctttaattgagttgaaagaattgtcgtacttaggggaatacttcgtagtttatcagtttg
cattacctcttactgataagaattagaatggatcatgacatctgacatctttttttttttttcgaatcaagggttgactgaattgacctttt
gatttctctccgcccccaccgaatgcatctggcatctgcgcgcccccataatgtttaaccgaaccctccttacggacagttttct
cccggtcgcgcttagtaccctaactccttgtgttgtctgtcctcaacttttttgagactcttcctcacttccaatacaaccaccaag SEQ ID NO: 32 (p[Phosphoinositide binding protein required for vesicle formation in autophagy]+pFDH1 (=Natbidi10); ←p[Phosphoinositide binding protein required for vesicle formation in autophagy]|pFDH1→)
tagatggttatcttgaatggtatttgtaaggattgatctcgaaggttgtatatagtcgtgccgtgcaagtggaggagaatgaaag
aagatgtaagaattctggcccttgcacctgatcgcgaaggtggaaatggcagaaggatcagcctggacgaagcaaccagt
tccaactgctaagtaaagaagatgctagacgaaggagacttcagaggtgaaaagtttgcaagaagagagctgcgggaaa
taaattttcaatttaaggacttgagtgcgtccatattcgtgtacgtgtccaactgttttccattacctaagaaaaacataaagattaa
aaagataaacccaatcgggaaactttagcgtgccgtttcggattccgaaaaacttttggagcgccagatgactatggaaga
ggagtgtaccaaaatggcaagtcgggggctactcaccggatagccaatacattctctaggaaccagggatgaatccaggttt
ttgttgtcacggtaggtcaagcattcacttcttaggaatatctcgttgaaagctacttgaaatcccattgggtgcggaaccagcttc
taattaaatagttcgatgatgttctctaagtgggactctacggctcaaacttctacacagcatcatcttagtagtcccttcccaaaa
caccattctaggtttcggaacgtaacgaaacaatgttcctctcttcacattgggccgttactctagccttccgaagaaccaataa
aagggaccggctgaaacgggtgtggaaactcctgtccagtttatggcaaaggctacagaaatcccaatcttgtcgggatgtt
gctcctcccaaacgccatattgtactgcagttggtgcgcattttagggaaaatttaccccagatgtcctgattttcgagggctacc
cccaactccctgtgcttatacttagtctaattctattcagtgtgctgacctacacgtaatgatgtcgtaacccagttaaatggccga

Figure 25 (continued)

aaaactatttaagtaagtttatttctcctccagatgagactctccttcttttctccgctagttatcaaactataaacctattttacctcaa
atacctccaacatcacccacttaaaca SEQ ID NO: 33 (pGUT1bidi; ← p[Probable aquaporin PIP1-2 2]|pGUT1→)
gaaaaggtttactatcccgatttaggcgaaaagagtagaccaaatatttgcgtcgttgatcaatttataaaaaaatatggcaac
tttcaccagcttagctctccagacttttcttcccgaattttttggttccgagaaatggacctttgctagccggtgggaaataacttga
gatgcatggacggaatcaaacacggaaaaatctaggtcatcctacagcaaacacctgcaaggccgggaaagaattgctc
ggtattttctattttgggagatttgttggcacggaagaatcggtaactttactaatccaatactccgctcctgactgtttcaagtcgg
accccaactttcaagtgacccaatttagcagcctgcattctcttgattttatgggggaaactaacaatagtgttgccttgatttaag
tggcattgttctttgaaatcgaaattggggataacgtcataccgaaaggtaaacaacttcggggaattgccctggttaaacattt
attaagcgagataaataggggatagcgagataggggggcggagaagaagaagggtgttaaattgctgaaatctctcaatctg
gaagaaacggaataaattaactccttcctgagataataagatccgactctgctatgaccccacacggtactgacctcggcat
accccattggatctggtgcgaagcaacaggtcctgaaacctttatcacgtgtagtagattgaccttccagcaaaaaaaggc
attatatattttgttgttgaagggggtgagggggaggtgcaggtggttctttattcgtcttgtagttaattttcccggggttgcggagcgt
caaaagtttgcccgatctgatagcttgcaagatgccaccgcttatccaacgcacttcagagagcttgccgtagaaagaacgtt
ttcctcgtagtattccagcacttcatggtgaagtcgctatttcaccgaagggggggtattaaggttgcgcacccctccccacac
cccagaatcgtttattggctgggttcaatggcgtttgagttagcacattttttccttaaacaccctccaaacacggataaaaatgc
atgtgcatcctgaaactggtagagatgcgtactccgtgctccgataataacagtggtgttggggttgctgttagctcacgcactc
cgttttttttcaaccagcaaaattcgatggggagaaacttggggtactttgccgactcctccaccatactggtatataaataatact
cgcccacttttcgtttgctgcttttatatttcaaggactgaaaaagactcttcttctacttttcacactataccacagatatatctactat
a SEQ ID NO: 34 (pHTX1bidi(=W1,2; natbidi2); ←HTA1|HTB1→)
tgttgtagttttaatatagtttgagtatgagatggaactcagaacgaaggaattatcaccagtttatatattctgaggaaagggtgt
gtcctaaattggacagtcacgatggcaataaacgctcagccaatcagaatgcaggagccataaattgttgtattattgctgca
agatttatgtgggttcacattccactgaatggttttcactgtagaattggtgtcctagttgttatgtttcgagatgttttcaagaaaaac
taaaatgcacaaactgaccaataatgtgccgtcgcgcttggtacaaacgtcaggattgccaccacttttttcgcactctggtaca
aaagttcgcacttcccactcgtatgtaacgaaaaacagagcagtctatccagaacgagacaaattagcgcgtactgtcccat
tccataaggtatcataggaaacgagagtcctcccccccatcacgtatatataaacacactgatatcccacatccgcttgtcacc
aaactaatacatccagttcaagttacctaaacaaatcaaa

Figure 25 (continued)

SEQ ID NO: 35 (pHHX1bidi (=W3,4); ←HHT1|HHF1→)

ttttctttacctggatataaataaaaaaaaggaaacacaatctctgtttcaagaaattagggattttagtctgcttatatacttcgcg
ctaccccgcgacccgagcaactactagccttacaaacgctttgcactcagaaaacaagtgcgacattttgcttttttcaaactg
tgacgttagcgacaaccctggtttgaactcgttttcgaccaataagatcatcgcaaccgatcagcccggtctcaattgtacgtgt
acaactcagcatggccgcaaataaggaacggtacctttgtggccaaatgagtggcgttgctgctaacaaggtgagccatca
actggtatatatagacgagttccctcctacctgctttttctccttttttttattgctcaactactatcgataaaac SEQ ID NO: 36 (pHHX2bidi (=W5,6; natbidi3); ←HHT2|HHF2→)

ttttactacgatagacacaagaagaagcaggaggggggaggatctggatatttataagagtctcccatagataacgatttggc
acttttgccatcagtgccaacagtatttcgcactgcgacactcccgactgaaatgggatgcaagtttattatgagttctggtagc
atagaaatgggacatgttcttacagtttcaaatttacgcacgctctgcctctaggagtacggctcagttcatcgcgtaccgtgtcg
tatcaacattacggtttggcactgcattgtccaccttaactcttttcatctataaatacaagacgagtgcgtccttttctagactcacc
cataaacaaataatcaataaat SEQ ID NO: 37 (pHHO1bidi (W7); ←pTBF1|pHHO1→)

ttgatccagctgtaaagggagaaggatgcagttccaaggctgattgagttaactactgatgcaagttagagaacctagaata
gagtctcaaattttcttgcacttttggcacagtgtgcaacaatgattaacataaattttcgcgtgttttgttttaataccatgaatataa
atacaaaagatgcacgtattccccttttctagtttgtttgtgttttgctaaatagtccataaagaagttgaacc SEQ ID NO: 38 (pCSE4bidi (W11); ←p[Actin or Component of both the SWI/SNF and RSC chromatin remodeling complexes, depending on which annotation you believe in]|pCSE4→)

cgttctactagcgtgaagcttttgttgtataaaggatgaagggctgaattatccaagtcgcgctctcaagcagatgttgggaggt
attctgattcattctggggatggttaagttagcttggcctacaagataaattcattcaaaataatcatgctttgaaactaaattcacg
agtaacaagtgaaccaagttgcctgcacctacgaggatgttgttttgaactcagtcatgaaccattgagtactgactccaagat
cgtaactgctccgtccttggaagactgactccatacatttgatgaaattcagcccggttgtcatgcttataaaaaatctctacttaa
gatctctcatctgtacagacagagactttgttagcactcattgacgactctctgttttctgccgttctgcctttctgtttgaccaggact

Figure 25 (continued)

atgatccaaagaattcttgggttattccaaatacgtcatattgattattacccttttaggtaataatatggaaattgaaaaatgaaat
ggctggtacaacctatcctcctctttagatcacattctcttccagatcaacaattgagctataactc

SEQ ID NO: 39(D1)

ggaggggggaggatctggatatttataagagtctcccatagataacgatttggcacttttgccatcagtgccaacagtatttcgc
actgcgacactcccgactgaaatgggatgcaagtttattatgagttctggtagcatagaaatgggacatgttcttacagtttcaa
atttacgcacgctctgcctctaggagtacggctcagttcatcgcgtaccgtgtcgtatcaacattacggtttggcactgcattgtcc
accttaactcttttcatctataaatacaagacgagtgcgtccttttctagactcacccataaacaaataatcaataaat

SEQ ID NO: 40(D2)

ttttactacgatagacacaagaagtaagagtctcccatagataacgatttggcacttttgccatcagtgccaacagtatttcgca
ctgcgacactcccgactgaaatgggatgcaagtttattatgagttctggtagcatagaaatgggacatgttcttacagtttcaaat
ttacgcacgctctgcctctaggagtacggctcagttcatcgcgtaccgtgtcgtatcaacattacggtttggcactgcattgtcca
ccttaactcttttcatctataaatacaagacgagtgcgtccttttctagactcacccataaacaaataatcaataaat

SEQ ID NO: 41(D3)

ttttactacgatagacacaagaagaagcaggaggggaggatctggatttggcacttttgccatcagtgccaacagtatttcg
cactgcgacactcccgactgaaatgggatgcaagtttattatgagttctggtagcatagaaatgggacatgttcttacagtttca
aatttacgcacgctctgcctctaggagtacggctcagttcatcgcgtaccgtgtcgtatcaacattacggtttggcactgcattgtc
caccttaactcttttcatctataaatacaagacgagtgcgtccttttctagactcacccataaacaaataatcaataaat

SEQ ID NO: 42(D4)

ttttactacgatagacacaagaagaagcaggaggggaggatctggatatttataagagtctcccatagataaacagtatttc
gcactgcgacactcccgactgaaatgggatgcaagtttattatgagttctggtagcatagaaatgggacatgttcttacagtttc
aaatttacgcacgctctgcctctaggagtacggctcagttcatcgcgtaccgtgtcgtatcaacattacggtttggcactgcattgt
ccaccttaactcttttcatctataaatacaagacgagtgcgtccttttctagactcacccataaacaaataatcaataaat

SEQ ID NO: 43(D5)

ttttactacgatagacacaagaagaagcaggaggggaggatctggatatttataagagtctcccatagataacgatttggc
acttttgccatcacccgactgaaatgggatgcaagtttattatgagttctggtagcatagaaatgggacatgttcttacagtttca

Figure 25 (continued)

aatttacgcacgctctgcctctaggagtacggctcagttcatcgcgtaccgtgtcgtatcaacattacggtttggcactgcattgtc
cacctlaactcttttcatctataaatacaagacgagtgcgtccttttctagactcacccataaacaaataatcaataaat

SEQ ID NO: 44(D6)

ttttactacgatagacacaagaagaagcaggaggggggaggatctggatatttataagagtctcccatagataacgatttggc
acttttttgccatcagtgccaacagtatttcgcactgcgtattatgagttctggtagcatagaaatgggacatgttcttacagtttcaa
atttacgcacgctctgcctctaggagtacggctcagttcatcgcgtaccgtgtcgtatcaacattacggtttggcactgcattgtcc
accttaactcttttcatctataaatacaagacgagtgcgtccttttctagactcacccataaacaaataatcaataaat

SEQ ID NO: 45(D7)

ttttactacgatagacacaagaagaagcaggaggggggaggatctggatatttataagagtctcccatagataacgatttggc
acttttttgccatcagtgccaacagtatttcgcactgcgacactcccgactgaaatgggatgcaatgggacatgttcttacagtttc
aaatttacgcacgctctgcctctaggagtacggctcagttcatcgcgtaccgtgtcgtatcaacattacggtttggcactgcattgt
ccaccttaactcttttcatctataaatacaagacgagtgcgtccttttctagactcacccataaacaaataatcaataaat

SEQ ID NO: 46(D8)

ttttactacgatagacacaagaagaagcaggaggggggaggatctggatatttataagagtctcccatagataacgatttggc
acttttttgccatcagtgccaacagtatttcgcactgcgacactcccgactgaaatgggatgcaagtttattatgagttctggtagc
aaatttacgcacgctctgcctctaggagtacggctcagttcatcgcgtaccgtgtcgtatcaacattacggtttggcactgcattgt
ccaccttaactcttttcatctataaatacaagacgagtgcgtccttttctagactcacccataaacaaataatcaataaat

SEQ ID NO: 47(D9)

ttttactacgatagacacaagaagaagcaggaggggggaggatctggatatttataagagtctcccatagataacgatttggc
acttttttgccatcagtgccaacagtatttcgcactgcgacactcccgactgaaatgggatgcaagtttattatgagttctggtagc
atagaaatgggacatgttcttacaggagtacggctcagttcatcgcgtaccgtgtcgtatcaacattacggtttggcactgcattg
tccaccttaactcttttcatctataaatacaagacgagtgcgtccttttctagactcacccataaacaaataatcaataaat

SEQ ID NO: 48(D10)

ttttactacgatagacacaagaagaagcaggaggggggaggatctggatatttataagagtctcccatagataacgatttggc
acttttttgccatcagtgccaacagtatttcgcactgcgacactcccgactgaaatgggatgcaagtttattatgagttctggtagc

Figure 25 (continued)

atagaaatgggacatgttcttacagtttcaaatttacgcacgctctgcaccgtgtcgtatcaacattacggtttggcactgcattgt
ccaccttaactcttttcatctataaatacaagacgagtgcgtccttttctagactcacccataaacaaataatcaataaat

SEQ ID NO: 49(D11)

ttttactacgatagacacaagaagaagcaggaggggaggatctggatatttataagagtctcccatagataacgatttggc
acttttgccatcagtgccaacagtatttcgcactgcgacactcccgactgaaatgggatgcaagtttattatgagttctggtagc
atagaaatgggacatgttcttacagtttcaaatttacgcacgctctgcctctaggagtacggctcagttcatttggcactgcattgt
ccaccttaactcttttcatctataaatacaagacgagtgcgtccttttctagactcacccataaacaaataatcaataaat

SEQ ID NO: 50(D12)

ttttactacgatagacacaagaagaagcaggaggggaggatctggatatttataagagtctcccatagataacgatttggc
acttttgccatcagtgccaacagtatttcgcactgcgacactcccgactgaaatgggatgcaagtttattatgagttctggtagc
atagaaatgggacatgttcttacagtttcaaatttacgcacgctctgcctctaggagtacggctcagttcatcgcgtaccgtgtcg
tatcaacattctcttttcatctataaatacaagacgagtgcgtccttttctagactcacccataaacaaataatcaataaat

SEQ ID NO: 51(D13)

ttttactacgatagacacaagaagaagcaggaggggaggatctggatatttataagagtctcccatagataacgatttggc
acttttgccatcagtgccaacagtatttcgcactgcgacactcccgactgaaatgggatgcaagtttattatgagttctggtagc
atagaaatgggacatgttcttacagtttcaaatttacgcacgctctgcctctaggagtacggctcagttcatcgcgtaccgtgtcg
tatcaacattacggtttggcactgcattgtccaccgagtgcgtccttttctagactcacccataaacaaataatcaataaat

SEQ ID NO: 52(D14)

ttttactacgatagacacaagaagaagcaggaggggaggatctggatatttataagagtctcccatagataacgatttggc
acttttgccatcagtgccaacagtatttcgcactgcgacactcccgactgaaatgggatgcaagtttattatgagttctggtagc
atagaaatgggacatgttcttacagtttcaaatttacgcacgctctgcctctaggagtacggctcagttcatcgcgtaccgtgtcg
tatcaacattacggtttggcactgcattgtccaccttaactcttttcatctataaatacccataaacaaataatcaataaat

SEQ ID NO: 53(D15)

ttttactacgatagacacaagaagaagcaggaggggaggatctggatatttataagagtctcccatagataacgatttggc
acttttgccatcagtgccaacagtatttcgcactgcgacactcccgactgaaatgggatgcaagtttattatgagttctggtagc

Figure 25 (continued)

atagaaatgggacatgttcttacagtttcaaatttacgcacgctctgcctctaggagtacggctcagttcatcgcgtaccgtgtcg
tatcaacattacggtttggcactgcattgtccaccttaactcttttcatctataaatacaagacgagtgcgtccttttctag

SEQ ID NO: 54(T1)

taaggtggacaatgcagtgccaaaccgtaatgttgatacgacacggtacgcgatgaactgagccgtactcctagaggcaga
gcgtgcgtaaatttgaaactgtaagaacatgtcccatttctatgctaccagaactcataataaacttgcatcccatttcagtcggg
agtgtcgcagtgcgaaatactgttggcactgatggcaaaaagtgccaaatcgttatctatgggagactcttataaatatccaga
tcctccccctcctgcttcttcttgtgtctatcgtagtaaaa

SEQ ID NO: 55(T2)

gaggcagagcgtgcgtaaatttgaaactgtaagaacatgtcccatttctatgctaccagaactcataataaacttgcatcccatt
tcagtcgggagtgtcgcagtgcgaaatactgttggcactgatggcaaaaagtgccaaatcgttatctatgggagactcttataa
atatccagatcctccccctcctgcttcttcttgtgtctatcgtagtaaaa

SEQ ID NO: 56(T3)

ttgcatcccatttcagtcgggagtgtcgcagtgcgaaatactgttggcactgatggcaaaaagtgccaaatcgttatctatggg
agactcttataaatatccagatcctccccctcctgcttcttcttgtgtctatcgtagtaaaa

SEQ ID NO: 57(T4)

ttatctatgggagactcttataaatatccagatcctccccctcctgcttcttcttgtgtctatcgtagtaaaa

SEQ ID NO: 58(T5)

cgatttggcacttttgccatcagtgccaacagtatttcgcactgcgacactcccgactgaaatgggatgcaagtttattatgagtt
ctggtagcatagaaatgggacatgttcttacagtttcaaatttacgcacgctctgcctctaggagtacggctcagttcatcgcgta
ccgtgtcgtatcaacattacggtttggcactgcattgtccaccttaactcttttcatctataaatacaagacgagtgcgtccttttcta
gactcacccataaacaaataatcaataaat

SEQ ID NO: 59(T6)

Figure 25 (continued)

gtttattatgagttctggtagcatagaaatgggacatgttcttacagtttcaaatttacgcacgctctgcctctaggagtacggctc
agttcatcgcgtaccgtgtcgtatcaacattacggtttggcactgcattgtccaccttaactcttttcatctataaatacaagacga
gtgcgtccttttctagactcacccataaacaaataatcaataaat

SEQ ID NO: 60(T7)

taggagtacggctcagttcatcgcgtaccgtgtcgtatcaacattacggtttggcactgcattgtccaccttaactcttttcatctata
aatacaagacgagtgcgtccttttctagactcacccataaacaaataatcaataaat

SEQ ID NO: 61(T8)

actcttttcatctataaatacaagacgagtgcgtccttttctagactcacccataaacaaataatcaataaat

SEQ ID NO: 62(S1)

ttttactacgatagacacaagaagaagcaggagggggaggatctggatatttataagagtctcccatagataacgatttggc
acttttttgccatcagtgccaacagtatttcgcactgcgacactcccgaccgcacgctctgcctctaggagtacggctcagttcat
cgcgtaccgtgtcgtatcaacattacggtttggcactgcattgtccaccttaactcttttcatctataaatacaagacgagtgcgtc
cttttctagactcacccataaacaaataatcaataaat

SEQ ID NO: 63(S2)

ttttactacgatagacacaagaagaagcaggagggggaggatctggatatttataagagtctcccatagataacgatttggc
acttttttgaaatgggatgcaagtttattatgagttctggtagcatagaaatgggacatgttcttacagtttcaaatttatgtcgtatca
acattacggtttggcactgcattgtccaccttaactcttttcatctataaatacaagacgagtgcgtccttttctagactcacccata
aacaaataatcaataaat

SEQ ID NO: 64(S3)

ttttactacgatagacacaagaagaagcaggagggggaggatctggatatttataagagtcttgaaatgggatgcaagtttatt
atgagttctggtagcatagaaatgggacatgttcttacagtttcaaatttaattgtccaccttaactcttttcatctataaatacaaga
cgagtgcgtccttttctagactcacccataaacaaataatcaataaat

SEQ ID NO: 65(S4)

ttttactacgatagacacaagaagaagcaggagggggaggatctggaagagtctcccatagataacgatttggcacttttgc
catcagtgccaacagtatttcgcactgcgacactcccgactgaaatgggatgcaagtttattatgagttctggtagcatagaaat

Figure 25 (continued)

gggacatgttcttacagtttcaaatttacgcacgctctgcctctaggagtacggctcagttcatcgcgtaccgtgtcgtatcaacat
tacggtttggcactgcattgtccaccttaactcttttcatccaagacgagtgcgtccttttctagactcacccataaacaaataatc
aataaat

SEQ ID NO: 66(S5)

ttttactacgatagacacaagaagaagcaggaggggaggatctggatatttataagagtctcccatagataacgatttgcca
tagtatttcgcactgcgacactcccgactgaaatgggatgcaagtttattatgagttctggtagcatagaaatgggacatgttctt
acagtttcaaatttacgcacgctctgcctctaggagtacggctcagttcatcgcgtaccgtgtcgtatcaacattacggcattgtc
caccttaactcttttcatctataaatacaagacgagtgcgtccttttctagactcacccataaacaaataatcaataaat SEQ ID NO: 67 (SynBidi1)

ttttactacgatagacacaagaagaagcaggaggggaggatctggatatttatatattgctgtcaagtaggggttagaacag
ttaaattttgatcatgaacgttaggctatcagcagtattcccaccagaatcttggaagcatacaatgtggagacaatgcataatc
atccaaaaagcgggtgtttccccatttgcgagttcaaatacctatctttggcaggacttttcctcctgccttttttagcctcaggtctc
ggttagcctctaggcaaattctggtcttcatacctatatcaacttttcatcagatagcctttgggttcaaaaaagaactaaagcag
gatgcctgatataaatacaagacgagtgcgtccttttctagactcacccataaacaaataatcaataaat SEQ ID NO: 68 (SynBidi2)

ttttactacgatagacacaagaagaagcaggaggggaggatctggatatttatatcaggcatcctgctttagttcttttttgaac
ccaaaggctatctgatgaaaagttgatataggtatgaagaccagaatttgcctagaggctaaccgagacctgaggctaaaa
aaggcaggaggaaaagtcctgccaaagataggtatttgaactcgcaaatggggaaacacccgcttttggatgattatgcatt
gtctccacattgtatgcttccaagattctggtgggaatactgctgatagcctaacgttcatgatcaaaatttaactgttctaacccct
acttgacagcaatatataaatacaagacgagtgcgtccttttctagactcacccataaacaaataatcaataaat SEQ ID NO: 69 (SynBidi3)

ttttactacgatagacacaagaagaagcaggaggggaggatctggatatttataagagtctcccatagataattaaattttga
tcatgaacgttaggctatcagcagtattcccaccagaatcttggaagcatacaatgtggagacaatgcataatcatccaaaaa
gcgggtgtttccccatttgcgagttcaaatacctatctttggcaggacttttcctcctgccttttttagcctcaggtctcggttagcctct
aggcaaattctggtcttcatacctatatcaacttttcatcagatagcctttgggttcaaaaaattaactcttttcatctataaatacaa
gacgagtgcgtccttttctagactcacccataaacaaataatcaataaat

Figure 25 (continued)

SEQ ID NO: 70 (SynBidi4)

ttttactacgatagacacaagaagaagcaggaggggggaggatctggatatttataagagtctcccatagataatttttttgaacc
caaaggctatctgatgaaaagttgatataggtatgaagaccagaatttgcctagaggctaaccgagacctgaggctaaaaa
aggcaggaggaaaagtcctgccaaagataggtatttgaactcgcaaatggggaaacacccgcttttttggatgattatgcattg
tctccacattgtatgcttccaagattctggtgggaatactgctgatagcctaacgttcatgatcaaaatttaattaactcttttcatcta
taaatacaagacgagtgcgtccttttctagactcacccataaacaaataatcaataaat SEQ ID NO: 71 (SynBidi5)

ttttactacgatagacacaagaagaagcaggaggggggaggatctggatatttatatattgctgtcaagtaggggttagaacag
ttaaattttgatcatgaacgttaggctatcagcagtattcccaccagaatcttggaagcatacaatgtggagacaatgcataatc
atccaaaaagcgggtgtttccccatttgcgttatttccgaatgcaacaagctccgcattacacccgaacatcactccagatgag
ggctttctgagtgtggggtcaaatagtttcatgttccccaaatggcccaaaactgacagtttaaacgctgtcttggaacttaactct
tttcatctataaatacaagacgagtgcgtccttttctagactcacccataaacaaataatcaataaat SEQ ID NO: 72 (SynBidi6)

ttttactacgatagacacaagaagaagcaggaggggggaggatctggatatttataagagtctcccatagataagttccaaga
cagcgtttaaactgtcagttttgggccatttggggaacatgaaactatttgaccccacactcagaaagccctcatctggagtgat
gttcgggtgtaatgcggagcttgttgcattcggaaataacgcaaatggggaaacacccgcttttttggatgattatgcattgtctcc
acattgtatgcttccaagattctggtgggaatactgctgatagcctaacgttcatgatcaaaatttaactgttctaaccccctacttga
cagcaatatataaatacaagacgagtgcgtccttttctagactcacccataaacaaataatcaataaat SEQ ID NO: 73 (SynBidi7)

ttttactacgatagacacaagaagaagcaggaggggggaggatctggatatttataagagtctcccatagataattaaattttga
tcatgaacgttaggctatcagcagtattcccaccagaatcttggaagcatacaatgtggagacaatgcataatcatccaaaaa
gcgggtgtttccccatttgcgttatttccgaatgcaacaagctccgcattacacccgaacatcactccagatgagggctttctga
gtgtggggtcaaatagtttcatgttccccaaatggcccaaaactgacagtttaaacgctgtcttggaacattgtccaccttaactc
ttttcatctataaatacaagacgagtgcgtccttttctagactcacccataaacaaataatcaataaat SEQ ID NO: 74 (SynBidi8)

Figure 25 (continued)

ttttactacgatagacacaagaagaagcaggaggggaggatctggatatttataagagtctcccatagataacgatttggc
acttttgttccaagacagcgtttaaactgtcagttttgggccatttggggaacatgaaactatttgaccccacactcagaaagcc
ctcatctggagtgatgttcgggtgtaatgcggagcttgttgcattcggaaataacgcaaatggggaaacacccgcttttggatg
attatgcattgtctccacattgtatgcttccaagattctggtgggaatactgctgatagcctaacgttcatgatcaaaatttaattaa
ctcttttcatctataaatacaagacgagtgcgtccttttctagactcacccataaacaaataatcaataaat SEQ ID NO: 75 (SynBidi9)

ttttactacgatagacacaagaagaagcaggaggggaggatctggatatttataagagtctcccatagataagttccaaga
cagcgtttaaactgtcagttttgggccatttggggaacatgaaactatttgaccccacactcagaaagccctcatctggagtgat
gttcgggtgtaatgcggagcttgttgcattcggaaataacgttccatcccttgttgagcaacaccatcgttagccagtacgaaa
gaggaaacttaaccgataccttggagaaatctaaggcgcgaatgagtttagcctagatatccttagtgaagggttgttccgata
cttctccacattcagtcatagatgggcagctttgttatcatgaagttaactcttttcatctataaatacaagacgagtgcgtccttttct
agactcacccataaacaaataatcaataaat SEQ ID NO: 76 (SynBidi10)

ttttactacgatagacacaagaagaagcaggaggggaggatctggatatttataagagtctcccatagataacttcatgata
acaaagctgcccatctatgactgaatgtggagaagtatcggaacaacccttcactaaggatatctaggctaaactcattcgcg
ccttagatttctccaaggtatcggttaagtttcctctttcgtactggctaacgatggtgttgctcaacaaagggatggaacgttatttc
cgaatgcaacaagctccgcattacacccgaacatcactccagatgagggcttctgagtgtggggtcaaatagtttcatgttcc
ccaaatggcccaaaactgacagtttaaacgctgtcttggaacttaactcttttcatctataaatacaagacgagtgcgtccttttct
agactcacccataaacaaataatcaataaat SEQ ID NO: 77 (SynBidi11)

ttttactacgatagacacaagaagaagcaggaggggaggatctggatatttataagagtctcccatagataatgatgttcgg
gtgtaatgcggagcttgttgtgcattgtctccacattgtatgcttccaagattctggtgggaatttaactcttttcatctataaatacaa
gacgagtgcgtccttttctagactcacccataaacaaataatcaataaat SEQ ID NO: 78 (SynBidi12)

Figure 25 (continued)

ttttactacgatagacacaagaagaagcaggaggggggaggatctggatatttataagagtctcccatagataaattcccacc
agaatcttggaagcatacaatgtggagacaatgcacaacaagctccgcattacacccgaacatcattaactcttttcatctata
aatacaagacgagtgcgtccttttctagactcacccataaacaaataatcaataaat SEQ ID NO: 79(pDAS1-D1)

aataaaaaaacgttatagaaagaaattggactacgatatgctccaatccaaattgtcaaaattgaccaccgaaaaagaaca
attggaatttgacaagaggaacaactcactagattctcaaacggagcgtcacctttggaaacagaagaggagtatctacaat
tgaattccaaacttaaagtcgagctgtccgaattcatgtcgctaaggctttcttacttggaccccattttgaaagtttcattaaagtt
cagtcaaaaattttcatggacatttatgacacattaaagagcggactaccttatgttgattctctatccaaagaggattatcagtc
caagatcttggactctagaatagataacattctgtcgaaaatggaagcgctgaaccttcaagcttacattgatgattagagcaa
tgatataaacaacaattgagtgacaggtctactttgttctcaaaaggccataaccatctgtttgcatctcttatcaccacaccatcc
tcctcatctggccttcaattgtggggaacaactagcatcccaacaccagactaactccacccagatgaaaccagttgtcgctt
accagtcaatgaatgttgagctaacgttccttgaaactcgaatgatcccagccttgctgcgtatcatccctccgctattccgccgc
ttgctccaaccatgtttccgccttttcgaacaagttcaaatacctatctttggcaggacttttcctcctgcctttttagcctcaggtctc
ggttagcctctaggcaaattctggtcttcatacctatatcaacttttcatcagatagcctttgggttcaaaaaagaactaaagcag
gatgcctgatatataaatcccagatgatctgcttttgaaactattttcagtatcttgattcgtttacttacaaacaactattgttgatttta
tctggagaataatcgaacaaa SEQ ID NO: 80(pDAS1-D2)

aataaaaaaacgttatagaaagaaattggactacgatatgctccaatccaaattgtcaaaattgaccaccgaaaaagaaca
attggaatttgacaagaggaacaactcactagattctcaaacggagcgtcacctagagtcagtttccaagtcaattacagaa
agtttggaaacagaagaggagtatctacaattgaattccaaacttaaagtcgagctgtccgaattcatgtcgctaaggctttctt
acttggaccccattttgaaagtttcattaaagttcagtcaaaaattttcatggacatttatgacacattaaagagcggactacctt
atgttgattctctatccaaagaggattatcagtccaagatcttggactctagaatagataacattctgtcgaaaatggaagcgct
gaaccttcaagcttacattcctcctcatctggccttcaattgtggggaacaactagcatcccaacaccagactaactccaccca
gatgaaaccagttgtcgcttaccagtcaatgaatgttgagctaacgttccttgaaactcgaatgatcccagccttgctgcgtatc
atccctccgctattccgccgcttgctccaaccatgtttccgccttttcgaacaagttcaaatacctatctttggcaggacttttcctc
ctgcctttttagcctcaggtctcggttagcctctaggcaaattctggtcttcatacctatatcaacttttcatcagatagcctttgggtt
caaaaaagaactaaagcaggatgcctgatatataaatcccagatgatctgcttttgaaactattttcagtatcttgattcgtttactt
acaaacaactattgttgattttatctggagaataatcgaacaaa

Figure 25 (continued)

SEQ ID NO: 81(pDAS1-D3)

aataaaaaaacgttatagaaagaaattggactacgatatgctccaatccaaattgtcaaaattgaccaccgaaaaagaaca
attggaatttgacaagaggaacaactcactagattctcaaacggagcgtcacctagagtcagtttccaagtcaattacagaa
agtttggaaacagaagaggagtatctacaattgaattccaaacttaaagtcgagctgtccgaattcatgtcgctaaggctttctt
acttggaccccattttttgaaagtttcattaaagttcagtcaaaaattttcatggacatttatgacacattaaagagcggactaccttt
atgttgattctctatccaaagaggattatcagtccaagatcttggactctagaatagataacattctgtcgaaaatggaagcgct
gaaccttcaagcttacattgatgattagagcaatgatataaacaacaattgagtgacaggtctactttgttctcaaaaggccata
accatctgtttgcatctcttatcaccacaccatcctcctcatctggccttcaattgtggggaacaactagcatcccaacaccaga
ctaactccacccagatgaaaccagttgtctaacgttccttgaaactcgaatgatcccagccttgctgcgtatcatcctccgctat
tccgccgcttgctccaaccatgtttccgcttttttcgaacaagttcaaatacctatctttggcaggacttttcctcctgccttttttagcc
tcaggtctcggttagcctctaggcaaattctggtcttcatacctatatcaacttttcatcagatagcctttgggttcaaaaaagaact
aaagcaggatgcctgatatataaatcccagatgatctgcttttgaaactattttcagtatcttgattcgtttacttacaaacaactatt
gttgattttatctggagaataatcgaacaaa SEQ ID NO: 82(pDAS1-D4)

aataaaaaaacgttatagaaagaaattggactacgatatgctccaatccaaattgtcaaaattgaccaccgaaaaagaaca
attggaatttgacaagaggaacaactcactagattctcaaacggagcgtcacctagagtcagtttccaagtcaattacagaa
agtttggaaacagaagaggagtatctacaattgaattccaaacttaaagtcgagctgtccgaattcatgtcgctaaggctttctt
acttggaccccattttttgaaagtttcattaaagttcagtcaaaaattttcatggacatttatgacacattaaagagcggactaccttt
atgttgattctctatccaaagaggattatcagtccaagatcttggactctagaatagataacattctgtcgaaaatggaagcgct
gaaccttcaagcttacattgatgattagagcaatgatataaacaacaattgagtgacaggtctactttgttctcaaaaggccata
accatctgtttgcatctcttatcaccacaccatcctcctcatctggccttcaattgtggggaacaactagcatcccaacaccaga
ctaactccacccagatgaaaccagttgtcgcttaccagtcaatgaatgttgagctaacgttccttgaaactcctccgctattccg
ccgcttgctccaaccatgtttccgcttttttcgaacaagttcaaatacctatctttggcaggacttttcctcctgccttttttagcctcag
gtctcggttagcctctaggcaaattctggtcttcatacctatatcaacttttcatcagatagcctttgggttcaaaaaagaactaaa
gcaggatgcctgatatataaatcccagatgatctgcttttgaaactattttcagtatcttgattcgtttacttacaaacaactattgttg
attttatctggagaataatcgaacaaa SEQ ID NO: 83(pDAS1-D5)

Figure 25 (continued)

aataaaaaaacgttatagaaagaaattggactacgatatgctccaatccaaattgtcaaaattgaccaccgaaaaagaaca
attggaatttgacaagaggaacaactcactagattctcaaacggagcgtcacctagagtcagtttccaagtcaattacagaa
agtttggaaacagaagaggagtatctacaattgaattccaaacttaaagtcgagctgtccgaattcatgtcgctaaggctttctt
acttggaccccattttttgaaagtttcattaaagttcagtcaaaaattttcatggacatttatgacacattaaagagcggactacctt
atgttgattctctatccaaagaggattatcagtccaagatcttggactctagaatagataacattctgtcgaaaatggaagcgct
gaaccttcaagcttacattgatgattagagcaatgatataaacaacaattgagtgacaggtctactttgttctcaaaaggccata
accatctgtttgcatctcttatcaccacaccatcctcctcatctggccttcaattgtggggaacaactagcatcccaacaccaga
ctaactccacccagatgaaaccagttgtcgcttaccagtcaatgaatgttgagctaacgttccttgaaactcgaatgatcccag
ccttgctgcgtatcatccctccgctattccgccgcttgctccaaccatgtttccgccttttttcgaacatcctgcctttttagcctcaggt
ctcggttagcctctaggcaaattctggtcttcatacctatatcaacttttcatcagatagcctttgggttcaaaaaagaactaaagc
aggatgcctgatatataaatcccagatgatctgcttttgaaactattttcagtatcttgattcgtttacttacaaacaactattgttgatt
ttatctggagaataatcgaacaaa SEQ ID NO: 84(pDAS1-D6)

aataaaaaaacgttatagaaagaaattggactacgatatgctccaatccaaattgtcaaaattgaccaccgaaaaagaaca
attggaatttgacaagaggaacaactcactagattctcaaacggagcgtcacctagagtcagtttccaagtcaattacagaa
agtttggaaacagaagaggagtatctacaattgaattccaaacttaaagtcgagctgtccgaattcatgtcgctaaggctttctt
acttggaccccattttttgaaagtttcattaaagttcagtcaaaaattttcatggacatttatgacacattaaagagcggactacctt
atgttgattctctatccaaagaggattatcagtccaagatcttggactctagaatagataacattctgtcgaaaatggaagcgct
gaaccttcaagcttacattgatgattagagcaatgatataaacaacaattgagtgacaggtctactttgttctcaaaaggccata
accatctgtttgcatctcttatcaccacaccatcctcctcatctggccttcaattgtggggaacaactagcatcccaacaccaga
ctaactccacccagatgaaaccagttgtcgcttaccagtcaatgaatgttgagctaacgttccttgaaactcgaatgatcccag
ccttgctgcgtatcatccctccgctattccgccgcttgctccaaccatgtttccgccttttttcgaacaagttcaaatacctatctttgg
caggacttttcctcctgcctttgcaaattctggtcttcatacctatatcaacttttcatcagatagcctttgggttcaaaaaagaacta
aagcaggatgcctgatatataaatcccagatgatctgcttttgaaactattttcagtatcttgattcgtttacttacaaacaactattg
ttgattttatctggagaataatcgaacaaa SEQ ID NO: 85(pDAS1-D7)

aataaaaaaacgttatagaaagaaattggactacgatatgctccaatccaaattgtcaaaattgaccaccgaaaaagaaca
attggaatttgacaagaggaacaactcactagattctcaaacggagcgtcacctagagtcagtttccaagtcaattacagaa

Figure 25 (continued)

agtttggaaacagaagaggagtatctacaattgaattccaaacttaaagtcgagctgtccgaattcatgtcgctaaggctttctt
acttggaccccattttgaaagtttcattaaagttcagtcaaaaattttcatggacatttatgacacattaaagagcggactacctt
atgttgattctctatccaagaggattatcagtccaagatcttggactctagaatagataacattctgtcgaaaatggaagcgct
gaaccttcaagcttacattgatgattagagcaatgatataaacaacaattgagtgacaggtctactttgttctcaaaaggccata
accatctgtttgcatctcttatcaccacaccatcctcctcatctggccttcaattgtggggaacaactagcatcccaacaccaga
ctaactccacccagatgaaaccagttgtcgcttaccagtcaatgaatgttgagctaacgttccttgaaactcgaatgatcccag
ccttgctgcgtatcatccctccgctattccgccgcttgctccaaccatgtttccgccttttcgaacaagttcaaatacctatctttgg
caggacttttcctcctgcctttttagcctcaggtctcggttagcctctaggcaaattctggtcttcataccggttcaaaaagaact
aaagcaggatgcctgatatataaatcccagatgatctgcttttgaaactattttcagtatcttgattcgtttacttacaaacaactatt
gttgattttatctggagaataatcgaacaaa SEQ ID NO: 86(pDAS1-D8)

aataaaaaaacgttatagaaagaaattggactacgatatgctccaatccaaattgtcaaaattgaccaccgaaaaagaaca
attggaatttgacaagaggaacaactcactagattctcaaacggagcgtcacctagagtcagttccaagtcaattacagaa
agtttggaaacagaagaggagtatctacaattgaattccaaacttaaagtcgagctgtccgaattcatgtcgctaaggctttctt
acttggaccccattttgaaagtttcattaaagttcagtcaaaaattttcatggacatttatgacacattaaagagcggactacctt
atgttgattctctatccaagaggattatcagtccaagatcttggactctagaatagataacattctgtcgaaaatggaagcgct
gaaccttcaagcttacattgatgattagagcaatgatataaacaacaattgagtgacaggtctactttgttctcaaaaggccata
accatctgtttgcatctcttatcaccacaccatcctcctcatctggccttcaattgtggggaacaactagcatcccaacaccaga
ctaactccacccagatgaaaccagttgtcgcttaccagtcaatgaatgttgagctaacgttccttgaaactcgaatgatcccag
ccttgctgcgtatcatccctccgctattccgccgcttgctccaaccatgtttccgccttttcgaacaagttcaaatacctatctttgg
caggacttttcctcctgcctttttagcctcaggtctcggttagcctctaggcaaattctggtcttcatacctatatcaacttttcatcag
atagcctttgggttcaaaaaagaactaaagcaggatgcctgatatataaatcccagatgatctgcttttgaaactattttcagtat
cttgattcgtttacttacatcgaacaaa SEQ ID NO: 87(pDAS1-D2+D5)

aataaaaaaacgttatagaaagaaattggactacgatatgctccaatccaaattgtcaaaattgaccaccgaaaaagaaca
attggaatttgacaagaggaacaactcactagattctcaaacggagcgtcacctagagtcagttccaagtcaattacagaa
agtttggaaacagaagaggagtatctacaattgaattccaaacttaaagtcgagctgtccgaattcatgtcgctaaggctttctt
acttggaccccattttgaaagtttcattaaagttcagtcaaaaattttcatggacatttatgacacattaaagagcggactacctt

Figure 25 (continued)

atgttgattctctatccaaagaggattatcagtccaagatcttggactctagaatagataacattctgtcgaaaatggaagcgct
gaaccttcaagcttacattcctcctcatctggccttcaattgtggggaacaactagcatcccaacaccagactaactccaccca
gatgaaaccagttgtcgcttaccagtcaatgaatgttgagctaacgttccttgaaactcgaatgatcccagccttgctgcgtatc
atccctccgctattccgccgcttgctccaaccatgtttccgcctttttcgaacatcctgccttttttagcctcaggtctcggttagcctct
aggcaaattctggtcttcatacctatatcaacttttcatcagatagcctttgggttcaaaaaagaactaaagcaggatgcctgat
atataaatcccagatgatctgcttttgaaactattttcagtatcttgattcgtttacttacaaacaactattgttgattttatctggagaat
aatcgaacaaa SEQ ID NO: 88(pDAS2-D1)

attactgttttgggcaatcctgttgataagacgcattctagagttgtttcatgaaagggttacgggtgttgattggtttgagatatgcc
agaggacagatcaatctgtggtttgctaaactggaagtctggtaaggactctagcataccaagtaagattacgtaacacctgg
gcatgactttctaagttagcaagtcaccaagagggtcctatttaacgtttggcggtatctgaaacacaagacttgcctatcccat
agtacatcatattacctgtcaagctatgctaccccacagaaataccccaaaagttgaagtgaaaaaatgaaaattactggta
acttcaccccataacaaacttaataatttctgtagccaatgaaagtaaaccccattcaatgttccgagatttagtatacttgcccct
ataagaaacgaaggatttcagcttccttaccccatgaacagaaatcttccatttaccccccactggagagatccgcccaaac
gaacagataatagaaaaagaaattcggacaaatagaacactttctcagccaattaaagtcattccatgcactcccttttagct
gccgttccatcccttgttgagcaacaccatcgttagccagtacgaaagaggaaacttaaccgataccttggagaaatctaag
gcgcgaatgagtttagcctagatatccttagtgaagggttgttccgatacttctccacattcagtcatagatgggcagctttgttatc
atgaagagacggaaacgggcattaagggttaaccgccaaattatataaagacaacatgtccccagtttaaagttttctttcct
attcttgtatcctgagtgaccgttgtgtttaatataacaagttcgttttaacttaagaccaaaaccagttacaacaaattataacccc
tctaaacactaaagttcactcttatcaaactatcaaacatcaaaa SEQ ID NO: 89(pDAS2-D2)

attactgttttgggcaatcctgttgataagacgcattctagagttgtttcatgaaagggttacgggtgttgattggtttgagatatgcc
agaggacagatcaatctgtggtttgctaaactggaagtctggtaaggactctagcaagtccgttactcaaaaagtcataccaa
gtaagattacgtaacacctgggcatgactttctaagttagcaagtcaccaagagggtcctatttatagtacatcatattacctgtc
aagctatgctaccccacagaaataccccaaaagttgaagtgaaaaaatgaaaattactggtaacttcaccccataacaaac
ttaataatttctgtagccaatgaaagtaaaccccattcaatgttccgagatttagtatacttgccccctataagaaacgaaggattt
cagcttccttaccccatgaacagaaatcttccatttaccccccactggagagatccgcccaaacgaacagataatagaaaa
aagaaattcggacaaatagaacactttctcagccaattaaagtcattccatgcactcccttttagctgccgttccatcccttgttga

Figure 25 (continued)

gcaacaccatcgttagccagtacgaaagaggaaacttaaccgataccttggagaaatctaaggcgcgaatgagtttagcct
agatatccttagtgaagggttgttccgatacttctccacattcagtcatagatgggcagctttgttatcatgaagagacggaaac
gggcattaagggttaaccgccaaattatataaagacaacatgtccccagtttaaagttttctttcctattcttgtatcctgagtgac
cgttgtgtttaatataacaagttcgttttaacttaagaccaaaaccagttacaacaaattataacccctctaaacactaaagttca
ctcttatcaaactatcaaacatcaaaa SEQ ID NO: 90(pDAS2-D3)

attactgttttgggcaatcctgttgataagacgcattctagagttgtttcatgaaagggttacgggtgttgattggtttgagatatgcc
agaggacagatcaatctgtggtttgctaaactggaagtctggtaaggactctagcaagtccgttactcaaaaagtcataccaa
gtaagattacgtaacacctgggcatgactttctaagttagcaagtcaccaagagggtcctatttaacgtttggcggtatctgaaa
cacaagacttgcctatcccatagtacatcatattacctgtcaagctatgctaccccacagaaataccccaaaagttgaagtga
aaaaatgaaaattactggtaacttcaccccataacaaacttaataatgagatttagtatacttgccccctataagaaacgaagg
atttcagcttccttaccccatgaacagaaatcttccatttaccccccactggagagatccgcccaaacgaacagataatagaa
aaaagaaattcggacaaatagaacactttctcagccaattaaagtcattccatgcactccctttagctgccgttccatcccttgtt
gagcaacaccatcgttagccagtacgaaagaggaaacttaaccgataccttggagaaatctaaggcgcgaatgagtttag
cctagatatccttagtgaagggttgttccgatacttctccacattcagtcatagatgggcagctttgttatcatgaagagacggaa
acgggcattaagggttaaccgccaaattatataaagacaacatgtccccagtttaaagttttctttcctattcttgtatcctgagtg
accgttgtgtttaatataacaagttcgttttaacttaagaccaaaaccagttacaacaaattataacccctctaaacactaaagtt
cactcttatcaaactatcaaacatcaaaa SEQ ID NO: 91(pDAS2-D4)

attactgttttgggcaatcctgttgataagacgcattctagagttgtttcatgaaagggttacgggtgttgattggtttgagatatgcc
agaggacagatcaatctgtggtttgctaaactggaagtctggtaaggactctagcaagtccgttactcaaaaagtcataccaa
gtaagattacgtaacacctgggcatgactttctaagttagcaagtcaccaagagggtcctatttaacgtttggcggtatctgaaa
cacaagacttgcctatcccatagtacatcatattacctgtcaagctatgctaccccacagaaataccccaaaagttgaagtga
aaaaatgaaaattactggtaacttcaccccataacaaacttaataatttctgtagccaatgaaagtaaaccccattcaatgttcc
gagatttagtatacttgccccctataagaaacgaaggattgagatccgcccaaacgaacagataatagaaaaaagaaattcg
gacaaatagaacactttctcagccaattaaagtcattccatgcactccctttagctgccgttccatcccttgttgagcaacacca
tcgttagccagtacgaaagaggaaacttaaccgataccttggagaaatctaaggcgcgaatgagtttagcctagatatcctta
gtgaagggttgttccgatacttctccacattcagtcatagatgggcagctttgttatcatgaagagacggaaacgggcattaag

Figure 25 (continued)

ggttaaccgccaaattatataaagacaacatgtccccagtttaaagtttttctttcctattcttgtatcctgagtgaccgttgtgtttaat
ataacaagttcgttttaacttaagaccaaaaccagttacaacaaattataaccccctctaaacactaaagttcactcttatcaaac
tatcaaacatcaaaa SEQ ID NO: 92(pDAS2-D5)

attactgttttgggcaatcctgttgataagacgcattctagagttgtttcatgaaagggttacgggtgttgattggtttgagatatgcc
agaggacagatcaatctgtggtttgctaaactggaagtctggtaaggactctagcaagtccgttactcaaaaagtcataccaa
gtaagattacgtaacacctgggcatgactttctaagttagcaagtcaccaagagggtcctatttaacgtttggcggtatctgaaa
cacaagacttgcctatcccatagtacatcatattacctgtcaagctatgctaccccacagaaataccccaaaagttgaagtga
aaaaatgaaaattactggtaacttcaccccataacaaacttaataatttctgtagccaatgaaagtaaaccccattcaatgttcc
gagatttagtatacttgccccctataagaaacgaaggatttcagcttccttaccccatgaacagaaatcttccatttaccccccact
ggagagatccgcccaaacgaacagataattgcactcccctttagctgccgttccatcccctttgttgagcaacaccatcgttagcc
agtacgaaagaggaaacttaaccgataccttggagaaatctaaggcgcgaatgagtttagcctagatatccttagtgaaggg
ttgttccgatacttctccacattcagtcatagatgggcagctttgttatcatgaagagacggaaacgggcattaagggttaaccg
ccaaattatataaagacaacatgtccccagtttaaagtttttctttcctattcttgtatcctgagtgaccgttgtgtttaatataacaag
ttcgttttaacttaagaccaaaaccagttacaacaaattataaccccctctaaacactaaagttcactcttatcaaactatcaaac
atcaaaa SEQ ID NO: 93(pDAS2-D6)

attactgttttgggcaatcctgttgataagacgcattctagagttgtttcatgaaagggttacgggtgttgattggtttgagatatgcc
agaggacagatcaatctgtggtttgctaaactggaagtctggtaaggactctagcaagtccgttactcaaaaagtcataccaa
gtaagattacgtaacacctgggcatgactttctaagttagcaagtcaccaagagggtcctatttaacgtttggcggtatctgaaa
cacaagacttgcctatcccatagtacatcatattacctgtcaagctatgctaccccacagaaataccccaaaagttgaagtga
aaaaatgaaaattactggtaacttcaccccataacaaacttaataatttctgtagccaatgaaagtaaaccccattcaatgttcc
gagatttagtatacttgccccctataagaaacgaaggatttcagcttccttaccccatgaacagaaatcttccatttaccccccact
ggagagatccgcccaaacgaacagataatagaaaaaagaaattcggacaaatagaacactttctcagccaattaaagtc
attccatgcactcccctttagctgcaagaggaaacttaaccgataccttggagaaatctaaggcgcgaatgagtttagcctagat
atccttagtgaagggttgttccgatacttctccacattcagtcatagatgggcagctttgttatcatgaagagacggaaacgggc
attaagggttaaccgccaaattatataaagacaacatgtccccagtttaaagtttttctttcctattcttgtatcctgagtgaccgttgt

Figure 25 (continued)

gtttaatataacaagttcgttttaacttaagaccaaaaccagttacaacaaattataaccccctctaaacactaaagttcactcttat caaactatcaaacatcaaaa SEQ ID NO: 94(pDAS2-D7)

attactgttttgggcaatcctgttgataagacgcattctagagttgtttcatgaaagggttacgggtgttgattggtttgagatatgcc agaggacagatcaatctgtggtttgctaaactggaagtctggtaaggactctagcaagtccgttactcaaaaagtcataccaa gtaagattacgtaacacctgggcatgactttctaagttagcaagtcaccaagagggtcctatttaacgtttggcggtatctgaaa cacaagacttgcctatcccatagtacatcatattacctgtcaagctatgctaccccacagaaataccccaaaagttgaagtga aaaaatgaaaattactggtaacttcaccccataacaaacttaataatttctgtagccaatgaaagtaaaccccattcaatgttcc gagatttagtatacttgcccctataagaaacgaaggatttcagcttccttaccccatgaacagaaatcttccatttaccccccact ggagagatccgcccaaacgaacagataatagaaaaagaaattcggacaaatagaacactttctcagccaattaaagtc attccatgcactcccttagctgccgttccatcccttgttgagcaacaccatcgttagccagtacgaaagaggaaacttaaccg ataccttggagaaagatatccttagtgaagggttgttccgatacttctccacattcagtcatagatgggcagctttgttatcatgaa gagacggaaacgggcattaagggttaaccgccaaattatataaagacaacatgtccccagtttaaagttttctttcctattcttg tatcctgagtgaccgttgtgtttaatataacaagttcgttttaacttaagaccaaaaccagttacaacaaattataaccccctctaaa cactaaagttcactcttatcaaactatcaaacatcaaaa SEQ ID NO: 95(pDAS2-D8)

attactgttttgggcaatcctgttgataagacgcattctagagttgtttcatgaaagggttacgggtgttgattggtttgagatatgcc agaggacagatcaatctgtggtttgctaaactggaagtctggtaaggactctagcaagtccgttactcaaaaagtcataccaa gtaagattacgtaacacctgggcatgactttctaagttagcaagtcaccaagagggtcctatttaacgtttggcggtatctgaaa cacaagacttgcctatcccatagtacatcatattacctgtcaagctatgctaccccacagaaataccccaaaagttgaagtga aaaaatgaaaattactggtaacttcaccccataacaaacttaataatttctgtagccaatgaaagtaaaccccattcaatgttcc gagatttagtatacttgcccctataagaaacgaaggatttcagcttccttaccccatgaacagaaatcttccatttaccccccact ggagagatccgcccaaacgaacagataatagaaaaagaaattcggacaaatagaacactttctcagccaattaaagtc attccatgcactcccttagctgccgttccatcccttgttgagcaacaccatcgttagccagtacgaaagaggaaacttaaccg ataccttggagaaatctaaggcgcgaatgagtttagcctagatatccttagtgaagggttgttcagacggaaacgggcattaa gggttaaccgccaaattatataaagacaacatgtccccagtttaaagttttctttcctattcttgtatcctgagtgaccgttgtgttta atataacaagttcgttttaacttaagaccaaaaccagttacaacaaattataaccccctctaaacactaaagttcactcttatcaa actatcaaacatcaaaa

Figure 25 (continued)

SEQ ID NO: 96(pCAT1, monodirectional MUT)
AGTGTGTAATCATATATATAATAAATGAGGAATAATAATTGAATAGAGATTTAACGAGT
CGAAGTTTCTGAAATATACGCACAGTTTATATTTATGATTTTGATATCTAACTACAGTC
TTCTCCATATATTTAACTATAAATAATAAAGTATATAACTCTTATGAAACTGTTTCACCA
CATTTTTTTCTACGTAATCGAACTCCGAATGCGGTTCTCCTGTAACCTTAATTGTAGCA
TAGATCACTTAAATAAACTCATGGCCTGACATCTGTACACGTTCTTATTGGTCTTTTAG
CAATCTTGAAGTCTTTCTATTGTTCCGGTCGGCATTACCTAATAAATTCGAATCGAGA
TTGCTAGTACCTGATATCATATGAAGTAATCATCACATGCAAGTTCCATGATACCCTC
TACTAATGGAATTGAACAAAGTTTAAGCTTCTCGCACGAGACCGAATCCATACTATGC
ACCCCTCAAAGTTGGGATTAGTCAGGAAAGCTGAGCAATTAACTTCCCTCGATTGGC
CTGGACTTTTCGCTTAGCCTGCCGCAATCGGTAAGTTTCATTATCCCAGCGGGGTGA
TAGCCTCTGTTGCTCATCAGGCCAAAATCATATATAAGCTGTAGACCCAGCACTTCAA
TTACTTGAAATTCACCATAACACTTGCTCTAGTCAAGACTTACAATTAAA SEQ ID NO: 97(pPEX14, monodirectional MUT)
ctaaatgctgtttctcttagcatagtcaatgattagttttcactcatttgtacaacaatcggtttggtatctgcaatgacactagagat
aattctggaggttagcttgcatacataagccggttctgttccttgataataattccaatcaaggtctagtttgcgaagataatctctg
gatagaccagctctttcttcttcgtttaggattttatcgctatgcaacaccgaaatattcctgtaaacccattgatctagtggttgatg
caatcctatcccgtgatacttagagcagctctcttttagagcccaatactgtgttagaatttcaaattgtctatcttctgtgtgtcgag
gaagttcacgttcaagaaagttcgtttcgtctgggtgaaaaatatcagaaaaggatcgtaaaagctgtattgggtcctcttgaa
actgtttgattgtttgtatatcagccaaatcgattcctaattgcttaatcgaaggttttcagactcacttcccagttttgtgcatctttct
tcgaaagacaattcctactacagattcatcgtctgccatattatattccaattgtttatagatggcttgccacacggtgccacagtt
atctcaggttcaaacagggtgtccatctcatagtttaaggacagaattgttcttagcaacaagcctcctagtaaggccatcctct
gatcatgtctattctttctcgctaggattctgttacgctgtttcaacgacaattgacgtaaacacagttccattaaataatcatcttcta
actcgttgccgactttgaccactacaagaatatttctttctccttctgtcaactgcttccaatgttgaaagacatcgtccattcttcaa
cgaagaagtttattagaacagtattacctaatctgagaagttcaaggcgacgtgtactgatccatatggtcccatcatcactgc SEQ ID NO: 98(pMSRAB, monodirectional ROS)

Figure 25 (continued)

aactgccacttatgcgaaacttcctagataagttcaaagctgtccacgtgtatacagaaaagaatgcgccagagacattctac
agggaggtacttacagtaaacgactgcgcgattgccaacaaactatgtaggtaacatgtggaaaattgtctccacactagat
aggccaaagagaacgcatcatcgttcgcttttagtatccaataagatttcatttacattctttttttaaatgatcttgcccttagatag
acatcgatttgggctcctttctgagaacatgtgtggggcaatggtaaccattaggattcttcatgagataatcttgatggtaatcgt
cagcatccaagtaactagttaacttttccacttgagtaacaatcttatggtgcggaaaccacttcttctgtgcttctgccagcgatt
gctccgttatctctttctccttctcatcgaggtaaaagacagcagatctgtattgacttccaatatcattaccttggcgatctttctgag
ttgggtcgtggactaggaaaaagaaatctatcaactcgttaaatgaagtgacgtctggattgtatgagatttgcagaacctcag
catggtgggtcattcccaggcaaatctgagtgtaagttggattggccacatttccattggcaaagccgacttgtgtatcaacaatt
ctgtctttaaaatgcattttgtagatgtgctctaatccccaaaaacagcctccagcgactgtcactactttgtcctgaggagattttc
tgatgttcgacgaaacaagactgctattgacgggcatatgagaagaactacgtttgaaaaaatttcggaaagagcccatgaa
tgcaaaaccgcttgccttgcttgaactgggagcaagcaagaatatatatcctttcattccgtttcgtttaatcaaatgatatttgaa
attttgggagctgtactgaaatgtgattggttcatttgatatgaaattgatgtgaa SEQ ID NO: 99(pGPX, monodirectional ROS)
atccgcgaggattccatcatcaattggatgcgaaatgaagatgaagagtcaataggtaaatcttcaatccaaggttattagtcc
tagaatatagcagtctatgatgctttgcgactggagttgtcactagtcagggagattgtataaattaaacatataaaaacaatctt
gcatgatagattacaatggacaagctccataaccgtttcaattacacgattgtaactagttcaatctggtaataattaagtacctc
ttataattagaatgaaatagcagcatgaaaatgattggggccatttgatcatcgtatcattaatccttgtccctcatcctagtctttc
gatgagatgtactccactatcactttccactatgtctgatatttcaccaacttgtaatgcaaatgcagctctttcaaatgatggatgc
attgtctttctcccaaaaaggcccaaatccccgttccgggcatgtgaggagcaatcactttcagtagcagccagttgacctaaa
gtggcagaaccatcaagaatctgtttttggaatcctctaagcttttcaattgcttcttccttagttcttgtaatctgaggctccttccag
gagctcggtttcctagagttcttgtgtttcaccagaagatgagcacaccgaacttgttctgggtcatgaaggcgtttcttgatgtact
cgcccagtgcttctaagttagttccagaagggggctcccaggaagattcttgtgtttccttgttatagaaatactcagattgatga
gttttgatattttaattgtccaattcctcggtaatccgttaaatgtatttgtcatgctacgttaatttagcatcacaagatctctcactaa
ttgaattcttaagccaccagcctcgaattctagattcgaaaattactaatgtcaagaatactcttaaccagaccatttgctctaag
aaatcttctcttcttcacgcattcctcaaagcaaataagaaca SEQ ID NO: 100(pMSR2c2, monodirectional ROS)
tgtctccacactaacttatttgataaatgattaattcaataaaaccttgttttgaggtattatttaggtacgtcagatggtacggttcat
cgatggatttccttcacaatggaccttattcttcttttcaattttgcttacatagtaacagaattcatagctgacatgtcgcttttcttgat

Figure 25 (continued)

ggaaggcatgtcagagttcatggccgacatgtcgctcttcttcatagaaggcatgtcagagttcatggccgacatgtcgctcttc
ttcacagaagacatgtcagttttttcatggaaggcatgtcagagttcatggccgacatgtgagaagaacttcgtttgaaaaagc
gtcggaaaaaggtcatgaaacaaaaagtcactgccttcttgatcatgggaagcaaatgcatttagatattttcgtttcgttcgta
ctacatgctatttgaaacttggaagctgttccaaaaggtcattggttcacttgatgtgaaattgatgtgaaatagtaaagactttta
ctccttttgcagaccttgattgcagaaaagtgatctgatcccataaacttcaatcgcgacttcgtttcaaaaattaggtaatctgga
gtgagaattctcgtttttatgttctgagcgttctttcttcttgacgggtggataaagagaagacctgaattacagagaagagctaa
aattccaagagcaattattattatcttttaaaccgcagttcccccctgacatggtaatagaggtattcacaaatttggcgccttgtca
gttcttcttgaattaccatttacggactcccaactcctcatccggtgctaagcctcaataaaaaaagaaagactaagttttgctca
aacctttctagttgccacctgccttgtagtccgaagcaaagtggctgaatatcacttcgcgcaatgctttccagttgccaccggct
gagaatgaggttcaactctgtttaaacagtaattgtttcgaa SEQ ID NO: 101(pMSR2c4, monodirectional ROS)

tgtctccacactaacttatttgataaatgattaattcaataaaaaccttgttttgaggtattatttaggtacgtcagatggtacggttcat
cgatggatttccttcacaatggaccttattcttcttttcaattttgcttacatagtaacagaattcatagctgacatgtcgcttttcttgat
ggaaggcatgtcagagttcatggccgacatgtcgctcttcttcatagaaggcatgtcagagttcatggccgacatgtcgctcttc
ttcacagaagacatgtcagttttttcatggaaggcatgtcagagttcatggccgacatgtgagaagaacttcgtttgaaaaagc
gtcggaaaaaggtcatgaaacaaaaagtcactgccttcttgatcatgggaagcaaatgcatttagatattttcgtttcgttcgta
ctacatgctatttgaaacttggaagctgttccaaaaggtcattggttcacttgatgtgaaattgatgtgaaatagtaaagactttta
ctccttttgcagaccttgattgcagaaaagtgatctgatcccataaacttcaatcgcgacttcgtttcaaaaattaggtaatctgga
gtgagaattctcgtttttatgttctgagcgttctttcttcttgacgggtggataaagagaagacctgaattacagagaagagctaa
aattccaagagcaattattattatcttttaaaccgcagttcccccctgacatggtaatagaggtattcacaaatttggcgccttgtca
gttcttcttgaattaccatttacggactcccaactcctcatccggtgctaagcctcaataaaaaaagaaagactaagttttgctca
aacctttctagttgccacctgccttgtagtccgaagcaaagtggctgaatatcacttcgcgcaatgctttccagttgccaccggct
gagaatgaggttcaactctgtttaaacagtaattgtttcgaa SEQ ID NO: 102(pZWF1, monodirectional PPP1)

actttcttttactgcttatttcattcgtatagccaatagatttcccatattttttccagagtacgtagatggtggattaggtaattgttggc
atttctagttgctagtgaacttagctctggattattgtagtaggtgaaaaataccaagggcgatggaaatttcaaaggccgatct
ggggatgtgtggggtaaagactttggatggaatccaggggcaaagacaagggctagacttcactatattggtggtaaaagtg
aatctactagaagtttgagtcaacgacgatatggagtaaccaagtgaagacgatatctttagttcgttatggccaccttaaaag

Figure 25 (continued)

aagcccactcagtccatgtgagttctgaaacttttaaagacagttaacccaaggttcacaattgtgtgaccttatgtcaactgtac
tagaaggccaaagattattggacgattgggttatctatttccttgataagcatgtgctccaatcaatacacccacctgtcagggg
atacacagtgcggagctccgttttctcccagaaaattcggttggagctcttttcttaaacttcgaaagtcccccgacagagaagtg
ccgttagccaatagtgtccctgcattctggttcctccccactgcagcgtcagctggaaagggctctattctaagctattctaaagc
aatccaaaggtgggggtcggatcaatgcgcgatctttcgtcgccagtgtcggggcccggcacgggggccgtaaccggctttt
ctctaggttgacaccatgggatatcccctgattgggcaaatcccacataagtatggcttgcggcttactaatcgcgtaagtcgc
gcattctcttttcctgatccttaatatcaatcctccggcaccatcatcgtagtttgcgagattccataaacttttggcccccctaacttt
tttttgttgccatcctttacttccatctaaaaaaaaccgacacagaatctgccaaaca SEQ ID NO: 103(pSOL3, monodirectional PPP2A)
aggaacccttaaaagtggaggtatccgtacttaaagagaatccattacaagaaaatgccacaacattcatgtttggtcattcc
ttggaacaaaaaattgataactatcgttaataaaaccgttgagagagtacttaattctctgttcgtaatgaatcaaatcaagctca
acagaaaatctccaaaagctgtagccttgctcctgatgaagcttgattacaggaaattcaccagttgaaatgacatccgatag
cagatgttccttcaagtcgtttcggtgagcgggtccaatatgatacctaattgttgggttcttcgaataatcactctcatcgtcttttgt
caccaccaaaatagttgccctgtaattattggacttattttcaaaagcggagaccaaacgaagaagtggaccggtagaaact
ttcaattttgggtctcctaagtgttcagtaactggaacttttggttgtccatgactaactgtagtttcccaggcttgttgatactccgata
aaggtaatgaattgaaccagttggaaagtatcgagtctgacattgatggcacgatgaaagaaactgaattaagcgagcaat
actaaaagaagtagaagtagctgaacgtgaataaactacaactctggaataacaaaggatggctctgagaagcgcgaca
aatgaatcactgaaaccatactcctacaacatcgtgttgcaaatcctcactatttgtctccctctccaattcgcagaacctatgcg
aaagatggaaaacttaaagactaaatcacaggttataaaattctttttgcatcagcttatagaaagatctgtataatcgaaaaga
aaaaaaaaaagggtaaacactggtattaccaaaaaaaacatcctaagactaatatacaccgacgagttcgctacacttctc
gaactgttaataaaaaggttggtaggtagccttagttattctcgtctgttaaccatcccataacaatatcgaa SEQ ID NO: 104(pSOL1, monodirectional PPP2B)
ccgaagggtgtaggtgtcgtcatatctacttcctgggggatgcctcaaatttggctgcctttcattagggttaaaaataggtggtt
caatgagggatacattccatgtccttctgtttgtagatcgctagcaaaaggcgatagtgaagggtgagcccctccaggaggca
acctatcaccctctccaattggtggaggccctgatggtgggcggaaattcgaagctacaggatcatccagtaactgatattcgt
ctgtaaattgtgggggagcttctcctagtggtggcgatattggatttgtttctcttaagcggctaaaactactctctccagtctgggtt
tgttcagctggctttggatcttccgttgacttcggaattggctcgcttgtgatcagactggcattgattatcctagtctctatgatatca
cccaacagtactaggagtatactgttgttatcaagttttgtaacaatacctttttgttccgccaacatcaatttcccgactctccaatg

Figure 25 (continued)

gcttcgagctgtgccattttgctacgtattcctccagcttgtccataattatttcaaagataattttatcgggaaaagcaattgatacg
gagttcttagacggggaaactttcaggttaaaggggatgagacccttttcgagcgtgatcgccctcttctcccgcctagaaaaat
ccagaaggagtgtgtgatgcttgggggttggttgctaatcaggtagtcgcaacccaaatcagccggcaacaagctagaat
ttacatctaaagctttcaaataaccctctaacgattcaattaatcgtttttcccattggtacacaccgagccttatagtcttatctgaa
tctacaaaaataccaaggaagagagtagtgcttcaaccaacaaaaagcctacctgtgtccattctttatctcctacaagtataa
tataaataccagagacccacaaaatcagtaatcgattcacaattggcctatt SEQ ID NO: 105(pPGD, monodirectional PPP3)

ttatggtagaatcatcaattggaatgaccctatcgttgctatacagactcgtagccccatttcttgtttgttggttttcgtcgtcaattgc
ctccaaaattgaagagatggcacttcgtcgcgtgggttcctgggaaatattttgaagtggaacatcgttgaaataaggcagtat
atcatgctgattctcagcattggagtcagtagcttcaagtgaatctatactgtatgagtcggaagaggatttccggctcgttttgtc
ttcattttgttattagaaggaatgataacgttgggaaaccggaggttggagattttgtatatataaaactttcttggagcttattaata
aatgcgggatgcagtaaacttgcatatatctattgtaacacttttgcaatagctgcatgccttgactcatcattcagtatcgtgtga
aaaccaatgatacatccgtacattcaaactacaaccttcctcattagtaattcttttgaattttcggaacccgaagctccgcctat
cccccaactaacacatcttccaatttgggtgggagaacacctagcaacatcacgatcattgcgcgaacgttcgcactgtattt
ttttctcccaaacacccaacttctaggccaaatatccacttctcggggttctattcacccatttaattgttggccttaaaagtcaattg
agttccaatcatagtcccctagttgattgcttgtagcaaatgccacaacagtaggcatttacgtcctcacagtctcttcccttgtccct
cattgatacctctttattctcccccaccaccatacactaccttcctcgcacccctgtcatcacaaccgcaatataatcgatgcgcg
gtttcttgcctaatccatcgtccaacagagaggtcgctctccttatatatatagttgatcccccttttttctacccttgcaattttttttgg
gaccaaagaaaagaaacaagactgatacaaat SEQ ID NO: 106(pRKI1, monodirectional PPP4A)

tgaagttattcctctacaaatcgaccgaatatttctatacgtgtaataacttcttcgtattagctgcaacgatgcctaaatatacattt
cccaaaaacaacgacgcttcgtagaaattataaagtttcacttgggatctcgaagacaacttgcttaccagtcagcttaccgta
gacagcctggaaagagtcaagcttgtagtcaatgttggaagagtccttggagtcaagcaaaactttggtgatttggtcaccac
cgaccaagtatctgattctcttaccgataatctcggttgggaaaaccaagtcctccaaaatcttctcgtgaacgaccttgacggtt
ctagatctaggtctcttctggacaacctttggtcctcttggaatctttggggtgatctttctctcagccaagaaaacgacatggcgg
tcagggaacttcttctccaactctctggtcaacttgatttgtaccttgtggaaagcagtcaacagaggaactggtacaaagatta
cgatggcagtctttccgctctcagtctcaatctccttgatggagttgaattgcaaaggtctcaagtcagcctttaagtctggggagt
tagcttccaagtcaacaaatgattgggcgacttgcagctccaactcagtgggctcttcgttcaggattttggctgatgacatcttgt

Figure 25 (continued)

gatactgctgttaccgtgtgagtttcgacagaattgaaaaagattgttaaggctctggaggaaaaactggattcgcgcacaa
cagtcccaagagaagagtagtaacaaaaaaaattacagtcatgtgatgtaggggatgtggttagggtcgaagcccagtac
ggtgttgggatgctaagaggttaatatctaatgcacaatacgcttatgtaagttcatgcttgaaatagcctattgatgaatgtaag
ggaaattagaccgtcctttgtgggtacttattcacgtcttgcctctagcatcttagacaacta SEQ ID NO: 107(pRPE1, monodirectional PPP5A)
atggttaaaacaattattgctccttcaatcctgtcggcagattttcaaacttgggatgtgaatgtcacaagatgtttaagctacgg
gctgactgggtccacattgacgtcatggacggccatttcgtccctaatttgaccatgggtcctccaattatctcgtcccttagaaa
agctgttccgaggggagagaaagatggacagacgacacacttctttgactgccatatgatggtggccaatcccgaacaatg
ggtcccagaggttgcaaaggcaggtggtgatcagtacacttttcactacgaagcaactaaggatccagtgaagttagtggaa
cttatcaagagccatggactgaaagctgcatgtgctatcaagcccggaacatcagtcgatgtcttgtaccctctagcagacaa
gcttgacatggctctggtaatgacagttgagccagggtttggtggacagaagtttatggctgatatgatgcccaaagttgaagc
attgcgggccaaatttccaaacttagatattcaggtcgatggtggtcttggaaaggagaccattggagtagcagctgatgctgg
ggcaaacgtaattgttgctggatcttctgttttggtgctaaagaccccggtgaggttatccgatatcttcgtgatacggtagaaaa
tgctcagaaaaaagctaaagccaaaccgaaacccaatttatgactgaatagtatattaagtaggatttgatatacgtctttaga
ggtgattgaaagaccgaatgagttttgctgggcggaatgcgattccttactgcgcgaacaaacgttccgtctagtgggttttcc
atccaccaattaatctgccccagatctcaaaccatatttccaattttactacctttccttcatatcacctagctattcgaaaaa SEQ ID NO: 108(pRPE2, monodirectional PPP5B)
agcgatggacagactgcctcacaacagttcgtcaaacagggaaaagacgccttgagagtctactggttgatgcttatctacat
gattatcatgatggccgcattcaactttagttctcactcctcccaagatctttaccctactcttctaacagttcaatatgaatttggtaa
agacagatctacagttactaacgtcgtggcaaatcttggagccattgtcggaggtattttctggggtcatatgtccaacttcattg
gtcgacgtcttgcagttttgctctgttgtatagtaggtggagctttcatttacccttgggcatttataaatggttcagggatcaatgctg
gtgctttcttcttacaatttgctgtccaaggtggatggggtgtatgtccagttcatcttgctgagatgtctccgccccatttccgagctt
ttgttacaggaaccacctaccagctaggaaacctggcatcatctggatcatctactatcctggccgatattggagaaagattcc
ccatttacgacgagaatggagtgcggaaagagggtgtttatgactatgccaaagtaatggctatatttatgggagctgtgtttgc
tttcctgtttattgtgatgttgctgggtccagaaagaagaggagcctccaatcttgatgatctccaggattacattgacgattggga
gcaaaaagatctggacaacaaaaaaggaattgaaactgagttcatcgaagatgttcagttaatggaggctgtctctaatgag
gacctttctgagaaaggcaatgagaaagtagaggcttttgaaggaaataagtaagattagggtacttcttagaaattactaata

Figure 25 (continued)

ctacacctctacattcgttatcttatcaggcttgtcgcgatgggctaaactatagcctatgagtgggggtcgtagttaaagaaat
atatactatatgcgaagatgggaaagtaaaactagttgaatactgtgtgagatc SEQ ID NO: 109(pTKL1, monodirectional PPP6,8A)

Gattccactgctcagagtcttttcatcaagctctaagaaaagtccggggatggaggagccagcgcaacagaaaactatgtc
gggactaaaaccaacttcctctaaaacacgctcacactggtcatatttggagatatctgctgccacgtaagaaattgtgttgcc
cttctcggtcccgtgaatatcaatagcgtcctttactacctgctttagtaaggattctgttctagccacaatcacaacggaacatcc
ttttccatacaaaagtttagcaaactcggctccaacaccctgggatgcacccgtaataattgcctttttgttggtgacatcaaaatt
atcaaacattccagttccctctacactttgtatgagaatgatagctgaaattgtgcaccagatgttagaagataaggtcgtgtcat
gaactaatatcatgaattccgagggtggctcaacaactattcacgtgacttggacgttggaagttgaggtggttggtggatgttg
cacggagtatcatttgtaagcatgaaatcagtctaaaaaacttgcagaatagcagagcggttcggaaattcattcaaaacca
cctcctcagattggatctgccctactctgtttagctctgggagattttctcggtcgtgttctttcgctggtctacccacgctataggaat
cgctgtgaacgctaccttcttcccaacttctcggtgactattataagccattcccactttgttttcaagcaccaacaacccacccc
accttatctactccatcttgggtgtccccgcgcctgttgcaaagtccgaaccatagaaccccgacctttgtcccactaaccctc
agacacccctcggaagtcagggagaaaccactccgaagtacattaatcatccctcgtattctcgacggtgcccatttctttata
aaaagggagacacaggttgcttcactaactctagacttgtattctacatccactctacaca SEQ ID NO: 110(pDAS1, monodirectional PPP6,8B)

Aataaaaaaacgttatagaaagaaattggactacgatatgctccaatccaaattgtcaaaattgaccaccgaaaaagaac
aattggaatttgacaagaggaacaactcactagattctcaaacggagcgtcacctagagtcagtttccaagtcaattacaga
aagtttggaaacagaagaggagtatctacaattgaattccaaacttaaagtcgagctgtccgaattcatgtcgctaaggctttct
tacttggaccccattttttgaaagtttcattaaagttcagtcaaaaattttcatggacatttatgacacattaaagagcggactaccft
atgttgattctctatccaaagaggattatcagtccaagatcttggactctagaatagataacattctgtcgaaaatggaagcgct
gaaccttcaagcttacattgatgattagagcaatgatataaacaacaattgagtgacaggtctactttgttctcaaaaggccata
accatctgtttgcatctcttatcaccacaccatcctcctcatctggccttcaattgtggggaacaactagcatcccaacaccaga
ctaactccacccagatgaaaccagttgtcgcttaccagtcaatgaatgttgagctaacgttccttgaaactcgaatgatcccag
ccttgctgcgtatcatccctccgctattccgccgcttgctccaaccatgtttccgccttttcgaacaagttcaaatacctatctttgg
caggacttttcctcctgccttttttagcctcaggtctcggttagcctctaggcaaattctggtcttcatacctatatcaacttttcatcag
atagcctttgggttcaaaaaagaactaaagcaggatgcctgatatataaatcccagatgatctgcttttgaaactattttcagtat
cttgattcgtttacttacaaacaactattgttgattttatctggagaataatcgaacaaa

Figure 25 (continued)

SEQ ID NO: 111(pDAS2, monodirectional PPP6,8C)

Attactgttttgggcaatcctgttgataagacgcattctagagttgtttcatgaaagggttacgggtgttgattggtttgagatatgcc
agaggacagatcaatctgtggtttgctaaactggaagtctggtaaggactctagcaagtccgttactcaaaaagtcataccaa
gtaagattacgtaacacctgggcatgactttctaagttagcaagtcaccaagagggtcctatttaacgtttggcggtatctgaaa
cacaagacttgcctatcccatagtacatcatattacctgtcaagctatgctaccccacagaaataccccaaaagttgaagtga
aaaaatgaaaattactggtaacttcaccccataacaaacttaataatttctgtagccaatgaaagtaaaccccattcaatgttcc
gagatttagtatacttgccccrataagaaacgaaggatttcagcttccttaccccatgaacagaaatcttccatttaccccccact
ggagagatccgcccaaacgaacagataatagaaaaaagaaattcggacaaatagaacactttctcagccaattaaagtc
attccatgcactccctttagctgccgttccatccctttgttgagcaacaccatcgttagccagtacgaaagaggaaacttaaccg
ataccttggagaaatctaaggcgcgaatgagtttagcctagatatccttagtgaagggttgttccgatacttctccacattcagtc
atagatgggcagctttgttatcatgaagagacggaaacgggcattaagggttaaccgccaaattatataaagacaacatgtc
cccagtttaaagttttctttcctattcttgtatcctgagtgaccgttgtgtttaatataacaagttcgttttaacttaagaccaaaacca
gttacaacaaattataaccccctctaaacactaaagttcactcttatcaaactatcaaacatcaaaa SEQ ID NO: 112(pTAL1, monodirectional PPP7A)

Cagagatcgtgttttgattaagattgctgctacctgggagggaatacaagcagccctggagttggagcaggtctacgatatac
actgcaacttgacactaatttttcttttgttcaagctgttgcgtgtgctgaagcgcaggtaacacttatctctccttttgttggacgtatt
cttgactggtacaaggcaaaaacaggtaagcaatatgaaggtgctgctgaccctggagttatttctgttgttcgtatattcaagta
tttcaaggcatacggatacaaaactatagtcatgggagcttctttccgaaatgtcagcgaaataaaagctctagctggatgcg
attatctaacaattgcaccaactttgttggatcaattacaaagctccacagatgctgtccctaaagtccttgaccctgcaacctca
gcggctgaggagcaggagccttttgtgtcgtttgtatccaacgaaactgctttccgttttgaactcaacgaggatcaaatggcca
cagaaaagttgtctgagggggttcgaaagttttcagctgactgcaatacccctgtttgatcttttgagagaaaaagtaaaagtcgc
tcaagaggaggtgaataatatctccaatggcgtgccatcacttttccgtcgtgttttatccaagttgtaagccattgggccaaacg
tttctggatcttgaagctaaccaaacctgatagggcaatgctcaggacagctaaacttagtttgaagtttccccaggttttcttcg
gaagatgttttcacccacaatcaccccactctaagtatgtttgcaataccaactccgcgcttattaccccattatcaggatttgc
tctcccgaacctcccgcaaactgcacctataccgatcgcggcgaactgtgctccacacacttgcccaatcttataaaagttctt
cctccgccacctgggttgcgctctttcttttactctaattgaaattttatttctaca SEQ ID NO: 113(pTAL2, monodirectional PPP7B)

Figure 25 (continued)

gatatcgatctacacttaatagtagatgacgaggcatctctccaataggtaccatatctggtgtttcttgtaatttaagaatctgttg
gtctatgaatgtagatttgtcatgaacaatgatatatgggtcaggaggacaagatggtttctctgagttgggttgttgaggtgcctg
gcaagacttcggagcgttgatatccccaagacttgtagtgaccgatagttgaagcgtgtgtttgcaggaacggcacatcaatg
caactttcgtaactttggaattgagagttgatgcactgatgacgatacccgaaattttgacgattttaccaatatgacttgaagac
aagtctctcattgaaaccttattatcgttactaagcaaaacgagctgacaagaagggaaggtggtcggtatttcctcgttgttca
aatatatgattctcctggcaatatctgtgatggcctgttcaaaaagtggaatcatttctgcaggatcatctaccaactttttattgag
ctcctcattgaatacgattaagtggtcattttgaatcgtcagtaagtacttgtttacaagtaaattctgtctgagttgttctctgtagatg
tactgattttccatacgaaactccaaaatgaacgaacggaatgccttaatgacctcactgaactggtcatcgttctgttctccgg
gaaggacacttgtgttaaagactgatgctctatcaaaggacattgcaacaaagtataaacggttgtgagcgggaaaaagat
gtgtaggtaattgtcgtagatgagactgattcagtagaaaacgcgtcctgcactattttttctttcttcattacatttcctaatcggga
caaaatgaatctaaagacgtggttatgtagtacacgcatcgataggctatccccataccaaaacactatttlaccccatccttg
acaggttataaatatgcgatagtatgagtatcttcaaattcagctgaaatatc SEQ ID NO: 114(pAOX1+pGAP)

cgtttcgaataattagttgttttttgatcttctcaagttgtcgttaaaagtcgttaaaatcaaaagcttgtcaattggaaccagtcgca
attatgaaagtaagctaataatgatgataaaaaaaaggtttaagacagggcagcttccttctgtttatatattgctgtcaagtagg
ggttagaacagttaaattttgatcatgaacgttaggctatcagcagtattcccaccagaatcttggaagcatacaatgtggaga
caatgcataatcatccaaaaagcgggtgtttccccatttgcgtttcggcacaggtgcaccggggttcagaagcgatagagag
actgcgctaagcattaatgagattattttttgagcattcgtcaatcaataccaaacaagacaaacggtatgccgacttttggaagt
ttcttttgaccaactggccgttagcatttcaacgaaccaaacttagttcatcttggatgagatcacgcttttgtcatattaggttcca
agacagcgtttaaactgtcagttttgggccatttggggaacatgaaactatttgaccccacactcagaaagccctcatctggag
tgatgttcgggtgtaatgcggagcttgttgcattcggaaataaacaaacatgaacctcgccaggggggccaggatagacag
gctaataaagtcatggtgttagtagcctaatagaaggaattggaatgagcgagctccaatcaagcccaataactgggctggtt
tttcgatggcaaaagtgggtgttgaggagaagaggagtggaggtcctgcgtttgcaacggtctgctgctagtgtatcccctcct
gttgcgtttggcacttatgtgtgagaatggacctgtggatgtcggatggcaaaaaggtttcattcaacctttcgtctttggatgttag
atcttttttgtagaaatgtcttggtgtcctcgtccaatcaggtagccatctctgaaatatctggctccgttgcaactccgaacgacct
gctggcaacgtaaaattctccggggtaaaacttaaatgtggagtaatggaaccagaaacgtctcttcccttctctctccttccac
cgcccgttaccgtccctaggaaattttactctgctggagagcttcttctacggccccctgcagcaatgctcttcccagcattacgt
tgcgggtaaaacggaggtcgtgtacccgacctagcagcccagggatggaaaagtcccggccgtcgctggcaataatagc

Figure 25 (continued)

gggcggacgcatgtcatgagattattggaaaccaccagaatcgaatataaaaggcgaacacctttcccaattttggtttctcct
gacccaaagactttaaatttaatttatttgtccctatttcaatcaattgaacaactatcaaaacaca SEQ ID NO: 115(pAOX1+pCAT1)

cgtttcgaataattagttgtttttgatcttctcaagttgtcgttaaaagtcgttaaaatcaaaagcttgtcaattggaaccagtcgca
attatgaaagtaagctaataatgatgataaaaaaaaggtttaagacagggcagcttccttctgtttatatattgctgtcaagtagg
ggttagaacagttaaattttgatcatgaacgttaggctatcagcagtattcccaccagaatcttggaagcatacaatgtggaga
caatgcataatcatccaaaaagcgggtgtttccccatttgcgtttcggcacaggtgcaccggggttcagaagcgatagagag
actgcgctaagcattaatgagattattttgagcattcgtcaatcaataccaaacaagacaaacggtatgccgacttttggaagt
ttcttttgaccaactggccgttagcatttcaacgaaccaaacttagttcatcttggatgagatcacgcttttgtcatattaggttcca
agacagcgtttaaactgtcagttttgggccatttggggaacatgaaactatttgaccccacactcagaaagccctcatctggag
tgatgttcgggtgtaatgcggagcttgttgcattcggaaataaacaaacatgaacctcgccaggggggccaggatagacag
gctaataaagtcatggtgttagtagcctaatagaaggaattggaatgagcgagctccaatcaagcccaataactgggctggtt
tttcgatggcaaaagtgggtgttgaggagaagaggagtggaggtcctgcgtttgcaacggtctgctgctagtgtatccctcct
gttgcgtttggcacttatgtgtgagaatggacctgtggatgtcggatggcaaaaaggtttcattcaacctttcgtctttggatgttag
atctAGTGTGTAATCATATATATAATAAATGAGGAATAATAATTGAATAGAGATTTAACGA
GTCGAAGTTTCTGAAATATACGCACAGTTTATATTTATGATTTTGATATCTAACTACAG
TCTTCTCCATATATTTAACTATAAATAATAAAGTATATAACTCTTATGAAACTGTTTCAC
CACATTTTTTTCTACGTAATCGAACTCCGAATGCGGTTCTCCTGTAACCTTAATTGTAG
CATAGATCACTTAAATAAACTCATGGCCTGACATCTGTACACGTTCTTATTGGTCTTTT
AGCAATCTTGAAGTCTTTCTATTGTTCCGGTCGGCATTACCTAATAAATTCGAATCGA
GATTGCTAGTACCTGATATCATATGAAGTAATCATCACATGCAAGTTCCATGATACCC
TCTACTAATGGAATTGAACAAAGTTTAAGCTTCTCGCACGAGACCGAATCCATACTAT
GCACCCCTCAAAGTTGGGATTAGTCAGGAAAGCTGAGCAATTAACTTCCCTCGATTG
GCCTGGACTTTTCGCTTAGCCTGCCGCAATCGGTAAGTTTCATTATCCCAGCGGGGT
GATAGCCTCTGTTGCTCATCAGGCCAAAATCATATATAAGCTGTAGACCCAGCACTTC
AATTACTTGAAATTCACCATAACACTTGCTCTAGTCAAGACTTACAATTAAA SEQ ID NO: 116(pGAP+pCAT1)

Figure 25 (continued)

Tgtgttttgatagttgttcaattgattgaaataggggacaaataaattaaatttaaagtctttgggtcaggagaaaccaaaattggg
aaaggtgttcgccttttatattcgattctggtggtttccaataatctcatgacatgcgtccgcccgctattattgccagcgacggccg
ggacttttccatccctgggctgctaggtcgggtacacgacctccgttttacccgcaacgtaatgctgggaagagcattgctgca
aggggggccgtagaagaagctctccagcagagtaaaatttcctagggacggtaacgggcggtggaaggagagagaagg
gaagagacgtttctggttccattactccacatttaagttttaccccggagaattttacgttgccagcaggtcgttcggagttgcaac
ggagccagatatttcagagatggctacctgattggacgaggacaccaagacatttctacaaaaaAGTGTGTAATCA
TATATATAATAAATGAGGAATAATAATTGAATAGAGATTTAACGAGTCGAAGTTTCTGA
AATATACGCACAGTTTATATTTATGATTTTGATATCTAACTACAGTCTTCTCCATATATT
TAACTATAAATAATAAAGTATATAACTCTTATGAAACTGTTTCACCACATTTTTTTCTAC
GTAATCGAACTCCGAATGCGGTTCTCCTGTAACCTTAATTGTAGCATAGATCACTTAA
ATAAACTCATGGCCTGACATCTGTACACGTTCTTATTGGTCTTTTAGCAATCTTGAAGT
CTTTCTATTGTTCCGGTCGGCATTACCTAATAAATTCGAATCGAGATTGCTAGTACCT
GATATCATATGAAGTAATCATCACATGCAAGTTCCATGATACCCTCTACTAATGGAATT
GAACAAAGTTTAAGCTTCTCGCACGAGACCGAATCCATACTATGCACCCCTCAAAGTT
GGGATTAGTCAGGAAAGCTGAGCAATTAACTTCCCTCGATTGGCCTGGACTTTTCGC
TTAGCCTGCCGCAATCGGTAAGTTTCATTATCCCAGCGGGGTGATAGCCTCTGTTGC
TCATCAGGCCAAAATCATATATAAGCTGTAGACCCAGCACTTCAATTACTTGAAATTC
ACCATAACACTTGCTCTAGTCAAGACTTACAATTAAA SEQ ID NO: 117(pGAP+pTEF1)

tgtgttttgatagttgttcaattgattgaaataggggacaaataaattaaatttaaagtctttgggtcaggagaaaccaaaattggg
aaaggtgttcgccttttatattcgattctggtggtttccaataatctcatgacatgcgtccgcccgctattattgccagcgacggccg
ggacttttccatccctgggctgctaggtcgggtacacgacctccgttttacccgcaacgtaatgctgggaagagcattgctgca
aggggggccgtagaagaagctctccagcagagtaaaatttcctagggacggtaacgggcggtggaaggagagagaagg
gaagagacgtttctggttccattactccacatttaagttttaccccggagaattttacgttgccagcaggtcgttcggagttgcaac
ggagccagatatttcagagatggctacctgattggacgaggacaccaagacatttctacaaaaaggtatttgacaggttggg
gagcaaataagtgatgatgtcccatgaaagtagaaaatggctagtagaaggcaaaaatttgaaattcttagagtcaaatagtt
agactccaagttctaatccacatttggtcagtttcatagcatccagagcttttgccactggtgaacatatctacccattgcgatgca
acaagtcactgaaagcctaaaacggagattcccctatcttacagcctcgttcaaaaaaactgctaccgtttatctgctatggcc
gatgtgaggatgcgctcatgcccaagagtccaactttatcaaaaacttgacccgtcatacaggctctagatcaagaagcaaa

Figure 25 (continued)

cttaatctcagcatctggttacgtaactctggcaaccagtaacacgcttaaggtttggaacaacactaaactaccttgcggtact
accattgacactacacatccttaattccaatcctgtctggcctccttcaccttttaaccatcttgcccattccaactcgtgtcagattg
cgtatcaagtgaaaaaaaaaaattttaaatctttaacccaatcaggtaataactgtcgcctcttttatctgccgcactgcatgagg
tgtccccttagtgggaaagagtactgagccaaccctggaggacagcaagggaaaaatacctacaacttgcttcataatggtc
gtaaaaacaatccttgtcggatataagtgttgtagactgtcccttatcctctgcgatgttcttcctctcaaagtttgcgatttctctctat
cagaattgccatcaagagactcaggactaatttcgcagtcccacacgcactcgtacatgattggctgaaatttccctaaagaa
tttcttttcacgaaaatttttttttacacaagattttcagcagatataaaatggagagcaggacctccgctgtgactcttcttttttttct
tttattctcactacatacattttagttattcgccaac SEQ ID NO 118: BZF1 (pFBA2-500+pTAL2-500)

atttatgaaattaatcaattaccttatcaaggtagaatttgggtgaatttgtatgtttaaataccggctaagagaataggctacgta
ccccacagactggaagtcgcatccgaaccgaaatggaaaaggcgtgtaagggttgcatggtacgaatagggggaagaag
agaactgggaagtgatcattgatagtgtgagtggcgggaaatattaggtgtgagtttgaaaggcctacaatagggatgcaaa
aatcctgctcatagggtcactggggagtatttattttctgttttcaggtttcccaccaatgtaaatgttcttcttagaatagaagaaag
ctttctgtttgcaggataacattttgtccagtaaaagatatcatttagtttgagttcatgtgatcacatttagatcacattaaaagca
aaagtgacggtacgtcttctataactgtttaaatggttgaggtttgaagtcctggtaaaagtcaagtcacaatgccaacttttattg
agctcctcattgaatacgattaagtggtcattttgaatcgtcagtaagtacttgtttacaagtaaattctgtctgagttgttctctgtag
atgtactgattttccatacgaaactccaaaatgaacgaacggaatgccttaatgacctcactgaactggtcatcgttctgttctcc
gggaaggacacttgtgttaaagactgatgctctatcaaaggacattgcaacaaagtataaacggttgtgagcgggaaaaag
atgtgtaggtaattgtcgtagatgagactgattcagtagaaaacgcgtcctgcactattttttttTctttcttcattacatttcctaatcg
ggacaaaatgaatctaaagacgtggttatgtagtacacgcatcgataggctatccccataccaaaacactattttaccccatc
cttgacaggttataaatatgcgatagtatgagtatcttcaaattcagctgaaatatc SEQ ID NO 119: BZF2 (pFDH1-564+pDAS1-552)

tgtttaagtgggtgatgttggaggtatttgaggtaaaataggtttatagtttgataactagcggagaaaagaaggagagtctcat
ctggaggagaaataaacttacttaaatagttttcggccatttaactgggttacgacatcattacgtgtaggtcagcacactgaat
agaattagactaagtataagcacagggagttggggtagccctcgaaaatcaggacatctgggtaaatttccctaaaatg
cgcaccaactgcagtacaatatggcgtttgggaggagcaacatcccgacaagattgggatttctgtagcctttgccataaact
ggacaggagtttccacacccgtttcagccggtcccttttattggttcttcggaaggctagagtaacggcccaatgtgaagagag
gaacattgtttcgttacgttccgaaacctagaatggtgttttgggaagggactactaagatgatgctgtgtagaagtttgagccgt

Figure 25 (continued)

agagtcccacttagagaacatcatcgaactatttaattagaagctggttccgcacccaagcaatgatataaacaacaattgag
tgacaggtctactttgttctcaaaaggccataaccatctgtttgcatctcttatcaccacaccatcctcctcatctggccttcaattgt
ggggaacaactagcatcccaacaccagactaactccacccagatgaaaccagttgtcgcttaccagtcaatgaatgttgag
ctaacgttccttgaaactcgaatgatcccagccttgctgcgtatcatccctccgctattccgccgcttgctccaaccatgtttccgc
cttttcgaacaagttcaaatacctatctttggcaggacttttcctcctgcctttttagcctcaggtctcggttagcctctaggcaaatt
ctggtcttcatacctatatcaacttttcatcagatagcctttgggttcaaaaaagaactaaagcaggatgcctgatatataaatcc
cagatgatctgcttttgaaactattttcagtatcttgattcgtttacttacaaacaactattgttgattttatctggagaataatcgaaca
aa SEQ ID NO 120: BZF3 (pFDH1-564+pCAT1-500)

tgtttaagtgggtgatgttggaggtatttgaggtaaaataggtttatagtttgataactagcggagaaaagaaggagagtctcat
ctggaggagaaataaaacttacttaaatagttttcggccatttaactgggttacgacatcattacgtgtaggtcagcacactgaat
agaattagactaagtataagcacagggagttgggggtagccctcgaaaatcaggacatctggggtaaattttccctaaaatg
cgcaccaactgcagtacaatatggcgtttggaggagcaacatcccgacaagattgggatttctgtagcctttgccataaact
ggacaggagtttccacacccgtttcagccggtccctttattggttcttcggaaggctagagtaacggcccaatgtgaagagag
gaacattgtttcgttacgttccgaaacctagaatggtgttttgggaagggactactaagatgatgctgtgtagaagtttgagccgt
agagtcccacttagagaacatcatcgaactatttaattagaagctggttccgcacccaTAATCGAACTCCGAATG
CGGTTCTCCTGTAACCTTAATTGTAGCATAGATCACTTAAATAAACTCATGGCCTGAC
ATCTGTACACGTTCTTATTGGTCTTTTAGCAATCTTGAAGTCTTTCTATTGTTCCGGTC
GGCATTACCTAATAAATTCGAATCGAGATTGCTAGTACCTGATATCATATGAAGTAAT
CATCACATGCAAGTTCCATGATACCCTCTACTAATGGAATTGAACAAAGTTTAAGCTT
CTCGCACGAGACCGAATCCATACTATGCACCCCTCAAAGTTGGGATTAGTCAGGAAA
GCTGAGCAATTAACTTCCCTCGATTGGCCTGGACTTTTCGCTTAGCCTGCCGCAATC
GGTAAGTTTCATTATCCCAGCGGGGTGATAGCCTCTGTTGCTCATCAGGCCAAAATC
ATATATAAGCTGTAGACCCAGCACTTCAATTACTTGAAATTCACCATAACACTTGCTCT
AGTCAAGACTTACAATTAAA SEQ ID NO 121: BZF4 (pDAS2-699+pDAS1-552)

ttttgatgtttgatagtttgataagagtgaactttagtgtttagaggggttataatttgttgtaactggttttggtcttaagttaaaacgaa
cttgttatattaaacacaacggtcactcaggatacaagaataggaaagaaaaactttaaactggggacatgttgtctttatata

Figure 25 (continued)

atttggcggttaacccttaatgcccgtttccgtctcttcatgataacaaagctgcccatctatgactgaatgtggagaagtatcgg
aacaaccccttcactaaggatatctaggctaaactcattcgcgccttagatttctccaaggtatcggttaagtttcctctttcgtactg
gctaacgatggtgttgctcaacaaagggatggaacggcagctaaagggagtgcatggaatgactttaattggctgagaaag
tgttctatttgtccgaatttctttttttctattatctgttcgtttgggcggatctctccagtggggggtaaatggaagatttctgttcatgggg
taaggaagctgaaatccttcgtttcttataggggcaagtatactaaatctcggaacattgaatgggtttactttcattggctacag
aaattattaagtttgttatggggtgaagttaccagtaatttcattttttcacttcaactttggggtatttctgtggggtagcatagagc
aatgatataaacaacaattgagtgacaggtctactttgttctcaaaaggccataaccatctgtttgcatctcttatcaccacacca
tcctcctcatctggccttcaattgtggggaacaactagcatcccaacaccagactaactccacccagatgaaaccagttgtcg
cttaccagtcaatgaatgttgagctaacgttccttgaaactcgaatgatcccagccttgctgcgtatcatccctccgctattccgcc
gcttgctccaaccatgtttccgccttttcgaacaagttcaaatacctatctttggcaggacttttcctcctgcctttttagcctcaggt
ctcggttagcctctaggcaaattctggtcttcatacctatatcaacttttcatcagatagcctttgggttcaaaaaagaactaaagc
aggatgcctgatatataaatcccagatgatctgcttttgaaactattttcagtatcttgattcgtttacttacaaacaactattgttgatt
ttatctggagaataatcgaacaaa SEQ ID NO 122: BZF5 (pFDH1-564+pPXR1-392)

tgtttaagtgggtgatgttggaggtatttgaggtaaaataggtttatagtttgataactagcggagaaaagaaggagagtctcat
ctggaggagaaataaacttacttaaatagtttttcggccatttaactgggttacgacatcattacgtgtaggtcagcacactgaat
agaattagactaagtataagcacagggagttgggggtagccctcgaaaatcaggacatctggggtaaattttccctaaaatg
cgcaccaactgcagtacaatatggcgtttgggaggagcaacatcccgacaagattgggatttctgtagcctttgccataaact
ggacaggagtttccacacccgtttcagccggtccctttattggttcttcggaaggctagagtaacggcccaatgtgaagagag
gaacattgtttcgttacgttccgaaacctagaatggtgttttgggaagggactactaagatgatgctgtgtagaagtttgagccgt
agagtcccacttagagaacatcatcgaactatttaattagaagctggttccgcacccaccaaaaagagaaaaaagaggga
atccctgttctttccaatggaaatgacgtaactttaacttgaaaaaatacccccaaccagaagggttcaaactcaacaaggattgc
gtaattcctacaagtagcttagagctgggggagagacaactgaaggcagcttaacgataacgcggggggattggtgcacg
actcgaaaggaggtatcttagtcttgtaacctcttttttccagaggctattcaagattcataggcgatatcgatgtggagaagggt
gaacaatataaaaggctggagagatgtcaatgaagcagctggatagatttcaaattttctagatttcagagtaatcgcacaaa
acgaaggaatcccaccaagcaaaaaaaaaatctaag SEQ ID NO 123: BZF6 (pFLD1-366+pAOX1-643)

Figure 25 (continued)

tgtgaatatcaagaattgtatgaacaagcaaagttggagctttgagcgatgtatttatatgagtagtgaaatcctgattgcgatca
ggtaaggctctaaaaatcgatgatggtcccgaattctttgataggctaaggacttcctcatcgggcagttcgaaggaagaagg
ggcatgagccctgcgaaaccatatgaggaagggagatagaagcagaagattatccttcgggagcaagtctttccagcccg
catcttgtgattggatgatagttttaactaaggaaagagtgcgacatccgttgtgtagtaatcatgcatacgtctattattctctctag
ttacccaactctgttatctcactaattcttatttccgaatgcaacaagctccgcattacacccgaacatcactccagatgagggct
ttctgagtgtggggtcaaatagtttcatgttccccaaatggcccaaaactgacagtttaaacgctgtcttggaacctaatatgaca
aaagcgtgatctcatccaagatgaactaagtttggttcgttgaaatgctaacggccagttggtcaaaaagaaacttccaaaag
tcggcataccgtttgtcttgtttggtattgattgacgaatgctcaaaaataatctcattaatgcttagcgcagtctctctatcgcttctg
aaccccggtgcacctgtgccgaaacgcaaatggggaaacacccgcttttggatgattatgcattgtctccacattgtatgcttc
caagattctggtgggaatactgctgatagcctaacgttcatgatcaaaatttaactgttctaaccccacttgacagcaatatata
aacagaaggaagctgccctgtcttaaaccttttttttttatcatcattattagcttactttcataattgcgactggttccaattgacaagc
ttttgattttaacgacttttaacgacaacttgagaagatcaaaaaacaactaattattcgaaacg SEQ ID NO 124: BZF7 (pAOX2-500+pCAT1-500)

ttttctcagttgatttgtttgtggggatttagtaagtcgtaaacttcgttaaaaaagatcaatgtagtcaatacagttgatccgaaata
gaaggaagaggtttgcaatgtgtaagaacaatgtagttaaaagcccgttttaagacaatattctttgatgctgatcagaaaagg
acaataagggattttggttgcttcttttataccaataatcgtctcctcatcgcttaattttctccccatctcaaccggtgaagggtagg
acgcttctgtaatctgttcacataaaagggggttttcactccgagacaaaaatttatgcgacaaaaatagcctatcttggaaggtg
atgtcttatcaacttgcattgtttgcaaggagaagcaaggacaactcaacatgggtaaaaattcaaaaccaaccaattggaa
actcccaactgtccactaggtagctgacagctgtcacttttgctgttcgttgtcttgtctctttcgcttaaTAATCGAACTCCG
AATGCGGTTCTCCTGTAACCTTAATTGTAGCATAGATCACTTAAATAAACTCATGGCC
TGACATCTGTACACGTTCTTATTGGTCTTTTAGCAATCTTGAAGTCTTTCTATTGTTCC
GGTCGGCATTACCTAATAAATTCGAATCGAGATTGCTAGTACCTGATATCATATGAAG
TAATCATCACATGCAAGTTCCATGATACCCTCTACTAATGGAATTGAACAAAGTTTAA
GCTTCTCGCACGAGACCGAATCCATACTATGCACCCCTCAAAGTTGGGATTAGTCAG
GAAAGCTGAGCAATTAACTTCCCTCGATTGGCCTGGACTTTTCGCTTAGCCTGCCGC
AATCGGTAAGTTTCATTATCCCAGCGGGGTGATAGCCTCTGTTGCTCATCAGGCCAA
AATCATATATAAGCTGTAGACCCAGCACTTCAATTACTTGAAATTCACCATAACACTTG
CTCTAGTCAAGACTTACAATTAAA

Figure 25 (continued)

SEQ ID NO 125: BZF8 (pFLD1-366+ pPXR1-392)

tgtgaatatcaagaattgtatgaacaagcaaagttggagctttgagcgatgtatttatatgagtagtgaaatcctgattgcgatca
ggtaaggctctaaaaatcgatgatggtcccgaattctttgataggctaaggacttcctcatcgggcagttcgaaggaagaagg
ggcatgagccctgcgaaaccatatgaggaagggagatagaagcagaagattatccttcgggagcaagtctttccagcccg
catcttgtgattggatgatagttttaactaaggaaagagtgcgacatccgttgtgtagtaatcatgcatacgtctattattctctctag
ttacccaactctgttatctcactaattcccaaaagagaaaaagagggaatccctgttctttccaatggaaatgacgtaacttt
aacttgaaaaatacccaaccagaagggttcaaactcaacaaggattgcgtaattcctacaagtagcttagagctggggga
gagacaactgaaggcagcttaacgataacgcgggggattggtgcacgactcgaaaggaggtatcttagtcttgtaacctct
tttttccagaggctattcaagattcataggcgatatcgatgtggagaagggtgaacaatataaaaggctggagagatgtcaat
gaagcagctggatagatttcaaattttctagatttcagagtaatcgcacaaaacgaaggaatcccaccaagcaaaaaaaaa
aatctaag SEQ ID NO 126: DDC1 (pDAS2-1000+pDAS1-1000)

ttttgatgtttgatagtttgataagagtgaactttagtgtttagaggggttataaatttgttgtaactggttttggtcttaagttaaaacgaa
cttgttatattaaacacaacggtcactcaggatacaagaataggaaagaaaaactttaaactggggacatgttgtctttatata
atttggcggttaacccttaatgcccgtttccgtctcttcatgataacaaagctgcccatctatgactgaatgtggagaagtatcgg
aacaacccttcactaaggatatctaggctaaactcattcgcgccttagatttctccaaggtatcggttaagtttcctctttcgtactg
gctaacgatggtgttgctcaacaaagggatggaacggcagctaaagggagtgcatggaatgactttaattggctgagaaag
tgttctatttgtccgaatttctttttctattatctgttcgtttgggcggatctctccagtgggggtaaatggaagatttctgttcatgggg
taaggaagctgaaatccttcgtttcttataggggcaagtatactaaatctcggaacattgaatgggtttactttcattggctacag
aaattattaagtttgttatgggtgaagttaccagtaattttcattttttcacttcaacttttggggtatttctgtggggtagcatagcttg
acaggtaatatgatgtactatgggataggcaagtcttgtgtttcagataccgccaaacgttaaataggaccctcttggtgacttg
ctaacttagaaagtcatgcccaggtgttacgtaatcttacttggtatgacttttgagtaacggacttgctagagtccttaccagact
tccagtttagcaaaccacagattgatctgtcctctggcatatctcaaaccaatcaacacccgtaacccttttcatgaaacaactct
agaatgcgtcttatcaacaggattgcccaaaacagtaataataaaaaaacgttatagaaagaaattggactacgatatgctc
caatccaaattgtcaaaattgaccaccgaaaagaacaattggaatttgacaagaggaacaactcactagattctcaaacg
gagcgtcacctagagtcagttccaagtcaattacagaaagtttggaaacagaagaggagtatctacaattgaattccaaact
taaagtcgagctgtccgaattcatgtcgctaaggctttcttacttggaccccatttttgaaagtttcattaaagttcagtcaaaaattt
tcatggacatttatgacacattaaagagcggactaccttatgttgattctctatccaaagaggattatcagtccaagatcttggac
tctagaatagataacattctgtcgaaaatggaagcgctgaaccttcaagcttacattgatgattagagcaatgatataaacaac Figure 26 — table illegible at this resolution.

Figure 26 (continued)

The page contains a rotated table that is largely illegible due to low resolution. The readable content appears to be sequence/promoter data which cannot be accurately transcribed.

| | | | | |
|---|---|---|---|---|
| pHHK2-09 | sTcon-HHK2-fwd (=sTcombies1365bpFW 0) | GAACTCATAATAAACTTGCATCCCAT TTC | s-eGFP-pHHK3650bp REV3 | TTGTTTATTGGGTGAGTCTTAG |
| | sTcon-HHK2-09-rev (=sTcombies1365bpRW 0) | CATtttaactaagaaatgtagaggttgcgttagttgcatgc cccataactgaaatggctgtggatgctctctaagtgctgac ctggcctgcaatgtggctgcacgtcaatcatgca | bnt-pHHK2-09-fwd | GACATGTCTTACAggcagagaactaatcacagcga acagga |
| pHHK2-010 | bnt-pHHK2-09-rev | aacagaaagtactcCTGTAAGAACATGT CCCATTTCATGCTACCAG | eGFP-pHHK2-010-REV3 | gaaaaagtggttccccttggaaAATTTATTGATTAAT TTGTTTATTGGTGAGTCTTAG |
| pHHK2-011 | sTcon-HHK2-fwd (=sTcombies1365bpFW 0) | CTTGATAAACTTCCTCACCCTTAGAAAAC CATtttactaagaaggaagaaggagtc | eGFP-pHHK2-010-REV3 | gaaatagttcatttaccttggtggcagccccatgccaagtctaagtgcctgctgctgtgccatcgat caagcttggcactgaaacatgtagctgagaaacctgacgatcggcgtgctgagttgcaaatttaag |
| | sTcon-HHK2-011-REV | aacagaaagtactcCTGTAAGAACATGT cccagaaggaagaagaaggaagcctgag tggagagatagatggatggagacaccta | bnt-pHHK2-011-fwd | tcgaggcaggtttcaTGGCACTGCATGCCACGTT AACTC |
| pHHK2-012 | sTcon-HHK2-fwd (=sTcombies1365bpFW 0) | CTTGATAAACTTCCTCACCCTTAGAAAAC CATtttactaagaagataagcgaagaa | eGFP-pHHK2-012-REV3 | gaaaaagtggtttccttggaggccgcaATTTATTGATTAAT TTGTTTATTGGTGAGTCTTAG |
| | bnt-pHHK2-012-rev | aataactgaaactgaagaagaagaagcatgagt gaaaccgcgttcagcagcaggctaag | eGFP-pHHK2-012-fwd | tggcggcctcaaaaagaacaCTTTTTATCATCAAAATAGAA GACGAGTGCGTCCCTTTCTAG |
| pHHK2-013 | sTcon-HHK2-fwd (=sTcombies1365bpFW 0) | gaagaagttgaataacatacaggaaggacctcagaaaAATGTTG | eGFP-pHHK2-013-rev | gaaaaagtggtttccttggcagcaATTTATTGATTAT TTGTTTATTGGTGAGTCTTAG |
| | sTcon-HHK2-012-rev | CTTGATAAACTTCCTCACCCTTAGAAAAC CATtttactaagaaggaagaaggagtcg aacaagaagcagaaggcagctggaggcc | eGFP-pHHK3650bp REV3 | TTGTTTATTGGGTGAGTCTTAG |

| | | | | | |
|---|---|---|---|---|---|
| pHHK2-SDA3 | | | | | |
| pHHK2-SDA4 | | | | | |
| pHHK2-SDA5 | | | | | |
| pHHK2-SynB6d1 | | | | | |
| pHHK2-SynB6d2 | | | | | |
| pHHK2-SynB6d3 | | | | | |
| pHHK2-SynB6d4 | | | | | |
| pHHK2-SynB6d5 | | | | | |
| pHHK2-SynB6d6 | | | | | |
| pHHK2-SynB6d7 | | | | | |
| pHHK2-SynB6d8 | | | | | |
| pHHK2-SynB6d9 | | | | | |
| pHHK2-SynB6d10 | | | | | |
| pHHK2-SynB6d11 | | | | | |
| pHHK2-SynB6d12 | | | | | |
| bAS1 variants | | | | | |
| pDAS1-del1 | "like wildtype" | pDAS1-Sd6-fwd | GTCACTTGCAGGAATAAAAAACGTTATA GAAAGAAATTGGACTACGAAGATATCCTC | pDAS1-d1-del8 | TCTCAAAACGAAGCCTCACTTTGGAAAACGGAAGA CGAGTATCTAAGATTGGATTCGAATTC |
| pDAS1-del2 | "moderately stronger than wildtype" | pDAS1-d2-fwd | AATTCAATCTAGTAGAATACATCTCTTTCTTCTGTTC CAAACGTGACGCTTCAGTTTGAAGAATTAG | pDAS1-d1-del8-rev | CCTTTGCTAGGCCATTTTTGTTCTTCCAAGCTTACAT AAATCAACAATACGTTAGTTGGTAAGG |
| pDAS1-del3 | "moderately stronger than wildtype" | pDAS1-Sd6-fwd | TTGTTCTCTCACGATTGAAGGCCTAAGATCAAG GAGGAATGTAAGGCTGCAGGCTTCAGGCTTC TC | pDAS1-d2-del8 | TCTCTCATCAGCATTTAGTCTTGCAATATAATCCCAGAT AAAATCAACGATAGGTAGTCTGTAAG |
| pDAS1-del4 | "like wildtype" | pDAS1-Sd6-fwd | GTCACTTGCAGGAATAAAAAACGTTATA GAAAGAAATGGACTACGAGATATCTC | pDAS1-d3-del8 | ACTAACTTGACTCAGATGAAGAAACAGTTGGTTAAC GTTCCTTCGAAACTCGAATGATCCCAG |
| | | pDAS1-d3-fwd | GGTGGGATCATTCGAGTTTCGAAGGAAAGT TAGACAACTGGGTCTCATCCGGGTGGAGTT AG | pDAS1-b-del-rev | CCTTTGCTAGGCCATTTGGTCGAATATATCCCAGAAT AAAATCAACATAGGTGTTTCTAAGG |
| | | pDAS1-Sd6-fwd | GTCACTTGCAGGAATAAAAAACGTTATA GAAAGAAATGGACTACGGAGATATCCTC | pDAS1-d4-del8 | CAGTCAATGATATTCGAAGCTAAGCATAAGCTTGAAA CTCTCCGTTACTCCGGGCCATGC |
| | | pDAS1-d4-fwd | TGGAGGAAAGCGGCGGAATTAGCGGAGGAG TTTCAAGGAAAGCAGGTAGGCTCAAACACATTCATTG AC | pDAS1-d4-del8 | CGTTTGCCTAGGATTTGGAATTCCAAACTGTTTCCAGAG AAAATCAAGAAGATAGTGGTTTTCGAAAG |
| pDAS1-del5 | "moderately stronger than wildtype" | pDAS1-Sd6-fwd | GTCACTTGCAGGAATAAAAAACGTTATA | pDAS1-d5-del8 | CTTGCCTAGGCCATTTCGAAACGAAGTTCGCAAGTTTCGAACAT |

[Figure: table too low-resolution to transcribe reliably]

Figure 26 (continued)

| | | fwd | algrev | DASaid containing WT REV PX2224 |
|---|---|---|---|---|
| pGA452-11030 pFF96.BC3 | ~2/3 of pAC382 | pGA452-1000-fwd | ctcatcgttcaggctatccaatcagtgtgataagac | DASaid containing WT REV PX2224 | tttcgattgttctaagattcgttgataagtgtagtttaatcag |
| pT4&1 (PFF74) | moderate, down regulated on NaeOH | pT4&1rev | caggaagttcgttttcagataacaagtthcgctgctca | pTA&1fwd | tghaggaaaataattttcaattagcaaaagaaagcgcaaa |
| pT4&2 (PFF78) | moderate NaeOH inducible | pT4&2rev | ggaatgctgcatcactctoataagtthcgctgatggccac | pTA&2fwd | ggaattccggcccgaacttgtaggcctcatctatcgcaatcat aac |

BIDIRECTIONAL PROMOTER

SEQUENCE LISTING

The entire content of a Sequence Listing titled "Sequence_Listing.txt," created on Apr. 11, 2016 and having a size of 253 kilobytes, which has been submitted in electronic form in connection with the present application, is hereby incorporated by reference herein in its entirety.

FIELD OF THE INVENTION

The invention relates to a library of bidirectional expression cassettes comprising a repertoire of bidirectional promoter sequences, methods of producing and screening such library, and bidirectional promoter sequences, including isolated Pichia pastoris or CHO cell promoter sequences.

BACKGROUND ART

The production of proteins for industry or pharmacy is most commonly achieved by recombinant gene expression using heterologous host systems. The methylotrophic yeast Pichia pastoris is an important host system for heterologous gene expression. P. pastoris provides fast growth on simple media and is capable of providing most eukaryotic post translational modifications. Along with high capacities for protein production, P. pastoris is the only microbial expression host that provides fully humanized glycosylation (including sialylation) in engineered strains. Furthermore P. pastoris reaches exceptionally high cell densities (up to 130 g/l cell dry weight) and has high secretory capacities. As P. pastoris secretes only negligible amounts of endogenous protein, heterologous secreted proteins consist the vast majority of protein in the supernatant, thereby drastically facilitating purification and downstream processing.

When expressing a single protein, several factors influence the expression efficiency and thereby the yields. An important key factor to regulate expression is the promoter. The transcription strength of the promoter strongly influences the achieved yields. Strong promoters tend to give higher yields, but the effect is protein dependent. If other factors such as protein folding or post translational modifications are the expression limiting factor, too strong promoters might overburden the cellular machinery. In this case a weaker promoter might lead to better yields. In addition also the regulation of the promoter can influence the yields. Constitutive promoters provide more or less constant expression during the entire production process. However, the constitutive production of a protein of interest (POI) might interfere with the cellular metabolism and hamper growth, especially if the POI is toxic or difficult to express.

The coexpression of two (or more) proteins even further complicates expression efforts.

Dual gene coexpression is required when producing dimeric proteins (such as antibodies, consisting of a heavy and a light chain), an enzyme and a redox partner (such as Cytochrome P450 enzymes (CYP), which require a reductase (CPR) that delivers electrons) or when expressing a gene of interest (GOI) together with a folding helper (chaperone). Even more proteins have to be coexpressed for multimeric proteins and metabolic pathways.

The coexpressed proteins have to be expressed at the most suitable expression level, ratio and most favorable regulatory profile (constitutive, inducible or tunable expression simultaneously or in consecutive manner).

As for a single gene, the expression levels of multiple genes depend on their properties and might require strong or weak promoters to drive transcription. In addition, also the ratio of the coexpressed proteins is important. Depending on their natural role, they provide strongest activity/yields when expressed at equal levels, or one of the two proteins is required in several fold excess. For human P450s and the associated reductase it has been shown that a specific ratio of CYP to CPR is required for highest activity [1].

Furthermore, for the coexpression of two genes also the time frame has to be considered as the two proteins can either be expressed simultaneously or separately with one protein preceding expression. Especially in the coexpression of a helper protein, different time windows can be beneficial. Placing the helper protein under the control of a constitutive promoter and the GOI under a regulated/inducible promoter or consecutive induction provides the helper protein as a folding catalyst before starting GOI expression with an inductor. Using this approach, the helper protein expression precedes the GOI and is abundantly available when the GOI is expressed and can right away assist in folding.

Most gene coexpression efforts in P. pastoris have relied on the use of two separate vectors, with each vector providing one of the two genes [1,2].

The two vectors can either be cotransformed in the same strain [1] or transformed in two separate strains, which are subsequently mated, resulting in a strain carrying both genes [2].

Using two vectors also requires the use of two resistance markers. Concerning transfer of the vector, mating is relatively time consuming and requires at first the generation of single strains that express the GOIs. Cotransformation of the two vectors in one strain is linked with lower transformation efficiencies and requires immediate double selection on two antibiotics which can be detrimental in a case a critical protein is expressed constitutively.

Additionally, the two GOIs have also been placed on the same vector. In this case the same monodirectional promoter was cloned in front of the two GOIs [3]. This approach solves the problem of multiple resistance markers, but poses a problem as the same promoter sequence is present on the vector twice, which can lead to undesired recombination events. In contrast to open reading frames where the same amino acid sequence can be encoded by different gene sequences due to different codons there is no general concept to diversify the DNA sequence of promoters. Therefore mostly identical or completely different promoters with different properties are used to generate expression cassettes by individual fusions of coding regions with individual promoter sequences.

Concerning monodirectional promoters, the methanol inducible AOX1 promoter and the constitutive GAP promoter are most commonly used to drive gene expression. A set number of other promoters have been reported but not described in detail and were rarely applied by a broader public so far [4].

Bidirectional promoters provide divergent expression in opposing (forward and reverse) orientations. This enables coexpression of two genes by placing them in opposing orientations and placing a bidirectional promoter in between them (see FIG. 1 B, C).

There are no bidirectional promoters described in P. pastoris. However, bidirectional promoters have been studied in Saccharomyces cerevisiae and some information on natural bidirectional promoters and their function is available.

There are few examples for bidirectional promoters in *S. cerevisiae* that have been described in detail. Most prominently, the divergent organization of the GAL1-GAL10 promoter was studied. The GAL1 and GAL10 genes are organized in opposite orientations, with the intergenic region constituting a bidirectional promoter [5]. Both genes are required for the galactose metabolism and are tightly transcriptionally regulated by the carbon source. The genes on both sides are strongly induced on galactose and repressed on other carbon sources [6]. Therefore this bidirectional promoter provides similar expression levels on both sides and they share the same regulatory profile with a fixed ratio between the two sides. The bidirectional GAL1-GAL10 promoter has also been provided as an expression vector for bidirectional gene expression (pESC vector series, Stratagene/Agilent, La Jolla, Calif., USA). The GAL1-GAL10 promoter was also used to study a human heterodimeric transcription factor composed of aryl hydrocarbon receptor and aryl hydrocarbon receptor nuclear translocator [7]. In frame of this work also a constitutive bidirectional promoter was described by fusing the GPD and ADH1 promoters in opposite directions to each other. A similar fusion of constitutive promoters was performed by [8] using TEF1 and PGK1 in opposite orientations. The GAL1 and GAL10 sides of the GAL1-GAL10 promoter have furthermore been coupled with the constitutive GPD promoter, leading to bidirectional promoters with constitutive expression on one side and inducible expression on the other [9]. The two differently regulated sides did not influence each other and retained their regulatory profile and more than 85% of their monodirectional activity.

Another specific example of a bidirectional promoter in yeast is the UGA3-GLT1 intergenic region, which was shown to be affected by chromatin organization, but which was not tested as a promoter for bidirectional expression vectors [10].

Recent publications on genome wide analysis of natural bidirectional promoters in *S. cerevisiae* have shown that they are rather not involved in specific, high level expression, but rather in cryptic and pervasive transcription of the entire genome at low levels [11,12]. Namely, it was shown that weak pervasive transcription occurs in bidirectional fashion, and that the number of bidirectional promoters is significantly higher than previously estimated. Bidirectional pervasive transcription occurs not only next to protein coding sequences but also in intergenic regions [11]. These studies also suggested that bidirectionality is an intrinsic trait of eukaryotic promoters, leading in the majority of cases to short-lived unstable transcripts but also stable transcripts with a possible regulatory role [12]. The exact function of this pervasive bidirectional transcription is not fully understood, but they might play regulatory roles or help in maintaining chromatin structure [11].

Bidirectional promoters have also been studied in higher eukaryotes, namely in plants [13] and mammalian cells. Concerning mammalian cells bidirectional expression has been engineered using antibiotic regulated synthetic bidirectional promoters by tetracycline [14,15], pristinamycin [16] and two antibiotics at the same time (using a macrolide antibiotic on one side and a streptogramin antibiotic on the other side) [17]. Also sequence based approaches for promoter engineering of bidirectional promoters and natural bidirectional promoters were used in mammalian expression systems [18,19]. However, no library approach was applied so far to optimize expression by testing different bidirectional promoters to influence expression levels and ratios of coexpressed proteins.

Currently available bidirectional expression vectors rely on a bidirectional promoter flanked by two multiple cloning sites to clone in the genes to be expressed (FIG. 1 B). Although they facilitate cloning compared to dual gene expression with monodirectional promoters (FIG. 1 A), these vectors contain only a single bidirectional promoter. If different bidirectional promoters should be tested, a separate cloning vector is required for each promoter. Concomitantly this requires also multiple cloning steps for each gene pair into the vectors. Examples for such vectors have been mentioned above in *S. cerevisiae* [7,9] and there are bidirectional expression vectors available for mammalian cells (Clontech) and a specific, restriction site based screening vector for bidirectional elements [20]. However restriction sites with their palindromic sequences in front of the translation start can influence heterologous protein expression.

The Clontech vectors provide either bidirectional constitutive or bidirectional inducible expression with identical expression levels on both sides. These vectors have been optimized to facilitate the screening of a single gene. Therefore both sides provide identical expression. One side drives the expression of the GOI whereas the other side drives the expression of a reporter gene. If no activity assay or easy way of detection of the GOI is available, the reporter gene can help to screen for efficient expression of the GOI thereby avoiding the frequently applied fusion of the GOI to a fluorescent reporter protein.

Currently available bidirectional vectors [7,9] rely on a fixed bidirectional promoter and subsequent cloning steps using multiple cloning sites (MCS) (see FIG. 1 B and FIG. 2 A). Polson et al. [20] describe a vector that allows to test different promoters by restriction/ligation cloning which depends on the introduction of specific restriction sites at the end of each of the tested promoter sequences.

US20130157308A1 describes a bidirectional expression vector that can be utilized to determine the existence and characteristics of bidirectional promoters. The bidirectional expression vector includes two different reporter genes in a head to head (5' to 5') arrangement. In addition, the bidirectional expression vector can include a polylinker region located between the heads of the two reporter genes that provides multiple cloning sites for nonexclusive examination of polynucleotide sequences.

Currently used bidirectional promoters provide a very limited set of expression levels, ratios and regulatory profiles. In *S. cerevisiae* only five bidirectional promoters have been tested for expression vectors: 1) the natural GAL1-GAL10 promoter providing galactose inducible expression with the same strength on both sides, 2) a GPD and ADH1 fusion promoter [7], 3) a TEF1 and PGK1 fusion promoter [8] providing constitutive expression with the same strength on both sides and fusions of the 4) GAL1 sides with the GPD promoter and 5) the GAL10 side with the GPD promoter [9].

Notably these promoters provide only identical expression levels (strong expression) and a fixed ratio (approximately equal 1:1 ratio) on both sides [7] and the regulatory profiles are limited to constitutive expression and inducible expression using galactose.

Therefore, there are no bidirectional promoters that provide intermediate or low expression and with the currently known four promoters it is not possible to achieve different expression ratios of multiple genes to tune expression ratios for maximal yields of recombinant proteins or cellular metabolites from expressed pathways. Furthermore inducible expression can only be achieved using galactose. For example no auto regulatory bidirectional promoters and feedback loops are available for expression in yeasts.

Fine-tuning and optimizing the expression of a gene pair or multiple genes requires a broader scope of expression levels, ratios and time profiles.

SUMMARY OF INVENTION

It is the object of the present invention to provide for alternative bidirectional promoter sequences suitable for recombinant production methods of producing composite proteins or metabolites of a metabolic pathway employing at least two different genes.

The object is solved by the subject matter as claimed.

According to the invention there is provided a library of bidirectional expression cassettes comprising a repertoire of bidirectional promoter sequences, each expression cassette comprising a promoter sequence operably linked to a first gene in one direction, and operably linked to an oppositely oriented second gene in the other direction which is different from the first gene.

According to the invention there is further provided a library of expression vectors, each comprising at least one expression cassette of the invention.

Hereinafter, the term "library" or "library of the invention" refers to any one or both of the library of expression cassettes and library of expression vectors.

The library of the invention is specifically characterized by the genes employed, which genes may include any GOI or pairs of GOI to be coexpressed. Specifically, the genes comprise a GOI and/or reporter gene, preferably genes encoding protein components of the same composite protein or protein complex, preferably wherein the composite protein is a heterodimeric protein, or preferably wherein the protein complex is formed by interaction of the protein components, or preferably wherein one protein supports folding and/or targeting of another protein or preferably wherein the genes are of the same metabolic or regulatory pathway, including signaling pathways and transcription factors, or of one pathway which supports other pathways, such as energy generating pathways, ATP production, cofactor regeneration.

Specifically, the promoter sequence is selected from the group consisting of a natural promoter sequence or pairs of natural promoter sequences of *Pichia pastoris* or CHO cells fused in opposite orientation, preferably selected from the group consisting of the sequences of SEQ ID NO:1-95 or SEQ ID NO:114-181, or functionally active variants thereof, preferably deletion variants, truncations or repeats thereof.

Specifically, the repertoire of the promoter sequences comprises at least one natural promoter sequence of *P. pastoris* or pairs of such natural promoter sequences fused in opposite orientation, preferably selected from the group consisting of the sequences of SEQ ID NO:1-38, or SEQ ID NO:96-125, or functionally active variants thereof, preferably deletion variants, truncations or repeats of any of SEQ ID NO:1-38 or SEQ ID NO:126-135, or methanol inducible variants thereof obtainable by fusing core promoter regions of any of SEQ ID 1-38 to cis-acting regulatory elements of methanol inducible promoters, preferably selected from the group consisting of the sequences of SEQ ID 39-95 or SEQ ID NO:136-165.

In addition, the invention refers to further functionally active variants or artificial promoter sequences as detailed below, e.g. in the examples section, including the tables and sequence listing. Specific bidirectional promoter sequences of the present invention are described in the tables or sequence listing below.

It is well understood that the bidirectional promoter sequences provided herein and specifically described in the tables or sequence listing below shall include the specified promoter sequences and the complementary sequences, which are used, e.g. for transcription in the opposite direction.

Specifically, the repertoire comprises at least 2 library members, each comprising the same promoter sequence in opposite orientation.

Specifically, the repertoire comprises artificial promoter sequences, preferably at least 50 different promoter sequences, more preferably at least 100, or at least 1000, or at least 10000, preferably wherein each of the different promoter sequences has a proven bidirectional transcription activity.

According to the invention there is further provided a method of producing a library of the invention, comprising
a) providing an expression cassette consisting of the first and second genes and a stuffer sequence separating them, which stuffer sequence comprises a recognition site for a type IIS restriction enzyme at both ends;
b) cleaving the stuffer sequence using the type IIS restriction enzyme resulting in ligation ends at the start codons of the genes;
c) introducing a repertoire of promoter sequences to obtain a repertoire of expression cassettes; and optionally
d) engineering a repertoire of expression vectors by introducing the repertoire of expression cassettes into a suitable vector.

The repertoire of promoter sequences may be introduced by a well-known cloning method, such as for example by a conventional cloning method or by TA cloning or Gibson assembly.

Specifically, the repertoire of promoter sequences comprises natural and/or synthetic nucleotide sequences of 100 base lengths to 5000 base lengths, preferably obtained by recombination of artificial random sequences, such as oligos, or mutagenesis of a parent promoter sequence, preferably wherein the parent promoter sequence is a natural promoter sequence or pairs of natural promoter sequences of *P. pastoris* fused in opposite orientation, preferably selected from the group consisting of the sequences of SEQ ID 1-38, or SEQ ID NO:96-125, or functionally active variants thereof, preferably deletion variants, truncations or repeats of any of SEQ ID NO:1-38 or SEQ ID NO:126-135, or methanol inducible variants thereof obtainable by fusing core promoter regions of any of SEQ ID 1-38 to cis-acting regulatory elements of methanol inducible promoters, preferably selected from the group consisting of the sequences of SEQ ID 39-95 or SEQ ID NO:136-165.

According to the invention there is further provided an isolated bidirectional *Pichia pastoris* promoter sequence, which when operably linked to a first gene in one direction and operably linked to an oppositely oriented second gene in the other direction, has bidirectional transcription activity, preferably with different transcription strength and/or ratios and/or regulatory profiles in each direction.

Specifically, the promoter sequence is selected from the group consisting of a natural promoter sequence or pairs of natural promoter sequences of *Pichia pastoris* fused in opposite orientation, preferably selected from the group consisting of the sequences of SEQ ID NO:1-165, or functionally active variants thereof, preferably deletion variants, truncations or repeats thereof.

More specifically, the promoter sequence is selected from the group consisting of a natural promoter sequence or pairs of natural promoter sequences of *Pichia pastoris* fused in opposite orientation, preferably selected from the group consisting of the sequences of SEQ ID NO:1-38, or SEQ ID NO:96-125 or functionally active variants thereof, preferably deletion variants, truncations or repeats of any of SEQ ID NO:1-38 or SEQ ID NO:126-135, or methanol inducible variants thereof obtainable by fusing core promoter regions of any of SEQ ID 1-38 to cis-acting regulatory elements of methanol inducible promoters, preferably selected from the group consisting of the sequences of SEQ ID 39-95 or SEQ ID NO:136-165.

According to the invention there is further provided an expression cassette or expression vector comprising the promoter sequence of the invention.

According to the invention there is further provided a host cell comprising the expression cassette or vector of the invention.

According to the invention there is further provided a method of screening or selecting a bidirectional promoter suitable for expressing at least two GOI in a host cell which comprises
a) providing a library of the invention, comprising the at least two GOI as the first and second genes;
b) selecting a library member which has a proven bidirectional transcription activity; and
c) identifying the bidirectional promoter sequence comprised in the selected library member and/or using the same for producing an expression construct to express said at least two GOI under the transcriptional control of said bidirectional promoter sequence.

Specifically, the transcription activity is qualitatively and/or quantitatively determined, preferably by in vitro or in vivo methods.

Specifically, the library member is selected according to the transcription activity of the first and second genes, which is differently regulated, preferably any of a constitutive activity, or activity induced or derepressed by a carbon source.

According to the invention there is further provided a kit for use in the method of the invention, comprising
a) an expression cassette consisting of the first and second genes and a stuffer sequence separating them, or an expression vector comprising such expression cassette, which stuffer sequence comprises a recognition site for a type IIS restriction enzyme at both ends;
b) the type IIS restriction enzyme;
c) and a repertoire of promoter, preferably a promoter library including bidirectional promoter.

Specifically, the library of the invention is used for screening or selecting a bidirectional promoter suitable for expressing at least two GOI by a single expression cassette or by a single vector.

BRIEF DESCRIPTION OF DRAWINGS

FIG. 1B: Conventional bidirectional expression vector with a fixed bidirectional promoter

FIG. 2A: Cloning of genes of interest into conventional bidirectional vectors. The two genes have to be cloned into the vector using four different enzymes from the two multiple cloning sites (MCS). The cloning steps can either be performed sequentially or with lower efficiencies simultaneously (dashed arrow). This procedure relies on the use of a single bidirectional promoter and does not allow simple testing of multiple promoters.

FIG. 2B: Vector generation and cloning strategy with new bidirectional vectors. An entry vector is assembled by fusing the coding sequences to a stuffer fragment by overlap extension PCR. This expression cassette is cloned into a starting vector by conventional restriction enzyme digestion and ligation. Subsequently the entry vector is digested with a type IIS restriction enzyme, thereby removing the stuffer fragment and allowing the direct cloning of a library of PCR amplified bidirectional promoters FIG. 3: type II restriction enzyme recognition sequences (EcoRI and EcoRV) and type IIS restriction enzyme recognition sequences (BsaI, MlyI, BmrI). The enzymes shown on top create sticky/cohesive ends, whereas the enzymes on the bottom create blunt ends.

FIG. 25: Promoter sequences

FIG. 26: Table 4

DESCRIPTION OF EMBODIMENTS

Figure 1A:
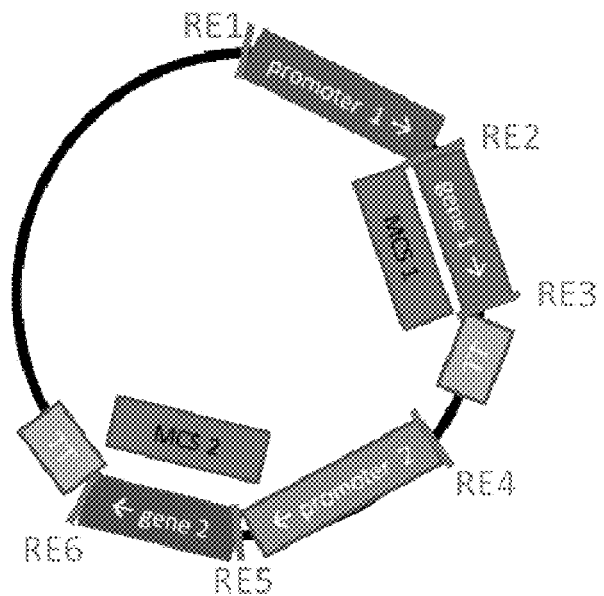
FIGS. 1A and 1B: Conventional dual gene expression vector with two monodirectional promoters

Specific terms as used throughout the specification have the following meaning.

The term "bidirectional" with respect to a promoter and transcription of a nucleotide sequence shall refer to transcription in both directions of a nucleic acid sequence.

In particular, bidirectional promoters are double-strand transcription control elements that can drive expression of at least two separate sequences, e.g. coding or non-coding sequences, in opposite directions. Such promoter sequences may be composed of two individual promoter sequences acting in opposite directions, such as one nucleotide sequence is linked to the other (complementary) nucleotide sequence, including packaging constructs comprising the two promoters in opposite directions, e.g. by hybrid, chimeric or fused sequences comprising the two individual promoter sequences, or at least core sequences thereof, or else by only one transcription regulating sequence that can initiate the transcription in both directions. The two individual promoter sequences may be juxtaposed or a linker sequence can be located between the first and second sequences. Specifically, a promoter sequence may be reversed to be combined with another promoter sequence in the opposite orientation. Still, genes located on both sides of a bidirectional promoter can be operably linked to a single transcription control sequence or region that drives the transcription in both directions.

For example, a first gene can be operably linked to the bidirectional promoter with or without further regulatory elements, such as a reporter or terminator elements, and a second gene can be operably linked to the bidirectional promoter in the opposite direction and by the complementary promoter sequence, again with or without further regulatory elements.

An expression construct incorporating such bidirectional promoter as described herein comprises a bidirectional arrangement of elements, e.g. a bidirectional architecture of a vector.

Though the sequences controlling the transcription in one and the other direction may be the same, it is preferred that the sequences are different in sequence, structure and function, e.g. promoter sequences of different transcriptional activity or strength, e.g. to obtain different transcription or expression levels and a specific transcription or expression ratio, or differently regulated with a specific regulatory profile. For example, the promoter may be constitutive, inducible and/or repressible and/or de-repressible, e.g. by a specific carbon source, such as methanol, or by specific chemicals, antibiotics or environmental factors. Therefore, the bidirectional promoter may e.g. be a constitutive promoter in one direction, and regulated differently in the other direction, e.g. inducible and/or repressible and/or de-repressible, which enables the specific co-expression of genes that is dependent on cultivation conditions. In another example, the bidirectional promoter can be inducible and/or repressible and/or de-repressible, however, by means of different trigger of the promoter activity, such as different carbon-source or a different amount or limitation of carbon-source.

The term "expression cassette" refers to nucleic acid molecules containing a desired coding sequence and control sequences in operable linkage, so that hosts transformed or transfected with these sequences are capable of producing the encoded polypeptides or host cell metabolites. In order to effect transformation, the expression system may be included in a vector; however, the relevant DNA may also be integrated into the host chromosome. Expression may refer to secreted or non-secreted expression products, including polypeptides or metabolites. Specifically, an expression cassette of the invention is also called "bidirectional expression cassette".

"Expression vectors" used herein are defined as constructs including DNA sequences that are required for the transcription of cloned recombinant nucleotide sequences, i.e. of recombinant genes and the translation of their mRNA in a suitable host organism. Expression vectors usually comprise an origin for autonomous replication in the host cells, selectable markers, a number of restriction enzyme cleavage sites, a suitable promoter sequence and a transcription terminator, which components are operably linked together. The term "vector" as used herein specifically includes autonomously replicating nucleotide sequences as well as genome integrating nucleotide sequences. Specifically, an expression vector of the invention is also called "bidirectional expression vector".

The expression cassette or vector of the invention specifically comprises a promoter of the invention, operably linked to two non-coding or coding regions of nucleotide sequences located on both sides of the promoter, in opposite directions, e.g. two different genes encoding a POI or reporter under the transcriptional control of said promoter, which promoter is not natively associated with the genes.

The term "gene of interest" or GOI as used herein shall refer to any coding gene, e.g. encoding a protein of interest (POI), including polypeptides, or else reporter compounds. A POI may either be a polypeptide or protein, e.g. a recombinant protein not naturally occurring in the host cell, i.e. a heterologous protein, or else may be native to the host cell, i.e. a homologous protein to the host cell, but is produced, for example, by transformation with a vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. The expression product of a gene of interest is typically a protein, or a metabolite mediated by such protein, e.g. a product of a metabolic pathway. Alternatively, genes of regulatory pathways may be included according to the invention, e.g. signaling pathways, or transcription factors.

The genes as used according to the invention may encode parts of a protein, e.g. protein chains or protein domains. By the co-expression of such genes, e.g. employing the bidirectional constructs of the invention, a composite protein may be expressed, e.g. a heterodimeric or multimeric protein comprising encoded by at least two different genes. Alternatively, a protein complex may be expressed by coexpressing at least two proteins, which either interact with each other, e.g. an enzyme and a co-factor or substrate, or a protein and a factor processing the protein, e.g. folding such protein, or cleaving such protein, e.g. for secretion or maturation purposes. Alternatively, a series of genes may be co-expressed, which are part of a metabolic pathway to produce a cell metabolite. Further examples refer to elements of pathways, such as energy generating pathways, ATP production, or cofactor regeneration.

Genes of interest may be e.g. the genes coding for any of the above-mentioned polypeptides of interest. The expression construct of the invention may also be used for expression of marker genes, reporter genes, amplifiable genes, or the like.

The term "cell" or "host cell" as used herein refers to a cell or an established clone of a particular cell type that has acquired the ability to proliferate over a prolonged period of time. A host cell particularly includes a recombinant construct, e.g. engineered to express recombinant genes or products. The term "host cell" also refers to a recombinant cell line as used for expressing a gene or products of a metabolic pathway to produce polypeptides or cell metabolites mediated by such polypeptides, including production cell lines, which are ready-to-use for cultivation in a bioreactor to obtain the product of a production process, such as a protein of interest (POI) or a cell metabolite. The cells may be specifically eukaryotic, including mammalian, insect, yeast, filamentous fungi and plant cells. It is well understood that the term does not include human beings.

The term "isolated" as used herein with respect to a nucleic acid such as a promoter of the invention shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized. This term specifically refers to a DNA molecule that is separated from sequences with which it is immediately contiguous in the naturally occurring genome of the organism in which it originated. For example, an "isolated promoter" may comprise a DNA molecule inserted into a vector, such as a plasmid, or integrated into the genomic DNA of a host organism. An isolated promoter may further represent a molecule produced directly by biological or synthetic means and separated from other components present during its production.

The term "repertoire" as used herein refers to a mixture or collection of nucleic acid sequences, such as promoter, expression cassettes, or vectors, or host cells comprising such repertoire, that are characterized by sequence diversity. The individual members of a repertoire may have common features, such as a common core structure and/or a common function, e.g. a specific promoter activity. Within a repertoire there are usually "variants" of a nucleic acid sequence, such as a variety of promoter sequences, which are derived from a parent sequence through mutagenesis methods, or synthetically produced, e.g. through randomization techniques. Likewise, the term "library" as used herein refers to a variety of nucleic acid sequences or constructs or cells comprising such nucleic acid sequences, e.g. including a repertoire or a selected population of library members with common features. The library is composed of members, each of which has a single nucleic acid sequence. To this extent, "library" is synonymous with "repertoire." Hereinafter the term "kit" is also used synonymous with "library".

Sequence differences between library members are responsible for the diversity present in the library.

The term "operably linked" as used herein refers to the association of nucleotide sequences on a single nucleic acid molecule, e.g. an expression cassette or a vector, in a way such that the function of one or more nucleotide sequences is affected by at least one other nucleotide sequence present on said nucleic acid molecule. For example, a promoter is operably linked with a coding sequence of a recombinant gene, when it is capable of effecting the expression of that coding sequence. As a further example, a nucleic acid encoding a signal peptide is operably linked to a nucleic acid sequence encoding a POI, when it is capable of expressing a protein.

The term "promoter" as used herein refers to a DNA sequence capable of controlling the expression of a coding sequence or functional RNA. The promoter of the invention specifically initiates, regulates, or otherwise mediates or controls the expression of a coding DNA. Promoter DNA and coding DNA may be from the same gene or from different genes, and may be from the same or different organisms.

Promoter activity is typically assessed by its transcriptional efficiency. This may be determined directly by measurement of the amount of mRNA transcription from the promoter, e.g. by Northern Blotting or indirectly by measurement of the amount of gene product expressed from the promoter.

The strength of the promoter of the invention specifically refers to its transcription strength, represented by the efficiency of initiation of transcription occurring at that promoter with high or low frequency. The higher transcription strength the more frequently transcription will occur at that promoter. Promoter strength is important, because it determines how often a given mRNA sequence is transcribed, effectively giving higher priority for transcription to some genes over others, leading to a higher concentration of the transcript. A gene that codes for a protein that is required in large quantities, for example, typically has a relatively strong promoter. The RNA polymerase can only perform one transcription task at a time and so must prioritize its work to be efficient. Differences in promoter strength are selected to allow for this prioritization.

The strength or relative strength of the bidirectional promoter activity, herein also referred to as transcription or expression ratio, may be determined by comparing the frequency of transcription or the transcription rate, e.g. as determined by the amount of a transcript in a suitable assay, e.g. qRT-PCR or Northern blotting. The strength of a promoter to express a gene of interest is commonly understood as the expression strength or the capability of support a high expression level or rate.

The transcription rate may be determined by the transcription strength on a microarray, or with quantitative real time PCR (qRT-PCR). Preferably the transcription analysis is qualitative, quantitative or semi-quantitative, e.g. employing a microarray, Northern Blot, RNA sequencing or qRT-PCR, or else in a cell culture, such as by measuring the quantity of respective gene expression products in recombinant cells.

The term "variant" as used herein in the context of the present invention shall specifically refer to any sequence derived from a parent sequence, e.g. by size variation, e.g. elongation or fragmentation, mutation, hybridization (including combination of sequences), or with a specific degree of homology, or analogy.

The invention specifically provides for bidirectional promoter which is a wild-type promoter, e.g. of *P. pastoris*, or a functionally active variant thereof, e.g. capable of controlling the transcription of a specific gene in a wild-type or recombinant eukaryotic cell.

The functionally active variant promoter may e.g. be derived from any of the natural promoter sequences of *P. pastoris*, specifically any one of SEQ ID 1-38, by mutagenesis, thus employing the wild-type sequence as a "parent" sequence, to produce sequences suitable for use as a promoter in recombinant cell lines. Such variant promoter may be obtained from a promoter library of artificial or mutant sequences by selecting those library members with predetermined properties. Variant promoters may have the same or even improved properties, e.g. improved in promoter strength to support POI production, or with the same or changed regulatory profile.

The variant promoter may also be derived from analogous sequences, e.g. from eukaryotic species other than *P. pastoris* or from a genus other than *Pichia*, such as from *K. lactis, Z. rouxii, P. stipitis, H. polymorpha*. Specifically, the analogous promoter sequences natively associated with genes analogous to the corresponding *P. pastoris* genes may be used as such or as parent sequences to produce functionally active variants thereof. The properties of such analogous promoter sequences or functionally active variants thereof may be determined using standard techniques.

The "functionally active" variant of a nucleotide or promoter sequence as used herein specifically means a mutant sequence, e.g. resulting from modification of a parent sequence by insertion, deletion or substitution of one or more nucleotides within the sequence or at either or both of the distal ends of the sequence, and which modification does not affect or impair the activity of this sequence.

Specifically, the functionally active variant of the promoter sequence according to the invention is selected from the group consisting of homologs with at least about 60% nucleotide sequence identity, preferably at least 70%, at least 80%, or at least 90% degree of homology or sequence identity to the parent sequence; and/or homologs obtainable by modifying the parent nucleotide sequence used as a template to provide for mutations, e.g. by insertion, deletion or substitution of one or more nucleotides within the sequence or at either or both of the distal ends of the sequence; and analogs derived from species other than *P. pastoris*.

The promoter of the invention may comprise or consist of a nucleotide sequence of 80 bp to 1500 bp, preferably at least 100 bp, at least 200 bp, preferably at least 300 bp, more preferred at least 400 bp, at least 500 bp, at least 600 bp, at least 700 bp, at least 800 bp, at least 900 bp, or at least 1000 bp.

Specifically preferred functionally active variants are those derived from a promoter according to the invention by modification, extension and/or fragments of the promoter sequence, which comprises e.g. a core promoter region and additional nucleotides.

The core promoter region is understood in the following way. The promoter of the invention may include an expression regulation system comprising a transcription factor region and a core promoter region. A transcription factor region can have various positions related to a core promoter region, e.g. upstream or downstream of a core promoter region, proximate or distal to a core promoter region, or even incorporated within a core promoter region. Transcription factors generally regulate gene expression by activating or repressing expression, e.g. upon a certain stimulus. Therefore, the core promoter is understood as the part of a promoter sequence excluding the part acting as transcription factor.

A functionally active variant of a parent promoter sequences as described herein may specifically obtained through mutagenesis methods. The term "mutagenesis" as used in the context of the present invention shall refer to a method of providing mutants of a nucleotide sequence, e.g. through insertion, deletion and/or substitution of one or more nucleotides, so to obtain variants thereof with at least one change in the nucleotide sequence. Mutagenesis may be through random, semi-random or site directed mutation. Typically large randomized promoter libraries are produced with a high gene diversity, which may be selected according to a specifically desired function, e.g. transcription strength, bidirectional transcription ratio, or regulation profile.

Some of the preferred functionally active variants of the promoter according to the invention are prolonged size variants or specifically fragments of any of SEQ ID 1-38, preferably those including the 3' end of a promoter nucleotide sequence, e.g. a nucleotide sequence derived from one of the promoter nucleotide sequences which has of a specific length and insertions or a deletion of the 5' terminal region, e.g. an elongation or cut-off of the nucleotide sequence at the 5' end, so to obtain a specific length with a range from the 3' end to a varying 5' end, such as with a length of the nucleotide sequence of at least 80 bp, preferably at least 100 bp, preferably at least 200 bp.

The functionally active variant of a promoter of the invention is also understood to encompass hybrids of any of SEQ ID 1-38, or any of the functionally active variants thereof, e.g. resulting from combination with one or more of any promoter sequences, e.g. bidirectional promoter sequences. In another embodiment, the hybrid is composed of at least one of the sequences selected from any of SEQ ID 1-38, or any of the functionally active variants thereof, a promoter sequence of a homologue gene from phylogenetically related yeast strains, and a heterologous sequence which is e.g. not natively associated with the wild-type sequence in P. pastoris.

Figure 23:
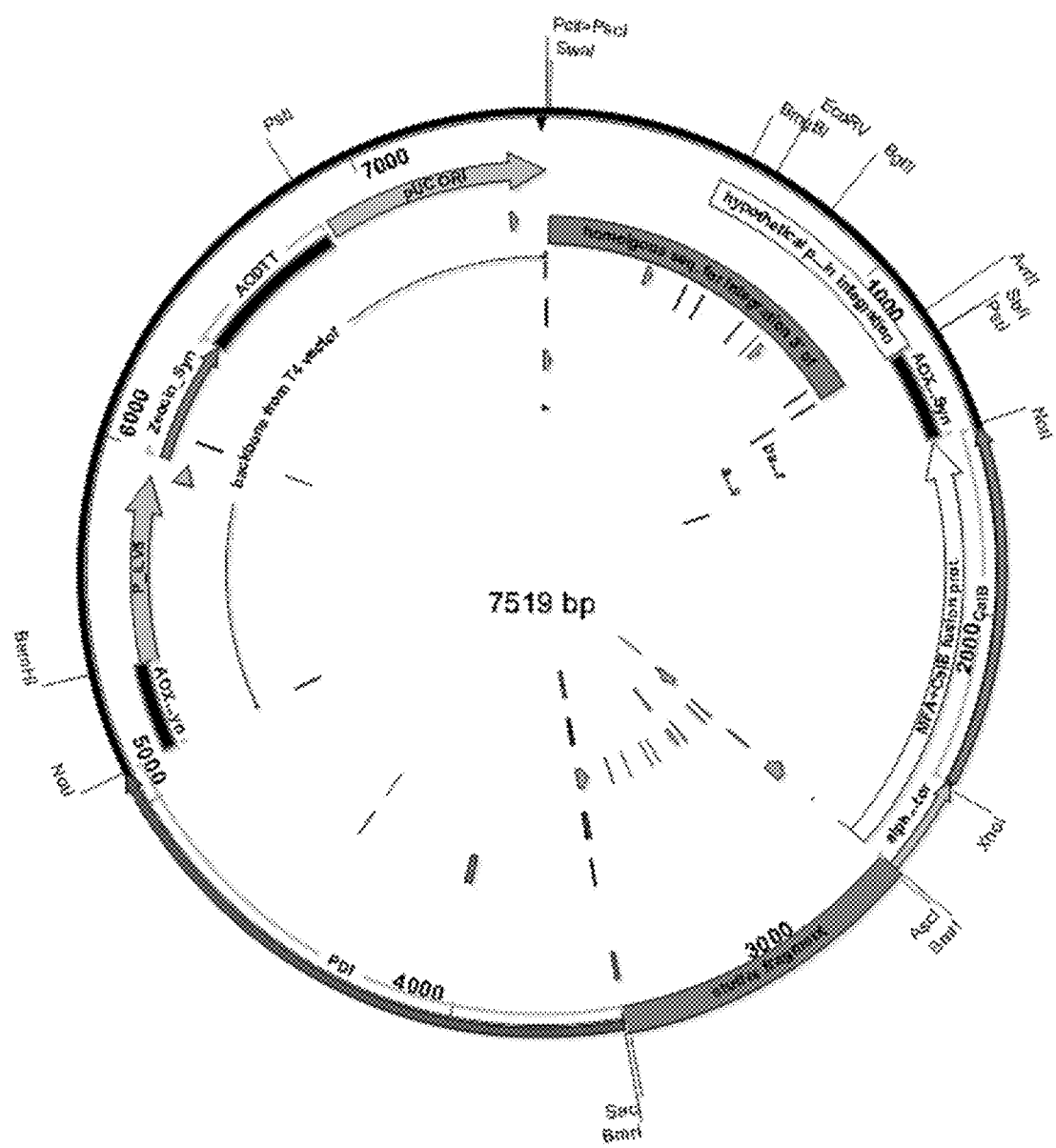
FIG. 23: Bidirectional entry vector for testing different bidirectional promoters for CalB+PDI coexpression.

The functionally active variant of a promoter of the invention is further understood to encompass a nucleotide sequence which hybridizes under stringent conditions to any of SEQ ID 1-38, or any of SEQ ID 39-95, or any of the bidirectional promoter sequences of Table 2 (FIG. 23).

As used in the present invention, the term "hybridization" or "hybridizing" is intended to mean the process during which two nucleic acid sequences anneal to one another with stable and specific hydrogen bonds so as to form a double strand under appropriate conditions. The hybridization between two complementary sequences or sufficiently complementary sequences depends on the operating conditions that are used, and in particular the stringency. The stringency may be understood to denote the degree of homology; the higher the stringency, the higher percent homology between the sequences. The stringency may be defined in particular by the base composition of the two nucleic sequences, and/or by the degree of mismatching between these two nucleic sequences. By varying the conditions, e.g. salt concentration and temperature, a given nucleic acid sequence may be allowed to hybridize only with its exact complement (high stringency) or with any somewhat related sequences (low stringency). Increasing the temperature or decreasing the salt concentration may tend to increase the selectivity of a hybridization reaction.

As used in the present invention the phrase "hybridizing under stringent hybridizing conditions" is preferably understood to refer to hybridizing under conditions of certain stringency. In a preferred embodiment the "stringent hybridizing conditions" are conditions where homology of the two nucleic acid sequences is at least 70%, preferably at least 80%, preferably at least 90%, i.e. under conditions where hybridization is only possible if the double strand obtained during this hybridization comprises preferably at least 70%, preferably at least 80%, preferably at least 90% of A-T bonds and C-G bonds.

The stringency may depend on the reaction parameters, such as the concentration and the type of ionic species present in the hybridization solution, the nature and the concentration of denaturing agents and/or the hybridization temperature. The appropriate conditions can be determined by those skilled in the art, e.g. as described in Sambrook et al. (Molecular Cloning: A Laboratory Manual, Cold Spring Harbor, 1989).

The functionally active variant of the invention is specifically characterized by exhibiting substantially the same activity as any of the wild-type P. pastoris sequences of the invention.

The term "recombinant" as used herein shall mean "being prepared by or the result of genetic engineering". Thus, a recombinant microorganism or host cell comprises at least one "recombinant nucleic acid". A recombinant microorganism specifically comprises an expression vector or cloning vector, or it has been genetically engineered to contain a recombinant nucleic acid sequence. A "recombinant protein" is produced by expressing a respective recombinant nucleic acid in a host. A "recombinant promoter" is a genetically engineered non-coding nucleotide sequence suitable for its use as a functionally active promoter as described herein.

The term "substantially the same activity" as used herein specifically refers to the activity as indicated by substantially the same or improved promoter strength, specifically the expression or transcriptional strength of the promoter, and its substantially the same or improved characteristics with respect to the promoter strength and regulation.

The term "homology" indicates that two or more nucleotide sequences have the same or conserved base pairs at a corresponding position, to a certain degree, up to a degree close to 100%. A homologous sequence of the invention typically has at least about 60% nucleotide sequence identity, preferably at least about 70% identity, more preferably at least about 80% identity, more preferably at least about 90% identity, more preferably at least about 95% identity, more preferably at least about 98% or 99% identity.

The homologous promoter sequence according to the invention preferably has a certain homology to any of the native promoter nucleotide sequences of P. pastoris in at least specific parts of the nucleotide sequence, such as including the 3' region of the respective promoter nucleotide sequence.

Analogous sequences are typically derived from other species or strains. It is expressly understood that any of the analogous promoter sequences of the present invention that are derived from species other than P. pastoris, e.g. from other yeast species, may comprise a homologous sequence, i.e. a sequence with a certain homology as described herein. Thus, the term "homologous" may also include analogous sequences. On the other hand, it is understood that the invention also refers to analogous sequences and homologs thereof that comprise a certain homology.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "stuffer sequence" sometimes called "stuffer fragment" as used herein shall refer to a coding or non-coding nucleotide sequence used to enlarge an expression construct, herein specifically used as placeholder for incorporating a promoter sequence. It particularly includes no functional elements that would interfere with the other elements of the expression cassette or the expression vector of the invention.

The term "type IIS restriction enzyme" is herein understood in the following way. Restriction enzymes or restriction endonucleases are proteins that are able to cleave or break double-stranded DNA sequences. Type IIS restriction endonucleases cleave DNA at a defined distance from their non-palindromic asymmetric recognition sites. The stuffer sequence as described herein specifically comprises at least one type IIS restriction enzyme recognition site. The respective enzyme recognizes and binds to the restriction enzyme recognition site and cleaves the polynucleotide chains within or near to the recognition site. The type II recognition sequences can be continuous or interrupted.

Type IIS restriction enzymes generally recognize non-palindromic sequences and cleave outside of their recognition site. Exemplary enzymes are BsaI, MlyI and BmrI, and further BsaI, BsmBI, BspQI, BtgZI, BsmFI, FokI, BbvI, or any other enzymes described herein, or any variant thereof. The term "type IIS restriction enzyme recognition site" shall particularly include a complement or reverse complement of the described recognition site for that particular enzyme.

Therefore, the invention specifically provides for promoter and expression constructs the improved coexpression of two (or more) proteins at the most suitable expression level, ratio and most favorable regulatory profile (constitutive, inducible or tunable expression). Here we describe a library and kit of bidirectional promoters that can be used to optimize the coexpression of two genes in *P. pastoris*. The bidirectional fashion allows to easily test multiple promoters and expression ratios between different genes, facilitates the vector design, reduces the size of expression cassettes and the chance of undesired recombination events compared to dual gene expression with separate promoters. Demonstrated with an example relying on TA cloning, the employed system allows to easily test a library of promoters and facilitates cloning compared to established cloning procedures. Alternatively, other cloning techniques such as cloning by restriction/ligation, ligase or polymerase based cloning or recombination techniques can be employed. By providing a library of natural and synthetic bidirectional promoters and expression constructs incorporating such promoter, with different overall expression levels, ratios and regulatory profiles the coexpression of two genes can be easily optimized and fine-tuned. In addition the kit contains an entry vector where the library of different bidirectional promoters can be randomly cloned in between to coexpressed genes by simple TA cloning, or similar simple cloning strategies such as recombination cloning and other ligase or polymerase based cloning techniques. The system is exemplified by expression in *P. pastoris* but can be transferred to other yeasts such as *Saccharomyces cerevisiae, Hansenula polymorpha, Schizzosaccharomyces pombe, Klyveromyces lactis, Yarrowia lipolytica* etc and other eukaryotic expression hosts such as filamentous fungi (*Aspergillus, Trichoderma, Penicillium*, etc), plants and mammalian hosts (e.g. CHO or human cell lines), too. Synthetic variants of bidirectional promoters can be designed to be shorter than natural promoters and due to the bidirectional mode of action can drive and regulate transcription of two different or sequence diversified genes and thereby employed for the design of compact expression cassettes for metabolic pathways.

The cloning strategy described in FIG. 2 B allows to easily test multiple promoters to find the most suitable bidirectional promoter for a certain gene pair to enable the production of maximized amounts of functional proteins. Therefore an expression cassette consisting of the two genes of interest and a stuffer fragment separating them is cloned into a starting vector using a single restriction enzyme. In a subsequent cloning step the stuffer fragment is cleaved out using a single Type IIS restriction enzyme resulting in vector ends suitable for ligation of PCR amplified bidirectional promoters. This approach does not require restriction digestion of the promoters and does not require MCS and maintains the natural sequence context without introducing any additional sequences.

Therefore any promoter sequence can be used, without having to worry about the presence of restriction sites and its possible negative influence on transcription and translation. Furthermore MCSs contain several sites of restriction enzymes and can lead to problems, as also such short sequences represent non-natural elements added to the 5' untranslated region of the mRNA that can interfere with mRNA structure thereby causing translation inhibition [21]. For example in *P. pastoris*, it has been shown that an increased length of the 5' UTR decreases the expression of the commonly used alcohol oxidase 1 promoter (PAOX1) [22].

Using the type IIS based cloning strategy the stuffer fragment is precisely cleaved out, removing all additional vector sequences up to the start codons of the genes to be expressed. Therefore bidirectional promoters can be PCR amplified with primers designed up to their natural start codons, using the first base of the translational start codon ATG for TA cloning.

Using this strategy, a completely natural promoter and 5'UTR sequence is achieved, omitting any bias from MCS or restriction enzyme sites.

The Type IIS strategy relies on a special group of restriction enzymes. Conventional type II enzymes such as EcoRI and EcoRV cleave within their palindromic recognition sequences creating sticky or blunt ends. Type IIS enzymes like BsaI, MlyI and BmrI recognize non palindromic sequences and cleave in a variable sequence outside of their recognition sequence (see FIG. 3).

Figure 4:
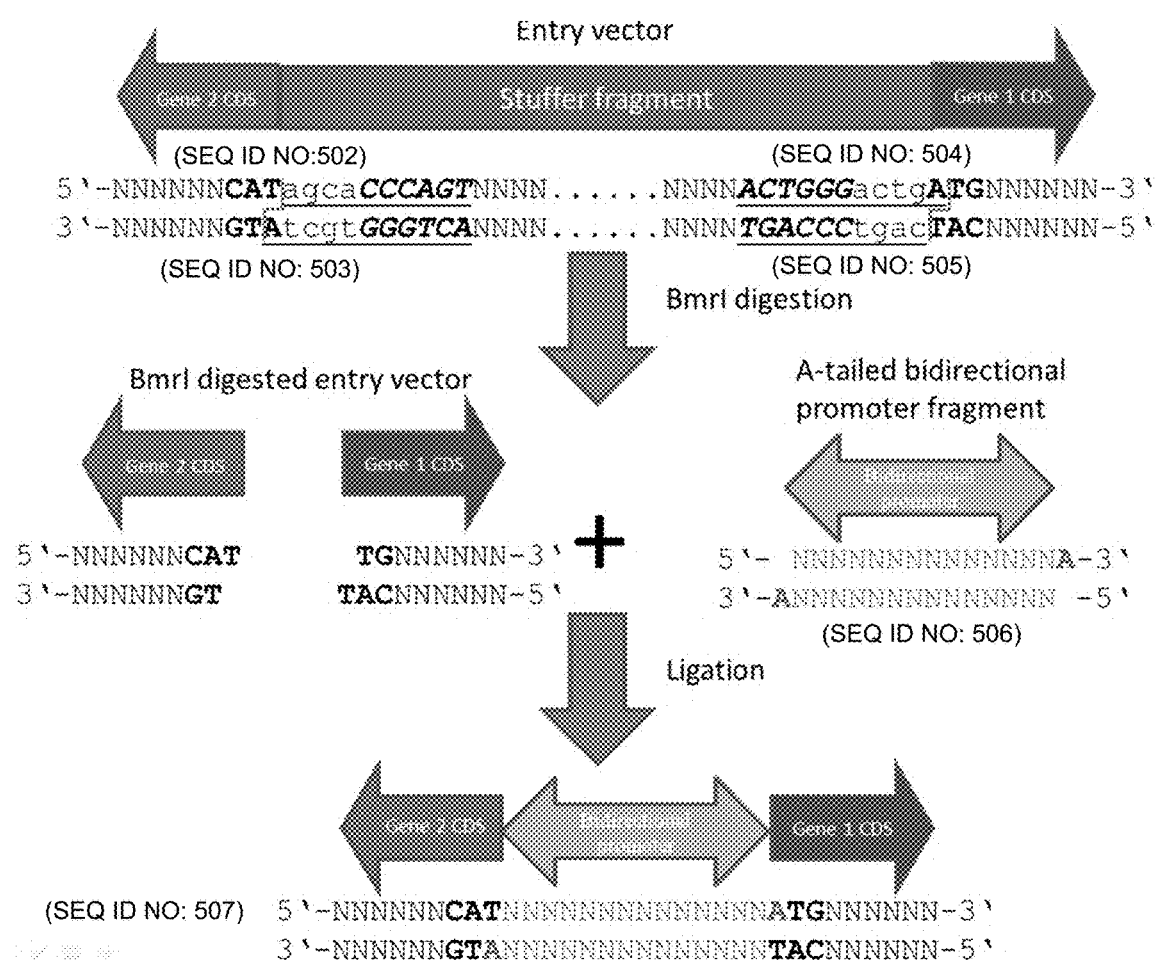
FIG. 4: Detailed depiction of TA cloning based vector assembly. The entry vector is digested with a type IIS restriction enzyme creating a 3' overhang. The figure shows the use of BmrI, the recognition sequence is written bold in uppercase in italics. The entire recognition sequence including variable parts is underlined. Note that the site was carefully placed to create a 3' thymidine overhang in the start codons on the vector that can be ligated with an adenine tailed PCR fragment of a bidirectional promoter. The start codons of the two genes are highlighted in bold and the cleavage pattern of BmrI is shown in italics and underlined. The bidirectional promoter can insert either in forward or reverse orientation.

By placing the two recognition sequences at the end of the stuffer fragment in reverse orientation, it can be cleaved out without leaving any undesired sequence in the vector (see FIG. 2 B and FIG. 4).

For the direct insertion of PCR amplified bidirectional promoters without digestion, either blunt end ligations or TA cloning is applicable. Blunt end ligations can be directly used to clone PCR fragments but they show only low efficiencies. TA cloning requires a 3' adenine overhang on the PCR product and a thymidine overhang on the vector leading to 50 fold higher ligation efficiencies than blunt end cloning [23]. Taq polymerase adds by default a 3' adenine overhang in PCR amplification that can ligate with a thymidine overhang created by digestion with a type IIS restriction enzyme (depicted in FIG. 4). We used the enzyme BmrI and placed the recognition sequences in opposite directions to cut the adenine of the start codons, thereby removing the stuffer fragment and leaving T overhangs suitable for cloning of A tailed fragments similar to [24]. The bidirectional promoters can be simply amplified by designing primers containing exactly the promoter sequences up to the start codons (FIG. 4). The A is either introduced directly by the polymerase such as taq polymerase or in an additional short enzymatic step following the major amplification.

Therefore the same bidirectional promoter fragments can be tested with any combination of target genes.

TA cloning is not directional, therefore the bidirectional promoters can either insert in forward or reverse orientation. This is a major disadvantage for the cloning of conventional promoters or coding sequences as only the forward orientation is required. In case of bidirectional promoters, it is however a beneficial trait, because the same bidirectional promoter can easily be tested in both orientations, thereby facilitating library generation.

Alternatively to TA cloning the bidirectional promoters can also be cloned by Gibson assembly [25] MEGAWHOP cloning (Methods Enzymol. 2011; 498:399-406) or other recombination techniques such as in vivo recombination, ligase cycling reaction (*ACS Synth. Biol.*, 2014, 3 (2), pp 97-106) and overlap extension PCR. This requires however overlapping regions with the vector and thereby for each orientation of the promoters and for each gene pair a separate set of primers or alternatively the addition of universal overlap regions into all promoters and the stuffer fragment which might cause undesired influences to the promoters due to these DNA fragments in the 5' UTR of the promoter and also undesired multimerization of the promoters.

Figure 1B:
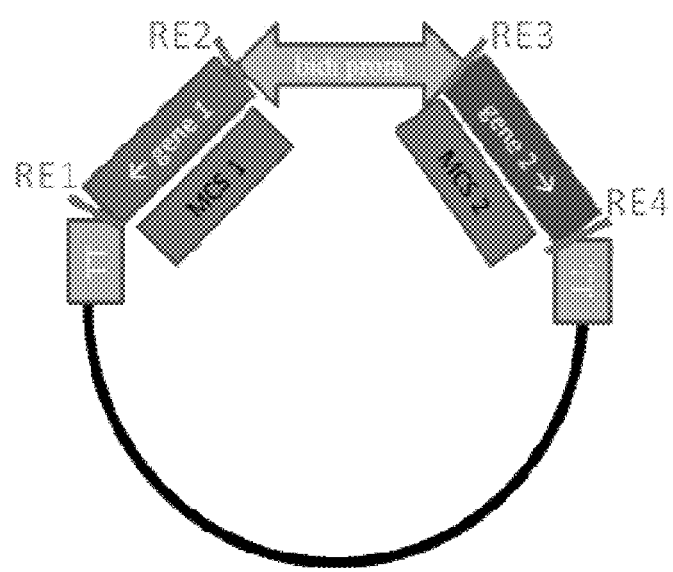
Figure 1C:
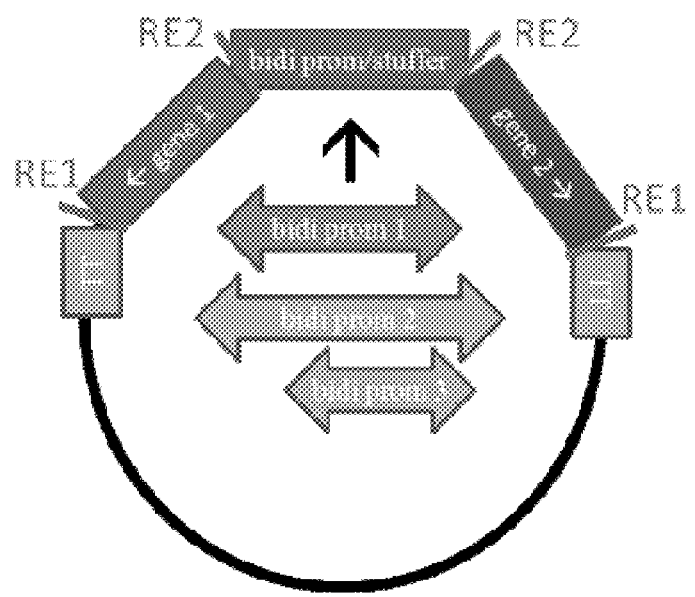
FIG. 1C: New bidirectional expression vector allowing the replacement of a stuffer fragment with a library of bidirectional promoters. The number of restriction enzymes (REs) and the respective sites required for cloning are indicated by the abbreviations RE1-6 and lines. Multiple cloning sites (MCS) and genes to be cloned are shown in parallel.

In comparison with currently used bidirectional vectors, the new strategy allows simple screening of a library of bidirectional promoters with a single entry vector and thereby to identify the most favorable expression condition for a certain gene pair. The cloning procedure is facilitated compared to all existing systems as the promoters can be directly PCR amplified and cloned without restriction digestion maintaining their fully natural sequence context and avoiding problems associated with the use of MCSs. Preparing the entry vector requires also only 2 restriction enzymes compared to 4 enzymes when using a conventional strategy (FIGS. 1 B and C). Cloning two different reporter genes into the entry vector the new system also allows to test and characterize bidirectional promoters similar to the system described by Polson et al. [20] but in a simple procedure and the possibility to avoid additional restriction site recognition sequences in the 5' UTR.

Cloning strategy for expression optimization using bidirectional promoters allows simple testing of multiple bidirectional promoters;
allows direct cloning of PCR amplified bidirectional promoters omitting restriction enzyme digestion of the promoters;
seamless cloning of the promoters avoiding problems associated with MCS.

We specifically describe a library approach for bidirectional promoters providing different overall expression levels ranging from strong to weak expression, different ratios (equal expression up to more than 20 fold difference) in *P. pastoris*. These libraries and individual promoters of such libraries can be used in combination with a random cloning strategy in order to optimize expression levels and ratios of several genes by compact and simple expression cassette design. Expression cassettes can be integrated into expression vectors such as plasmids, phages and other viruses and also be simple linear DNA fragments for integration into nucleic acids of the host. The bidirectional promoter libraries contain different (at least 2) bidirectional promoters either from natural origin, or made as hybrid promoters by head to head fusion or designed as fully synthetic or semi synthetic promoters combining core promoters with transcription factor binding sites or other regulatory DNA elements. Positive and negative regulatory DNA sequences can either be used in a unidirectional mode or bidirectional and thereby shared by both sides of the bidirectional promoter. Alternatively bidirectional promoters can also be designed by head to head fusion of natural or synthetic core promoter sequences without additional regulatory DNA elements. In addition to their application as promoter library also individual single bidirectional promoters with different expression strength on both sides of the promoter can be employed in random cloning approaches and expression ratios are optimized due to the different orientation of the promoter. The effect of different expression levels obtained by the two different promoter sides can be enhanced by the application of multiple copies of the expression cassette in the host strain.

The *S. cerevisiae* prime example of a regulated bidirectional promoter (GAL1-GAL10) is not present in *P. pastoris* as this yeast even lacks the enzymes required for galactose metabolism. Therefore the obviously known approach and homologs of *S. cerevisiae* could not be used.

However, *P. pastoris* is capable of growing on methanol as a sole carbon source and the genes involved in the methanol metabolism are tightly regulated by the carbon source. Namely, they are completely repressed on glucose and strongly induced on methanol. These promoters have predominately been used to drive protein expression in *P. pastoris* [4]. Due to their tight regulation and to get access to interesting bidirectional promoters for a promoter kit and gene expression optimization by random cloning of promoters we have tested all potentially bidirectional promoters of the MUT pathway. Therefore the genomic organization was analyzed and MUT genes with upstream genes annotated in reverse orientation were analyzed for their expression levels with green and red fluorescent proteins as reporters (GFP and RFP). In addition we also tested genes involved in the defense of radical oxygen species (ROS), as the methanol metabolism form considerable amounts of $H_2O_2$. To identify constitutive promoters, we searched for housekeeping genes organized in a bidirectional fashion that could be assumed to be expressed at high levels. These promoters included gene pairs involved in transcription, translation and primary metabolism.

Surprisingly, these important housekeeping genes were often expressed at rather low levels, despite their anticipated important physiological roles. But in some cases we could identify natural bidirectional promoters with similar or even higher expression levels than the currently used AOX1 and GAP promoters on at least one side. Some promoters provided also strong methanol inducible ($P_{DAS1,2}$) or constitutive (histone promoters) expression on both sides. This was surprising, as bidirectional promoters in *S. cerevisiae* were reported to be a source for cryptic and pervasive transcription at low expression levels with unclear function [11,12]. Therefore the strong and in some cases even tightly regulated expression was unexpected. The constitutive bidirectional histone promoters ($P_{HTX1}$, $P_{HHX1}$, $P_{HHX2}$,) reached similar or higher expression levels than the commonly used monodirectional GAP promoter. These bidirectional promoters are of similar length or even shorter than the monodirectional GAP promoter ($P_{GAP}$: 486 bp; $P_{HHX1}$: 550 bp; $P_{HTX1}$: 416 bp; $P_{HHX2}$: 365 bp). For comparison a simple head to head fusion of the most commonly used promoters for constitutive expression in P. pastoris ($P_{TEF1}$ and $P_{GAP}$) is about 1 kbp to 1.5 kbp, depending on the promoter length used. Therefore even the new natural bidirectional histone promoters allow the design of smaller vectors thereby increasing transformation efficiency and allowing the construction of small expression cassettes. Furthermore these short natural promoters provide a valuable source for promoter parts such as core promoter elements or regulatory DNA elements. In addition we found promoters providing also intermediate and low overall expression levels and promoters with different expression ratios on the two sides. However the ratios of the two sides of natural promoters were limited. We aimed to identify promoters providing a range of expression ratios, e.g. an equal expression ratio (1:1) but also promoters with stronger expression on side and half or one tenth of the expression on the other side. These promoters should ideally be available with different regulatory profiles (e.g. constitutive or inducible) and different overall expression strength (e.g. a strong expression on one side and half of that expression on the other side but also intermediate expression on one side and half of that expression on the other side).

The natural promoters met some of these requirements but did not provide the aspired range of ratios of the two sides of the bidirectional promoters. Also the regulatory profiles of the natural promoters were limited. The natural promoters provided only inducible or constitutive expression on both sides, but we did not find any natural bidirectional promoters providing mixed regulatory profiles such as constitutive expression on one side and inducible expression on the other side.

To extend the range of overall expression levels, ratios and regulatory profiles of the bidirectional promoters, we engineered the most promising natural bidirectional promoters and created synthetic bidirectional fusion promoters.

The engineering approaches were based on semi rational and systematic deletion and truncation approaches. The engineered variants of bidirectional $P_{DAS1,2}$ and $P_{HTX2}$ variants exceeded in some cases the expression levels of the natural wild type promoter in terms of expression, but provided also new ratios.

To achieve new regulatory profiles, we fused differently regulated monodirectional promoters in opposite orientation to each other, thereby creating synthetic bidirectional fusion promoters.

We fused the two constitutive promoters $P_{TEF1}$ and $P_{GAP}$ to each other, thereby creating a bidirectional promoter with strong constitutive expression on both sides. We fused also the commonly used $P_{AOX1}$ and $P_{GAP}$ promoters to each other, thereby creating a promoter with methanol inducible expression on one side and inducible expression on the other side.

Induction in these fusion promoters relies on the use of methanol. We also aimed to create bidirectional promoters providing methanol free regulated expression. This was achieved by using derepressed promoters $P_{PEX5}$, $P_{ADH2}$, $P_{CAT1}$. Similar to the commonly used AOX1 promoter, derepressed promoters are completely repressed on glucose, but they do not require methanol for induction, but auto-induce expression when the glucose in the medium is depleted. This unites the advantage of an inducible promoter (allowing to separate cell growth and heterologous gene expression) with the benefits of constitutive promoters (easy process design, no requirement for the use of an inducer). For P. pastoris, this allows even to avoid the usage of the toxic and flammable inducer methanol. The handling of large quantities of methanol for industrial protein production is a considerable problem solved by derepressed promoters.

In P. pastoris, so far only certain synthetic variants of the AOX1 promoter showed derepressed expression [28], however at significantly lower expression levels than the methanol induced AOX1 wildtype promoter, but the strength can be further increased by fusion with positive regulatory elements. Here we identified, to our knowledge the first naturally derepressed monodirectional promoters in P. pastoris: $P_{CAT1}$, $P_{ADH2}$ and $P_{PEX5}$.

The bidirectional fusion promoters tested here include combinations of $P_{AOX1}$ with $P_{CAT1}$, providing inducible and derepressed expression on the two sides of the bidirectional promoter. Notably $P_{CAT1}$ can even be further induced with methanol.

Also a combination of $P_{GAP}$ and $P_{CAT1}$ was tested, providing constitutive and derepressed expression on the two sides of the bidirectional promoter. So far no such combination was known for any yeast. Derepressed expression on both sides can be achieved by using fusions of $P_{CAT1}+P_{ADH2}$, $P_{PEX5}+P_{ADH2}$ or $P_{PEX5}+P_{CAT1}$.

Bidirectional promoter kit and its individual parts
  new bidirectional promoters exceeding on single sides the expression levels of commonly used monodirectional promoters ($P_{AOX1}$, $P_{GAP}$)
  set of natural bidirectional promoters providing . . .
    different overall expression levels
    different ratios of the two sides
    and different regulatory profiles (constitutive, inducible and derepressed (=derepressed is inducer free regulated expression)

In S. cerevisiae just five bidirectional expression promoters are described providing strong expression with a fixed equal ratio and constitutive and inducible expression.

Engineered synthetic bidirectional promoters and variants of $P_{DAS1,2}$ and $P_{HTX2}$ provide
  shorter promoter sequences
  improved expression
  a range of expression ratios
  unprecedented regulatory profiles The foregoing description will be more fully understood with reference to the following examples. Such examples are, however, merely representative of methods of practicing one or more embodiments of the present invention and should not be read as limiting the scope of invention.

In general, the recombinant nucleic acids or organisms as referred to herein may be produced by recombination techniques well known to a person skilled in the art. In accordance with the present invention there may be employed conventional molecular biology, microbiology, and recombinant DNA techniques within the skill of the art. Such techniques are explained fully in the literature (see, e.g., Maniatis, Fritsch & Sambrook, "Molecular Cloning: A Laboratory Manual, Cold Spring Harbor, (1982)). Specifically, a recombinant expression construct may be obtained by ligating the promoter and relevant genes into a vector or expression construct. These genes can be stably integrated into a host cell genome by transforming a host cell using such vectors or expression constructs.

EXAMPLES

Example 1—Bidirectional (TA) Cloning Vectors

At first we aimed to test the applicability of the TA cloning strategy for inserting bidirectional promoters into a vector. We aimed to link this evaluation with the establishment of a screening vector to easily assess the properties of various bidirectional promoters. Common sticky end cloning strategies require digestion of the vector and the insert with restriction enzymes. However, not all bidirectional promoters can be cloned using the same enzymes. Therefore also the position where the promoter is inserted in a MCS influences the screening, thereby biasing it. The same problem becomes evident when cloning several bidirectional promoters into an entry vector with genes to be expressed.

We based our bidirectional screening and expression plasmid on the *P. pastoris* vector pPpT4_S plasmid described [29]. *P. pastoris* vectors are by standard integrated into the genome by targeting a homologous recombination event. Most commonly, therefore the vectors are linearized in the promoter sequence used to target a recombination event. This strategy is not applicable with bidirectional promoters used here, as especially the semi-synthetic fusion promoters provide non-natural sequences hampering recombination. In addition, homologous recombination is occurring in *P pastoris* at rather low frequencies, therefore a linearization in the bidirectional promoter would in many cases not even be reconstituted, thereby compromising its functionality.

To this end we added an additional integration sequence to the plasmid; we used a 1.2 kbp sequence downstream of the ARG4 resistance marker gene.

Figure 5:
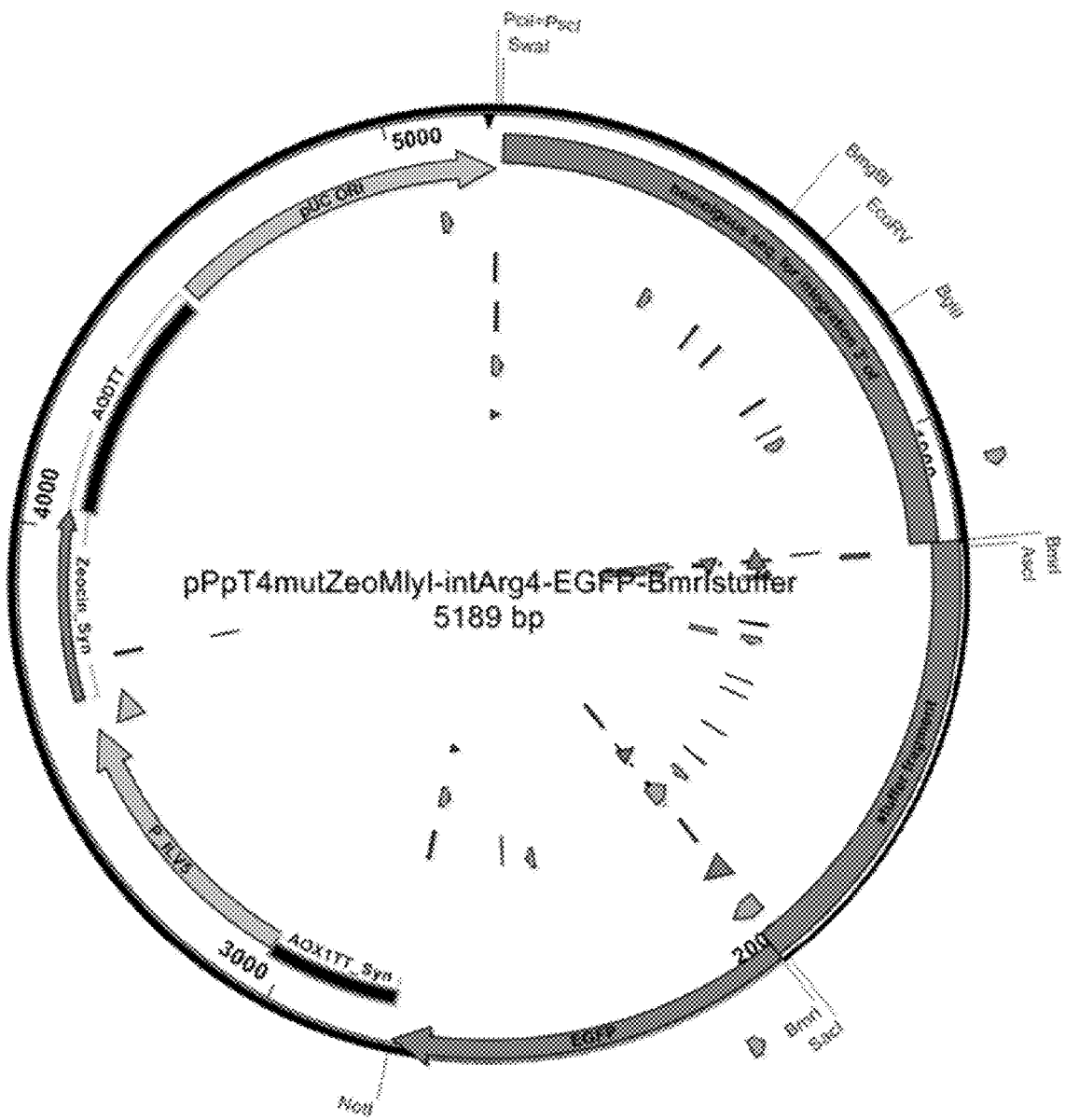
FIG. 5: TA cloning vector for screening of promoters with a single reporter gene.

At first we designed a reporter vector, where any PCR amplified promoter can be cloned in front of a reporter gene. We relied on a stuffer replacement strategy and used a variant of the green fluorescent protein (referred to as GFP) as reporter gene. The AOX1 promoter present in the pPpT4_S vector was removed by PciI and NotI digestion. The part was replaced by an olePCR assembly consisting of the ARG4 integration sequence (intARG4), a stuffer fragment and the GFP gene. We chose a sequence without any sequence homology to *P. pastoris* or *E. coli*, we used therefore a *S. cerevisiae* sequence present in neither organism. The TA cloning part of the stuffer was designed as outlined in section "Type IIS cloning strategy of bidirectional promoters", and FIG. 4). We added SacI and AscI sites next to the BmrI sites to allow easy exchange of vector parts (FIG. 4). The intARG4 sequence was PCR amplified using Phusion polymerase and *P. pastoris* genomic DNA as template using primers int.arg.fwd and int.arg.rev (see Tab. 1). The stuffer fragment was amplified from *S. cerevisiae* genomic DNA using primers stufferTHI5.fwd and stufferTHI5.rev. The GFP gene was amplified using primers EGFPfwd.stufferTHI5 and EGFPrevNotI from a *P. pastors* cloning plasmid. For olePCR, the fragments were gel purified and mixed in equimolar ratios. After 20 cycles of primerless PCR the primers int.arg.fwd and EGFPrevNotI were added. The obtained fragment of the correct size was gel purified, PciI and NotI digested and subsequently cloned into the PciI and NotI digested backbone of pPpT4_S. A MlyI site present in the vector was removed by PCR amplifying the vector using primers ZeoCDS_mut_MlyI_fwd and ZeoCDS_mut_MlyI_rev Pfu Ultra polymerase followed by DpnI digestion. After confirming the sequence by Sanger sequencing the vector was used for the following cloning steps. The final vector is shown in FIG. 5.

To test the suitability of the system, the PCR amplified promoters of the methanol metabolism and ROS defense were cloned into the vector (for promoters and primers see Tab. 2). The vector was BmrI digested, dephosphorylated and gel purified. The promoters were PCR amplified using Phusion polymerase and the phosphorylated primers, subsequently spin column purified and A-tailed using Taq polymerase. The vector backbone and promoters were then mixed in a molar 1:3 ratio and ligated using T4 ligase. The orientation of the promoters was confirmed by colony PCRs using Taq polymerase and primers seqintARG4fwd or seqGFPrev together with the respective primer used for amplification of the promoter.

Figure 6:
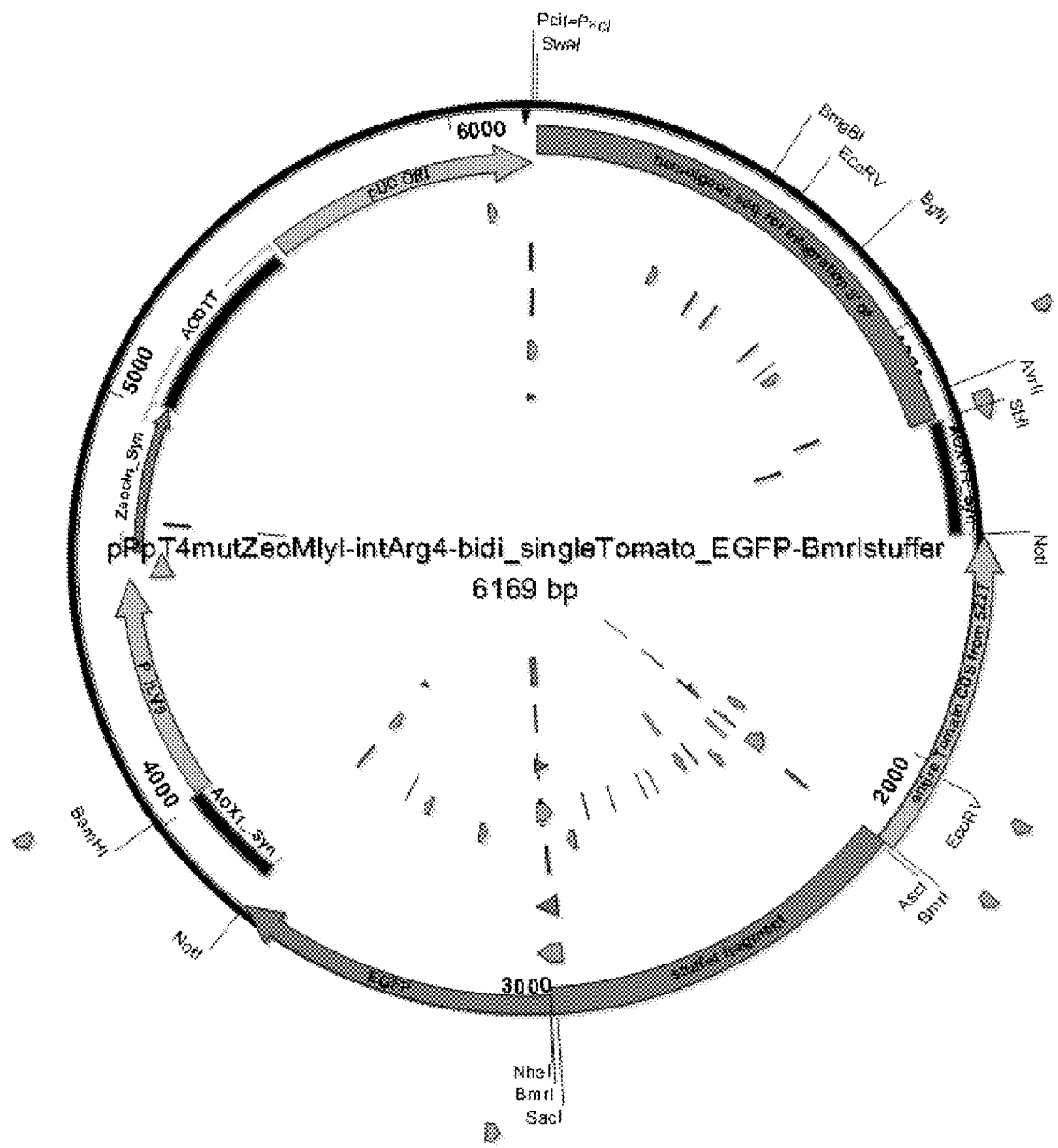
FIG. 6: TA cloning vector for screening of bidirectional promoters with two reporter genes.

With the single reporter vector, bidirectional promoters had to be cloned twice, once in forward and once in reverse orientation. To reduce the cloning effort and allow simultaneous detection of both sides, we designed a bidirectional screening vector. Based on the single reporter vector, we inserted a second reporter gene (a red fluorescent protein variant termed Tomato, the names are used here synonymously except explicitly stated otherwise), between the integration sequence and the stuffer fragment (FIG. 6). We also tested different fluorescent proteins and designed different vector variants of the RFP (data not shown). The vector was assembled by digesting the single reporter vector with AscI and AvrII. Subsequently the RFP fused to a *P. pastoris* transcription terminator sequence was PCR amplified from a *P. pastoris* cloning vector using primers newTomatoAscIBmrIFWD and AOXTTSbfIAvrIIREV1 (Tab. 1). To add an additional SbfI restriction site, the obtained PCR fragment was used as template for a 2nd PCR using primers newTomatoAscIBmrIFWD and AOXTTSbfIAvrIIREV2. The newly inserted part was confirmed by Sanger sequencing.

Subsequently we cloned several natural bidirectional promoters and semi synthetic fusion promoters into this vector. The promoters were either inserted in random orientation by TA cloning or directional by Gibson assembly [25].

The bidirectional reporter vector described here can also be used for the creation of an entry vector for the coexpression of any gene pair. Therefore a cassette consisting of the two genes to be coexpressed with a stuffer fragment between them is assembled by olePCR, digested with NotI and cloned in the NotI digested bidirectional double reporter vector backbone.

A set of more than 30 putative natural bidirectional promoters driving the expression of genes involved in different cellular functions were selected (Tab. 2). The putative natural bidirectional promoters stem from different pathways (methanol metabolism, ROS defense, housekeeping genes) and were PCR amplified and cloned into a reporter vector between a green and a red fluorescent protein, thereby allowing separate detection of both sides. The PCR amplification was performed using Thermo Scientific Phusion High-Fidelity DNA Polymerase according to the manufacturers' recommendations. Primers were phosphorylated using Thermo Scientific/Fermentas T4 Polynucleotide Kinase according to the manufacturers' recommendations. The blunt ended PCR fragments were A-tailed using Promega GoTaq® DNA Polymerase according to the manufacturers' recommendations and ligated with the vector using Thermo Scientific T4 DNA Ligase according to the manufacturers' recommendations. The GFP/RFP reporter vector was digested with NEB BmrI according to the manufacturers' recommendations, the correct band was gel purified and used for the ligation with the A tailed promoter fragments.

Figure 7:
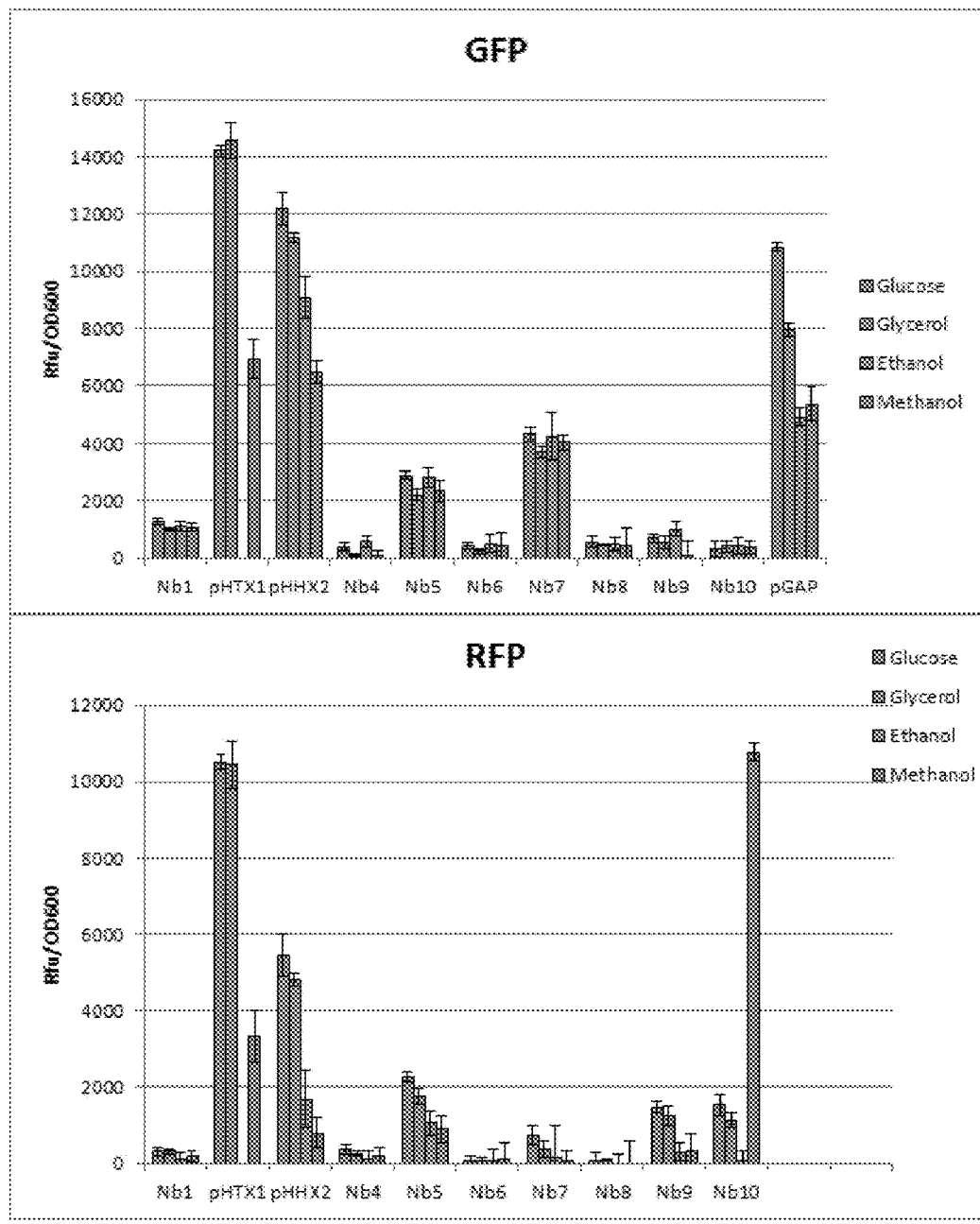
FIG. 7: Expression levels of several natural bidirectional promoters on different carbon sources. The strains were grown on the respective carbon sources for 24 h and assayed for reporter gene fluorescence. The GFP fluorescence represents the downstream side of the promoter, whereas RFP reflects the upstream side. For the GFP side, the commonly used GAP promoter was included as a reference. Nb1 and 4 to 10 are Natbidi 1 and 4 to 10 (SEQ ID NO:25 to 32).
Figure 26:
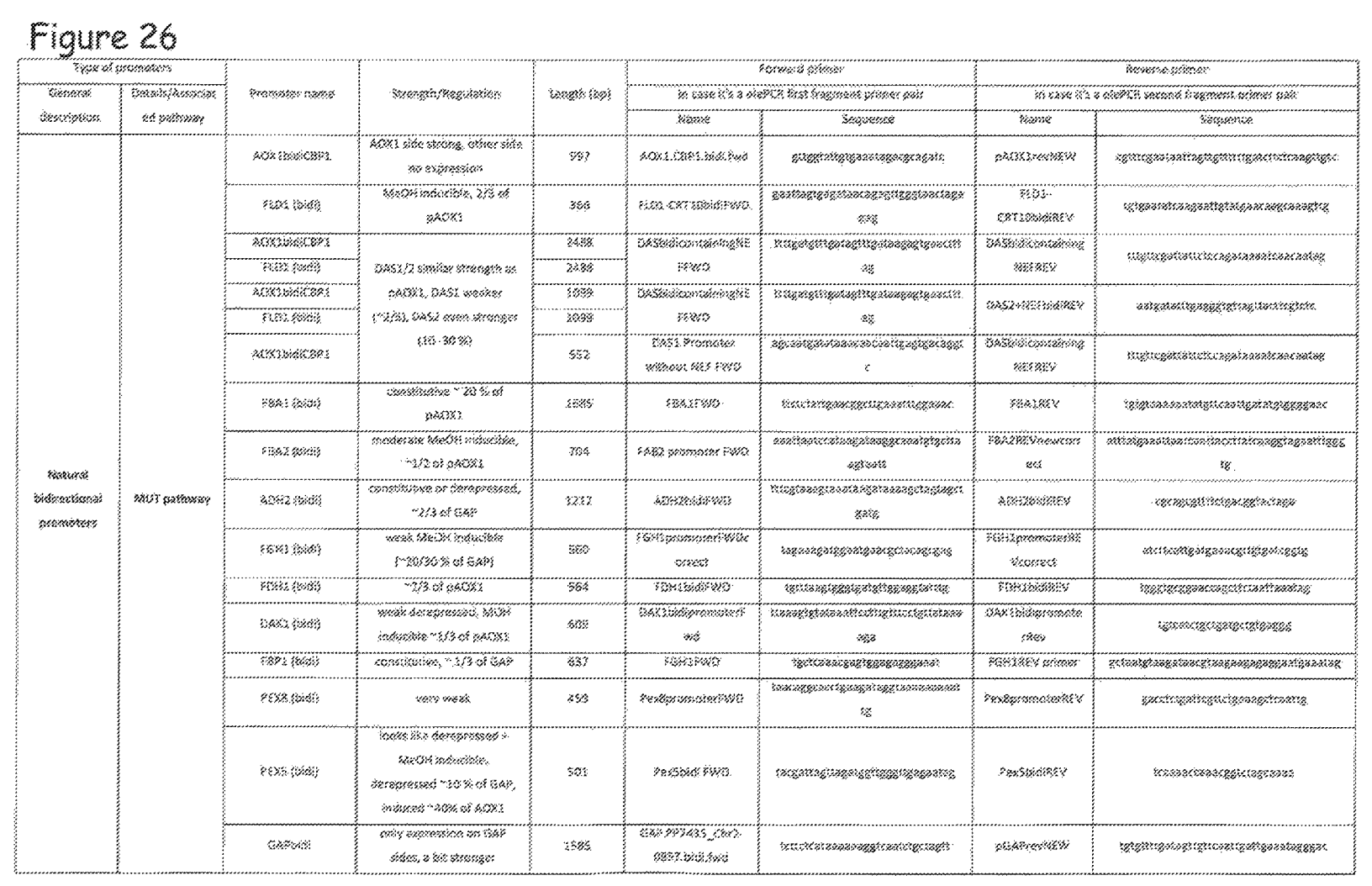
Figure 26:
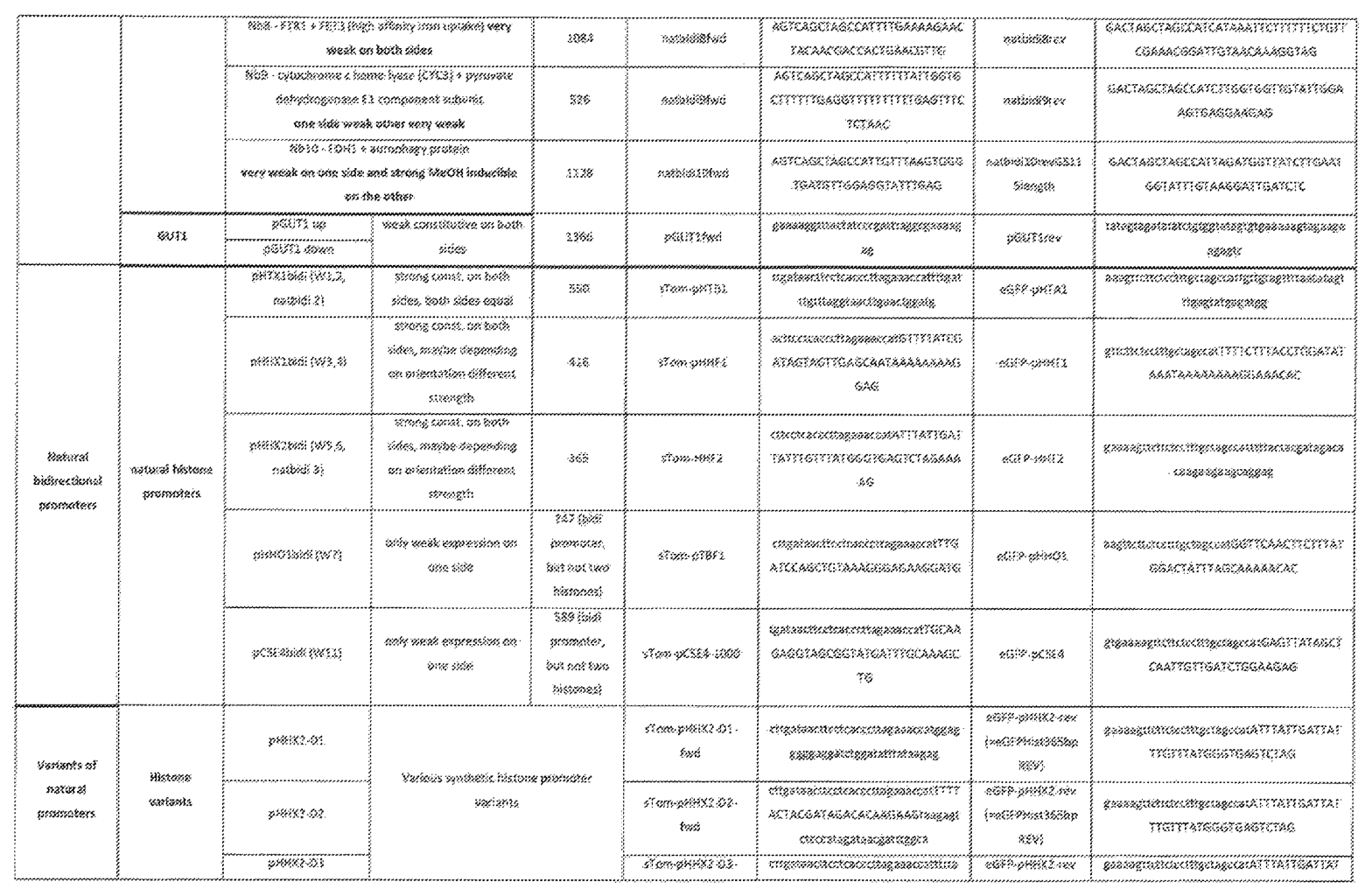
Figure 26:
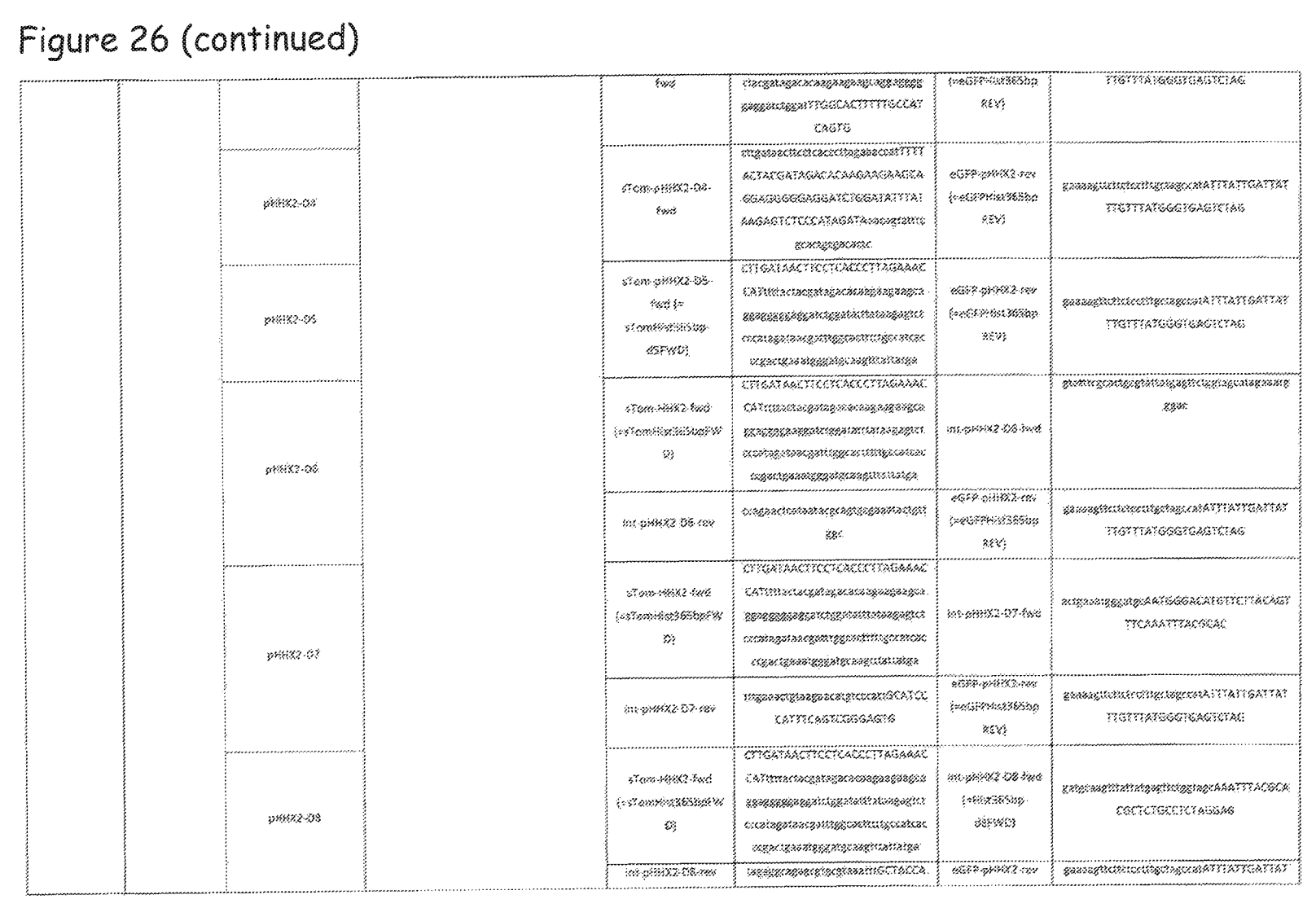
Figure 26:
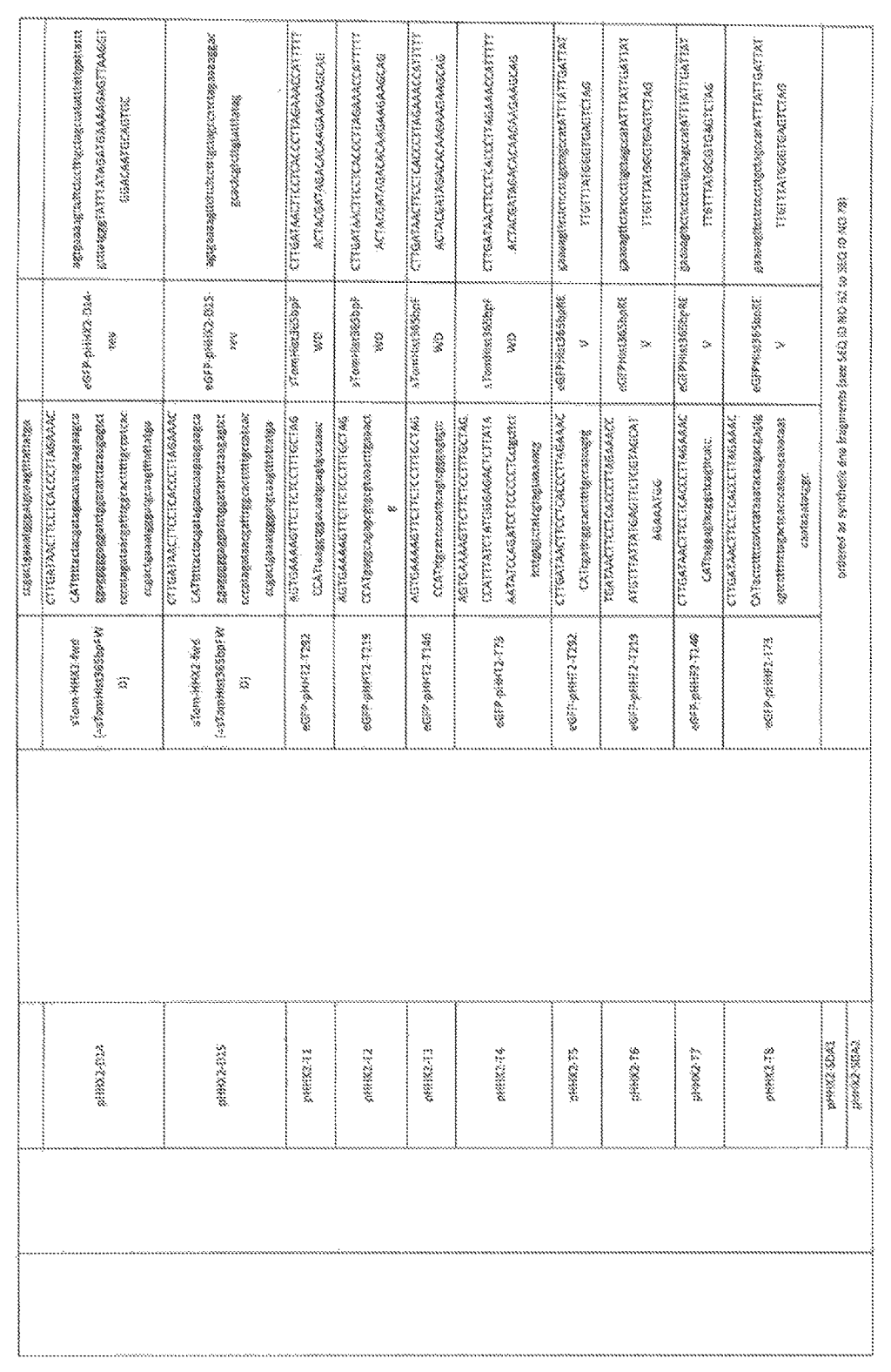
Figure 26:
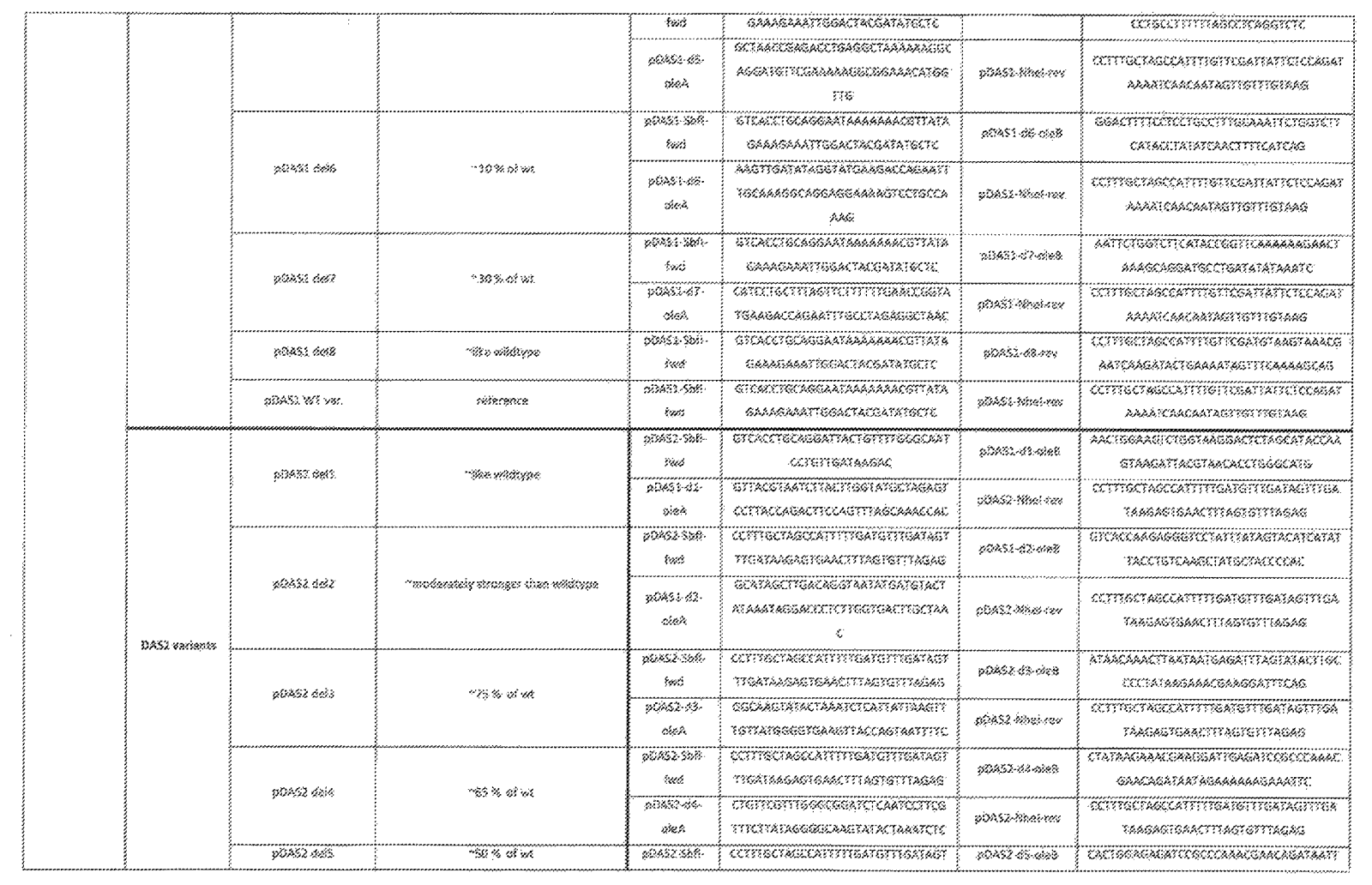
Figure 26:
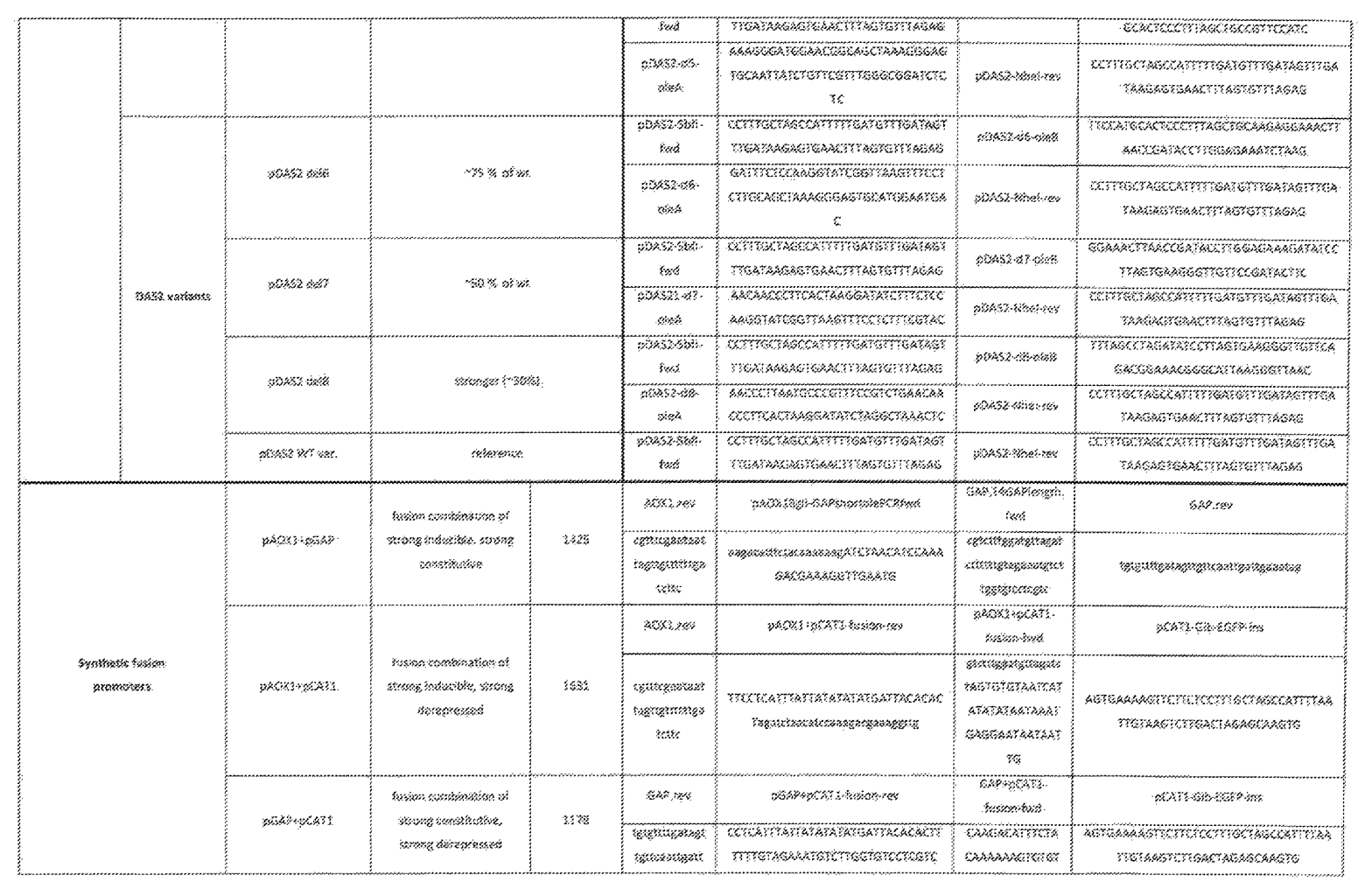

The bidirectional promoters exhibited the expression levels summarized in (Tab. 2, FIG. 26). The majority of the tested promoters were giving low expression levels (data not shown), possibly as expected from the frequent role in low level pervasive and cryptic transcription described in *S. cerevisiae* [11,12]. Several bidirectional promoters provided strong or intermediate expression on one side, and low expression on the other side. These bidirectional promoters can be used for low level coexpression of regulator (e.g. Hac1 [30]) or to achieve strongly different ratios. The expression of the promoters was also effected by the carbon source (FIG. 7).

Figure 8:
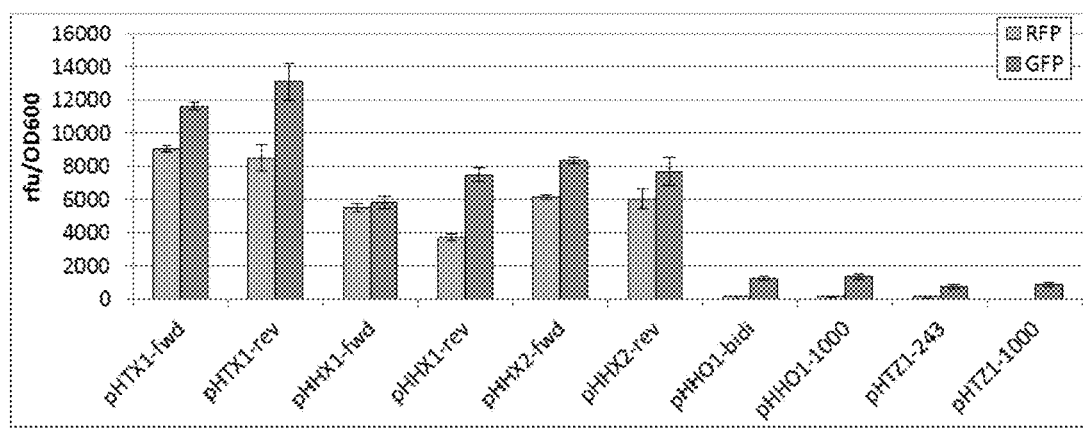
FIG. 8: Expression levels of wild type histone promoters. The putative bidirectional promoters were cloned into the reporter vector and tested in both orientation (forward, fwd and reverse, rev). pHTX1, pHHX1 and pHHX2 showed strong expression, whereas the other histone promoters showed rather weak expression.

Surprisingly, a few promoters showed strong expression most with an equal ratio on both sides. Several histone promoters ($P_{HTX1}$, $P_{HHX1}$, $P_{HHX2}$) provided strong constitutive expression (FIG. 8). Unexpectedly, these bidirectional histone promoters provided on each side similar or even higher expression levels than the monodirectional state of the art GAP promoter (FIG. 7). Yet their sequences, acting as a bidirectional promoter, were significantly shorter than the monodirectional GAP promoter ($P_{GAP}$: 486 bp; $P_{HHX1}$: 550 bp; $P_{HTX1}$: 416 bp; $P_{HHX2}$: 365 bp). A fusion of the most commonly used promoters for constitutive expression in *P. pastoris* ($P_{TEF1}$ and $P_{GAP}$) is about 1 kbp to 1.5 kbp, depending on the promoter length used. Therefore the novel bidirectional histone promoters allow the design of smaller vectors thereby increasing transformation efficiency, while exceeding expression levels of the commonly used GAP promoter.

The $P_{DAS1,2}$ pair provided strong inducible expression, the DAS2 promoter has already been described as a strong promoter, but the DAS1 promoter and their bidirectional organization had not been tested with functional reporter gene assays. Yet, the expression ratios of these promoters were rather limited; therefore we aimed to design synthetic variants.

For the bidirectional promoters see FIG. 25; the MUT pathway SEQ ID NO:1-19, ROS defense SEQ ID NO:20-24 and Natbidis SEQ ID NO:25-38.

Example 2: Synthetic Variants of Natural Bidirectional Promoters

Figure 9A:
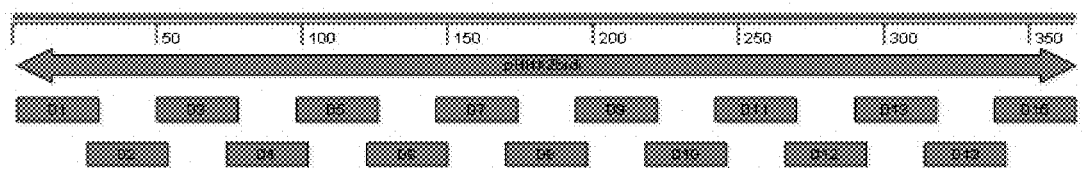
FIG. 9: Deletion variants and truncations of the pHHX2 promoter. A: Single deletion variants (D1 to D15) B: Both-sided truncations. C: Deletion variants S1 to S5 of longer stretches and two or three simultaneous deletions.
Figure 9B:
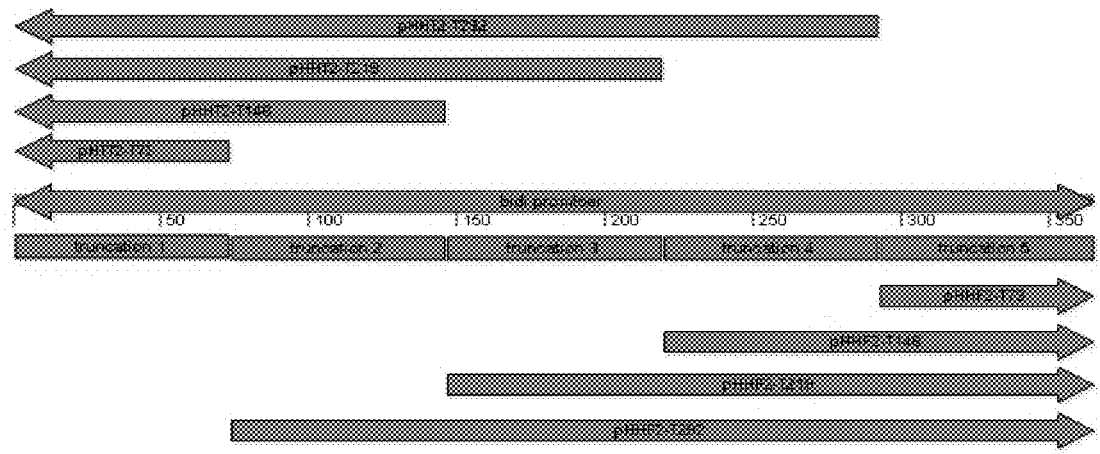
Figure 9C:
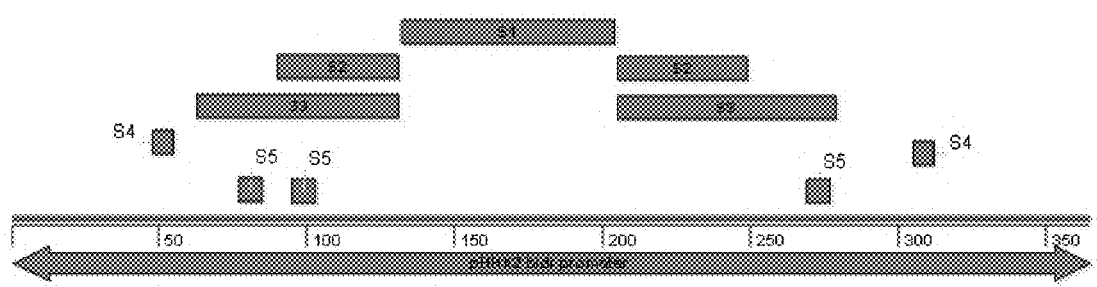
Figure 10:
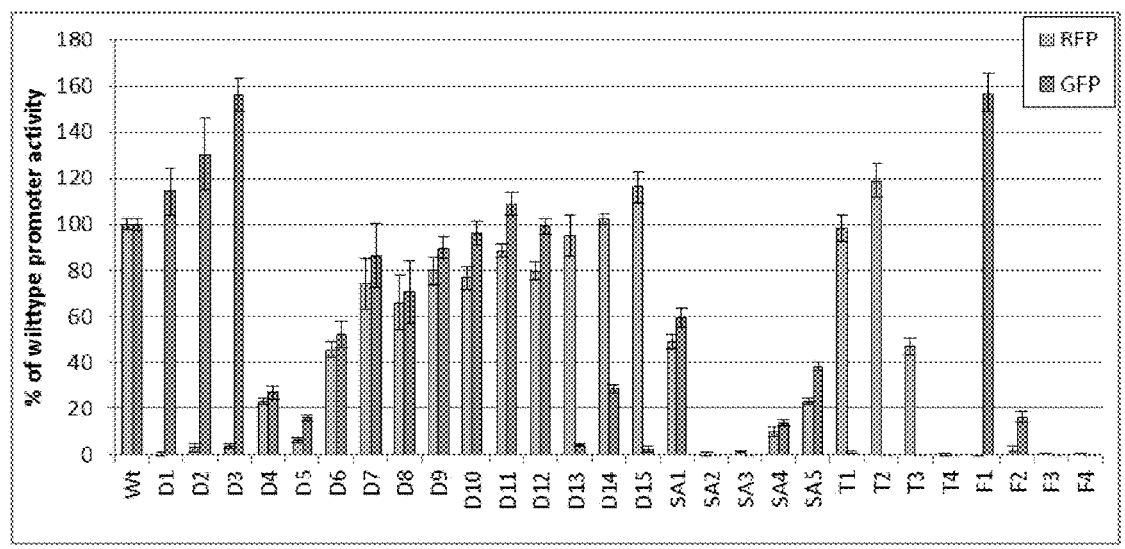
FIG. 10: Reporter fluorescence of deletion variants and truncations of the pHHX2 promoter. The variants exhibit up to 55% increased expression levels, different expression levels and ratios.

The overall expression levels and ratios of these promoters were fixed and thereby limited; therefore we aimed to design synthetic variants with various overall expression levels and several ratios. We selected the pHHX2 promoter as it had shown strong comparable expression levels as the other histone promoters while having the shortest length (365 bp). This short length favored deletion approaches, as variants of the promoter can be easily assembled from two long primers or a single synthetic double stranded fragment. We performed deletion studies (FIGS. 9 A and C) and truncations (FIG. 9 B) of the pHHX2 sequence. The deletion variants were either assembled by overlap extension PCR (olePCR) [28], from two primer fragments or ordered as synthetic double stranded fragment and cloned by Gibson assembly. All constructs were sequenced to confirm the correct cloning and assembly. The deletion variants showed different overall expression levels and altered ratios, resulting in a profound library for constitutive expression FIG. 10.

Figure 11:
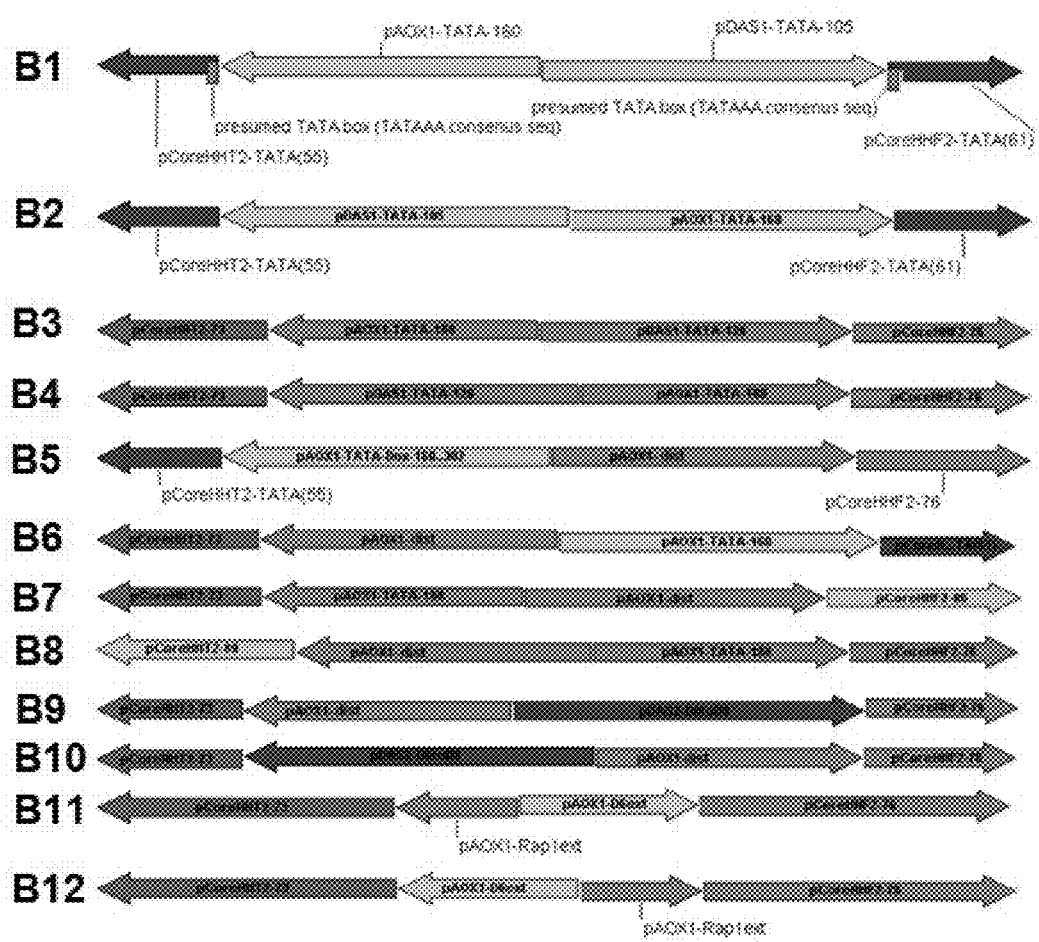
FIG. 11: Synthetic bidirectional promoters based on histone core promoters and regulatory elements of methanol inducible promoters. Different lengths of core promoters and different regulatory elements from methanol inducible promoters were tested. Elements are not drawn to scale. The artificially designed promoters were ordered as fully synthetic DNA fragments (see SEQ ID NO: 67 to SEQ ID NO: 78).

In addition we also designed synthetic promoters consisting of the core promoter regions of pHHX2 and cis-acting regulatory elements of methanol inducible promoters (pAOX1, pDAS1, pDAS2) named SynBidi1 to Synbidi12 (FIG. 11).

The SynBidi constructs were all ordered as synthetic double stranded fragments. All constructs were sequenced to confirm the correct cloning and assembly.

Figure 12:
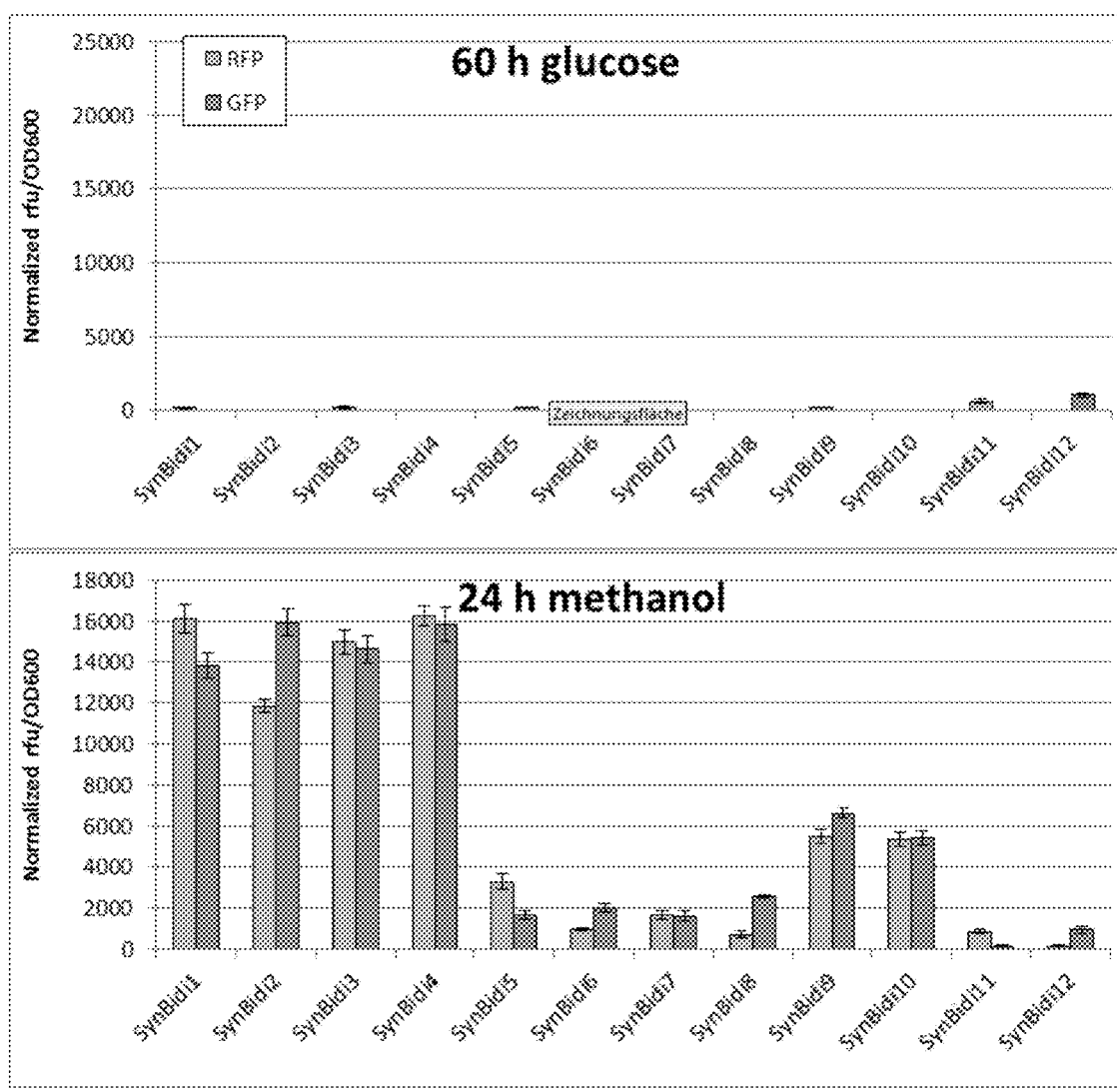
FIG. 12: Expression levels of the synthetic bidirectional promoters cloned into a reporter vector. The promoters were cloned into the vector in forward orientation; therefore GPP fluorescence correlates with the expression of the HHF2 side and RFP with the HHT2 side. The promoters were at first grown on glucose for 60 h showing a tight repression of all promoters except SynBidi11 and 12. Subsequently, the promoters were induced with methanol showing strong expression (Synbidi 1 to 4), intermediate expression (Synbidi 9 and 10) and low expression (Synbidi 5 to 8). Synbidi 11 and 12 showed either a constitutive or derepressed regulatory profile.

The synthetic bidirectional promoters showed strong a tight repression on glucose and strong bidirectional expression on methanol, despite their short length, making them excellent bidirectional promoters for inducible gene coexpression or pathway overexpression for metabolic engineering (FIG. 12).

Histone genes and also their organization in gene pairs flanking a bidirectional promoter are highly conserved between eukaryotes. Therefore also bidirectional histone promoters from Chinese hamster ovary (CHO) cells (SEQ ID NO 49 to SEQ ID NO 64) and other eukaryotes can be used to drive heterologous protein production and as a general eukaryotic engineering framework to design synthetic promoters, as demonstrated for *P. pastoris* with methanol induction.

For the synthetic variants of natural bidirectional promoters see FIG. 25; pHHX2 variants—systematic deletions SEQ ID NO:39-53; truncations SEQ ID NO:54-61; longer/multiple deletions SEQ ID NO:62-66; synthetic methanol inducible variants SEQ ID NO:67-78; and CHO bidirectional histone promoters SEQ ID NO:166-181.

Figure 13:
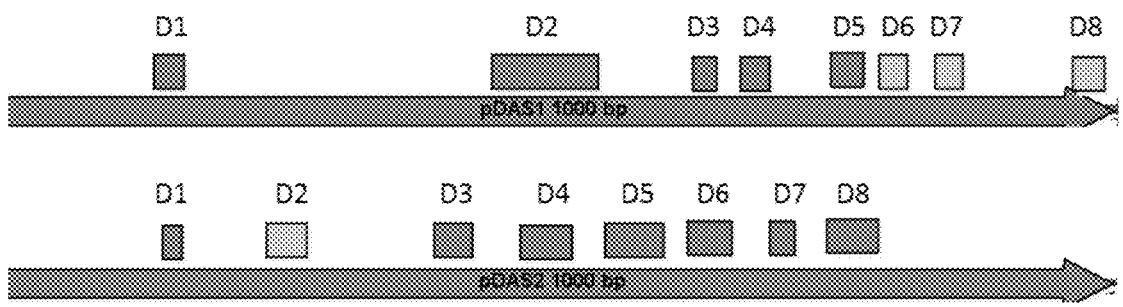
FIG. 13: Deletion variants of 1000 bp fragments of the DAS1 and DAS2 promoters. The deletions were selected based on homologies between the DAS1 and DAS2 promoters and the sequences of other strong methanol inducible promoters.

Similar to the constitutive bidirectional histone promoters, the overall expression levels and ratios of the methanol inducible DAS1,2 promoter were also fixed and thereby limited. Therefore we aimed to design synthetic variants with various overall expression levels and several ratios. In contrast to the short pHHX2, the DAS1,2 promoter is relatively long (2488 bp), therefore performing the same deletion approaches used for pHHX2 were not applicable. We relied on sequence comparisons between the DAS1 and DAS2 promoter sides and other methanol inducible genes to identify possible regulatory regions (deletions illustrated in FIG. 13). We made eight monodirectional deletion variants of 1000 bp fragments of DAS1 and DAS2. The deletions were assembled by olePCR [28] and cloned in front of a eGFP reporter after SbfI+NheI digestion. All constructs were sequenced to confirm the correct cloning and assembly. In addition, the monodirectional deletion variants were also assembled into bidirectional fusion promoters by cloning them via Gibson assembly into the bidirectional eGFP/sTom reporter vector resulting in variants DDC1 (pDAS2-1000+pDAS1-1000), DDC2 (pDAS2-del8+pDAS1-del2del5), DDC3 (pDAS2-del2+pDAS1-del2del5), DDC4 (pDAS2-del6+pDAS1-del6), DDC5 (pDAS2-del8+pDAS1-del6), DDC6 (pDAS2-del6+pDAS1-del2del5), DDC7 (pDAS2-del5+pDAS1-del6), DDC8 (pDAS2-del6+pDAS1-del7), DDC9 (pDAS2-trunc386+pDAS1-del6), DDC10 (pDAS2-trunc261+pDAS1-del6). For primers see Table 2, the respective monodirectional deletion promoters were used as template, therefore the same primers could be used in most cases.

Figure 14:
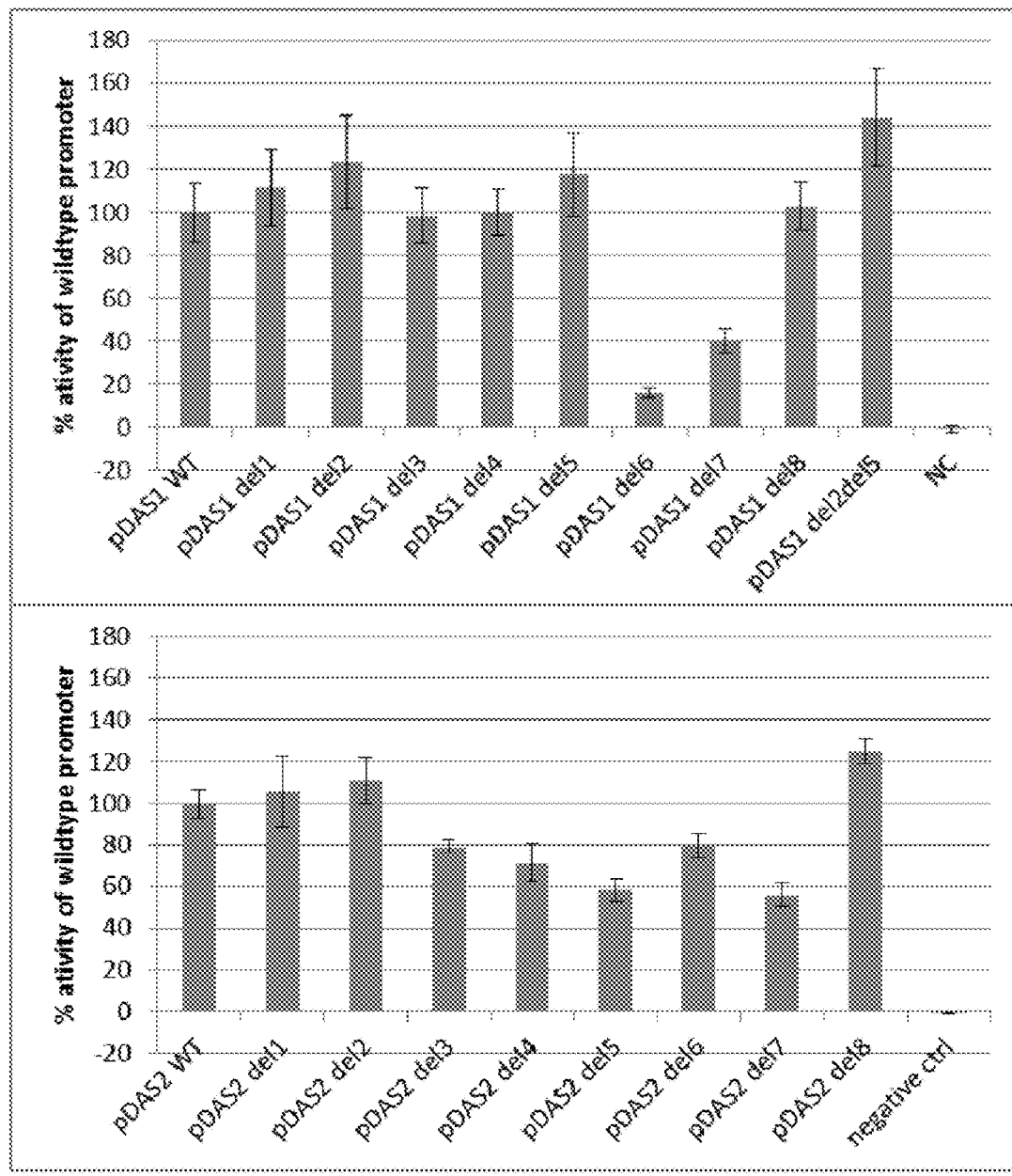
FIG. 14: Expression levels of the DAS1,2 deletion variants shown in FIG. 13. The variants were assembled by olePCR, cloned in front of a GFP reporter promoter, induced with methanol and compared to the wild type promoter (WT). NC denotes a negative control of the untransformed wildtype strain.
Figure 15:
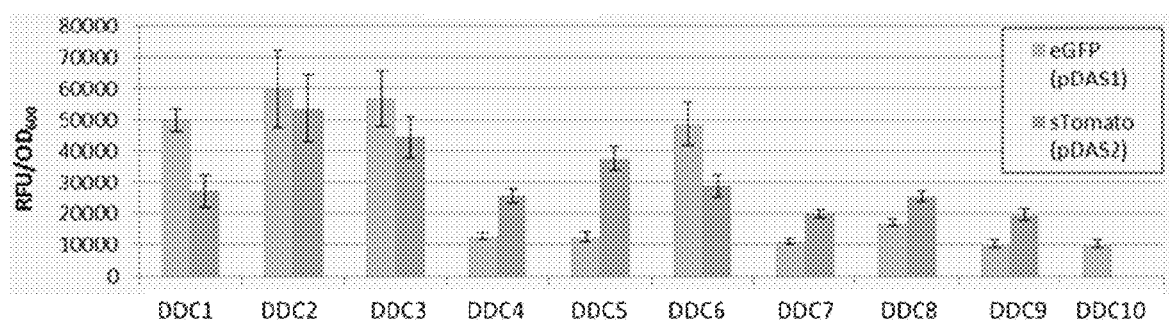
FIG. 15: Screening data for fusions of bidirectional pDAS1 and pDAS2 deletion variants. The RFU/OD600 values of three representative rescreening clones per construct were averaged; the strains were grown in DWPs for 48 h on methanol.

The monodirectional variants showed a range of different expression levels, between 16 and 144% of the wildtype promoters (FIG. 14). These monodirectional pDAS1 and pDAS2 variants were combined to form bidirectional promoters providing a wide range of inducible expression with different overall expression levels and ratios (FIG. 15). These fusions of the monodirectional promoters showed also in a bidirectional context in most cases the same expression levels. In some cases synergistic effects were noticed leading to improved expression and a set of methanol-inducible promoters sufficient to fine-tune expression.

For the bidirectional promoters see FIG. 25; pDAS1 deletions SEQ ID NO:79-87, pDAS2 deletions SEQ ID NO:88-95 and fusions of pDAS1 and pDAS2 deletions Natbidis SEQ ID NO:126-135.

As the natural bidirectional promoters identified provided only constitutive or inducible regulation on both sides, we aimed to design artificial promoters with different regulatory profiles. Therefore we tried to fuse monodirectional promoters to each other, thereby creating synthetic bidirectional promoters with different tailor-made regulatory profiles.

As most well characterized state of the art promoters of *P. pastoris* provide only methanol inducible or constitutive expression, we aimed to identify differently regulated promoters. Recent efforts on newly regulated promoters in *P. pastoris* focused on different means of induction [31] or repression [32]

In contrast, we aimed to identify autoregulated promoters not requiring an inducer or repressor, as this would drastically facilitate process design. We favored derepressed promoters, as they are tightly repressed on glucose like the commonly used AOX1 promoter. However they do not need an inducer such as methanol, but simply start expression when glucose is depleted. This can be used for process design to grow cells at first in a fed batch on glucose until the glucose is depleted. After glucose depletion the feed rate is decreased and maintained at a low level providing derepressed conditions. Under these conditions, added glucose is immediately taken up thereby sustaining energy for protein production. At the same time glucose repression cannot occur because added glucose is immediately metabolized.

Derepressed promoters are known from other methylotrophic yeast such as *Hansenula polymorpha*, and *Candida boidinii* [33]. In *P. pastoris* only certain deletion variants of the AOX1 promoter showed a derepressed regulatory profile, although clearly weaker than the methanol induced promoter (approximately one third of the expression on methanol) [28]. However, in *P. pastoris* no natural strong derepressed promoters have been described.

The monodirectional promoters were selected from different pathways (methanol metabolism, ROS defense and pentose phosphate pathway) and cloned in front of a GFP reporter protein.

Figure 16:
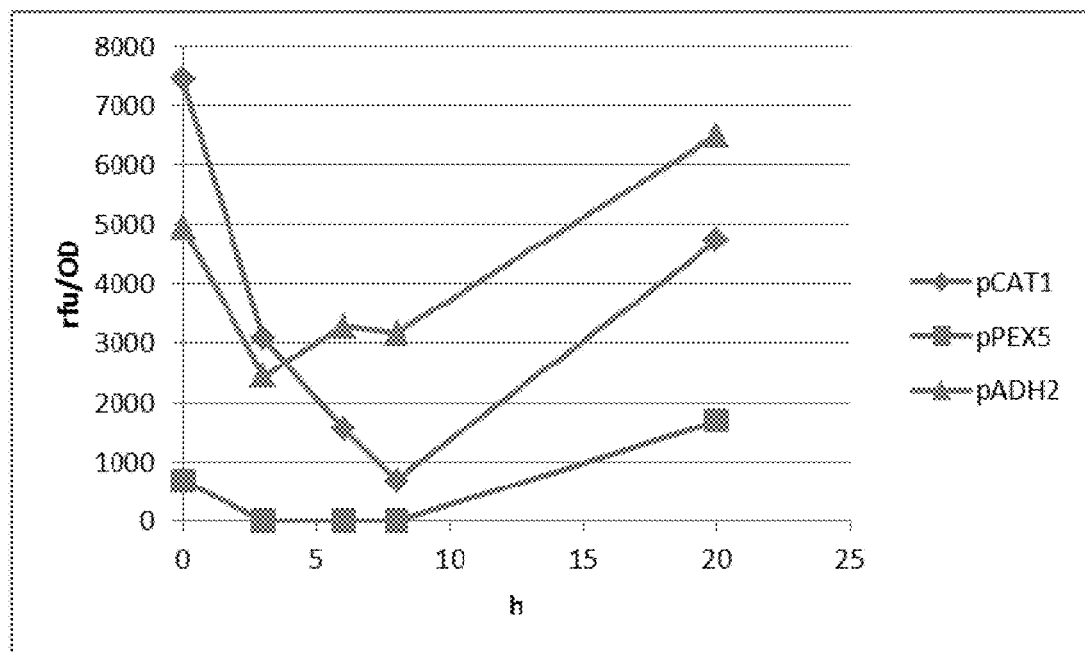
FIG. 16: pCAT1 and pPEX5 show clearly derepression, pADH2 a partially derepression effect. Pre-cultures of reporter strains with the three promoters were grown under derepressing conditions (starting phase on glucose followed by starvation without a carbon source). Subsequently the cultures were shifted to fresh glucose medium and a time series was measured. The expression levels of pCAT1 and pPEX5 decreased strongly, indicating repression on glucose. Subsequently, after glucose was depleted (approximately at 12 to 16 h, data of glucose measurements not shown), there expression increased drastically in an auto-regulated fashion.
Figure 17:
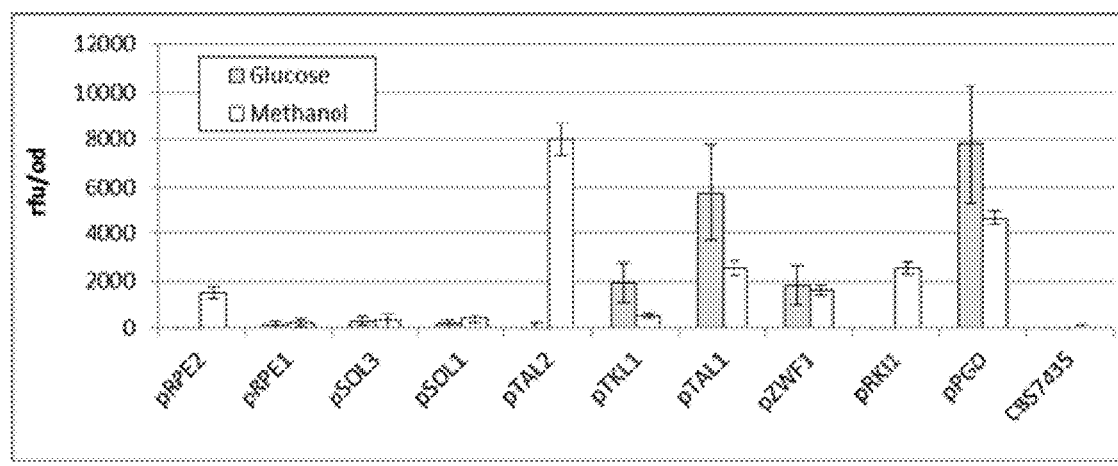
FIG. 17: Expression levels of monodirectional promoters of the pentose phosphate pathway. The promoters show different expression levels and regulatory profiles. RPE2, TAL2, RKI1 are methanol inducible, TKL1 and TAL1 down regulated on methanol and ZWF1 is constitutive. CBS7435 is the untransformed wildtype strain.

Thereby we identified the new derepressed promoters CAT1 (FIG. 16). The ADH2 and PEX5 promoters had been screened as potential bidirectional promoters but only shown strong derepressed expression on one side (FIG. 16) making them also suitable for such fusion approaches. However the monodirectional CAT1 promoter showed stronger derepressed expression than ADH2 and PEX5 making it the most suitable target for the fusion promoter strategy. The ADH2 promoter showed also rather a mix of constitutive expression and derepression. The other tested monodirectional promoters aside CAT1 showed also different expression levels and regulatory profiles (FIG. 17). Most notably certain promoters of the PPP (TKL1, TAL1) were downregulated on methanol, thereby providing a new regulatory profile. Such repression can be used to turn off a gene while inducing expression with a methanol inducible promoter.

For the monodirectional promoters see FIG. 25; MUT SEQ ID NO:96-97; ROS SEQ ID NO:98-101; and PPP SEQ ID NO:102-113.

As the natural bidirectional promoters identified provided only constitutive or inducible regulation on both sides, we aimed to design artificial promoters with different regulatory profiles. Therefore we tried to fuse previously identified and new monodirectional promoters to each other, thereby creating synthetic bidirectional promoters with different tailor-made regulatory profiles and expression ratios.

We aimed to design a bidirectional promoter providing strong inducible on one side and strong constitutive expression on the other. Therefore we fused the methanol inducible AOX1 promoter to the constitutive GAP promoter (pAOX1+pGAP). In addition we also aimed to link derepressed expression with either inducible or constitutive expression. To this end we fused the methanol inducible AOX1 promoter to the derepressed CAT1 promoter (pAOX1+pCAT1), in another construct the GAP promoter was fused to the CAT1 promoter (pGAP+pCAT1). We also tried to achieve constitutive expression on both sides by fusing the constitutive GAP promoter to the constitutive TEF promoter (pGAP+pTEF1). In addition fusions of methanol inducible promoters were tested to achieve different expression ratios and reduced promoter lengths compared to pDAS1,2. The variants tested include BZF1 (pFBA2-500+pTAL2-500), BZF2 (pFDH1-564+pDAS1-552), BZF3 (pFDH1-564+pCAT1-500), BZF4 (pDAS2-699+pDAS1-552), BZF5 (pFDH1-564+pPXR1-392), BZF6 (pFLD1-366+pAOX1-643), BZF7 (pAOX2-500+pCAT1-500) and BZF8 (pFLD1-366+pPXR1-392).

The promoters to be fused were PCR amplified and assembled by olePCR (primers see Table 2) and subsequently cloned into a reporter vector, in which the bidirectional promoter is flanked by a green and red fluorescent protein, allowing simultaneous detection of the expression of both promoter sides.

Figure 18:
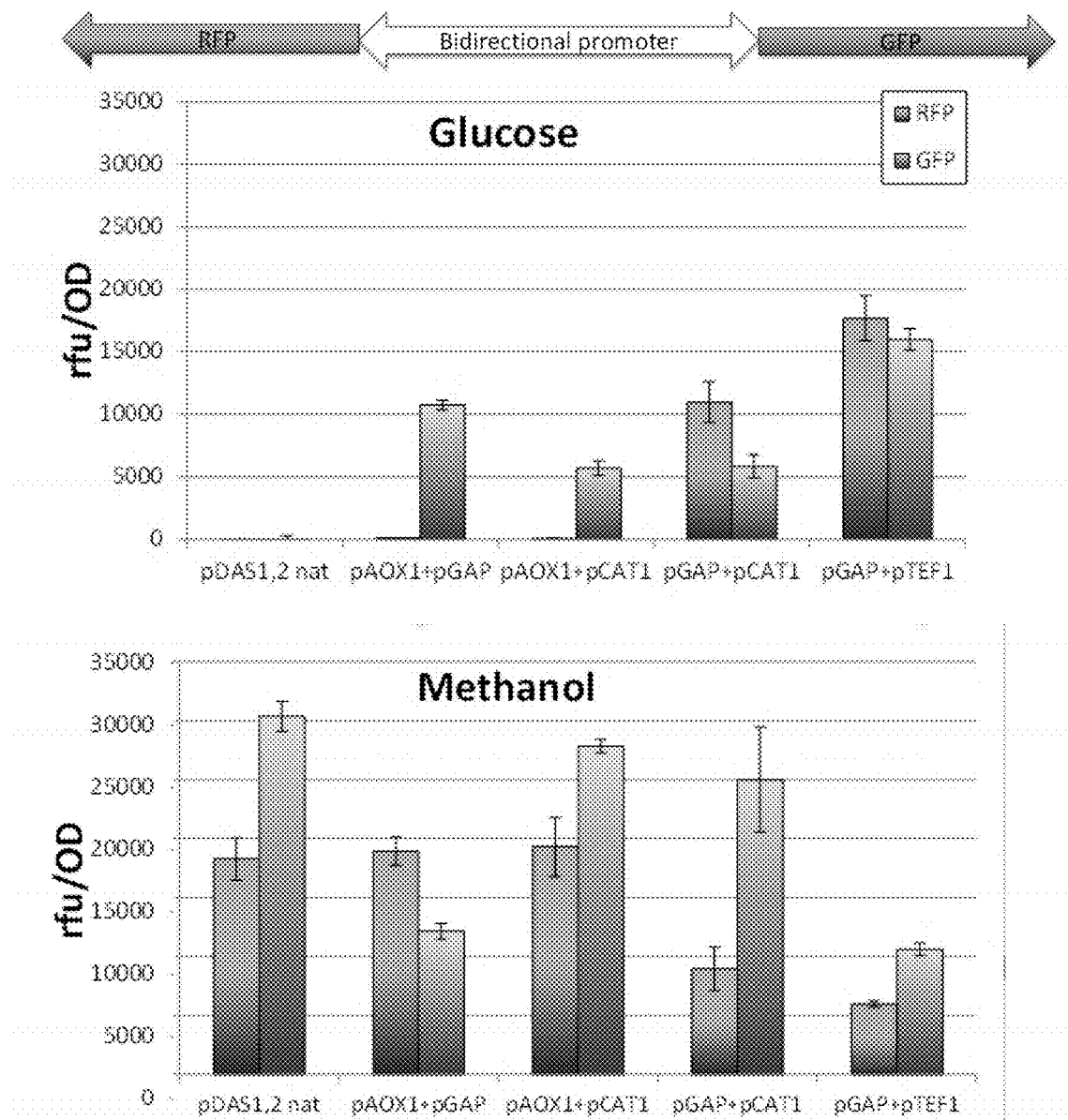
FIG. 18: Expression levels of semi-synthetic bidirectional fusion promoters. The natural bidirectional promoter of the DAS1,2 genes is shown as a reference.

The results are shown in FIG. 18. Even though showing strongly divergent regulation on both sides, surprisingly the two promoters did not infer with each other, maintaining their strength and regulation, thereby forming fully functional semi synthetic bidirectional promoters. Especially the fusion promoters pAOX1+pGAP, pAOX1+pCAT1, and pGAP+pCAT1 show promising properties. The constitutive pGAP+pTEF1 promoter provided strong expression comparable to the histone promoters, but was larger in size (2 to 3 fold difference). Still this bidirectional fusion promoter provides a different regulatory profile, as the GAP side is down-regulated on methanol whereas the TEF1 side remains on. This promoter makes pGAP+pTEF1 a valuable asset for the library of bidirectional promoters. Fusions of methanol inducible promoters maintained their tight regulation and offered different expression ratios on both sides FIG. 19.

For the semi synthetic bidirectional fusion promoters see FIG. 25; SEQ ID NO:114-125.

In addition to synthetic bidirectional fusion promoters, also monodirectional promoters were bidirectionalized. Since core promoters are rather short (ca. 100 bp), this enables the creation of short bidirectional promoters. Fusion promoters have always the length of both monodirectional parts and are therefore typically longer (although fusion promoters may provide beneficial effects by synergism between the two halves). Bidirectionalization was tested for different promoters by fusing different lengths of histone core promoters to the 5' end of the promoters of interest: BZ1 (pCoreHHT2-73+pAOX1BgIII), BZ2 (pCoreHHT2-73+pAOX1-711), BZ3 (pCoreHHT2-73+pAOX1-643), BZ4 (pCoreHHF2-76+pDAS1-552), BZ5 (pCoreHHF2-76+pDAS1-1000), BZ6 (pCoreHTA1-81+pDAS2-699), BZ7 (pCoreHTA1-81+pDAS2-1000), BZ8 (pCoreHTB1-86+pPXR1-478CBS), BZ9 (pCoreHTB1-86+pPXR1-392CBS), BZ10 (pCoreHTB1-86+pPXR1-480GS), BZ11 (pCoreHHT1-91+pFLD1-366), BZ12 (pCoreHHF1-80+pFDH1-564), BZ13 (pCoreHHT1-91+pFBA2-500), BZ14 (pCoreHHT1-91+pFBA2-704), BZ15 (pCoreHHF1-80+pTAL2-1000), BZ16 (pCoreHHF1-80+pTAL2-500), BZ17 (pCoreHHT2-73+pCAT1-692), BZ18 (pCoreHHT2-73+ pCAT1-500), BZ19 (pCoreHHF2-76–pGAP-486), BZ20 (pCoreHTA1-81-pTEF1-424), BZ21 (pCoreHTB1-86–pADH2-500), BZ23 (pCoreHHT2-89+pAOX1-711), BZ24 (pCoreHHT2-105+pAOX1-711), BZ25 (pCoreHTB1-106+pPXR1-392CBS), BZ26 (pCoreHTB1-126+pPXR1-392CBS), BZ27 (pCoreHHT1-111+pFLD1-366), BZ28 (pCoreHHT1-131+pFLD1-366), BZ29 (pCoreHHF1-80+pAOX1-711), BZ30 (pCoreHHF1-100+pAOX1-711), BZ31 (pCoreHHF1-121+pAOX1-711). These promoters were created by attaching the core promoter on a PCR primer and cloning them via Gibson assembly into the bidirectional reporter vector. Primers are listed in Table 2. The fluorescence measurement results are shown in FIG. 3, demonstrating that bidirectionalization was in some cases highly successful (e.g. BZ6) and is also a feasible strategy to achieve different expression ratios and short, sequence diversified promoters.

For the bidirectional synthetic fusion promoters see FIG. 25; SEQ ID NO:136-165.

To evaluate the library approach to optimize the coexpression of a gene pair with a set of bidirectional promoters, we selected two gene pairs. The first pair consisted of a cytochrome P450 enzyme (CYP) and the associated reductase (CPR). The second gene pair was *Candida antarctica* lipase B (CalB), a disulfide rich protein, and a protein disulfide isomerase (PDI) to assist in folding.

Cytochrome P450 enzymes are of high pharmaceutical interest, as these enzymes are responsible for the conversion of human drugs. CYPs are also versatile biocatalysts used in biotechnology [34]. The expression of CYPs is however difficult, as it requires to coexpression of the enzyme (CYP) and an associated reductase (CPR) that delivers electrons from NADPH. To complicate matters further, the CYP and CPR are integral membrane proteins localized in the ER, therefore they require to enter the sec pathway to achieve correct localization. They need to be expressed at high levels and it is necessary to achieve a suitable ratio between the CYP and CPR [1].

Therefore such a gene pair was an excellent target to test the bidirectional expression system, as common expression approaches in *P. pastoris* relied on the use of the use of two separate vectors with the identical promoter [1].

We used CYP52A13 and the associated reductase from *Candida tropicalis*. The genes were codon optimized for *P. pastoris* and subsequently cloned in a bidirectional entry vector with a stuffer fragment between them. Subsequently, the stuffer fragment was replaced with a set of bidirectional promoters providing different regulatory profiles and expression ratios. We focused only on strong bidirectional promoters and omitted weaker ones, as in previous work best expression was even achieved using multi copy strains bearing the strong AOX1 promoter [1]. Therefore we omitted the weak bidirectional promoters from the screening. The bidirectional entry vector was created by digesting the bidirectional reporter vector (FIG. 6) with NotI and gel purifying the backbone.

Figure 21:
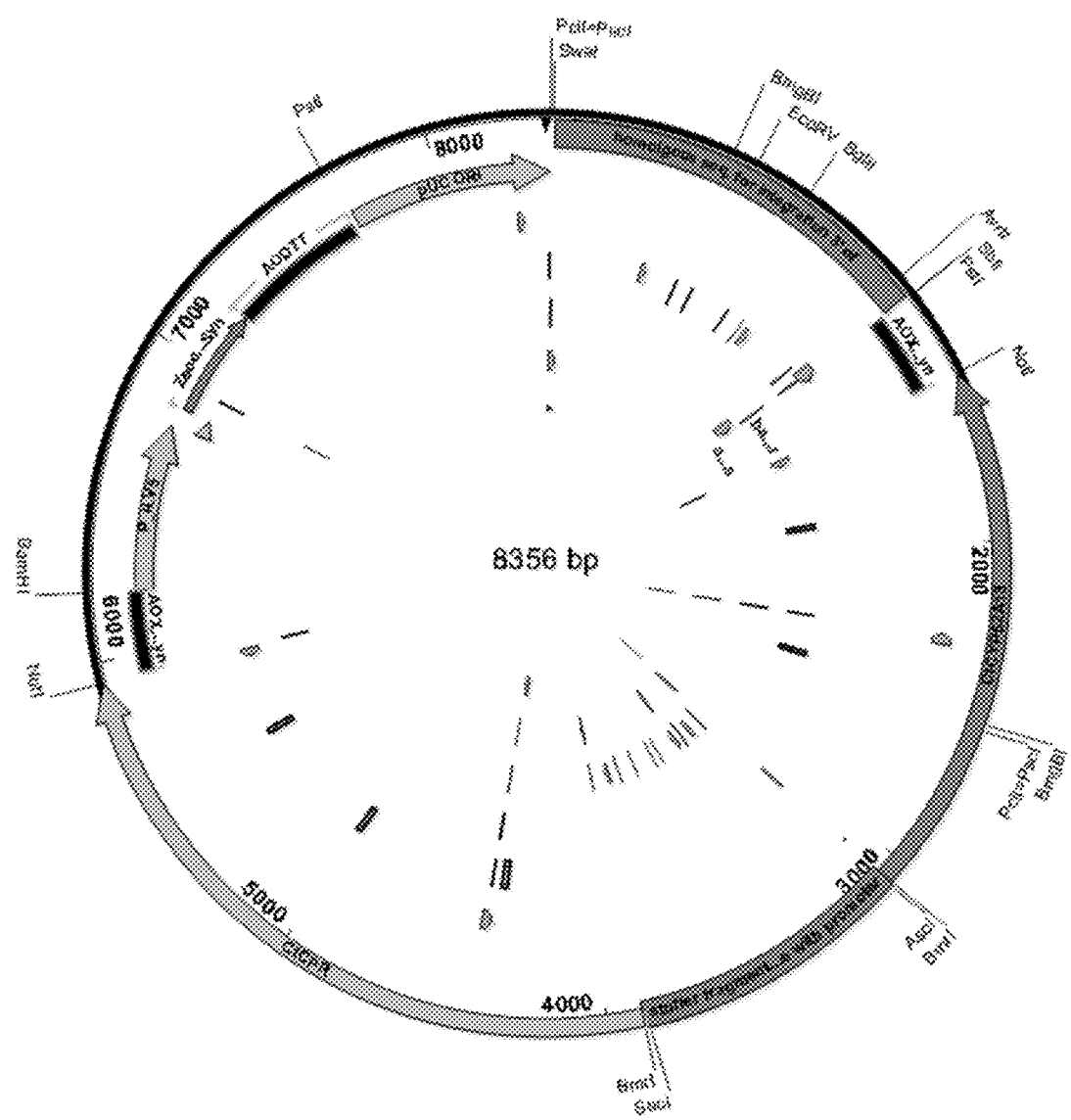
FIG. 21: Bidirectional entry vector for testing different bidirectional promoters for CYP+CPR coexpression.
Figure 22:
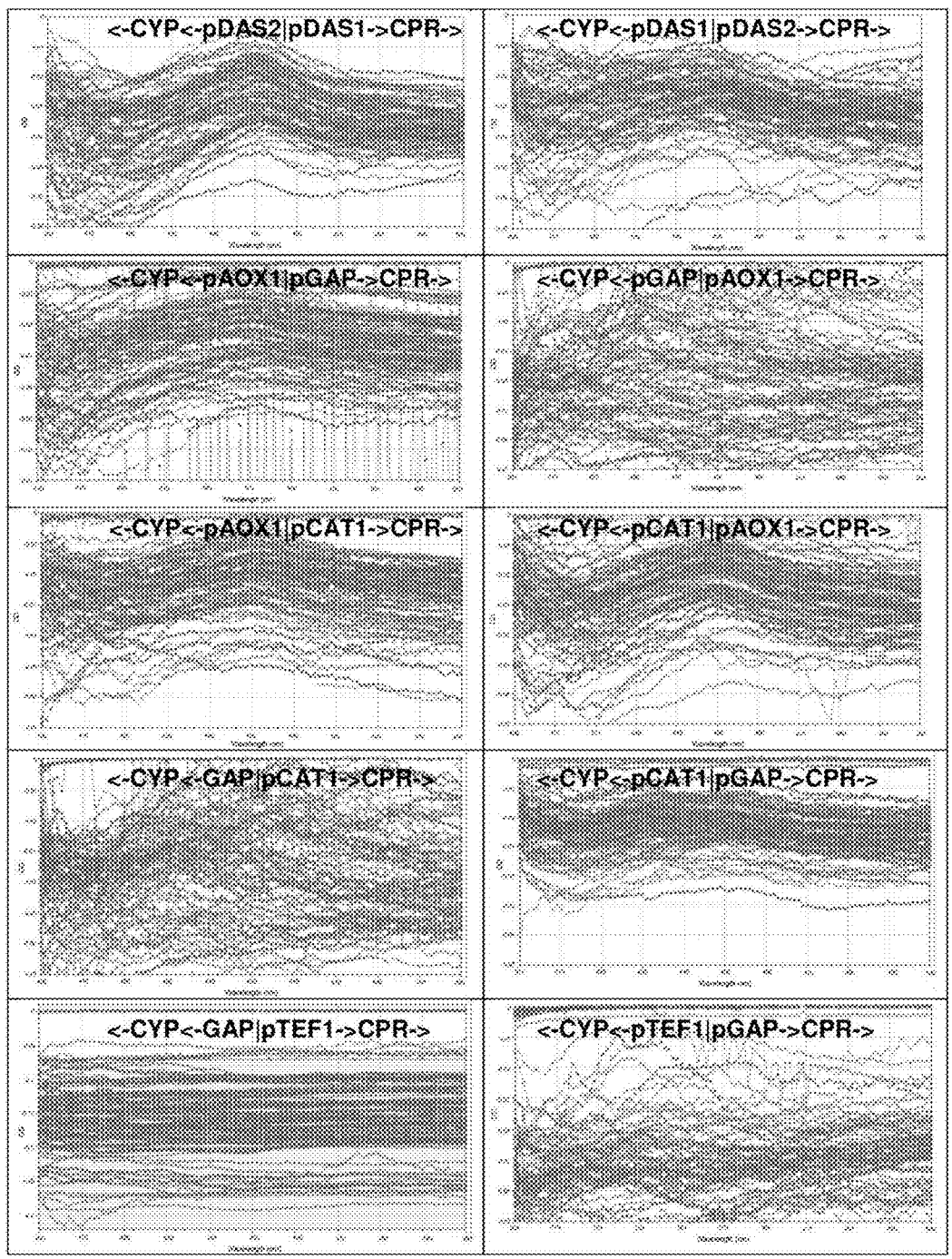
FIG. 22: CYP expression levels monitored by CO differential spectra. The screening landscapes from approximately 75 transformants per construct are shown. High expression is reflected by a pronounced peak at 450 nm. Constructs with the CYP under control methanol inducible promoters (DAS, AOX1, CAT1) were grown on methanol whereas constructs with the CYP under control of a constitutive promoter (GAP, TEF1) were grown on glucose.

BmrI sites present in the genes were removed by PCR amplifying the template vectors using primers pairs CtCYP52A13mutFWD+CtCYP52A13mutFWD and CtCPRmutFWD+CtCPRmutREV (introducing silent mutations in the BmrI recognition sequence, see Tab. 3 for the primer sequences) and Pfu Ultra polymerase followed by DpnI digestion. After confirming the sequence by Sanger sequencing the vectors were used as templates for the following cloning steps. An expression cassette consisting of the CYP and CPR genes in reverse orientation separated by a stuffer fragment was assembled by olePCR. The CYP gene was amplified using primers CtCYP52A13olePCRfwd and CtCYP52A13NotIrev from the above mentioned BmrI mutated vector template. The CPR gene was amplified using primers CtCPRolePCRfwd and CtCPRNotIrev from the above mentioned BmrI mutated vector template. The stuffer fragment was amplified from the bidirectional entry vector using primers stufferCYP-CPRolePCRfwd and stufferCYP-CPRolePCRrev. For olePCR, the fragments were gel purified and mixed in equimolar ratios. After 20 cycles of primerless PCR the primers CtCYP52A13NotIrev and CtCPRNotIrev were added. The obtained fragment of the correct size was gel purified, and NotI digested and subsequently cloned into the above mentioned NotI digested vector backbone. The inserted cassette was confirmed by Sanger sequencing. The final bidirectional entry vector is shown in FIG. 21.

Subsequently we removed the stuffer fragment by BmrI digestion and cloned a set of strong bidirectional promoters providing different regulatory profiles and ratios. We selected the natural bidirectional DAS1,2 promoter (strong inducible expression on both sides with slightly divergent ratio) and various semi-synthetic fusion promoters. The pAOX1+pGAP promoter provides on side strong inducible and on the other strong constitutive expression. The pAOX1+pCAT1 promoter provides on one side strong inducible and on the other strong derepressed expression. The pGAP+pCAT1 promoter provides on one side strong constitutive and on the other strong derepressed expression. The pGAP+pTEF1 promoter provides strong constitutive expression on both sides. We tested these five bidirectional promoters in both orientations, thereby doubling the different regulatory profiles and ratios.

The bidirectional promoters were cloned by Gibson assembly [25] after amplification with primers pDAS2-Gib-CtCYP-ins, pDAS1-Gib-CtCPR-ins, pDAS1-Gib-CtCYP-ins, pDAS2-Gib-CtCPR-ins, pAOX1-Gib-CtCYP-ins, pGAP-Gib-CtCPR-ins, pGAP-Gib-CtCYP-ins, pAOX1-Gib-CtCPR-ins, pCAT1-Gib-CtCPR-ins, pCAT1-Gib-CtCYP-ins, pTEF1-Gib-CtCPR-ins and pTEF1-Gib-CtCYP-ins.

The inserted bidirectional promoters were sequenced using primers seqCtCYP-141 . . . 174-rev and seqCtCPR-217 . . . 240-rev. For this application we used Gibson assembly as we were dealing with a low number of constructs and aimed to insert the promoters with a specific orientation. Compared to TA cloning, Gibson assembly does not require A-tailing of PCR fragments and verification of the orientation by colony PCR.

Figure 19:
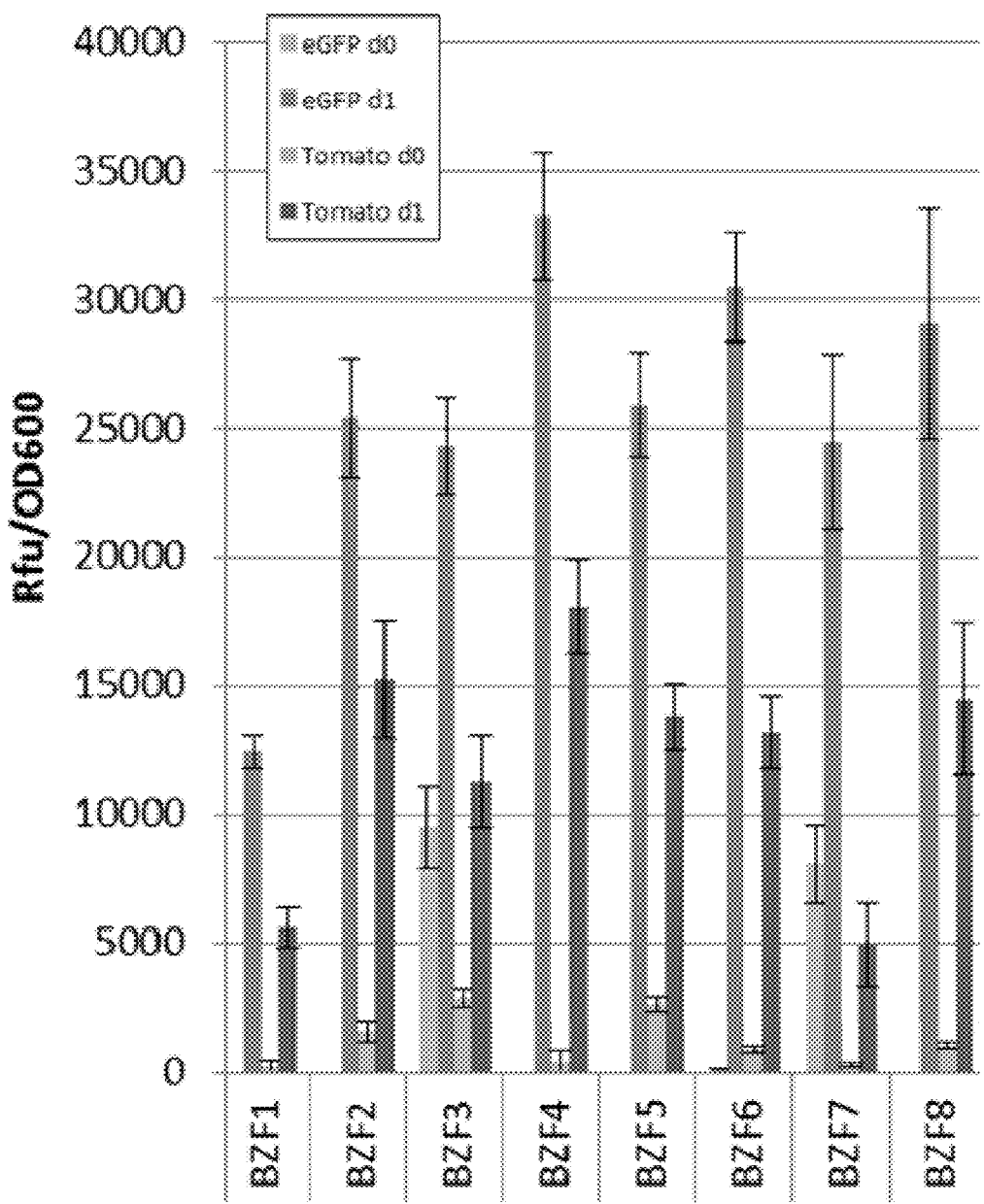
FIG. 19: eGFP reporter fluorescence of methanol inducible fusion promoters BZF1 to BZF8. Strains were grown of 60 h on glucose and subsequently induced for 24 h with methanol and reporter gene fluorescence measured.
Figure 20:
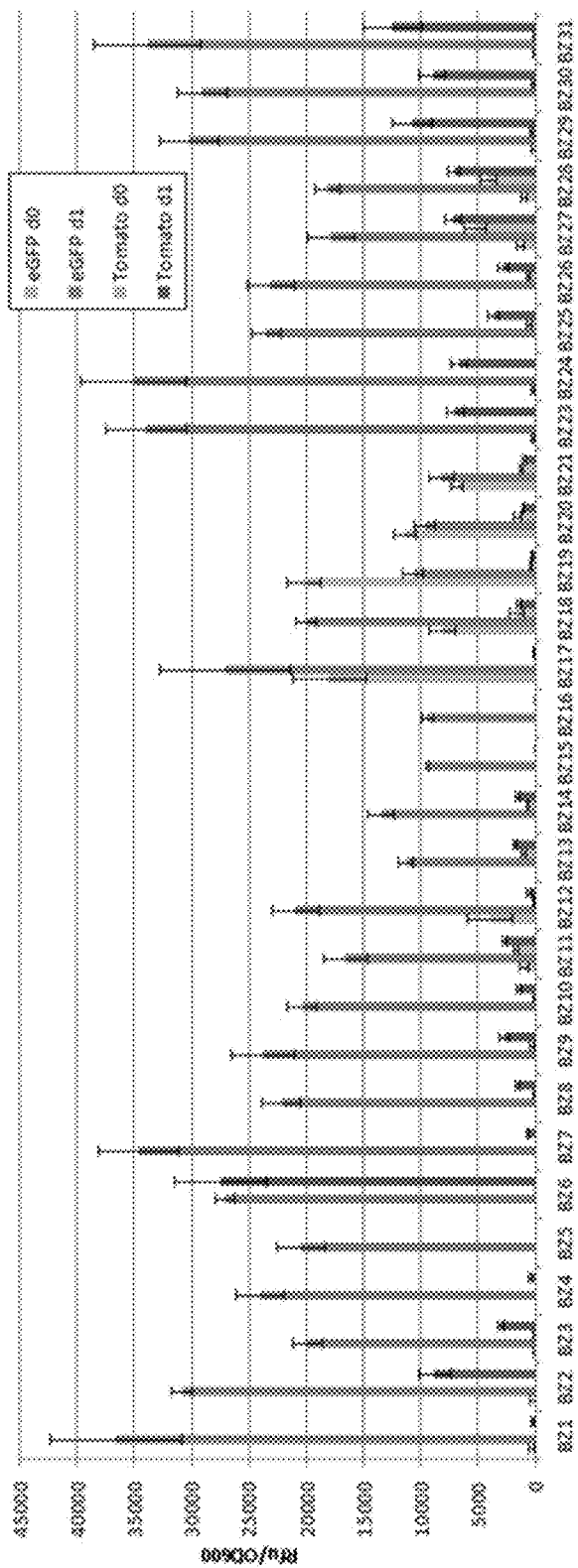
FIG. 20: Screening data for bidirectionalized promoters. The RFU/OD600 after growth on glucose for 60 h (d0) and subsequent methanol induction (24 h) are shown.

The results of the CYP expressions are shown in FIG. 19. As expression in *P. pastoris* varies between different transformants, we have analyzed landscapes of 50 to 100 transformants per construct to rule out bias of clonal variation. The bidirectional promoter used had a drastic and unexpected effect on expression. The construct ←CYP←pDAS2|pDAS1→CPR→ in which the CYP is under control of a methanol regulated construct showed the clearest peak at 450 nm, a hallmark of CYP expression. Interestingly, the same promoter in reverse orientation (←CYP←pDAS1|pDAS2→CPR→) indicated lower expression and much more background noise. This hints an effect of the expression ratio as pDAS2 appeared in the screening stronger than pDAS1 (FIG. 18). The CYP under control of the state of the art promoter pAOX1 showed clearly lower expression levels than the pDAS2 side, irrespectively of the fusion promoter (←CYP←pAOX1|pGAP→CPR→ or ←CYP←pAOX1|pCAT1→CPR→). Interestingly, CYP expression levels under the novel CAT1 promoter (←CYP←-pCAT1|pAOX1→CPR→) reached similarly high expression levels as the CYP under control of pDAS2, although the landscape clone to clone variation appeared higher (also transformants with lower expression). In this case the CPR was under control of the methanol inducible AOX1 promoter).

The CYP under control of the CAT1 promoter showed lower expression when fused to the constitutive GAP promoter (←CYP←pCAT1|pGAP→CPR→). This suggests that also the regulatory profile of the CPR expression affects CYP levels.

Strikingly, when the CYP was under control of a constitutive promoter (←CYP←pGAP|pAOX1→CPR→, ←CYP←GAP|pCAT1→CPR→, ←CYP←GAP|pTEF1→CPR→ and ←CYP←pTEF1|pGAP→CPR→) no expression was detectable, even when measured after multiple time points (data not shown). This shows that different regulatory profiles (e.g. inducible, constitutive, depressed expression and bidirectional combinations thereof) can drastically influence expression.

Our results suggest that CYP/CPR coexpression is highly complex and affected by several factors such as the expression ratio and the time profile. The bidirectional promoter library approach allowed to find an optimal expression condition for this gene pair, thereby highlighting its relevance and applicability.

*Candidia antarctica* lipase B (CalB) is an important biocatalyst which catalyzes a wide variety of organic reactions and is applied in many different regio- and enantio-selective syntheses. CalB expression is difficult as the protein contains three disulfide bonds. Therefore we aimed to coexpress protein disulfide isomerase (PDI), which assists in the formation of disulfide bonds in secretory and cell-surface proteins and unscrambles non-native disulfide bonds.

We aimed to optimize the coexpression of the two genes by using the bidirectional promoters expression approach. Therefore we used codon optimized genes for *P. pastoris* and cloned them cloned in a bidirectional entry vector with a stuffer fragment between them. Subsequently, the stuffer fragment was replaced with a set of bidirectional promoters providing different regulatory profiles and expression ratios. We focused only on strong bidirectional promoters and omitted weaker ones, as in previous work best expression was even achieved using multi copy strains bearing the strong AOX1 promoter (similar to the CYP, CPR coexpression). Therefore we omitted the weak bidirectional promoters from the screening.

The bidirectional entry vector was created by digesting the bidirectional reporter vector (FIG. 6) with NotI and gel purifying the backbone. We assembled an expression cassette consisting of the CalB and PDI in genes in reverse orientation separated by a stuffer fragment. Therefore the CalB gene was amplified from a plasmid where it was in frame linked to a Mating factor alpha signal sequence (to target secretion) using primers MFalphaolePCRfwd and CalB-NotIrev (see Tab. 3). The stuffer fragment was amplified from the bidirectional entry vector using primers 5'stufferMFalphaolePCRfwd and stufferCalB-PDIolePCRrev. The PDI gene was amplified using primers PDImutBmrI-olePCRfwd+PDINotIrev. For olePCR, the fragments were gel purified and mixed in equimolar ratios. After 20 cycles of primerless PCR the primers CalB-NotIrev and PDI-NotIrev were added. The obtained fragment of the correct size was gel purified, NotI digested and subsequently cloned into the above mentioned NotI digested vector backbone. The inserted cassette was confirmed by Sanger sequencing. The final bidirectional entry vector is shown in FIG. 23.

Subsequently we removed the stuffer fragment by BmrI digestion and cloned a set of strong bidirectional promoters providing different regulatory profiles and ratios. We selected the natural bidirectional DAS1,2 promoter (strong inducible expression on both sides with slightly divergent ratio) and various semi-synthetic fusion promoters. The pAOX1+pGAP promoter provides on one side strong inducible and on the other strong constitutive expression. The pAOX1+pCAT1 promoter provides on one side strong inducible and on the other strong derepressed expression. The pGAP+pCAT1 promoter provides on one side strong constitutive and on the other strong derepressed expression. In addition we tested two histone promoters (pHTX1 and pHHX2) in both orientations, as they provide strong constitutive expression in different ratios.

The bidirectional promoters were cloned by Gibson assembly [25] after amplification with primers pDAS2-Gib-MFalpha-ins, pDAS1-Gib-PDI-ins, pDAS1-Gib-MFalpha-ins, pDAS2-Gib-PDI-ins, pAOX1-Gib-MFalpha-ins, pGAP-Gib-PDI-ins, pGAP-Gib-MFalpha-ins, pAOX1-Gib-PDI-ins, pCAT1-Gib-PDI-ins, pCAT1-Gib-MFalpha-ins, pHTA1-Gib-MFalpha-ins, pHTB2-Gib-PDI-ins, pHTB2-Gib-MFalpha-ins, pHTA1-Gib-PDI-ins, pHistH3-Gib-MFalpha-ins, pHistH4-Gib-PDI-ins, pHistH4-Gib-MFalpha-ins, pHistH3-Gib-PDI-ins.

The inserted bidirectional promoters were sequenced using primers seqMFalpha132 . . . 109rev and seqPDI103 . . . 126rev. For this application we used again Gibson assembly as we were dealing with a low number of constructs and aimed to insert the promoters with a specific orientation, for the same reasons as mentioned for CYP+CPR coexpression.

Figure 24:
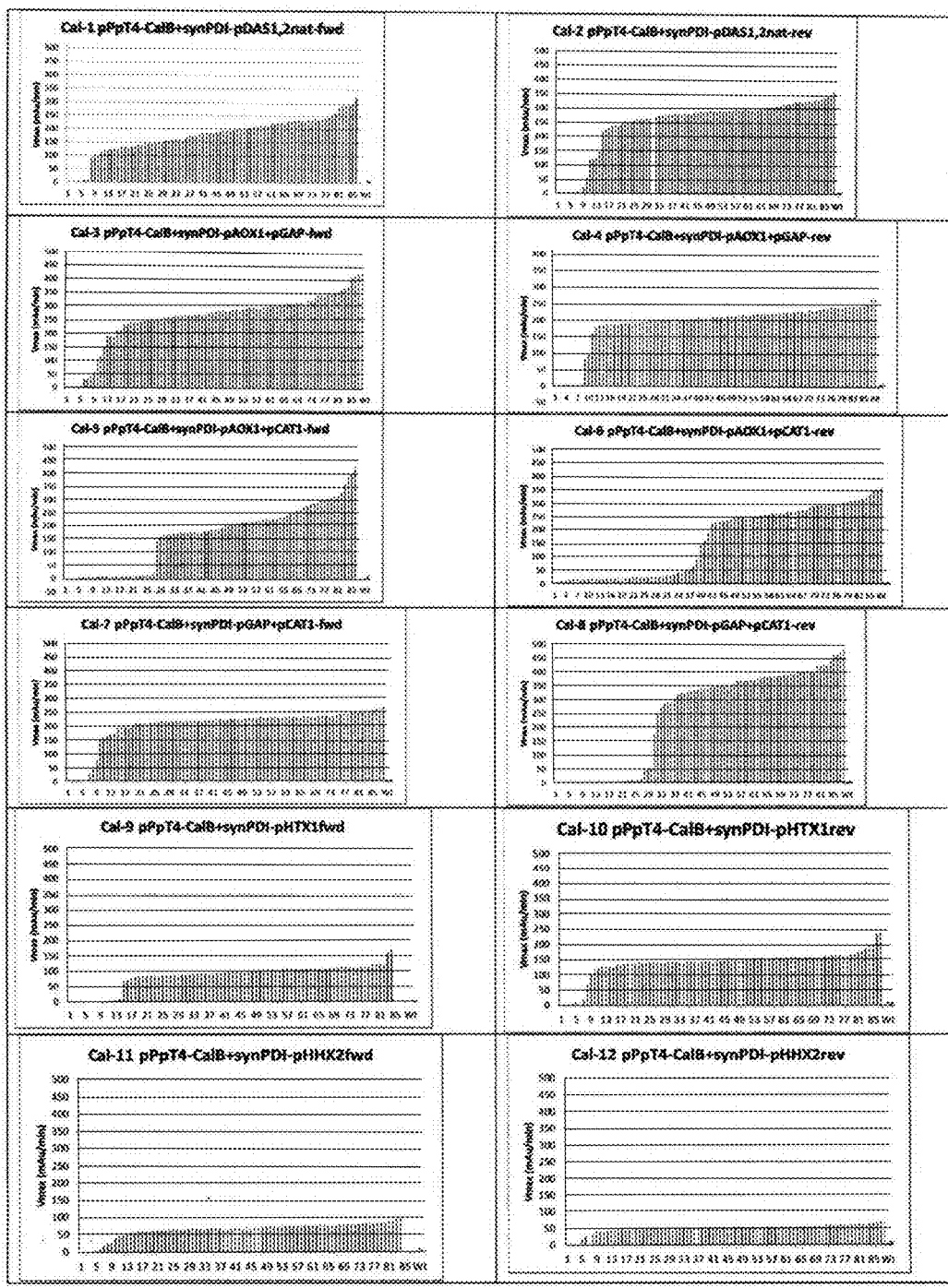
FIG. 24: CalB activities in strains with various bidirectional promoters used for coexpressing PDI. The screening landscapes from approximately 75 transformants per construct are shown. Constructs with CalB under control of methanol inducible promoters (DAS, AOX1, CAT1) were grown on methanol whereas constructs with the CYP under control of a constitutive promoter (GAP, HTX1, HHX2) were grown on glucose

The results are of the expression in *P. pastoris* are shown in FIG. 24. We could detect CalB activity with all tested bidirectional promoters; however there appeared strong differences between the constructs. The best promoters for inducible expression (Constructs Cal1,2,3,5,6,8) and constitutive expression (4,7,11,12) performed roughly similar. The novel CAT1 promoter resulted in the highest expression of all constructs and outperformed the state of the art AOX1 promoter when PDI was under control of the GAP promoter (CAL8). The data suggests also that too strong constitutive expression might overburden the cellular machinery, therefore the constitutive histone promoters showed lower expression than fusions of the GAP promoter to either AOX1 or CAT1.

Yet, the bidirectional expression strategy helped again to optimize the expression, with the novel fusion promoter consisting of CAT1 and GAP outperforming state of the art AOX1 expression.

Tables

TABLE 1

Primers used for assembling the single and double reporter vectors

| | |
|---|---|
| int.arg.fwd | GCCCACATGTATTTAAATTGCCAGTGTATGTGCACTTATAGAGG |
| int.arg.rev | CAACAGAGGTCGGCGCGCCACTGGGTGCTAGGACCTTCTCGCAGAATGGTATAAATATC |
| stufferTHI5.fwd | CTGCGAGAAGGTCCTAGCACCCAGTGGCGCGCCGACCTCTGTTGCCTCTTTGTTGGACG |

TABLE 1-continued

Primers used for assembling the single and double reporter vectors

| | |
|---|---|
| stufferTHI5.rev | CCTTTGCTAGCCATCAGTCCCAGTGAGCTCTTAAGCTGGAAGAGCCAATCTCTTGAAAG |
| EGFPfwd.stufferTHI5 | GGCTCTTCCAGCTTAAGAGCTCACTGGGACTGATGGCTAGCAAAGGAGAAGAACTTTTC |
| EGFPrevNotI | GATCGCGGCCGCTTACTTGTACAATTCATCCATGCCATG |
| ZeoCDS_mut_MlyI_fwd | agttctggactgataggctcggtttctcccgtg |
| ZeoCDS_mut_MlyI_rev | cacgggagaaaccgagcctatcagtccagaact |
| seqintARG4fwd | ctagatacccgtgaactttgtctc |
| seqGFPrev | ttccgtatgtagcatcaccttcac |
| newTomatoAscIBmrIFWD | GGTCggcgcgccACTGGGtgctATGGTTTCTAAGGGTGAGGAA |
| AOXTTSbfIAvrIIREV1 | TTATACCATTCTGCGAGAAGGTCCCCTGCAGGGCACAAACGAAGGTCTCACTTAATCTTC |
| AOXTTSbfIAvrIIREV2 | GACCCCTAGGCCGTACGACAGTCAGTTAGTAGATATTTATACCATTCTGCGAGAAGGTCC |

Tab. 2: List of Bidirectional Promoters (See FIG. 26)

The promoters were PCR amplified and cloned in a reporter vector with a green fluorescent protein on one side and a red fluorescent protein on the other side. If relevant, the length, primers used and approximate expression levels are outlined.

TABLE 3

Primers used for assembling the constructs for testing the applications of bidirectional expression system for gene coexpression

| | |
|---|---|
| CtCYP52A13mutREV | accattcaaaacccaatacagttgttgcatcacagctc |
| CtCPRmutFWD | gtaggaagttcgacagattacttggtgagaaaggtgg |
| CtCPRmutREV | ccacctttctcaccaagtaatctgtcgaacttcctac |
| CtCYP52A13olePCRfwd | GCAACAGAGGTCggcgcgccACTGGGtgctATGACGGTTCATGACATCATCGCTACTTAC |
| CtCYP52A13NotIrev | ACTTGCGGCCGCTTAATACATTTCAATGTTTGCACCATCGAACAAAGACATAGTC |
| stufferCYP-CPRolePCRfwd | catgaaccgtcatagcaCCCAGTggcgcgccGACCTCTGTTGCCTCTTTGTTGGACGAAC |
| stufferCYP-CPRolePCRrev | atcaagtgccatcagtCCCAGTgagctcTTAAGCTGGAAGAGCCAATCTCTTGAAAGTAC |
| CtCPRolePCRfwd | AgagctcACTGGGactgatggcacttgataaactagatttgtacgtgattatcaccttag |
| CtCPRNotIrev | TAATGCGGCCGCTTACCAAACATCCTCCTGATAACGATTTTGAACTTTCCAG |
| pDAS2-Gib-CtCYP-ins | aagtagcgatgatgtcatgaaccgtcattttgatgtttgatagtttgataagagtgaac |
| pDAS1-Gib-CtCPR-ins | acgtacaaatctagtttatcaagtgccatttttgttcgattattctccagataaaatcaac |
| pDAS1-Gib-CtCYP-ins | taagtagcgatgatgtcatgaaccgtcattttgttcgattattctccagataaaatcaac |
| pDAS2-Gib-CtCPR-ins | cgtacaaatctagtttatcaagtgccattttttgatgtttgatagtttgataagagtgaac |
| pAOX1-Gib-CtCYP-ins | aagtagcgatgatgtcatgaaccgtcatcgtttcgaataattagttgttttttgatcttc |
| pGAP-Gib-CtCPR-ins | atcacgtacaaatctagtttatcaagtgccattgtgttttgatagttgttcaattgattg |
| pGAP-Gib-CtCYP-ins | gtagcgatgatgtcatgaaccgtcattgtgttttgatagttgttcaattgattgaaatag |
| pAOX1-Gib-CtCPR-ins | cgtacaaatctagtttatcaagtgccatcgtttcgaataattagttgttttttgatcttc |

TABLE 3-continued

Primers used for assembling the constructs for testing the applications of bidirectional expression system for gene coexpression

| Primer | Sequence |
|---|---|
| pCAT1-Gib-CtCPR-ins | cacgtacaaatctagtttatcaagtgccatTTTAATTGTAAGTCTTGACTAGAGCAAGTG |
| pCAT1-Gib-CtCYP-ins | gtaagtagcgatgatgtcatgaaccgtcatTTTAATTGTAAGTCTTGACTAGAGCAAGTG |
| pTEF1-Gib-CtCPR-ins | acgtacaaatctagtttatcaagtgccatgttggcgaataactaaaatgtatgtagtgag |
| pTEF1-Gib-CtCYP-ins | taagtagcgatgatgtcatgaaccgtcatgttggcgaataactaaaatgtatgtagtgag |
| seqCtCYP-141 . . . 174-rev | agccttaaaaccgaaacaaccgtc |
| seqCtCPR-217 . . . 240-rev | acgggacagtttgttggcgtaatc |
| MFalphaolePCRfwd | CAACAGAGGTCggcgcgccACTGGGtgctATGAGATTCCCATCTATTTTCACCGCTGTCT |
| CalB-NotIrev | TAATGCGGCCGCTTATGGGGTCACGATACCGGAACAAGTTCTC |
| 5'stufferMFalphaolePCRfwd | atagatgggaatctcatagcaCCCAGTggcgcgccGACCTCTGTTGCCTCTTTGTTGGAC |
| stufferCalB-PDIolePCRrev | AttgaattgcatcagtCCCAGTgagctcTTAAGCTGGAAGAGCCAATCTCTTGAAAGTAC |
| PDImutBmrIolePCRfwd | AGCTTAAgagctcACTGGGactgatgcaattcaaTtgggacatcaagacagttgcatcca |
| PDINotIrev | ttttGCGGCCGCTTACAATTCGTCGTGAGCATCAGCTTCAGAC |
| pDAS2-Gib-MFalpha-ins | cagcggtgaaaatagatgggaatctcattttttgatgtttgatagtttgataagagtgaac |
| pDAS1-Gib-PDI-ins | actgtcttgatgtcccaAttgaattgcattttgttcgattattctccagataaaatcaac |
| pDAS1-Gib-MFalpha-ins | acagcggtgaaaatagatgggaatctcattttgttcgattattctccagataaaatcaac |
| pDAS2-Gib-PDI-ins | ctgtcttgatgtcccaAttgaattgcattttgatgtttgatagtttgataagagtgaac |
| pAOX1-Gib-MFalpha-ins | cagcggtgaaaatagatgggaatctcatcgtttcgaataattagttgttttttgatcttc |
| pGAP-Gib-PDI-ins | gtcttgatgtcccaAttgaattgcattgtgttttgatagttgttcaattgattgaaatag |
| pGAP-Gib-MFalpha-ins | gcggtgaaaatagatgggaatctcattgtgttttgatagttgttcaattgattgaaatag |
| pAOX1-Gib-PDI-ins | ctgtcttgatgtcccaAttgaattgcatcgtttcgaataattagttgttttttgatcttc |
| pCAT1-Gib-PDI-ins | aactgtcttgatgtcccaAttgaattgcatTTTAATTGTAAGTCTTGACTAGAGCAAGTG |
| pCAT1-Gib-MFalpha-ins | gacagcggtgaaaatagatgggaatctcatTTTAATTGTAAGTCTTGACTAGAGCAAGTG |
| pHTA1-Gib-MFalpha-ins | gcggtgaaaatagatgggaatctcattgttgtagttttaatatagtttgagtatgagatg |
| pHTB2-Gib-PDI-ins | actgtcttgatgtcccaAttgaattgcattttgatttgtttaggtaacttgaactggatg |
| pHTB2-Gib-MFalpha-ins | acagcggtgaaaatagatgggaatctcattttgatttgtttaggtaacttgaactggatg |
| pHTA1-Gib-PDI-ins | gtcttgatgtcccaAttgaattgcattgttgtagttttaatatagtttgagtatgagatg |
| pHistH3-Gib-MFalpha-ins | gacagcggtgaaaatagatgggaatctcatttttactacgatagacacaagaagaagcag |

TABLE 3-continued

Primers used for assembling the constructs for testing the applications of bidirectional expression system for gene coexpression

| | |
|---|---|
| pHistH4-Gib-PDI-ins | tgtcttgatgtcccaAttgaattgcatatttattgattatttg tttatgggtgagtctag |
| pHistH4-Gib-MFalpha-ins | agcggtgaaaatagatgggaatctcatatttattgattatttg tttatgggtgagtctag |
| pHistH3-Gib-PDI-ins | aactgtcttgatgtcccaAttgaattgcatttttactacgata gacacaagaagaagcag |
| seqMFalpha132 . . . 109rev | aaggtcagagtaaccgataactgc |
| seqPDI103 . . . 126rev | agtagcctcagtcaacttcacaac |

LITERATURE

[1] Geier M, Braun A, Emmerstorfer A, Pichler H, Glieder A. Production of human cytochrome P450 2D6 drug metabolites with recombinant microbes—a comparative study. Biotechnol J 2012:1-13.

[2] Chen M-T, Lin S, Shandil I, Andrews D, Stadheim T A, Choi B-K. Generation of diploid Pichia pastoris strains by mating and their application for recombinant protein production. Microb Cell Fact 2012; 11:91.

[3] Gudiminchi R K, Geier M, Glieder A, Camattari A. Screening for cytochrome P450 expression in Pichia pastoris whole cells by P450-carbon monoxide complex determination. Biotechnol J 2013; 8:146-52.

[4] Vogl T, Glieder A. Regulation of Pichia pastoris promoters and its consequences for protein production. New Biotechnol 2013; 30:385-404.

[5] St John T P, Davis R W. The organization and transcription of the galactose gene cluster of Saccharomyces. J Mol Biol 1981; 152:285-315.

[6] Lohr D, Venkov P, Zlatanova J. Transcriptional regulation in the yeast GAL gene family: a complex genetic network. FASEB J 1995; 9:777-87.

[7] Miller C A, Martinat M A, Hyman L E. Assessment of aryl hydrocarbon receptor complex interactions using pBEVY plasmids: expressionvectors with bi-directional promoters for use in Saccharomyces cerevisiae. Nucleic Acids Res 1998; 26:3577-83.

[8] Partow S, Siewers V, Bjorn S, Nielsen J, Maury J. Characterization of different promoters for designing a new expression vector in Saccharomyces cerevisiae. Yeast 2010; 27:955-64.

[9] Li A, Liu Z, Li Q, Yu L, Wang D, Deng X. Construction and characterization of bidirectional expression vectors in Saccharomyces cerevisiae. FEMS Yeast Res 2008; 8:6-9.

[10] Ishida C, Aranda C, Valenzuela L, Riego L, Deluna A, Recillas-Targa F, et al. The UGA3-GLT1 intergenic region constitutes a promoter whose bidirectional nature is determined by chromatin organization in Saccharomyces cerevisiae. Mol Microbiol 2006; 59:1790-806.

[11] Xu Z, Wei W, Gagneur J, Perocchi F, Clauder-Münster S, Camblong J, et al. Bidirectional promoters generate pervasive transcription in yeast. Nature 2009; 457:1033-7.

[12] Neil H, Malabat C, d'Aubenton-Carafa Y, Xu Z, Steinmetz L M, Jacquier A. Widespread bidirectional promoters are the major source of cryptic transcripts in yeast. Nature 2009; 457:1038-42.

[13] Xie M, He Y, Gan S. Bidirectionalization of polar promoters in plants. Nat Biotechnol 2001; 19:677-9.

[14] Sammarco M C, Grabczyk E. A series of bidirectional tetracycline-inducible promoters provides coordinated protein expression. Anal Biochem 2005; 346:210-6.

[15] Baron U, Freundlieb S, Gossen M, Bujard H. Co-regulation of two gene activities by tetracycline via a bidirectional promoter. Nucleic Acids Res 1995; 23:3605-6.

[16] Fux C, Fussenegger M. Bidirectional expression units enable streptogramin-adjustable gene expression in mammalian cells. Biotechnol Bioeng 2003; 83:618-25.

[17] Weber W, Marty R R, Keller B, Rimann M, Kramer B P, Fussenegger M. Versatile macrolide-responsive mammalian expression vectors for multiregulated multigene metabolic engineering. Biotechnol Bioeng 2002; 80:691-705.

[18] Amendola M, Venneri M A, Biffi A, Vigna E, Naldini L. Coordinate dual-gene transgenesis by lentiviral vectors carrying synthetic bidirectional promoters. Nat Biotechnol 2005; 23:108-16.

[19] Andrianaki a, Siapati E K, Hirata R K, Russell D W, Vassilopoulos G. Dual transgene expression by foamy virus vectors carrying an endogenous bidirectional promoter. Gene Ther 2010; 17:380-8.

[20] Polson A, Durrett E, Reisman D. A bidirectional promoter reporter vector for the analysis of the p53/WDR79 dual regulatory element. Plasmid 2011.

[21] Crook N C, Freeman E S, Alper H S. Re-engineering multicloning sites for function and convenience. Nucleic Acids Res 2011; 39:e92.

[22] Staley C A, Huang A, Nattestad M, Oshiro K T, Ray L E, Mulye T, et al. Analysis of the 5' untranslated region (5'UTR) of the alcohol oxidase 1 (AOX1) gene in recombinant protein expression in Pichia pastoris. Gene 2012; 496:118-27.

[23] Mead D A, Pey N K, Herrnstadt C, Marcil R A, Smith L M. A universal method for the direct cloning of PCR amplified nucleic acid. Biotechnology (N Y) 1991; 9:657-63.

[24] Rao B, Zhong X, Wang Y, Wu Q, Jiang Z, Ma L. Efficient vectors for expression cloning of large numbers of PCR fragments in P. pastoris. Yeast 2010:285-92.

[25] Gibson D G, Young L, Chuang R, Venter J C, Hutchison C A, Smith H O. Enzymatic assembly of DNA molecules up to several hundred kilobases. Nat Methods 2009; 6:343-5.

[26] Foster T J, Lundblad V, Hanley-Way S, Halling S M, Kleckner N. Three Tn10-associated excision events: relationship to transposition and role of direct and inverted repeats. Cell 1981; 23:215-27.

[27] Egner C, Berg D E. Excision of transposon Tn5 is dependent on the inverted repeats but not on the transposase function of Tn5. Proc Natl Acad Sci USA 1981; 78:459-63.
[28] Hartner F S, Ruth C, Langenegger D, Johnson S N, Hyka P, Lin-Cereghino G P, et al. Promoter library designed for fine-tuned gene expression in *Pichia pastoris*. Nucleic Acids Res 2008; 36:e76.
[29] Näätsaari L, Mistlberger B, Ruth C, Hajek T, Hartner F S, Glieder A. Deletion of the *Pichia pastoris* KU70 homologue facilitates platform strain generation for gene expression and synthetic biology. PLoS One 2012; 7:e39720.
[30] Guerfal M, Ryckaert S, Jacobs P P, Ameloot P, Van Craenenbroeck K, Derycke R, et al. The HAC1 gene from *Pichia pastoris*: characterization and effect of its overexpression on the production of secreted, surface displayed and membrane proteins. Microb Cell Fact 2010; 9:49-60.
[31] Prielhofer R, Maurer M, Klein J, Wenger J, Kiziak C, Gasser B, et al. Induction without methanol: novel regulated promoters enable high-level expression in *Pichia pastoris*. Microb Cell Fact 2013; 12:5.
[32] Delic M, Mattanovich D, Gasser B. Repressible promoters—A novel tool to generate conditional mutants in *Pichia pastoris*. Microb Cell Fact 2013; 12:6.
[33] Hartner F S, Glieder A. Regulation of methanol utilisation pathway genes in yeasts. Microb Cell Fact 2006; 5:39-59.
[34] Bernhardt R. Cytochromes P450 as versatile biocatalysts. J Biotechnol 2006; 124:128-45.

The invention claimed is:

1. A library of bidirectional expression cassettes comprising a plurality of bidirectional promoter sequences, each expression cassette comprising a bidirectional promoter sequence operably linked to a first gene in one direction, and operably linked to an oppositely oriented second gene in the other direction which is different from the first gene, wherein the bidirectional promoter sequences are functional in a *Pichia pastoris* or CHO cell, and wherein the bidirectional promoter sequences comprise two sequences selected from the group consisting of (i) SEQ ID NO:39-78, (ii) SEQ ID NO: 126-135, and (iii) SEP ID NO: 136-165.

2. A library of expression vectors each comprising at least one expression cassette as defined in claim 1.

3. The library of claim 1, wherein the genes comprise a gene of interest (GOI) or a reporter gene, and wherein (i) the genes encode protein components of a composite protein or protein complex, (ii) the first gene encodes a first protein which supports folding or targeting of a second protein, (iii) the genes are of the same metabolic or regulatory pathway, or (iv) the genes are of different pathways wherein one pathway supports other pathways.

4. The library of claim 1, wherein the plurality of bidirectional promoter sequences comprises at least 50 different bidirectional promoter sequences.

5. A method of screening or selecting a bidirectional promoter suitable for expressing at least two GOI in a host cell which comprises
   a) providing the library of claim 1, comprising the at least two GOI as the first and second genes;
   b) selecting a library member which has a proven bidirectional transcription activity; and c) identifying the bidirectional promoter sequence comprised in the selected library member and/or using the same for producing an expression construct to express said at least two GOI under the transcriptional control of said bidirectional promoter sequence.

6. The method according to claim 5, wherein the transcription activity is qualitatively and/or quantitatively determined.

7. The method of claim 5, wherein the library member is selected according to the transcription activity of the first and second genes, which is differently regulated, preferably any of a constitutive activity, or activity induced or de-repressed by a carbon source.

8. The library of claim 3, wherein the composite protein is a heterodimeric protein.

9. The library of claim 3, wherein the protein complex is formed by interaction of the protein components.

* * * * *

SEQUENCE LISTING

```
<160> NUMBER OF SEQ ID NOS: 507

<210> SEQ ID NO 1
<211> LENGTH: 997
<212> TYPE: DNA
<213> ORGANISM: Artificial Sequence
<220> FEATURE:
<223> OTHER INFORMATION: Promotor

<400> SEQUENCE: 1
gttggtattg tgaaatagac gcagatcggg aacactgaaa aataacagtt attattcgag      60
atctaacatc caaagacgaa aggttgaatg aaacttttt gccatccgac atccacaggt     120
ccattctcac acataagtgc caaacgcaac aggaggggat acactagcag cagaccgttg     180
caaacgcagg acctccactc ctcttctcct caacacccac ttttgccatc gaaaaaccag     240
cccagttatt gggcttgatt ggagctcgct cattccaatt ccttctatta ggctactaac     300
accatgactt tattagcctg tctatcctgg cccccctggc gaggttcatg tttgtttatt     360
tccgaatgca acaagctccg cattacaccc gaacatcact ccagatgagg gctttctgag     420
tgtggggtca aatagtttca tgttcccaa atggcccaaa actgacagtt taaacgctgt     480
cttggaacct aatatgacaa aagcgtgatc tcatccaaga tgaactaagt ttggttcgtt     540
gaaatgctaa cggccagttg gtcaaaaaga aacttccaaa agtcggcata ccgtttgtct     600
tgtttggtat tgattgacga atgctcaaaa ataatctcat taatgcttag cgcagtctct     660
ctatcgcttc tgaaccccgg tgcacctgtg ccgaaacgca aatggggaaa caccegcttt     720 ttggatgatt atgcattgtc tccacattgt atgcttccaa gattctggtg ggaatactgc     780
tgatagccta acgttcatga tcaaaattta actgttctaa cccctacttg acagcaatat     840
ataaacagaa ggaagctgcc ctgtcttaaa cctttttttt atcatcatta ttagcttact     900
ttcataattg cgactggttc caattgacaa gcttttgatt ttaacgactt ttaacgacaa     960
cttgagaaga tcaaaaaaca actaattatt cgaaacg                             997

<210> SEQ ID NO 2
<211> LENGTH: 366
<212> TYPE: DNA
<213> ORGANISM: Artificial Sequence
<220> FEATURE:
<223> OTHER INFORMATION: Promotor

<400> SEQUENCE: 2
gaattagtga gataacagag ttgggtaact agagagaata atagacgtat gcatgattac      60
tacacaacgg atgtcgcact cttttccttag ttaaaactat catccaatca caagatgcgg    120
```

```
gctggaaaga cttgctcccg aaggataatc ttctgcttct atctcccttc ctcatatggt    180
ttcgcagggc tcatgcccct tcttccttcg aactgcccga tgaggaagtc cttagcctat    240
caaagaattc gggaccatca tcgatttta  gagccttacc tgatcgcaat caggatttca    300
ctactcatat aaatacatcg ctcaaagctc caactttgct tgttcataca attcttgata    360
ttcaca                                                                366

<210> SEQ ID NO 3
<211> LENGTH: 2488
<212> TYPE: DNA
<213> ORGANISM: Artificial Sequence
<220> FEATURE:
<223> OTHER INFORMATION: Promotor

<400> SEQUENCE: 3
ttttgatgtt tgatagtttg ataagagtga actttagtgt ttagaggggt tataatttgt     60
tgtaactggt tttggtctta agttaaaacg aacttgttat attaaacaca acggtcactc    120
aggatacaag aataggaaag aaaaacttta aactggggac atgttgtctt tatataattt    180
ggcggttaac ccttaatgcc cgtttccgtc tcttcatgat aacaaagctg cccatctatg    240
actgaatgtg gagaagtatc ggaacaaccc ttcactaagg atatctaggc taaactcatt    300
cgcgccttag atttctccaa ggtatcggtt aagtttcctc tttcgtactg ctaacgatg     360 gtgttgctca acaaagggat ggaacggcag ctaaagggag tgcatggaat gactttaatt    420
ggctgagaaa gtgttctatt tgtccgaatt tcttttttct attatctgtt cgtttgggcg    480
gatctctcca gtggggggta aatggaagat ttctgttcat ggggtaagga agctgaaatc    540
cttcgtttct tataggggca agtatactaa atctcggaac attgaatggg gtttactttc    600
attggctaca gaaattatta agtttgttat ggggtgaagt taccagtaat tttcatttt     660 tcacttcaac ttttgggta  tttctgtggg gtagcatagc ttgacaggta atatgatgta    720
ctatgggata ggcaagtctt tgtttcaga  taccgccaaa cgttaaatag gaccctcttg    780
gtgacttgct aacttagaaa gtcatgccca ggtgttacgt aatcttactt ggtatgactt    840
tttgagtaac ggacttgcta gagtccttac cagacttcca gtttagcaaa ccacagattg    900
atctgtcctc tggcatatct caaaccaatc aacacccgta acccctttcat gaaacaactc    960 tagaatgcgt cttatcaaca ggattgccca aaacagtaat tggggcggtg gaatctacat   1020
gggagttcca tcgttgtctc ggttttttctc cctataagct actctggaga cgaagtaact   1080
aacaccctca aatatcatta tgtcctggtc agggttcaag aaagccgtca atagagctgg   1140
aacgcaggtc cttatgaaga caaaccatct tgatgagagt ctggatgaag agtttgattt   1200
ccaggagaag aacttccgga ttatccaaca atttactcaa gagctctaca atcgactttc   1260
aagcttattg gaaaatcatc atagttgtct aaaggctaat ctagccgttg ctaccacttt   1320 gaactctat  tatggaacct ccactacgga tggatttgaa ggaaaatatc tggagatcgt   1380
caacaggata aaagacgatg tgttacccaa ttcagtggaa ccgttcaatt atacaatatt   1440
gcaaccgtta gagactctta aacagtacaa tgaagagttt gacttgttaa taaaaaaacg   1500
ttatagaaag aaattggact acgatatgct ccaatccaaa ttgtcaaaat tgaccaccga   1560
aaaagaacaa ttggaatttg acaagaggaa caactcacta gattctcaaa cggagcgtca   1620
cctagagtca gtttccaagt caattacaga aagtttggaa acagaagagg agtatctaca   1680
attgaattcc aaacttaaag tcgagctgtc cgaattcatg tcgctaaggc tttcttactt   1740
```

```
ggacccacatt tttgaaagtt tcattaaagt tcagtcaaaa attttcatgg acatttatga    1800
cacattaaag agcggactac cttatgttga ttctctatcc aaagaggatt atcagtccaa    1860
gatcttggac tctagaatag ataacattct gtcgaaaatg gaagcgctga accttcaagc    1920
ttacattgat gattagagca atgatataaa caacaattga gtgacaggtc tactttgttc    1980
tcaaaaggcc ataaccatct gtttgcatct cttatcacca caccatcctc ctcatctggc    2040
cttcaattgt ggggaacaac tagcatccca acaccagact aactccaccc agatgaaacc    2100
agttgtcgct taccagtcaa tgaatgttga gctaacgttc cttgaaactc gaatgatccc    2160
agccttgctg cgtatcatcc ctccgctatt ccgccgcttg ctccaaccat gtttccgcct    2220
ttttcgaaca agttcaaata cctatctttg gcaggacttt tcctcctgcc ttttttagcc    2280
tcaggtctcg gttagcctct aggcaaaatt tggtcttcat acctatatca acttttcatc    2340
agatagcctt tgggttcaaa aaagaactaa agcaggatgc ctgatatata aatcccagat    2400
gatctgcttt tgaaactatt ttcagtatct tgattcgttt acttacaaac aactattgtt    2460
gattttatct ggagaataat cgaacaaa                                      2488

<210> SEQ ID NO 4
<211> LENGTH: 1099
<212> TYPE: DNA
<213> ORGANISM: Artificial Sequence
<220> FEATURE:
<223> OTHER INFORMATION: Promotor

<400> SEQUENCE: 4
ttttgatgtt tgatagtttg ataagagtga actttagtgt ttagaggggt tataatttgt      60
tgtaactggt tttggtctta agttaaaacg aacttgttat attaaacaca acggtcactc     120
aggatacaag aataggaaag aaaaacttta aactggggac atgttgtctt tatataattt     180
ggcggttaac ccttaatgcc cgtttccgtc tcttcatgat aacaaagctg cccatctatg     240
actgaatgtg gagaagtatc ggaacaaccc ttcactaagg atatctaggc taaactcatt     300
cgcgccttag atttctccaa ggtatcggtt aagtttcctc tttcgtactg gctaacgatg     360
gtgttgctca acaaagggat ggaacggcag ctaaagggag tgcatggaat gactttaatt     420
ggctgagaaa gtgttctatt tgtccgaatt tcttttttct attatctgtt cgtttgggcg     480
gatctctcca gtgggggta aatggaagat ttctgttcat ggggtaagga agctgaaatc     540
cttcgtttct tataggggca agtatactaa atctcggaac attgaatggg gtttactttc     600
attggctaca gaaattatta agtttgttat ggggtgaagt taccagtaat tttcattttt     660
tcacttcaac ttttggggta tttctgtggg gtagcatagc ttgacaggta atatgatgta     720
ctatgggata ggcaagtctt gtgtttcaga taccgccaaa cgttaaatag gaccctcttg     780
gtgacttgct aacttagaaa gtcatgccca ggtgttacgt aatcttactt ggtatgactt     840
tttgagtaac ggacttgcta gagtccttac cagacttcca gtttagcaaa ccacagattg     900
atctgtcctc tggcatatct caaaccaatc aacacccgta acccttcat gaaacaactc     960 tagaatgcgt cttatcaaca ggattgccca aaacagtaat tggggcggtg gaatctacat    1020
gggagttcca tcgttgtctc ggttttttctc cctataagct actctggaga cgaagtaact    1080
aacaccctca aatatcatt                                                 1099

<210> SEQ ID NO 5
<211> LENGTH: 552
<212> TYPE: DNA
<213> ORGANISM: Artificial Sequence
```

```
<220> FEATURE:
<223> OTHER INFORMATION: Promotor

<400> SEQUENCE: 5
agcaatgata taaacaacaa ttgagtgaca ggtctacttt gttctcaaaa ggccataacc      60
atctgtttgc atctcttatc accacaccat cctcctcatc tggccttcaa ttgtggggaa     120
caactagcat cccaacacca gactaactcc acccagatga aaccagttgt cgcttaccag     180
tcaatgaatg ttgagctaac gttccttgaa actcgaatga tcccagcctt gctgcgtatc     240
atccctccgc tattccgccg cttgctccaa ccatgtttcc gccttttttcg aacaagttca    300 aatacctatc tttggcagga cttttcctcc tgccttttt agcctcaggt ctcggttagc      360
ctctaggcaa attctggtct tcatacctat atcaactttt catcagatag cctttgggtt     420
caaaaaagaa ctaaagcagg atgcctgata tataaatccc agatgatctg cttttgaaac     480
tattttcagt atcttgattc gtttacttac aaacaactat tgttgatttt atctggagaa    540
taatcgaaca aa                                                         552

<210> SEQ ID NO 6
<211> LENGTH: 1685
<212> TYPE: DNA
<213> ORGANISM: Artificial Sequence
<220> FEATURE:
<223> OTHER INFORMATION: Promotor

<400> SEQUENCE: 6
ttctctattg aacggcttga aatttggaaa ccagatgaaa aataaaagga atggaagaag      60
aatgagaaaa ggataattaa tctttggttt agctaaattc ttcattgcac tttgacctta    120
aaggggctga tttaaggtta tgccggggaa gaagaaatag cgcgatgagc aaagtcgatg    180
cctaaaggag tggttttgct acctcattta agaagagaat aggacgtgca tccagcgatg    240
cgtgctagga caaagaaccg cacttggcgg gtacaaacct gacgtcattt cctgatatta    300
ttgacatttg agctgaccaa ttaaggtgcc catccacaat agccacctgg atagcggaat    360 gcaccccat tgagttgatc aaactaccat tttgcttata cctcaagtta atgttgaact     420
accattcttc acatgctcct cctagatccc ctgtccccct tctccccctc tttcatcctt    480
taatttgcat tcttgacgg tcttctatcc ctagaaagtt tggaacgcct gctatatggt     540
taggacacga ctgactagct ataaaatttt tcagaccaga ctctttctct tcttaacgca    600
aatttaacag gcagacaaca acataggaaa gaatcaccat ataggttgga ctctttacag    660
acgtccttgg ccgttgacca tggtggtaca gttgtccaag ttctacaagt ttgtctgaag    720
aatgaagtta ttggtcttgg gtgcagcttt ccatctgttc gatttattcg gctaagagtt    780
taccattgtg tgctcgtatg gggaagggtg caaggatcag taatacagtc gaacctggag    840
tatctaccat agtggggata caatgtagtt tatctgttat ctcgattgtt cctaattaag    900
gttttctttg atcctcttct agtccacacc tcctagatga cattcgagct gcctggattg    960
gatgcctagg tttattgcct agttcaatac aattcgtgcg ggctacagta gaaggccctt   1020
acataatccg gaaagcatgg tccccacca aattgagagc ttttcagcc ttcactggtg     1080 gtatcatttt cgggagataa taaggttccg attgggaatt cccaccagag aacactatag    1140
agggaccaag ctgatgctag cctgacatcc ccaaagcaca cttcgtaatt gaaaaccgtt   1200
acctctagca cactgtccag actacccccg tcaaaaaaac gctctttttc tcgactaatt   1260
gagtcttcaa ctcatcccgt ccttgccgaa ttacttgaat tcatttcaca cctccgttgc   1320
```

| | |
|---|---|
| ttacgtactc tcaccggtct ccggtgtaca tggatccgct attgccagat atttctcata | 1380 |
| caacaatcac cagatcaagg tcgtgaacgg accaatggca tccagagcaa tcctgaacag | 1440 |
| ataggggtcc gggctgtata agtgaaata cgtgacttg aaccagcaac tatgtcccag | 1500 |
| ttgtgctaca cttaacacgc gattaccccg gagctcacca ggcctcttcc ccctctcatt | 1560 |
| ggaaccctcc tagcgcttcg aaataatggc tgcgtactat ttaactggtg ccagttcccg | 1620 |
| ctgacaatat cctttttctt ctcccttag ttccccacat atcaattgaa catatttttt | 1680 |
| acaca | 1685 |

<210> SEQ ID NO 7
<211> LENGTH: 704
<212> TYPE: DNA
<213> ORGANISM: Artificial Sequence
<220> FEATURE:
<223> OTHER INFORMATION: Promotor

<400> SEQUENCE: 7

| | |
|---|---|
| aaattaatcc ataagataag gcaaatgtgc ttaagtaatt gaaaacagtg ttgtgattat | 60 |
| ataagcatgg tatttgaata gaactactgg ggttaactta tctagtagga tggaagttga | 120 |
| gggagatcaa gatgcttaaa gaaaaggatt ggccaatatg aaagccataa ttagcaatac | 180 |
| ttatttaatc agataattgt ggggcattgt gacttgactt ttaccaggac ttcaaacctc | 240 |
| aaccatttaa acagttatag aagacgtacc gtcacttttg cttttaatgt gatctaaatg | 300 |
| tgatcacatg aactcaaact aaaatgatat cttttactgg acaaaaatgt tatcctgcaa | 360 |
| acagaaagct ttcttctatt ctaagaagaa catttacatt ggtgggaaac ctgaaaacag | 420 |
| aaaataaata ctccccagtg accctatgag caggattttt gcatccctat tgtaggcctt | 480 |
| tcaaactcac acctaatatt tcccgccact cacactatca atgatcactt cccagttctc | 540 |
| ttcttcccct attcgtacca tgcaaccctt acacgccttt tccatttcgg ttcggatgcg | 600 |
| acttccagtc tgtggggtac gtagcctatt ctcttagccg gtatttaaac atacaaattc | 660 |
| acccaaattc taccttgata aggtaattga ttaatttcat aaat | 704 |

<210> SEQ ID NO 8
<211> LENGTH: 1212
<212> TYPE: DNA
<213> ORGANISM: Artificial Sequence
<220> FEATURE:
<223> OTHER INFORMATION: Promotor

<400> SEQUENCE: 8

| | |
|---|---|
| tttcgtaaag taaataagat aaaagctagt agctgatgga agaaggaaaa aagaatttgg | 60 |
| gagcaggaca gggtatttta tagtgaggtg aattgtgaat attagagatt ggggagggt | 120 |
| ggaccaattg ttggtgtgat cattggggt gcgctatatt cgcaccagat gcggttgac | 180 |
| gtctacaata ggcagggtga aaggaattgg cacgaattc gcaccccgga gagcgctcac | 240 |
| ccccgttttc aaacagcggg gggagcacaa aatgttgaaa actacacaga tcttttcgga | 300 |
| caccggtcgc tttatgtagt cgacatgcag attctcccaa atggaaaacg agattggaca | 360 |
| atttgtggag ttgaaaggg gggtgggaat caacgaaatt agcagattca tgggcaattg | 420 |
| gcaggactgg gcagaagggg tgagaattgc aatcgaatgg aacaggcact cccgttgcga | 480 |
| aatcaaaaaa gtctcgctat ctgaactgat ttttttaag cagcaactta cggtcaatac | 540 |
| atctccgatg gaggaatttt tcacccctcg ctaactagat gggcccttc taagaaattt | 600 |
| gggtttaagg ttgggcagtc agtcagtgca ccaatgctaa ctgccatttg tccaaagagg | 660 |

```
ggtgcaagga tgagggaccg ttgagaataa gatttggggt gttaatcggt gatactgatt        720
tgtcaaagag tggggaggac tgctgggcat tgttcacccc cctagttgtt agagttcgat        780
agccggccga atcacccccc tcttcttaca taatcattgt cactatgtgg ggtctctaca        840
gtctcaccct gcgatccggg acgacgccgc gaaattaggg ggcaagtctc ctccgggcat        900
gcaatattgg taacaggatc aattgatgcg agaaagttg gaggggtgt aaaattcaag         960 cccacaaagt cacacccctta tgcctgtaga ggggcaatcg gagagcagcc atggggtgtt     1020
tcactcgcac ttgggtggta aaaggaaga aacggtttac caccatccgg catccactct       1080
ggtcgtgcaa tttggcgaga tcgcgcatcc acacctagtc tcctattcca tccaaaattt     1140
gcttacctaa tatgatcttt attgattcta ccttccccta agagtcctct agtaccgtca     1200
gaaaacgctg cg                                                          1212
```

```
<210> SEQ ID NO 9
<211> LENGTH: 560
<212> TYPE: DNA
<213> ORGANISM: Artificial Sequence
<220> FEATURE:
<223> OTHER INFORMATION: Promotor

<400> SEQUENCE: 9
tagaaagatg gaatgaacgc tacagcgagg aagagcaatt gctatatata accccagagt         60
attgcttagg ctaagttgtc aagattgggt aaacaattcg agaatcaaag attaagtaag        120
aagtgttatg ttgtaggctt gaagcttcac gcaaggaaga ctgggagaag tagttgattc        180
ctgtggtgat tgtcctgaaa tgactgtgag cgggtccgcc tagagtgttg gatccctttc        240 agtgttttcca ctaatggggt ctacattgcg tcccagatcg atagaccagg agatcaatta      300
aaccctacgc aaactatagg gcatgaatca agagtatcaa ttggcatact cggatcattt       360
tctaccgttt cataccaaga gaagatggca aaatgggact tctgcgttat catgagttgg       420
ctccatcgga atttttccaca cttcaggttt ttcagatgta ttacccttttt gagccattca    480 caatgatatc ttggtatttc aaacagttgt agcttttact ataaaagtca caccgatcac       540
aacgtttcat caatgaagat                                                   560
```

```
<210> SEQ ID NO 10
<211> LENGTH: 564
<212> TYPE: DNA
<213> ORGANISM: Artificial Sequence
<220> FEATURE:
<223> OTHER INFORMATION: Promotor

<400> SEQUENCE: 10
tgtttaagtg ggtgatgttg gaggtatttg aggtaaaata ggtttatagt ttgataacta         60
gcggagaaaa gaaggagagt ctcatctgga ggagaaataa acttacttaa atagtttttc       120
ggccatttaa ctgggttacg acatcattac gtgtaggtca gcacactgaa tagaattaga       180
ctaagtataa gcacagggag ttgggggtag ccctcgaaaa tcaggacatc tggggtaaat      240
tttccctaaa atgcgcacca actgcagtac aatatggcgt ttgggaggag caacatcccg       300
acaagattgg gatttctgta gcctttgcca taaactggac aggagtttcc acaccgtttt     360
cagccggtcc ctttttattgg ttcttcggaa ggctagagta acggcccaat gtgaagagag    420
gaacattgtt tcgttacgtt ccgaaaccta gaatggtgtt ttgggaaggg actactaaga     480
tgatgctgtg tagaagtttg agccgtagag tcccacttag agaacatcat cgaactatttt    540
```
aattagaagc tggttccgca ccca                                          564

<210> SEQ ID NO 11
<211> LENGTH: 609
<212> TYPE: DNA
<213> ORGANISM: Artificial Sequence
<220> FEATURE:
<223> OTHER INFORMATION: Promotor

<400> SEQUENCE: 11
ttaaagtgta taaattcctt tgtttcctgt tataaaagaa gaagcaacaa gcaaaggatc     60
gggaaaggag tcgaaggttg agcaagcggg ttctttatat agtgagccat tatgacatat   120
tagacatcct taccccctcga ttagagagct caaacagccg actagctagc cgctctagta   180
tgacccacgc gaaaatgagc cgagcgatgc cctctatgga acgtattgga ataggaaatg   240
gtaagcttta atgggctggg ggggaaggga attgtccttc tggtgtgatt ttttttttggc   300 attggcgcta ccagatgtct ctttcgtaag ggttcaacct cggaggccga tctttgtggt   360
ttatgtttac acatcgtatt tttcaggact aagaaaatca ctggatggca gatgtcggtc   420
tggagacttg aaacgggctt acttagtagc tttgaaactt atcagataat ccgaatgtgt   480
tgcatattgt tgcatggtca cttttccaca actttgaaac gctaatcttt gatctgaaac   540
aaacatgctt tgcctataaa ccatgtatca cccctacttc tttctccctc acagcatcag   600
cagatgaca                                                          609

<210> SEQ ID NO 12
<211> LENGTH: 637
<212> TYPE: DNA
<213> ORGANISM: Artificial Sequence
<220> FEATURE:
<223> OTHER INFORMATION: Promotor

<400> SEQUENCE: 12
tgctcaaacg agtggagagg gaaatcgatt cagcagttaa atcaatgctg gaaaatattc     60
gagattacct aatcggatct ggaacttact tcgacctgac attttcttgc ctggggagcc   120
acgatcgatt atgtaatcaa gaatatggac agagggaaac agatttagct gtcaaaagcc   180
caagagaagc taccgatcaa tggatgcgga tagataaaga aaagcctttt tttttcatta   240
gccatccgag ttgtccaatc aaatgtctgc ctgctacgct ggagaggaat cacgcgtgtt   300
taacattcgg attgtcgcct aaaataagcc tattacctac acagtaaaac ccgggggggtg   360 ctttggtatc aatgaccccg ggattttatc caccagtttt tttctttctg gcaagagtgc   420
attgcatccc cgtacaaata gtagcaacct ccacaagagg aatcccctat gagcgagaag   480
tccatagtaa taccccccgcg gaaaagagat attttgtttc cgtgttgccc ttgaacttca   540
gtttccccca tcagtttata tagtagccgg gttcccaatc tctagcccctt ctttcctcct   600 atttcattcc tctcttctta cgttatctta cattagc                            637

<210> SEQ ID NO 13
<211> LENGTH: 459
<212> TYPE: DNA
<213> ORGANISM: Artificial Sequence
<220> FEATURE:
<223> OTHER INFORMATION: Promotor

<400> SEQUENCE: 13
taacaggcac ctgaagatag gtaaaaaaaa attgcttcgt cttgttgatc tgaggacgca     60
gaggctattt atacgggtcg gctctttgaa gtggggttgg ttgaccccccc agccttatcg   120

| | | |
|---|---|---|
| aatcctaagt tcacatgtag ttcgcgcaag tattacataa gcaagaattc agctgatatc | 180 |
| tgaggaggaa tcaatcgcat ggattcgtac ttcactttag tgtaaaaaga caaatagata | 240 |
| agaaaacact ggttaatgtc ttccctgata cccaaaggat tccaccaggt tccacgatgt | 300 |
| aaggcgttca cagtgttgct gatattgctc ccaattttg catcactttt tgacctcaag | 360 |
| tatgtgttta tccttagcta cgaccccttt atcagtcagt ggagacaata ctggaggata | 420 |
| ttgatctacc aattgagctt tcagaacgaa tcagaggtc | 459 |

<210> SEQ ID NO 14
<211> LENGTH: 501
<212> TYPE: DNA
<213> ORGANISM: Artificial Sequence
<220> FEATURE:
<223> OTHER INFORMATION: Promotor

<400> SEQUENCE: 14

| | | |
|---|---|---|
| tacgattagt tagatggttg ggttgagaat agttggatgt gttcaacaaa cggaggggga | 60 |
| tttcgccacc tttaaatacc cttgccaaaa ctgattgaat tgatctgacc cctatcgcta | 120 |
| acggtaaaaa aaaaatgcgg aggagatgac cagagacgga tcggaccgaa acagatgaat | 180 |
| ggaagaggga aggagagcta aacaaagttt aaaaggttgc tagcacggta aattctacag | 240 |
| caacaaaaaa aagagagctg atagcacaga ctatcataaa tccacaagtg ttgaatggtg | 300 |
| gagctcaatt tcctctgctg acaatctctg ttgtgtaggg aatgtgagca gcgagcatgt | 360 |
| gacactttag gctacgctat cccagttgcg aaaaatgtga ggagaagaac cgaaggcaga | 420 |
| ggtagtaaac cggtggtagt gtacaaaacc aattgaaaag ttctttaaag ttatcgtttt | 480 |
| tgctagaccg tttggtttgg a | 501 |

<210> SEQ ID NO 15
<211> LENGTH: 1585
<212> TYPE: DNA
<213> ORGANISM: Artificial Sequence
<220> FEATURE:
<223> OTHER INFORMATION: Promotor

<400> SEQUENCE: 15

| | | |
|---|---|---|
| tcttctcata aaaaaggtca atctgctagt taaaatatat gctgtaaacg gattatggta | 60 |
| catcccttaa atgcagcgtt aaagaccttc ttattgggca gtatgaatgg tacttcaagg | 120 |
| tgattctgtc gagtaaggct tgaaagagta gtcgttagat ttaagtaata atagagcaga | 180 |
| gcgaatacta aacacgaaac gcgcgagcat aaaatgacaa tataaccata ttaggaagca | 240 |
| aggagatata taccaaaaac gaagacctgg tcggatctga tcagatcaca ttctttcact | 300 |
| ctacaaaatg accagagtac gaaatatacg catacattcg attcaagttt tttaaagcct | 360 |
| tacatcgtat gtctggcaaa atcagagaat gcctcgtgaa agaaaaagac tgaatccatt | 420 |
| aacttgcatg ccaactcaat cccgactgtc aatcattcat ccttgcgtct tttgaacatc | 480 |
| tatgcttcca caagtcaatt cttgatttag tatacacata accaaatttg gatcaagttt | 540 |
| gaagtaaaac tttaacttca gctccttaca tttgcactaa gatctctgct actctggtcc | 600 |
| caagtgaacc accttttgga ccctattgac cggaccttaa cttgccaaac ctaaacgctt | 660 |
| aatgcctcag acgttttaat gcctctcaac acctccaagg ttgctttctt gagcatgcct | 720 |
| actaggaact ttacgaact gtggggttgc agacagtttc aggcgtgtcc cgaccaatat | 780 |
| ggcctactag actctctgaa aaatcacagt tttccagtag ttccgatcaa attaccatcg | 840 |

```
aaatggtccc ataaacggac atttgacatc cgttcctgaa ttatagtctt ccaccgtgga      900
tcatggtgtt ccttttttc ccaaagaata tcagcatccc ttaactacgt taggtcagtg      960
atgacaatgg accaaattgt tgcaaggttt ttcttttct ttcatcggca catttcagcc     1020
tcacatgcga ctattatcga tcaatgaaat ccatcaagat tgaaatctta aaattgcccc     1080
tttcacttga caggatcctt ttttgtagaa atgtcttggt gtcctcgtcc aatcaggtag     1140
ccatctctga aatatctggc tccgttgcaa ctccgaacga cctgctggca acgtaaaatt     1200
ctccggggta aacttaaat gtggagtaat ggaaccagaa acgtctcttc ccttctctct      1260
ccttccaccg cccgttaccg tccctaggaa atttactct gctggagagc ttcttctacg      1320
gcccccttgc agcaatgctc ttcccagcat tacgttgcgg gtaaaacgga ggtcgtgtac     1380
ccgacctagc agcccaggga tggaaaagtc ccggccgtcg ctggcaataa tagcgggcgg     1440
acgcatgtca tgagattatt ggaaaccacc agaatcgaat ataaaggcg aacacctttc      1500 ccaattttgg tttctcctga cccaaagact taaatttaa tttatttgtc cctatttcaa      1560
tcaattgaac aactatcaaa acaca                                           1585

<210> SEQ ID NO 16
<211> LENGTH: 408
<212> TYPE: DNA
<213> ORGANISM: Artificial Sequence
<220> FEATURE:
<223> OTHER INFORMATION: Promotor

<400> SEQUENCE: 16
tgtttgtttg tgtaattgaa agttgttact gacaaaatag aggcacttaa gctaggggc       60 agaagtatcc ttatatatgg aggttgtgcc cactaggaat agtgaaatcc gtctgagtcc     120
tgtccgggat tcgcggcatg gatgtacgat tcccggggta acgccagaag catgagaggg     180
agccagggta tggtgtgcgc gcagcagggc aagagtcaat cgaaaactga gaactgaaag     240
ctcagactga cggatgtgat gagatgaggt cgagaaaaca ggatgcctga tggcacttaa     300
aggtcgtgta gcactggttc ttttgtttcc ctcctcccaa aaaatctggc aaaatcgtaa     360
cctaaacaga aaaataacgg acactactaa taacccaagg tattgata                  408

<210> SEQ ID NO 17
<211> LENGTH: 915
<212> TYPE: DNA
<213> ORGANISM: Artificial Sequence
<220> FEATURE:
<223> OTHER INFORMATION: Promotor

<400> SEQUENCE: 17
tttatcaatt ggttggagtt gaattattcc ggaagaatgg aaaggttggg actcgaatag      60 atttttaaatt taagcaacct aggaggttta aatagacaag gggatgggac gtcagattgt     120
ctgcaatcgc ttatatattt attgcctgac ggaataaggg ctacctggaa ttttctttttc    180 tgcgaacggg caagtgtggt gcgcggcgaa aagacttcca caaagtataa ggtgggcgga     240
actttgcgtg gtgggtgggc gagaaaggcg tccgagctcg gtgggggag atatcctga      300 aaggtagaca gctgaccgaa tgccgggtgt tactgcaatc acagacatcc gacatctagt     360
aacacaggtg acctattacg tcaaagcaac gtttctaagt tctgatgtag tatcttccaa     420
gtcttgaagc ttctgcctgt atgcagtttc gtcttgatgc ctagactgct gaatttcagc     480
caactcttgc atttctttca acagcttcac ttgcaacccc tttagtgatt ttatcttgga     540
gtaatgatct ttagggaaga cgaatccttt cccttcctgt tccatctgcg ttgacagttg     600
```

```
tttaacatca tcaagaatgt ctatttcggt caatagtttg tcctggtagt tgattccagg    660
acggatggtt tcgatgttat cagccatttg gttacaactt ctcgaatagt agaaggtaag    720 agataaattac acgatggcct ttcttgtatg gggaaaaaag tattacctca gcaattgaat   780
tttgttctca aatttgggga aaggccagcc aaagacattc ggttcccatc ctgaccatcg    840
attactaatc tccagagaaa gtgctttcga gtagccctct agaaacgttg tcacttttgc    900
gccgagtcca ctcaa                                                    915
```

<210> SEQ ID NO 18
<211> LENGTH: 671
<212> TYPE: DNA
<213> ORGANISM: Artificial Sequence
<220> FEATURE:
<223> OTHER INFORMATION: Promotor

<400> SEQUENCE: 18

```
ctgtaattcg atttgagtct aacaagcaaa caaaatacta atttatgatt gttctcctta     60
gcagttcaag acggaaccaa ttgcaatcaa tgttatgctt tgttgaatcg attaaactct    120
gtatgaataa tgtttgattt atagcaagag aagaaagatc ttctccctgg ctgcatcgct    180
cttttttatg gatttgacac cttcgagact aagaaaatca ccttacgata atagctcatc    240
gccggagcag agaaattcag gaacaaattc gggcctaact ggtgcgttta agcataata     300 tatgcttgcg attatctagt ttttattaat tgctcaagag cagctgaatc ttttccaaaa    360
tcgatgattt ttcaacgttc taaaagctaa aagttgtagt tcactctgtc agcctcgatc    420
ttagtacgtg agacggtgtc ccgagcggtt cccagacgac catttcaagg ctaatgaaaa    480
agcgcgctga cttcgcgtat ggtctatcag ttaccatttt cgtacgtctc tttcatcacc    540
tttcactttg gtgcctagta actagatctt cgaaccactg aagacagcac agtcggatta    600
atttgtcctc aaagtatcat atctgaatta ctggtcttca attgagtact tttgatacat    660
tcagaaggta g                                                         671
```

<210> SEQ ID NO 19
<211> LENGTH: 562
<212> TYPE: DNA
<213> ORGANISM: Artificial Sequence
<220> FEATURE:
<223> OTHER INFORMATION: Promotor

<400> SEQUENCE: 19

```
gaattccgag ggtggctcaa caactattca cgtgacttgg acgttggaag ttgaggtggt     60
tggtggatgt tgcacggagt atcatttgta agcatgaaat cagtctaaaa aacttgcaga    120
atagcagagc ggttcggaaa ttcattcaaa accacctcct cagattggat ctgccctact    180
ctgtttagct ctgggagatt ttctcggtcg tgttctttcg ctggtctacc cacgctatag    240
gaatcgctgt gaacgctacc ttcttcccaa cttctcggtg actattataa gccattccca    300
ctttgttttc aagcaccaac aacccacccc caccttatct actccatctt gggtgtcccc    360
gcgcctgttg caaagtccga accatagaac ccccgacctt tgtcccacta accctcagac    420
accctcggga agtcagggag aaaccactcc gaagtacatt aatcatccct cgtattctcg    480
acggtgccca ttttctttat aaaaagggag acacaggttg cttcactaac tctagacttg    540
tattctacat ccactctaca ca                                             562
```

<210> SEQ ID NO 20

<210> SEQ ID NO 20
<211> LENGTH: 478
<212> TYPE: DNA
<213> ORGANISM: Artificial Sequence
<220> FEATURE:
<223> OTHER INFORMATION: Promotor

<400> SEQUENCE: 20

```
cttagatttt ttttttttgct tggtgggatt ccttcgtttt gtgcgattac tctgaaatct    60
agaaaatttg aaatctatcc agctgcttca ttgacatctc tccagccttt tatattgttc   120
acccttctcc acatcgatat cgcctatgaa tcttgaatag cctctggaaa aagaggtta    180
caagactaag atacctcctt tcgagtcgtg caccaatccc ccgcgttat cgttaagctg    240
ccttcagttg tctctccccc agctctaagc tacttgtagg aattacgcaa tccttgttga   300
gtttgaaccc ttctggttgg ggtattttc aagttaaagt tacgtcattt ccattggaaa    360
gaacagggat tccctctttt ttctcttttt ggcaggtctg tttgaatcac tttcctccgc   420
gagcccctag acaacctcct tcatagcctt ttatcactac tgttttgaca ctccagaa     478
```

<210> SEQ ID NO 21
<211> LENGTH: 966
<212> TYPE: DNA
<213> ORGANISM: Artificial Sequence
<220> FEATURE:
<223> OTHER INFORMATION: Promotor

<400> SEQUENCE: 21

```
ggtcgaacca atcaaggagg aagggacagc aactaaaaaa agattggctt atctatgcaa    60
aatgatgata tgttttaat caacgtgaag agaacgacag agataaaag cgactcaatg    120
ttgtgtatag aaaatgcttg tggggctagg gatttgaaga aagtaggag actaataacc   180
tggttgagga gatatgcgat atgatgatct gttaatatgg taaagaaaa gaatttcccg   240
atttggatat ggagcgattt ggtgcaactt ttatatatga catactcttg atgtgtacaa   300
cttcaagtat ccgcagtgaa gttaactacc tgaagaatga aagccagcgc agtagagtaa   360
acaagcgaca aaagactaa tattatgaaa gactatgtag atatgaatta aaatcccgaa    420
acaaaccatc aggaaaacgt tacaaatcct tcagtcagtt attccccggt cgggaaaacg   480
agtatagtat gagcaggcta atccagtact ttggcaagcc tcatcctgtg caacgaaaga   540
actaaatact ataacccaat ggctcaattg attcaaaacc tccttactcg tcctatttaa   600
cttctgtaac cattacaatt ccaacgtaag aaccaactaa agttgctcct aaaatcatta   660
aaactaccgg gagttggatg gccagttccc gatttggaaa tagagacatc agaaaagtgc   720
cttcatctaa gaatggtgat agaaatagcc ataaggtgta gtagataaac agaactgtgg   780
tcactataag ccacatacag ttaaccaact agaatttgcc ttaatctttt ccgagtccga   840
gacggctctt gcacgtgatc tttaaacata gcagtttgct gattgttgct ttctaagcta   900
cactcccttc tcttttatct tgaaccagag agcggaatca tctacttacc tttgacctaa   960
attaac                                                              966
```

<210> SEQ ID NO 22
<211> LENGTH: 402
<212> TYPE: DNA
<213> ORGANISM: Artificial Sequence
<220> FEATURE:
<223> OTHER INFORMATION: Promotor

<400> SEQUENCE: 22

```
ctgaaaaaaa ctacgtttgg aaaaacgtgg gaaggaactt atgaaacgca aactcgttgg    60
```

```
tcttttctgg gatttggcgg aagctaaggt atttatatat tttcattcc gttctacggt    120 atttgaaatt tagtaaccgt tctgacgtgc tattagttga tgtcacgtgt aatggtgaaa    180
tttttcatgt tttttcttcc tacaaagcgt ttcttttgc agagctcatc acaaaaacag    240
caattgccga gatccgaccc ccaaaagcca gagccttgaa tcgcgacatt attcccgagt    300
cttaggtaat aatgtgggtt gagacatgtc gttttttaaa ctttctcaaa tcctgggctt    360
agaagtggag ttgacagaaa tcacggcgca actgcactaa aa                      402
```

<210> SEQ ID NO 23
<211> LENGTH: 389
<212> TYPE: DNA
<213> ORGANISM: Artificial Sequence
<220> FEATURE:
<223> OTHER INFORMATION: Promotor

<400> SEQUENCE: 23

```
agttaatttt caagcagttg agagaaaaaa atgcgagaga tgcaccgtta tttacccgaa     60
tatagtttgt tcgcggacat ctctcatgct aatcttgctc caaagatcaa agtcccgaga    120
actcggctca gattttccca tgtgctttcg gtaagatggt ttactgccaa ctttaagttt    180
gcccactatc gattattgga ataaagtttt tgagattatt ctgattcgaa tcgacaggga    240
aaggaatacg ttgactcact cagtacctta aactctgtaa cgccgtaga catactagca     300 agtacactac tagacctagc cacagcacga accaagaggc gagcctctca gctctgttca    360
aactttatac cccccaataa gactacaag                                      389
```

<210> SEQ ID NO 24
<211> LENGTH: 1608
<212> TYPE: DNA
<213> ORGANISM: Artificial Sequence
<220> FEATURE:
<223> OTHER INFORMATION: Promotor

<400> SEQUENCE: 24

```
ggcactggat gatgttcaaa tcttattctc gtctgaacga tcgaaaaatt tgtcttgtgg     60
gcttctgagt ggaattttct taggcgcacg gaaatacaga ggtgaatggt ttctcttggg    120
gagatacttt tttcgcgtgc tcctccgtgc ggaacttcct tctgagcttc tacctctcag    180
attagtctaa tcgcatcagg aataagactg agaatgcttt taaggagagg cttgagattg    240
gctaattgcg ttccgaagta ctctttcaaa aggagttata cccctctcaa ctacgattct    300
ctaaagaatt atcgtaggca tgctcaggcg cctcaacccc atcagtttga cgccactaga    360
tgggaccaac aaccagttac taatgagcaa ggagtaatac tcccatccga ctcaattgca    420
aacattctga gacaaccaac tctggtcata aacggcaaaa tggaaatgat gaatatattt    480
ttaggatttg agcaggcgaa ccgatatgtt atcatggatc ctacaggaag tattttgggt    540
tacatgctag aaagggatct gggcatcacc aaagctatat tgagacagat ctaccgtttg    600
catcgacctt ttacagtgga tgtaatggat actgcaggaa atgtattaat gacaatcaag    660
aggccgttta gtttcatcaa ttcgcacatc aaagctatat tacccccttt caggaacagc    720
gacccagacg aacatgtaat tggagaatcc gttcaaagct ggcatccttg agacgaaga     780 tacaatctat ttacagcaca aattggcgaa aaggacactg tctacgatca gttcgggtac    840
attgacgcac cgtttctttc ctttgagttt cctgtacttt cagaatctag gcaaacgcta    900
ggtgctgtct ctagaaactt cgtgggcttt gcaagagagc ttttcacaga tacaggagtt    960
```

```
tacatcatcc gtatggggcc tgaatctttt gtagggctag aagggaacta cgggaacaat    1020
gtggcccaac atgcccttac gctggaccaa agggctgtat tattagccaa tgccgtttca    1080
attgactttg attactttc taggcactcg tcacacagtg gtggcttcat tgggtttgag     1140
gaatagacag ggtctcgtca actcagctcc tgccaccaaa ccaatcattg atcaacgagc    1200
acacttttgt ccacgtgaga tcgctttcgc ttgcagaaag agcaatgcat gaaaacggca    1260
aacgcaaaac gagcaaaaaa acgagtaaat aactacaatt tcaccaccaa cagggtcaaa    1320
gagcttttga gacactataa aaggggcct tcccccag gttccttgaa atcctcattc       1380
aattatgttt tttactcata atttgactca attggcatct tcttctttgt tcatatacag    1440
taattgatat gacgcttagt cattattagt gttctcgact agcagtggcg aaaaaagggg    1500
gagttatttt ctagaaccga ccgcaaacta taaagaaag ctgcccctca tatacctttc     1560
gaattcttta ttttctgtgt tcttcccta tttaacatct acacaaaa                  1608
```

<210> SEQ ID NO 25
<211> LENGTH: 657
<212> TYPE: DNA
<213> ORGANISM: Artificial Sequence
<220> FEATURE:
<223> OTHER INFORMATION: Promotor

<400> SEQUENCE: 25

```
gtttctgctt ctagaagaat gtgatgtgat gagtgccaaa ctagtatcgt agatggaaga     60
gtcgcgaaaa gttatggtta ggagcaccag tatatctaat cttgcaagtg agaagaagtc   120
aagcagaaga gggatagtgt tcgatagcca cttgggccca ttaaccagct aaagggccct   180
agagatttac tttgtataga tgatatttt ctatgcttcg gggactgtgt agaccaccta    240
ttgttcaagt gcagtattaa gtgagcacct tgtgaaaaat ttccttatgg ggtataatca   300
gtaattgaag tgcgcgcctt gacttatcgc atagctttcc actgttagtc agttaaccac   360
aggaaaaagt gatggaaagc taccgtaaaa acttccgctc gtcaaattgg gtttctctaa   420
catcaactaa cgttatagga agctgaattt cccactcaat tctattagac tcacctatta   480
tgaagatgca gtcaagacgt agcaatgatt acccggatat aaataagaaa actatataag   540
cagcgcgatt tcccttctca tctacatttg agttttctta ggggtaacta attgcataag   600
cctgagaatc attaaattgc attctctttc tcttccttct cccttcaaag tcacaca      657
```

<210> SEQ ID NO 26
<211> LENGTH: 737
<212> TYPE: DNA
<213> ORGANISM: Artificial Sequence
<220> FEATURE:
<223> OTHER INFORMATION: Promotor

<400> SEQUENCE: 26

```
gttgtcaatt aaagaggtga tatattcaga agaaaggggc ctgttgctta aactaacttt    60
ggatgcacga ggctactccg ggatggcatg tcgcggattt gaaaaagaca gatcgcgaat   120
tcactgtcac tatcaagatg gattgatcag ataacgtgac acgaaagaga actggtaaag   180
gagagggtga gcaatgacag cagacaacag caatcagggg agcaatcaac cggggtaaca   240
aaggaaaagt tgagtggtta tgaattttc aggaaataaa tcgtgtctgc tatttaatat   300
atagctattg atctgtataa tattgcgtat gcaactttcc ttctcgaata aaatgcgtaa   360
ttgtaagctg ctcattgggt tcaattaaat attaattgcc cgtcactgtg ggctcccaga   420
tcaagaaaca gcagcaaaag accacgagta ccaatggaaa tcttggttct agttccgatt   480
```

```
cgtacagatg ataaaccaac aatcaatttc caacgaaaga tgtaagttgt ggatttgctt      540
gatgacttgg gacgcaataa atacccagtt gttgtacatc taacatctcg gccatcgaca      600
cgtccgttta tctcgtgcac taccgatttc caccctataa gtaaacccct ttttcctctc      660
gattatgtaa acagcttcat ttttccttac cttctgttgg ctatggttc ctggctgtta       720 agtttcatcc aaccgta                                                      737

<210> SEQ ID NO 27
<211> LENGTH: 512
<212> TYPE: DNA
<213> ORGANISM: Artificial Sequence
<220> FEATURE:
<223> OTHER INFORMATION: Promotor

<400> SEQUENCE: 27
tgttactctt acaaagaaca agtttttgt tagcaatttt tttcacaatc cgagagagag        60
cgtgagcgat caggtagtgt gtcgcacaat aagagttaac gttttcagag gtttgactgg      120
gagggtgaaa cagttagtgt gtagccattg actgttagtg cacgacttga ataactgtt       180 tgcaaagaaa tctaaatctc gaatttgtga ctgctgtaac tgaactagga aggccagacc      240
tgtaaataca cgcgatttat ctcccaaaac tagagcgatc acgtgcatta taagactaaa      300
ttgctttgtg aaaaatagtc caccctgggga accgagcatc gtccgcccat ctccaaagaa     360
gacccgcgca tactctcccg ccagcacttt tcccttcaga ttttggttac gaagcccctg      420
ctcgaaatct ttctcgatct gtgccttcac tcacctttta caaattttca ccaagttaaa     480
aaaagcttcc aggttaacta caacaatcaa ag                                    512

<210> SEQ ID NO 28
<211> LENGTH: 220
<212> TYPE: DNA
<213> ORGANISM: Artificial Sequence
<220> FEATURE:
<223> OTHER INFORMATION: Promotor

<400> SEQUENCE: 28
tgcttacttt tgtttccaaa aaaccacccc tttctgtgct gataactaaa agcacttgga       60
gagaaatcaa atcaaaagtt tcagaaaaaa aaatgctaa ctacaaacag cttacaaatt      120
ttcttggaaa atgtttacat aagcttcgat actcagatgt ctctacaaaa aatctgatcc      180
tagagataga gatcttttgg cacatttcag ggacaggaac                            220

<210> SEQ ID NO 29
<211> LENGTH: 422
<212> TYPE: DNA
<213> ORGANISM: Artificial Sequence
<220> FEATURE:
<223> OTHER INFORMATION: Promotor

<400> SEQUENCE: 29
tgtaaatgat aattgataac ttgtttagaa gtttgtatga ggagaagaaa gcttgaggat       60 ttttttctt agactccacg acgcactgaa aattttatgg aacgcgcgaa attgttttca      120
gaaagtttgc gtggtgttac ccgactgtgt ttatttcaga gagttaccct gaattctgga      180
tttggaatca gacgatttat ccgtgctcat ctgacgcgcg aattttattt ggcacatgga      240
gtctcaacat ccatcggcct ttggcctaaa ttattcaagg gagagtactg atagtcacgt      300
gacgtttcac catgtagtaa gtctttttttt ttttcagagt gactctttca cagataacag     360
```

```
cataactata tagacttcac agaggtctgt catctctaga tacctgcaca caaacttaaa    420
ca                                                                   422
```

```
<210> SEQ ID NO 30
<211> LENGTH: 1084
<212> TYPE: DNA
<213> ORGANISM: Artificial Sequence
<220> FEATURE:
<223> OTHER INFORMATION: Promotor

<400> SEQUENCE: 30
tttgaaaaga actacaacga ccactgaacg ttgagtggca ctgctattgg aaggaagttc     60
gagaaatgac ttgaaggcga gatttgtgga aggaaggatc gagtttatat agctctgaaa    120
cttttctccc taaaacacat aagccaataa aactttaaga aactagcttc tatattgtaa    180
atttaagatt attatctact ggtgcatgaa catgcacgca ttgcatcaaa aatagcattt    240
tagtaacaaa ttatcgaatt ttttaaacag tggtgcgaaa tgatattaat tatcagatca    300
tctctgggct gtgcacatta acgaccccaa aagtcaagta cagtcgtgtg gttcgtgggc    360
tttcgtacca aatggaaaaa tcacgtacaa gtatgcccag agctaagcta atcggatggc    420
aagtagaaag tggatgggtt tcacagaaca ataaagaatg agtgacggat attattggct    480
ggcaggcatt aaagatgcat aatttaagct ttctgttttc tacttttgga attgtcacaa    540
atttgaactg tggatgttat tgaaacacag acccgtataa atacctcttg agagaaattt    600
gaaagtgaag ctatttcagt gaattaatca ctcgccatac acgaggtaga taattcacgt    660
agacgaattt cttttgatcc attttattca gggtggacag tcagaagtgt tcgttcacct    720
gatatgttct agatgcagct cgaaacgctg taaaaaaaaa agtcccaaaa gtcacgtgca    780
taaaggtgta gttcaattta atggagataa cataacatct atgactcctt tcatgaatcc    840
atctcaaaaa cacaaacttt gctagaatat ctggtggcac cgattttttca tcatttcacg    900
agtttatata gcatatgcgc caacagaacg ttgcctgaca caatgttaag gcttttaaat    960
tttgcttgtg tagtaaaaag ttagtagtgt gttactcgat atcatatttc tatcagaagt   1020
ggaatattct aatctctcct ctacctttgt tacaatccgt ttcgaacaga aaaagaatt   1080
tatg                                                                1084
```

```
<210> SEQ ID NO 31
<211> LENGTH: 526
<212> TYPE: DNA
<213> ORGANISM: Artificial Sequence
<220> FEATURE:
<223> OTHER INFORMATION: Promotor

<400> SEQUENCE: 31
tttttattgg tgcttttttg aggttttttt tttgagtttc tctaactgag gcggattccc     60
tggaaggata gcgacggagc aaataggagg agacagcagg aggtgctggt tgcaaactag    120
agtaaattca tgctaccaac tgagtcgcga atcgacaggg attgctcaat attatgcagt    180
ctatcttaat tctggagaag cctttaattg agttgaaaga attgtcgtac ttaggggaat    240
acttcgtagt ttatcagttt gcattacctc ttactgataa gaattagaat ggatcatgac    300
atctgacatc tttttttttt tttcgaatca agggttgact gaattgacct tttgatttct    360
ctccgccccc accgaatgca tctggcatct gcgcgcccccc ataatgttta accgaacccc    420
tccttacgga cagtttttctc ccggtcgcgc ttagtaccct aactccttgt gttgtctgtc    480
ctcaactttt ttgagactct tcctcacttc caatacaacc accaag                   526
```

<210> SEQ ID NO 32
<211> LENGTH: 1128
<212> TYPE: DNA
<213> ORGANISM: Artificial Sequence
<220> FEATURE:
<223> OTHER INFORMATION: Promotor

<400> SEQUENCE: 32

```
tagatggtta tcttgaatgg tatttgtaag gattgatctc gaaggttgta tatagtcgtg      60
ccgtgcaagt ggaggagaat gaaagaagat gtaagaattc tggcccttgc acctgatcgc     120
gaaggtggaa atggcagaag gatcagcctg gacgaagcaa ccagttccaa ctgctaagta     180
aagaagatgc tagacgaagg agacttcaga ggtgaaaagt ttgcaagaag agagctgcgg     240
gaaataaatt ttcaatttaa ggacttgagt gcgtccatat tcgtgtacgt gtccaactgt     300
tttccattac ctaagaaaaa cataaagatt aaaaagataa acccaatcgg gaaactttag     360
cgtgccgttt cggattccga aaacttttg gagcgccaga tgactatgga agaggagtg      420
taccaaaatg gcaagtcggg ggctactcac cggatagcca atacattctc taggaaccag     480
ggatgaatcc aggttttgt tgtcacggta ggtcaagcat tcacttctta ggaatatctc      540
gttgaaagct acttgaaatc ccattgggtg cggaaccagc ttctaattaa atagttcgat     600
gatgttctct aagtgggact ctacggctca aacttctaca cagcatcatc ttagtagtcc     660
cttcccaaaa caccattcta ggtttcggaa cgtaacgaaa caatgttcct ctcttcacat     720
tgggccgtta ctctagcctt ccgaagaacc aataaaaggg accggctgaa acgggtgtgg     780
aaactcctgt ccagtttatg gcaaaggcta cagaaatccc aatcttgtcg ggatgttgct     840
cctcccaaac gccatattgt actgcagttg gtgcgcattt tagggaaaat ttaccccaga     900
tgtcctgatt ttcgagggct accccaact ccctgtgctt atacttagtc taattctatt     960
cagtgtgctg acctacacgt aatgatgtcg taacccagtt aaatggccga aaaactattt    1020
aagtaagttt atttctcctc cagatgagac tctccttctt ttctccgcta gttatcaaac    1080
tataaaccta ttttacctca aatacctcca acatcaccca cttaaaca               1128
```

<210> SEQ ID NO 33
<211> LENGTH: 1366
<212> TYPE: DNA
<213> ORGANISM: Artificial Sequence
<220> FEATURE:
<223> OTHER INFORMATION: Promotor

<400> SEQUENCE: 33

```
gaaaaggttt actatcccga tttaggcgaa agagtagac caaatatttg cgtcgttgat       60
caatttataa aaaatatgg caactttcac cagcttagct ctccagactt tttcttcccg      120
aattttggt tccgagaaat ggacctttgc tagccggtgg gaaataactt gagatgcatg      180
gacggaatca aacacggaaa atctaggtc atcctacagc aaacacctgc aaggccggga     240
aagaattgct cggtattttc tattttggga gatttgttgg cacggaagaa tcggtaactt      300
tactaatcca atactccgct cctgactgtt tcaagtcgga ccccaacttt caagtgaccc      360
aatttagcag cctgcattct cttgatttta tgggggaaac taacaatagt gttgccttga     420
ttttaagtgg cattgttctt tgaaatcgaa attggggata acgtcatacc gaaaggtaaa      480
caacttcggg gaattgccct ggttaaacat ttattaagcg agataaatag gggatagcga     540
gataggggc ggagaagaag aagggtgtta aattgctgaa atctctcaat ctggaagaaa     600
```

| | |
|---|---|
| cggaataaat taactccttc ctgagataat aagatccgac tctgctatga ccccacacgg | 660 |
| tactgacctc ggcataccccc attggatctg gtgcgaagca acaggtcctg aaaccttat | 720 |
| cacgtgtagt agattgacct tccagcaaaa aaaaggcatt atatattttg ttgttgaagg | 780 |
| ggtgaggga ggtgcaggtg gttcttttat tcgtcttgta gttaattttc ccggggttgc | 840 |
| ggagcgtcaa aagtttgccc gatctgatag cttgcaagat gccaccgctt atccaacgca | 900 |
| cttcagagag cttgccgtag aaagaacgtt ttcctcgtag tattccagca cttcatggtg | 960 |
| aagtcgctat ttcaccgaag ggggggtatt aaggttgcgc accccctccc cacacccag | 1020 |
| aatcgtttat tggctgggtt caatggcgtt tgagttagca cattttttcc ttaaacacc | 1080 |
| tccaaacacg gataaaaatg catgtgcatc ctgaaactgg tagagatgcg tactccgtgc | 1140 |
| tccgataata acagtggtgt tggggttgct gttagctcac gcactccgtt tttttttcaac | 1200 |
| cagcaaaatt cgatggggag aaacttgggg tactttgccg actcctccac catactggta | 1260 |
| tataaataat actcgcccac ttttcgtttg ctgcttttat atttcaagga ctgaaaaga | 1320 |
| ctcttcttct acttttcac actataccac agatatatct actata | 1366 |

<210> SEQ ID NO 34
<211> LENGTH: 550
<212> TYPE: DNA
<213> ORGANISM: Artificial Sequence
<220> FEATURE:
<223> OTHER INFORMATION: Promotor

<400> SEQUENCE: 34

| | |
|---|---|
| tgttgtagtt ttaatatagt ttgagtatga gatggaactc agaacgaagg aattatcacc | 60 |
| agtttatata ttctgaggaa agggtgtgtc ctaaattgga cagtcacgat ggcaataaac | 120 |
| gctcagccaa tcagaatgca ggagcctaaa attgttgtat tattgctgca agatttatgt | 180 |
| gggttcacat tccactgaat ggttttcact gtagaattgg tgtcctagtt gttatgtttc | 240 |
| gagatgtttt caagaaaaac taaaatgcac aaactgacca ataatgtgcc gtcgcgcttg | 300 |
| gtacaaacgt caggattgcc accactttt tcgcactctg gtacaaaagt tcgcacttcc | 360 |
| cactcgtatg taacgaaaaa cagagcagtc tatccagaac gagacaaatt agcgcgtact | 420 |
| gtcccattcc ataaggtatc ataggaaacg agagtcctcc ccccatcacg tatatataaa | 480 |
| cacactgata tcccacatcc gcttgtcacc aaactaatac atccagttca agttacctaa | 540 |
| acaaatcaaa | 550 |

<210> SEQ ID NO 35
<211> LENGTH: 416
<212> TYPE: DNA
<213> ORGANISM: Artificial Sequence
<220> FEATURE:
<223> OTHER INFORMATION: Promotor

<400> SEQUENCE: 35

| | |
|---|---|
| ttttctttac ctggatataa ataaaaaaaa ggaaacacaa tctctgtttc aagaaattag | 60 |
| ggatttagt ctgcttatat acttcgcgct accccgcgac ccgagcaact actagcctta | 120 |
| caaacgcttt gcactcagaa aacaagtgcg acatttgct tttttcaaa ctgtgacgtt | 180 |
| agcgacaacc ctggtttgaa ctcgttttcg accaataaga tcatcgcaac cgatcagccc | 240 |
| ggtctcaatt gtacgtgtac aactcagcat ggccgcaaat aaggaacggt accttttgtg | 300 |
| gccaaatgag tggcgttgct gctaacaagg tgagccatca actggtatat atagacgagt | 360 |
| tccctcctac ctgcttttc tccttttttt tattgctcaa ctactatcga taaaac | 416 |

<210> SEQ ID NO 36
<211> LENGTH: 365
<212> TYPE: DNA
<213> ORGANISM: Artificial Sequence
<220> FEATURE:
<223> OTHER INFORMATION: Promotor

<400> SEQUENCE: 36

```
ttttactacg atagacacaa gaagaagcag gaggggggagg atctggatat ttataagagt      60
ctcccataga taacgatttg gcacttttg ccatcagtgc caacagtatt tcgcactgcg       120
acactcccga ctgaaatggg atgcaagttt attatgagtt ctggtagcat agaaatggga      180
catgttctta cagtttcaaa tttacgcacg ctctgcctct aggagtacgg ctcagttcat      240
cgcgtaccgt gtcgtatcaa cattacggtt tggcactgca ttgtccacct taactctttt     300
catctataaa tacaagacga gtgcgtcctt ttctagactc acccataaac aaataatcaa     360
taaat                                                                 365
```

<210> SEQ ID NO 37
<211> LENGTH: 247
<212> TYPE: DNA
<213> ORGANISM: Artificial Sequence
<220> FEATURE:
<223> OTHER INFORMATION: Promotor

<400> SEQUENCE: 37

```
ttgatccagc tgtaaaggga gaaggatgca gttccaaggc tgattgagtt aactactgat      60
gcaagttaga gaacctagaa tagagtctca aattttcttg cacttttggc acagtgtgca     120
acaatgatta acataaattt tcgcgtgttt tgttttaata ccatgaatat aaatacaaaa     180
gatgcacgta ttcccctttt ctagtttgtt tgtgttttg ctaaatagtc cataaagaag      240
ttgaacc                                                                247
```

<210> SEQ ID NO 38
<211> LENGTH: 589
<212> TYPE: DNA
<213> ORGANISM: Artificial Sequence
<220> FEATURE:
<223> OTHER INFORMATION: Promotor

<400> SEQUENCE: 38

```
cgttctacta gcgtgaagct tttgttgtat aaaggatgaa gggctgaatt atccaagtcg      60
cgctctcaag cagatgttgg gaggtattct gattcattct ggggatggtt aagttagctt     120
ggcctacaag ataaattcat tcaaataat catgctttga aactaaattc acgagtaaca      180
agtgaaccaa gttgcctgca cctacgagga tgttgttttg aactcagtca tgaaccattg     240
agtactgact ccaagatcgt aactgctccg tccttggaag actgactcca tacatttgat     300
gaaattcagc ccggttgtca tgcttataaa aaatctctac ttaagatctc tcatctgtac     360
agacagagac tttgttagca ctcattgacg actctctgtt ttctgccgtt ctgcctttct     420
gtttgaccag gactatgatc caaagaattc ttgggttatt ccaaatacgt catattgatt     480
attacccttt taggtaataa tatggaaatt gaaaatgaa atggctggta caacctatcc       540
tcctctttag atcacattct cttccagatc aacaattgag ctataactc                 589
```

<210> SEQ ID NO 39
<211> LENGTH: 336
<212> TYPE: DNA

<213> ORGANISM: Artificial Sequence
<220> FEATURE:
<223> OTHER INFORMATION: Promotor

<400> SEQUENCE: 39

```
ggaggggggag gatctggata tttataagag tctcccatag ataacgattt ggcactttt      60
gccatcagtg ccaacagtat ttcgcactgc gacactcccg actgaaatgg gatgcaagtt    120
tattatgagt tctggtagca tagaaatggg acatgttctt acagtttcaa atttacgcac    180
gctctgcctc taggagtacg gctcagttca tcgcgtaccg tgtcgtatca acattacggt    240
ttggcactgc attgtccacc ttaactcttt tcatctataa atacaagacg agtgcgtcct    300
tttctagact cacccataaa caaataatca ataaat                              336
```

<210> SEQ ID NO 40
<211> LENGTH: 336
<212> TYPE: DNA
<213> ORGANISM: Artificial Sequence
<220> FEATURE:
<223> OTHER INFORMATION: Promotor

<400> SEQUENCE: 40

```
ttttactacg atagacacaa gaagtaagag tctcccatag ataacgattt ggcactttt      60
gccatcagtg ccaacagtat ttcgcactgc gacactcccg actgaaatgg gatgcaagtt    120
tattatgagt tctggtagca tagaaatggg acatgttctt acagtttcaa atttacgcac    180
gctctgcctc taggagtacg gctcagttca tcgcgtaccg tgtcgtatca acattacggt    240
ttggcactgc attgtccacc ttaactcttt tcatctataa atacaagacg agtgcgtcct    300
tttctagact cacccataaa caaataatca ataaat                              336
```

<210> SEQ ID NO 41
<211> LENGTH: 336
<212> TYPE: DNA
<213> ORGANISM: Artificial Sequence
<220> FEATURE:
<223> OTHER INFORMATION: Promotor

<400> SEQUENCE: 41

```
ttttactacg atagacacaa gaagaagcag gaggggagg atctggattt ggcactttt       60
gccatcagtg ccaacagtat ttcgcactgc gacactcccg actgaaatgg gatgcaagtt    120
tattatgagt tctggtagca tagaaatggg acatgttctt acagtttcaa atttacgcac    180
gctctgcctc taggagtacg gctcagttca tcgcgtaccg tgtcgtatca acattacggt    240
ttggcactgc attgtccacc ttaactcttt tcatctataa atacaagacg agtgcgtcct    300
tttctagact cacccataaa caaataatca ataaat                              336
```

<210> SEQ ID NO 42
<211> LENGTH: 336
<212> TYPE: DNA
<213> ORGANISM: Artificial Sequence
<220> FEATURE:
<223> OTHER INFORMATION: Promotor

<400> SEQUENCE: 42

```
ttttactacg atagacacaa gaagaagcag gaggggagg atctggatat ttataagagt     60
ctcccataga taaacagtat ttcgcactgc gacactcccg actgaaatgg gatgcaagtt   120
tattatgagt tctggtagca tagaaatggg acatgttctt acagtttcaa atttacgcac   180
gctctgcctc taggagtacg gctcagttca tcgcgtaccg tgtcgtatca acattacggt   240
```

```
ttggcactgc attgtccacc ttaactcttt tcatctataa atacaagacg agtgcgtcct    300
tttctagact cacccataaa caaataatca ataaat                              336

<210> SEQ ID NO 43
<211> LENGTH: 336
<212> TYPE: DNA
<213> ORGANISM: Artificial Sequence
<220> FEATURE:
<223> OTHER INFORMATION: Promotor

<400> SEQUENCE: 43
ttttactacg atagacacaa gaagaagcag gaggggagg atctggatat ttataagagt     60
ctcccataga taacgatttg gcacttttg ccatcacccg actgaaatgg gatgcaagtt    120
tattatgagt tctggtagca tagaaatggg acatgttctt acagtttcaa atttacgcac   180
gctctgcctc taggagtacg gctcagttca tcgcgtaccg tgtcgtatca acattacggt   240
ttggcactgc attgtccacc ttaactcttt tcatctataa atacaagacg agtgcgtcct   300
tttctagact cacccataaa caaataatca ataaat                              336

<210> SEQ ID NO 44
<211> LENGTH: 336
<212> TYPE: DNA
<213> ORGANISM: Artificial Sequence
<220> FEATURE:
<223> OTHER INFORMATION: Promotor

<400> SEQUENCE: 44
ttttactacg atagacacaa gaagaagcag gaggggagg atctggatat ttataagagt     60
ctcccataga taacgatttg gcacttttg ccatcagtgc caacagtatt tcgcactgcg    120
tattatgagt tctggtagca tagaaatggg acatgttctt acagtttcaa atttacgcac   180
gctctgcctc taggagtacg gctcagttca tcgcgtaccg tgtcgtatca acattacggt   240
ttggcactgc attgtccacc ttaactcttt tcatctataa atacaagacg agtgcgtcct   300
tttctagact cacccataaa caaataatca ataaat                              336

<210> SEQ ID NO 45
<211> LENGTH: 336
<212> TYPE: DNA
<213> ORGANISM: Artificial Sequence
<220> FEATURE:
<223> OTHER INFORMATION: Promotor

<400> SEQUENCE: 45
ttttactacg atagacacaa gaagaagcag gaggggagg atctggatat ttataagagt     60
ctcccataga taacgatttg gcacttttg ccatcagtgc caacagtatt tcgcactgcg    120
acactcccga ctgaaatggg atgcaatggg acatgttctt acagtttcaa atttacgcac   180
gctctgcctc taggagtacg gctcagttca tcgcgtaccg tgtcgtatca acattacggt   240
ttggcactgc attgtccacc ttaactcttt tcatctataa atacaagacg agtgcgtcct   300
tttctagact cacccataaa caaataatca ataaat                              336

<210> SEQ ID NO 46
<211> LENGTH: 336
<212> TYPE: DNA
<213> ORGANISM: Artificial Sequence
<220> FEATURE:
<223> OTHER INFORMATION: Promotor
```

<400> SEQUENCE: 46

```
tttactacg atagacacaa gaagaagcag gaggggagg atctggatat ttataagagt    60
ctcccataga taacgatttg gcacttttg ccatcagtgc aacagtatt tcgcactgcg   120
acactcccga ctgaaatggg atgcaagttt attatgagtt ctggtagcaa atttacgcac  180
gctctgcctc taggagtacg gctcagttca tcgcgtaccg tgtcgtatca acattacggt  240
ttggcactgc attgtccacc ttaactcttt tcatctataa atacaagacg agtgcgtcct  300
tttctagact cacccataaa caaataatca ataaat                            336
```

<210> SEQ ID NO 47
<211> LENGTH: 336
<212> TYPE: DNA
<213> ORGANISM: Artificial Sequence
<220> FEATURE:
<223> OTHER INFORMATION: Promotor

<400> SEQUENCE: 47

```
tttactacg atagacacaa gaagaagcag gaggggagg atctggatat ttataagagt    60
ctcccataga taacgatttg gcacttttg ccatcagtgc aacagtatt tcgcactgcg   120
acactcccga ctgaaatggg atgcaagttt attatgagtt ctggtagcat agaaatggga  180
catgttctta caggagtacg gctcagttca tcgcgtaccg tgtcgtatca acattacggt  240
ttggcactgc attgtccacc ttaactcttt tcatctataa atacaagacg agtgcgtcct  300
tttctagact cacccataaa caaataatca ataaat                            336
```

<210> SEQ ID NO 48
<211> LENGTH: 336
<212> TYPE: DNA
<213> ORGANISM: Artificial Sequence
<220> FEATURE:
<223> OTHER INFORMATION: Promotor

<400> SEQUENCE: 48

```
tttactacg atagacacaa gaagaagcag gaggggagg atctggatat ttataagagt    60
ctcccataga taacgatttg gcacttttg ccatcagtgc aacagtatt tcgcactgcg   120
acactcccga ctgaaatggg atgcaagttt attatgagtt ctggtagcat agaaatggga  180
catgttctta cagtttcaaa tttacgcacg ctctgcaccg tgtcgtatca acattacggt  240
ttggcactgc attgtccacc ttaactcttt tcatctataa atacaagacg agtgcgtcct  300
tttctagact cacccataaa caaataatca ataaat                            336
```

<210> SEQ ID NO 49
<211> LENGTH: 336
<212> TYPE: DNA
<213> ORGANISM: Artificial Sequence
<220> FEATURE:
<223> OTHER INFORMATION: Promotor

<400> SEQUENCE: 49

```
tttactacg atagacacaa gaagaagcag gaggggagg atctggatat ttataagagt    60
ctcccataga taacgatttg gcacttttg ccatcagtgc aacagtatt tcgcactgcg   120
acactcccga ctgaaatggg atgcaagttt attatgagtt ctggtagcat agaaatggga  180
catgttctta cagtttcaaa tttacgcacg ctctgcctct aggagtacgg ctcagttcat  240
ttggcactgc attgtccacc ttaactcttt tcatctataa atacaagacg agtgcgtcct  300
tttctagact cacccataaa caaataatca ataaat                            336
```

<210> SEQ ID NO 50
<211> LENGTH: 336
<212> TYPE: DNA
<213> ORGANISM: Artificial Sequence
<220> FEATURE:
<223> OTHER INFORMATION: Promotor

<400> SEQUENCE: 50
ttttactacg atagacacaa gaagaagcag gagggggagg atctggatat ttataagagt 60
ctcccataga taacgatttg gcactttttg ccatcagtgc caacagtatt tcgcactgcg 120
acactcccga ctgaaatggg atgcaagttt attatgagtt ctggtagcat agaaatggga 180
catgttctta cagtttcaaa tttacgcacg ctctgcctct aggagtacgg ctcagttcat 240
cgcgtaccgt gtcgtatcaa cattctcttt tcatctataa atacaagacg agtgcgtcct 300
tttctagact cacccataaa caaataatca ataaat 336

<210> SEQ ID NO 51
<211> LENGTH: 336
<212> TYPE: DNA
<213> ORGANISM: Artificial Sequence
<220> FEATURE:
<223> OTHER INFORMATION: Promotor

<400> SEQUENCE: 51
ttttactacg atagacacaa gaagaagcag gagggggagg atctggatat ttataagagt 60
ctcccataga taacgatttg gcactttttg ccatcagtgc caacagtatt tcgcactgcg 120
acactcccga ctgaaatggg atgcaagttt attatgagtt ctggtagcat agaaatggga 180
catgttctta cagtttcaaa tttacgcacg ctctgcctct aggagtacgg ctcagttcat 240
cgcgtaccgt gtcgtatcaa cattacggtt tggcactgca ttgtccaccg agtgcgtcct 300
tttctagact cacccataaa caaataatca ataaat 336

<210> SEQ ID NO 52
<211> LENGTH: 336
<212> TYPE: DNA
<213> ORGANISM: Artificial Sequence
<220> FEATURE:
<223> OTHER INFORMATION: Promotor

<400> SEQUENCE: 52
ttttactacg atagacacaa gaagaagcag gagggggagg atctggatat ttataagagt 60
ctcccataga taacgatttg gcactttttg ccatcagtgc caacagtatt tcgcactgcg 120
acactcccga ctgaaatggg atgcaagttt attatgagtt ctggtagcat agaaatggga 180
catgttctta cagtttcaaa tttacgcacg ctctgcctct aggagtacgg ctcagttcat 240
cgcgtaccgt gtcgtatcaa cattacggtt tggcactgca ttgtccacct taactctttt 300
catctataaa tacccataaa caaataatca ataaat 336

<210> SEQ ID NO 53
<211> LENGTH: 336
<212> TYPE: DNA
<213> ORGANISM: Artificial Sequence
<220> FEATURE:
<223> OTHER INFORMATION: Promotor

<400> SEQUENCE: 53
ttttactacg atagacacaa gaagaagcag gagggggagg atctggatat ttataagagt 60

```
ctcccataga taacgatttg gcacttttg ccatcagtgc caacagtatt tcgcactgcg    120
acactcccga ctgaaatggg atgcaagttt attatgagtt ctggtagcat agaaatggga    180
catgttctta cagtttcaaa tttacgcacg ctctgcctct aggagtacgg ctcagttcat    240
cgcgtaccgt gtcgtatcaa cattacggtt tggcactgca ttgtccacct taactctttt    300
catctataaa tacaagacga gtgcgtcctt ttctag                              336
```

<210> SEQ ID NO 54
<211> LENGTH: 292
<212> TYPE: DNA
<213> ORGANISM: Artificial Sequence
<220> FEATURE:
<223> OTHER INFORMATION: Promotor

<400> SEQUENCE: 54

```
taaggtggac aatgcagtgc caaaccgtaa tgttgatacg acacggtacg cgatgaactg     60
agccgtactc ctagaggcag agcgtgcgta aatttgaaac tgtaagaaca tgtcccattt    120
ctatgctacc agaactcata ataaacttgc atcccatttc agtcgggagt gtcgcagtgc    180
gaaatactgt tggcactgat ggcaaaaagt gccaaatcgt tatctatggg agactcttat    240
aaatatccag atcctccccc tcctgcttct cttgtgtct atcgtagtaa aa             292
```

<210> SEQ ID NO 55
<211> LENGTH: 219
<212> TYPE: DNA
<213> ORGANISM: Artificial Sequence
<220> FEATURE:
<223> OTHER INFORMATION: Promotor

<400> SEQUENCE: 55

```
gaggcagagc gtgcgtaaat ttgaaactgt aagaacatgt cccatttcta tgctaccaga     60
actcataata aacttgcatc ccatttcagt cgggagtgtc gcagtgcgaa atactgttgg    120
cactgatggc aaaaagtgcc aaatcgttat ctatgggaga ctcttataaa tatccagatc    180 ctcccccctcc tgcttcttct tgtgtctatc gtagtaaaa                          219
```

<210> SEQ ID NO 56
<211> LENGTH: 146
<212> TYPE: DNA
<213> ORGANISM: Artificial Sequence
<220> FEATURE:
<223> OTHER INFORMATION: Promotor

<400> SEQUENCE: 56

```
ttgcatccca tttcagtcgg gagtgtcgca gtgcgaaata ctgttggcac tgatggcaaa     60
aagtgccaaa tcgttatcta tgggagactc ttataaatat ccagatcctc cccctcctgc    120
ttcttcttgt gtctatcgta gtaaaa                                         146
```

<210> SEQ ID NO 57
<211> LENGTH: 73
<212> TYPE: DNA
<213> ORGANISM: Artificial Sequence
<220> FEATURE:
<223> OTHER INFORMATION: Promotor

<400> SEQUENCE: 57

```
ttatctatgg gagactctta taaatatcca gatcctcccc ctcctgcttc ttcttgtgtc     60
tatcgtagta aaa                                                        73
```

```
<210> SEQ ID NO 58
<211> LENGTH: 292
<212> TYPE: DNA
<213> ORGANISM: Artificial Sequence
<220> FEATURE:
<223> OTHER INFORMATION: Promotor

<400> SEQUENCE: 58
cgatttggca cttttgcca tcagtgccaa cagtatttcg cactgcgaca ctcccgactg      60
aaatgggatg caagtttatt atgagttctg gtagcataga aatgggacat gttcttacag    120
tttcaaattt acgcacgctc tgcctctagg agtacggctc agttcatcgc gtaccgtgtc    180
gtatcaacat tacggtttgg cactgcattg tccaccttaa ctcttttcat ctataaatac    240
aagacgagtg cgtcctttc tagactcacc cataaacaaa taatcaataa at             292

<210> SEQ ID NO 59
<211> LENGTH: 219
<212> TYPE: DNA
<213> ORGANISM: Artificial Sequence
<220> FEATURE:
<223> OTHER INFORMATION: Promotor

<400> SEQUENCE: 59
gtttattatg agttctggta gcatagaaat gggacatgtt cttacagttt caaatttacg     60
cacgctctgc ctctaggagt acggctcagt tcatcgcgta ccgtgtcgta tcaacattac    120
ggtttggcac tgcattgtcc accttaactc ttttcatcta aaatacaag acgagtgcgt    180 ccttttctag actcacccat aaacaaataa tcaataaat                           219

<210> SEQ ID NO 60
<211> LENGTH: 146
<212> TYPE: DNA
<213> ORGANISM: Artificial Sequence
<220> FEATURE:
<223> OTHER INFORMATION: Promotor

<400> SEQUENCE: 60
taggagtacg gctcagttca tcgcgtaccg tgtcgtatca acattacggt ttggcactgc     60
attgtccacc ttaactcttt tcatctataa atacaagacg agtgcgtcct tttctagact    120
cacccataaa caaataatca ataaat                                         146

<210> SEQ ID NO 61
<211> LENGTH: 73
<212> TYPE: DNA
<213> ORGANISM: Artificial Sequence
<220> FEATURE:
<223> OTHER INFORMATION: Promotor

<400> SEQUENCE: 61
actcttttca tctataaata caagacgagt gcgtcctttt ctagactcac ccataaacaa     60
ataatcaata aat                                                        73

<210> SEQ ID NO 62
<211> LENGTH: 292
<212> TYPE: DNA
<213> ORGANISM: Artificial Sequence
<220> FEATURE:
<223> OTHER INFORMATION: Promotor

<400> SEQUENCE: 62
ttttactacg atagacacaa gaagaagcag gaggggagg atctggatat ttataagagt      60
```

```
ctcccataga taacgatttg gcactttttg ccatcagtgc caacagtatt tcgcactgcg    120
acactcccga ccgcacgctc tgcctctagg agtacggctc agttcatcgc gtaccgtgtc    180
gtatcaacat tacggtttgg cactgcattg tccaccttaa ctcttttcat ctataaatac    240
aagacgagtg cgtccttttc tagactcacc cataaacaaa taatcaataa at            292
```

<210> SEQ ID NO 63
<211> LENGTH: 278
<212> TYPE: DNA
<213> ORGANISM: Artificial Sequence
<220> FEATURE:
<223> OTHER INFORMATION: Promotor

<400> SEQUENCE: 63

```
ttttactacg atagacacaa gaagaagcag gagggggagg atctggatat ttataagagt    60
ctcccataga taacgatttg gcactttttt gaaatgggat gcaagtttat tatgagttct    120
ggtagcatag aaatgggaca tgttcttaca gtttcaaatt tatgtcgtat caacattacg    180
gtttggcact gcattgtcca ccttaactct tttcatctat aaatacaaga cgagtgcgtc    240
cttttctaga ctcacccata aacaataat caataaat                              278
```

<210> SEQ ID NO 64
<211> LENGTH: 221
<212> TYPE: DNA
<213> ORGANISM: Artificial Sequence
<220> FEATURE:
<223> OTHER INFORMATION: Promotor

<400> SEQUENCE: 64

```
ttttactacg atagacacaa gaagaagcag gagggggagg atctggatat ttataagagt    60
cttgaaatgg gatgcaagtt tattatgagt tctggtagca tagaaatggg acatgttctt    120
acagtttcaa atttaattgt ccaccttaac tcttttcatc tataaataca agacgagtgc    180
gtccttttct agactcaccc ataaacaaat aatcaataaa t                         221
```

<210> SEQ ID NO 65
<211> LENGTH: 349
<212> TYPE: DNA
<213> ORGANISM: Artificial Sequence
<220> FEATURE:
<223> OTHER INFORMATION: Promotor

<400> SEQUENCE: 65

```
ttttactacg atagacacaa gaagaagcag gagggggagg atctggaaga gtctcccata    60
gataacgatt tggcactttt tgccatcagt gccaacagta tttcgcactg cgacactccc    120
gactgaaatg ggatgcaagt ttattatgag ttctggtagc atagaaatgg gacatgttct    180
tacagtttca aatttacgca cgctctgcct ctaggagtac ggctcagttc atcgcgtacc    240
gtgtcgtatc aacattacgg tttggcactg cattgtccac cttaactctt tcatccaag     300 acgagtgcgt ccttttctag actcacccat aaacaaataa tcaataaat                 349
```

<210> SEQ ID NO 66
<211> LENGTH: 335
<212> TYPE: DNA
<213> ORGANISM: Artificial Sequence
<220> FEATURE:
<223> OTHER INFORMATION: Promotor

<400> SEQUENCE: 66

```
ttttactacg atagacacaa gaagaagcag gagggggagg atctggatat ttataagagt    60
```

```
ctcccataga taacgatttg ccatagtatt tcgcactgcg acactcccga ctgaaatggg      120
atgcaagttt attatgagtt ctggtagcat agaaatggga catgttctta cagtttcaaa      180
tttacgcacg ctctgcctct aggagtacgg ctcagttcat cgcgtaccgt gtcgtatcaa      240
cattacggca ttgtccacct taactctttt catctataaa tacaagacga gtgcgtcctt      300
ttctagactc acccataaac aaataatcaa taaat                                 335
```

```
<210> SEQ ID NO 67
<211> LENGTH: 413
<212> TYPE: DNA
<213> ORGANISM: Artificial Sequence
<220> FEATURE:
<223> OTHER INFORMATION: Promotor

<400> SEQUENCE: 67
ttttactacg atagacacaa gaagaagcag gaggggagg atctggatat ttatatattg       60
ctgtcaagta ggggttagaa cagttaaatt ttgatcatga acgttaggct atcagcagta     120
ttcccaccag aatcttggaa gcatacaatg tggagacaat gcataatcat ccaaaaagcg     180
ggtgtttccc catttgcgag ttcaaatacc tatctttggc aggactttc ctcctgcctt      240 ttttagcctc aggtctcggt tagcctctag gcaaattctg gtcttcatac ctatatcaac     300
ttttcatcag atagcctttg ggttcaaaaa agaactaaag caggatgcct gatataaata     360
caagacgagt gcgtcctttt ctagactcac ccataaacaa ataatcaata aat            413
```

```
<210> SEQ ID NO 68
<211> LENGTH: 413
<212> TYPE: DNA
<213> ORGANISM: Artificial Sequence
<220> FEATURE:
<223> OTHER INFORMATION: Promotor

<400> SEQUENCE: 68
ttttactacg atagacacaa gaagaagcag gaggggagg atctggatat ttatatcagg       60
catcctgctt tagttctttt ttgaacccaa aggctatctg atgaaaagtt gatataggta     120
tgaagaccag aatttgccta gaggctaacc gagacctgag gctaaaaaag gcaggaggaa     180
aagtcctgcc aaagataggt atttgaactc gcaaatgggg aaacacccgc ttttggatg      240 attatgcatt gtctccacat tgtatgcttc caagattctg gtgggaatac tgctgatagc     300
ctaacgttca tgatcaaaat ttaactgttc taacccctac ttgacagcaa tatataaata     360
caagacgagt gcgtcctttt ctagactcac ccataaacaa ataatcaata aat            413
```

```
<210> SEQ ID NO 69
<211> LENGTH: 397
<212> TYPE: DNA
<213> ORGANISM: Artificial Sequence
<220> FEATURE:
<223> OTHER INFORMATION: Promotor

<400> SEQUENCE: 69
ttttactacg atagacacaa gaagaagcag gaggggagg atctggatat ttataagagt       60
ctcccataga taattaaatt ttgatcatga acgttaggct atcagcagta ttcccaccag     120
aatcttggaa gcatacaatg tggagacaat gcataatcat ccaaaaagcg ggtgtttccc     180
catttgcgag ttcaaatacc tatctttggc aggactttc ctcctgcctt ttttagcctc      240
aggtctcggt tagcctctag gcaaattctg gtcttcatac ctatatcaac ttttcatcag     300
```

```
atagcctttg ggttcaaaaa attaactctt ttcatctata aatacaagac gagtgcgtcc    360 tttttctagac tcacccataa acaaataatc aataaat                             397
```

<210> SEQ ID NO 70
<211> LENGTH: 397
<212> TYPE: DNA
<213> ORGANISM: Artificial Sequence
<220> FEATURE:
<223> OTHER INFORMATION: Promotor

<400> SEQUENCE: 70

```
ttttactacg atagacacaa gaagaagcag gaggggagg atctggatat ttataagagt      60
ctcccataga taatttttttg aacccaaagg ctatctgatg aaaagttgat ataggtatga   120
agaccagaat ttgcctagag gctaaccgag acctgaggct aaaaaaggca ggaggaaaag   180
tcctgccaaa gataggtatt tgaactcgca aatggggaaa cacccgcttt ttggatgatt   240
atgcattgtc tccacattgt atgcttccaa gattctggtg ggaatactgc tgatagccta   300
acgttcatga tcaaaattta attaactctt ttcatctata aatacaagac gagtgcgtcc   360 tttttctagac tcacccataa acaaataatc aataaat                           397
```

<210> SEQ ID NO 71
<211> LENGTH: 407
<212> TYPE: DNA
<213> ORGANISM: Artificial Sequence
<220> FEATURE:
<223> OTHER INFORMATION: Promotor

<400> SEQUENCE: 71

```
ttttactacg atagacacaa gaagaagcag gaggggagg atctggatat ttatatattg      60
ctgtcaagta ggggttagaa cagttaaatt ttgatcatga acgttaggct atcagcagta   120
ttcccaccag aatcttggaa gcatacaatg tggagacaat gcataatcat ccaaaaagcg   180
ggtgtttccc catttgcgtt atttccgaat gcaacaagct ccgcattaca cccgaacatc   240
actccagatg agggctttct gagtgtgggg tcaaatagtt tcatgttccc caaatggccc   300
aaaactgaca gtttaaacgc tgtcttggaa cttaactctt ttcatctata aatacaagac   360
gagtgcgtcc tttttctagac tcacccataa acaaataatc aataaat                 407
```

<210> SEQ ID NO 72
<211> LENGTH: 410
<212> TYPE: DNA
<213> ORGANISM: Artificial Sequence
<220> FEATURE:
<223> OTHER INFORMATION: Promotor

<400> SEQUENCE: 72

```
ttttactacg atagacacaa gaagaagcag gaggggagg atctggatat ttataagagt      60
ctcccataga taagttccaa gacagcgttt aaactgtcag ttttgggcca tttggggaac   120
atgaaactat ttgaccccac actcagaaag ccctcatctg gagtgatgtt cgggtgtaat   180
gcggagcttg ttgcattcgg aaataacgca aatggggaaa cacccgcttt ttggatgatt   240
atgcattgtc tccacattgt atgcttccaa gattctggtg ggaatactgc tgatagccta   300
acgttcatga tcaaaattta actgttctaa cccctacttg acagcaatat ataaatacaa   360
gacgagtgcg tccttttcta gactcaccca taaacaaata tcaataaat                410
```

<210> SEQ ID NO 73
<211> LENGTH: 407

-continued

```
<212> TYPE: DNA
<213> ORGANISM: Artificial Sequence
<220> FEATURE:
<223> OTHER INFORMATION: Promotor

<400> SEQUENCE: 73
ttttactacg atagacacaa gaagaagcag gaggggagg atctggatat ttataagagt    60
ctcccataga taattaaatt ttgatcatga acgttaggct atcagcagta ttcccaccag   120
aatcttggaa gcatacaatg tggagacaat gcataatcat ccaaaaagcg ggtgtttccc   180
catttgcgtt atttccgaat gcaacaagct ccgcattaca cccgaacatc actccagatg   240
agggctttct gagtgtgggg tcaaatagtt tcatgttccc caaatggccc aaaactgaca   300
gtttaaacgc tgtcttggaa cattgtccac cttaactctt ttcatctata aatacaagac   360
gagtgcgtcc ttttctagac tcacccataa acaaataatc aataaat                407

<210> SEQ ID NO 74
<211> LENGTH: 413
<212> TYPE: DNA
<213> ORGANISM: Artificial Sequence
<220> FEATURE:
<223> OTHER INFORMATION: Promotor

<400> SEQUENCE: 74
ttttactacg atagacacaa gaagaagcag gaggggagg atctggatat ttataagagt    60
ctcccataga taacgatttg gcactttttg ttccaagaca gcgtttaaac tgtcagtttt   120
gggccatttg gggaacatga aactatttga ccccacactc agaaagccct catctggagt   180
gatgttcggg tgtaatgcgg agcttgttgc attcggaaat aacgcaaatg gggaaacacc   240 cgcttttttgg atgattatgc attgtctcca cattgtatgc ttccaagatt ctggtgggaa   300
tactgctgat agcctaacgt tcatgatcaa aatttaatta actctttttca tctataaata   360 caagacgagt gcgtcctttt ctagactcac ccataaacaa ataatcaata aat           413

<210> SEQ ID NO 75
<211> LENGTH: 457
<212> TYPE: DNA
<213> ORGANISM: Artificial Sequence
<220> FEATURE:
<223> OTHER INFORMATION: Promotor

<400> SEQUENCE: 75
ttttactacg atagacacaa gaagaagcag gaggggagg atctggatat ttataagagt    60
ctcccataga taagttccaa gacagcgttt aaactgtcag ttttgggcca tttggggaac   120
atgaaactat ttgaccccac actcagaaag ccctcatctg gagtgatgtt cgggtgtaat   180
gcggagcttg ttgcattcgg aaataacgtt ccatcccttt gttgagcaac accatcgtta   240
gccagtacga aagaggaaac ttaaccgata ccttggagaa atctaaggcg cgaatgagtt   300
tagcctagat atccttagtg aagggttgtt ccgatacttc tccacattca gtcatagatg   360
ggcagctttg ttatcatgaa gttaactctt ttcatctata aatacaagac gagtgcgtcc   420
ttttctagac tcacccataa acaaataatc aataaat                            457

<210> SEQ ID NO 76
<211> LENGTH: 457
<212> TYPE: DNA
<213> ORGANISM: Artificial Sequence
<220> FEATURE:
<223> OTHER INFORMATION: Promotor
```

<400> SEQUENCE: 76

```
ttttactacg atagacacaa gaagaagcag gaggggagg atctggatat ttataagagt        60
ctcccataga taacttcatg ataacaaagc tgcccatcta tgactgaatg tggagaagta      120
tcggaacaac ccttcactaa ggatatctag gctaaactca ttcgcgcctt agatttctcc      180
aaggtatcgg ttaagtttcc tctttcgtac tggctaacga tggtgttgct caacaaaggg     240
atggaacgtt atttccgaat gcaacaagct ccgcattaca cccgaacatc actccagatg      300
agggctttct gagtgtgggg tcaaatagtt tcatgttccc caaatggccc aaaactgaca      360
gtttaaacgc tgtcttggaa cttaactctt ttcatctata aatacaagac gagtgcgtcc      420
ttttctagac tcacccataa acaataatc aataaat                                457
```

<210> SEQ ID NO 77
<211> LENGTH: 223
<212> TYPE: DNA
<213> ORGANISM: Artificial Sequence
<220> FEATURE:
<223> OTHER INFORMATION: Promotor

<400> SEQUENCE: 77

```
ttttactacg atagacacaa gaagaagcag gaggggagg atctggatat ttataagagt        60
ctcccataga taatgatgtt cgggtgtaat gcggagcttg ttgtgcattg tctccacatt     120
gtatgcttcc aagattctgg tgggaattta actcttttca tctataaata caagacgagt     180
gcgtcctttt ctagactcac ccataaacaa ataatcaata aat                         223
```

<210> SEQ ID NO 78
<211> LENGTH: 223
<212> TYPE: DNA
<213> ORGANISM: Artificial Sequence
<220> FEATURE:
<223> OTHER INFORMATION: Promotor

<400> SEQUENCE: 78

```
ttttactacg atagacacaa gaagaagcag gaggggagg atctggatat ttataagagt        60
ctcccataga taaattccca ccagaatctt ggaagcatac aatgtggaga caatgcacaa      120
caagctccgc attacacccg aacatcatta actcttttca tctataaata caagacgagt     180
gcgtcctttt ctagactcac ccataaacaa ataatcaata aat                         223
```

<210> SEQ ID NO 79
<211> LENGTH: 969
<212> TYPE: DNA
<213> ORGANISM: Artificial Sequence
<220> FEATURE:
<223> OTHER INFORMATION: Promotor

<400> SEQUENCE: 79

```
aataaaaaaa cgttatagaa agaaattgga ctacgatatg ctccaatcca aattgtcaaa       60
attgaccacc gaaaagaac aattggaatt tgacaagagg aacaactcac tagattctca      120
aacggagcgt cacctttgga aacagaagag gagtatctac aattgaattc caaacttaaa     180
gtcgagctgt ccgaattcat gtcgctaagg ctttcttact tggacccccat ttttgaaagt    240 ttcattaaag ttcagtcaaa aattttcatg gacatttatg acacattaaa gagcggacta     300
ccttatgttg attctctatc caaagaggat tatcagtcca agatcttgga ctctagaata     360
gataacattc tgtcgaaaat ggaagcgctg aaccttcaag cttacattga tgattagagc    420
aatgatataa acaacaattg agtgacaggt ctactttgtt ctcaaaaggc ataaccatc      480
```

```
tgtttgcatc tcttatcacc acaccatcct cctcatctgg ccttcaattg tggggaacaa    540
ctagcatccc aacaccagac taactccacc cagatgaaac cagttgtcgc ttaccagtca    600
atgaatgttg agctaacgtt ccttgaaact cgaatgatcc cagccttgct gcgtatcatc    660
cctccgctat tccgccgctt gctccaacca tgtttccgcc ttttttcgaac aagttcaaat   720 acctatcttt ggcaggactt ttcctcctgc cttttttagc ctcaggtctc ggttagcctc    780
taggcaaatt ctggtcttca tacctatatc aactttcat cagatagcct ttgggttcaa     840
aaaagaacta aagcaggatg cctgatatat aaatcccaga tgatctgctt ttgaaactat    900
tttcagtatc ttgattcgtt tacttacaaa caactattgt tgattttatc tggagaataa    960
tcgaacaaa                                                            969
```

<210> SEQ ID NO 80
<211> LENGTH: 901
<212> TYPE: DNA
<213> ORGANISM: Artificial Sequence
<220> FEATURE:
<223> OTHER INFORMATION: Promotor

<400> SEQUENCE: 80

```
aataaaaaaa cgttatagaa agaaattgga ctacgatatg ctccaatcca aattgtcaaa     60
attgaccacc gaaaagaac aattggaatt tgacaagagg aacaactcac tagattctca     120
aacggagcgt cacctagagt cagtttccaa gtcaattaca gaaagtttgg aaacagaaga    180
ggagtatcta caattgaatt ccaaacttaa agtcgagctg tccgaattca tgtcgctaag    240
gctttcttac ttggaccccca ttttgaaag tttcattaaa gttcagtcaa aaattttcat    300
ggacatttat gacacattaa agagcggact accttatgtt gattctctat ccaaagagga    360
ttatcagtcc aagatcttgg actctagaat agataacatt ctgtcgaaaa tggaagcgct    420
gaaccttcaa gcttacattc ctcctcatct ggccttcaat tgtggggaac aactagcatc    480
ccaacaccag actaactcca cccagatgaa accagttgtc gcttaccagt caatgaatgt    540
tgagctaacg ttccttgaaa ctcgaatgat cccagccttg ctgcgtatca tccctccgct    600
attccgccgc ttgctccaac catgtttccg ccttttttcga acaagttcaa ataccctatct   660 ttggcaggac ttttcctcct gccttttttta gcctcaggtc tcggttagcc tctaggcaaa    720
ttctggtctt catacctata tcaacttttc atcagatagc ctttgggttc aaaaaagaac    780
taaagcagga tgcctgatat ataaatccca gatgatctgc ttttgaaact attttcagta    840
tcttgattcg tttacttaca aacaactatt gttgatttta tctggagaat aatcgaacaa    900
a                                                                     901
```

<210> SEQ ID NO 81
<211> LENGTH: 975
<212> TYPE: DNA
<213> ORGANISM: Artificial Sequence
<220> FEATURE:
<223> OTHER INFORMATION: Promotor

<400> SEQUENCE: 81

```
aataaaaaaa cgttatagaa agaaattgga ctacgatatg ctccaatcca aattgtcaaa     60
attgaccacc gaaaagaac aattggaatt tgacaagagg aacaactcac tagattctca     120
aacggagcgt cacctagagt cagtttccaa gtcaattaca gaaagtttgg aaacagaaga    180
ggagtatcta caattgaatt ccaaacttaa agtcgagctg tccgaattca tgtcgctaag    240
```

```
gctttcttac ttggacccca tttttgaaag tttcattaaa gttcagtcaa aaattttcat      300
ggacatttat gacacattaa agagcggact accttatgtt gattctctat ccaaagagga      360
ttatcagtcc aagatcttgg actctagaat agataacatt ctgtcgaaaa tggaagcgct      420
gaaccttcaa gcttacattg atgattagag caatgatata aacaacaatt gagtgacagg      480
tctactttgt tctcaaaagg ccataaccat ctgtttgcat ctcttatcac cacaccatcc      540
tcctcatctg gccttcaatt gtggggaaca actagcatcc caacaccaga ctaactccac      600
ccagatgaaa ccagttgtct aacgttcctt gaaactcgaa tgatcccagc cttgctgcgt      660
atcatccctc cgctattccg ccgcttgctc caaccatgtt ccgccttttt tcgaacaagt      720
tcaaatacct atctttggca ggacttttcc tcctgccttt tttagcctca ggtctcggtt      780
agcctctagg caaattctgg tcttcatacc tatatcaact tttcatcaga tagcctttgg      840
gttcaaaaaa gaactaaagc aggatgcctg atatataaat cccagatgat ctgcttttga      900
aactattttc agtatcttga ttcgtttact tacaaacaac tattgttgat tttatctgga      960
gaataatcga acaaa                                                      975

<210> SEQ ID NO 82
<211> LENGTH: 970
<212> TYPE: DNA
<213> ORGANISM: Artificial Sequence
<220> FEATURE:
<223> OTHER INFORMATION: Promotor

<400> SEQUENCE: 82
aataaaaaaa cgttatagaa agaaattgga ctacgatatg ctccaatcca aattgtcaaa       60
attgaccacc gaaaagaac aattggaatt tgacaagagg aacaactcac tagattctca      120
aacggagcgt cacctagagt cagtttccaa gtcaattaca gaaagtttgg aaacagaaga      180
ggagtatcta caattgaatt ccaaacttaa agtcgagctg tccgaattca tgtcgctaag      240
gctttcttac ttggacccca tttttgaaag tttcattaaa gttcagtcaa aaattttcat      300
ggacatttat gacacattaa agagcggact accttatgtt gattctctat ccaaagagga      360
ttatcagtcc aagatcttgg actctagaat agataacatt ctgtcgaaaa tggaagcgct      420
gaaccttcaa gcttacattg atgattagag caatgatata aacaacaatt gagtgacagg      480
tctactttgt tctcaaaagg ccataaccat ctgtttgcat ctcttatcac cacaccatcc      540
tcctcatctg gccttcaatt gtggggaaca actagcatcc caacaccaga ctaactccac      600
ccagatgaaa ccagttgtcg cttaccagtc aatgaatgtt gagctaacgt tccttgaaac      660
tcctccgcta ttccgccgct tgctccaacc atgtttccgc cttttcgaa caagttcaaa      720 tacctatctt tggcaggact tttcctcctg cctttttag cctcaggtct cggttagcct      780
ctaggcaaat tctggtcttc atacctatat caacttttca tcagatagcc tttgggttca      840 aaaagaact aaagcaggat gcctgatata taaatcccag atgatctgct ttgaaacta      900 ttttcagtat cttgattcgt ttacttacaa acaactattg ttgattttat ctggagaata      960
atcgaacaaa                                                            970

<210> SEQ ID NO 83
<211> LENGTH: 967
<212> TYPE: DNA
<213> ORGANISM: Artificial Sequence
<220> FEATURE:
<223> OTHER INFORMATION: Promotor

<400> SEQUENCE: 83
```

```
aataaaaaaa cgttatagaa agaaattgga ctacgatatg ctccaatcca aattgtcaaa    60
attgaccacc gaaaaagaac aattggaatt tgacaagagg aacaactcac tagattctca   120
aacggagcgt cacctagagt cagtttccaa gtcaattaca gaaagtttgg aaacagaaga   180
ggagtatcta caattgaatt ccaaacttaa agtcgagctg tccgaattca tgtcgctaag   240
gctttcttac ttggacccca tttttgaaag tttcattaaa gttcagtcaa aaattttcat   300
ggacatttat gacacattaa agagcggact accttatgtt gattctctat ccaaagagga   360
ttatcagtcc aagatcttgg actctagaat agataacatt ctgtcgaaaa tggaagcgct   420
gaaccttcaa gcttacattg atgattagag caatgatata aacaacaatt gagtgacagg   480
tctactttgt tctcaaaagg ccataaccat ctgtttgcat ctcttatcac cacaccatcc   540
tcctcatctg gccttcaatt gtggggaaca actagcatcc caacaccaga ctaactccac   600
ccagatgaaa ccagttgtcg cttaccagtc aatgaatgtt gagctaacgt tccttgaaac   660
tcgaatgatc ccagccttgc tgcgtatcat ccctccgcta ttccgccgct tgctccaacc   720
atgtttccgc ttttttcgaa catcctgcct tttttagcct caggtctcgg ttagcctcta   780
ggcaaattct ggtcttcata cctatatcaa cttttcatca gatagccttt gggttcaaaa   840
aagaactaaa gcaggatgcc tgatatataa atcccagatg atctgctttt gaaactattt   900
tcagtatctt gattcgttta cttacaaaca actattgttg attttatctg gagaataatc   960
gaacaaa                                                             967

<210> SEQ ID NO 84
<211> LENGTH: 971
<212> TYPE: DNA
<213> ORGANISM: Artificial Sequence
<220> FEATURE:
<223> OTHER INFORMATION: Promotor

<400> SEQUENCE: 84
aataaaaaaa cgttatagaa agaaattgga ctacgatatg ctccaatcca aattgtcaaa    60
attgaccacc gaaaaagaac aattggaatt tgacaagagg aacaactcac tagattctca   120
aacggagcgt cacctagagt cagtttccaa gtcaattaca gaaagtttgg aaacagaaga   180
ggagtatcta caattgaatt ccaaacttaa agtcgagctg tccgaattca tgtcgctaag   240
gctttcttac ttggacccca tttttgaaag tttcattaaa gttcagtcaa aaattttcat   300
ggacatttat gacacattaa agagcggact accttatgtt gattctctat ccaaagagga   360
ttatcagtcc aagatcttgg actctagaat agataacatt ctgtcgaaaa tggaagcgct   420
gaaccttcaa gcttacattg atgattagag caatgatata aacaacaatt gagtgacagg   480
tctactttgt tctcaaaagg ccataaccat ctgtttgcat ctcttatcac cacaccatcc   540
tcctcatctg gccttcaatt gtggggaaca actagcatcc caacaccaga ctaactccac   600
ccagatgaaa ccagttgtcg cttaccagtc aatgaatgtt gagctaacgt tccttgaaac   660
tcgaatgatc ccagccttgc tgcgtatcat ccctccgcta ttccgccgct tgctccaacc   720
atgtttccgc ttttttcgaa caagttcaaa tacctatctt tggcaggact tttcctcctg   780
cctttgcaaa ttctggtctt catacctata tcaacttttc atcagatagc ctttgggttc   840
aaaaaagaac taaagcagga tgcctgatat ataaatccca gatgatctgc ttttgaaact   900
attttcagta tcttgattcg tttacttaca acaactatt gttgatttta tctggagaat   960
aatcgaacaa a                                                        971
```

<210> SEQ ID NO 85
<211> LENGTH: 971
<212> TYPE: DNA
<213> ORGANISM: Artificial Sequence
<220> FEATURE:
<223> OTHER INFORMATION: Promotor

<400> SEQUENCE: 85

```
aataaaaaaa cgttatagaa agaaattgga ctacgatatg ctccaatcca aattgtcaaa      60
attgaccacc gaaaagaac aattggaatt tgacaagagg aacaactcac tagattctca     120
aacggagcgt cacctagagt cagtttccaa gtcaattaca gaaagtttgg aaacagaaga    180
ggagtatcta caattgaatt ccaaacttaa agtcgagctg tccgaattca tgtcgctaag    240
gctttcttac ttggaccca tttttgaaag tttcattaaa gttcagtcaa aaattttcat     300
ggacatttat gacacattaa agagcggact accttatgtt gattctctat ccaaagagga    360
ttatcagtcc aagatcttgg actctagaat agataacatt ctgtcgaaaa tggaagcgct    420
gaaccttcaa gcttacattg atgattagag caatgatata acaacaatt gagtgacagg      480
tctactttgt tctcaaaagg ccataaccat ctgtttgcat ctcttatcac cacaccatcc    540
tcctcatctg gccttcaatt gtggggaaca actagcatcc caacaccaga ctaactccac    600
ccagatgaaa ccagttgtcg cttaccagtc aatgaatgtt gagctaacgt tccttgaaac    660
tcgaatgatc ccagccttgc tgcgtatcat ccctccgcta ttccgccgct tgctccaacc    720
atgtttccgc cttttcgaa caagttcaaa tacctatctt tggcaggact tttcctcctg     780
cctttttag cctcaggtct cggttagcct ctaggcaaat tctggtcttc ataccggttc     840
aaaaaagaac taaagcagga tgcctgatat ataaatccca gatgatctgc ttttgaaact    900
attttcagta tcttgattcg tttacttaca aacaactatt gttgatttta tctggagaat    960
aatcgaacaa a                                                          971
```

<210> SEQ ID NO 86
<211> LENGTH: 968
<212> TYPE: DNA
<213> ORGANISM: Artificial Sequence
<220> FEATURE:
<223> OTHER INFORMATION: Promotor

<400> SEQUENCE: 86

```
aataaaaaaa cgttatagaa agaaattgga ctacgatatg ctccaatcca aattgtcaaa      60
attgaccacc gaaaagaac aattggaatt tgacaagagg aacaactcac tagattctca     120
aacggagcgt cacctagagt cagtttccaa gtcaattaca gaaagtttgg aaacagaaga    180
ggagtatcta caattgaatt ccaaacttaa agtcgagctg tccgaattca tgtcgctaag    240
gctttcttac ttggaccca tttttgaaag tttcattaaa gttcagtcaa aaattttcat     300
ggacatttat gacacattaa agagcggact accttatgtt gattctctat ccaaagagga    360
ttatcagtcc aagatcttgg actctagaat agataacatt ctgtcgaaaa tggaagcgct    420
gaaccttcaa gcttacattg atgattagag caatgatata acaacaatt gagtgacagg      480
tctactttgt tctcaaaagg ccataaccat ctgtttgcat ctcttatcac cacaccatcc    540
tcctcatctg gccttcaatt gtggggaaca actagcatcc caacaccaga ctaactccac    600
ccagatgaaa ccagttgtcg cttaccagtc aatgaatgtt gagctaacgt tccttgaaac    660
tcgaatgatc ccagccttgc tgcgtatcat ccctccgcta ttccgccgct tgctccaacc    720
atgtttccgc cttttcgaa caagttcaaa tacctatctt tggcaggact tttcctcctg     780
```

```
cctttttag    cctcaggtct   cggttagcct   ctaggcaaat   tctggtcttc   atacctatat    840
caacttttca   tcagatagcc   tttgggttca   aaaaagaact   aaagcaggat   gcctgatata    900
taaatcccag   atgatctgct   tttgaaacta   ttttcagtat   cttgattcgt   ttacttacat    960
cgaacaaa                                                                      968
```

<210> SEQ ID NO 87
<211> LENGTH: 868
<212> TYPE: DNA
<213> ORGANISM: Artificial Sequence
<220> FEATURE:
<223> OTHER INFORMATION: Promotor

<400> SEQUENCE: 87

```
aataaaaaaa   cgttatagaa   agaaattgga   ctacgatatg   ctccaatcca   aattgtcaaa     60
attgaccacc   gaaaagaac    aattggaatt   tgacaagagg   aacaactcac   tagattctca    120
aacggagcgt   cacctagagt   cagtttccaa   gtcaattaca   gaaagtttgg   aaacagaaga    180
ggagtatcta   caattgaatt   ccaaacttaa   agtcgagctg   tccgaattca   tgtcgctaag    240
gctttcttac   ttggaccca   ttttttgaaag   tttcattaaa   gttcagtcaa   aaattttcat    300
ggacatttat   gacacattaa   agagcggact   acctatgtt   gattctctat   ccaagagga     360 ttatcagtcc   aagatcttgg   actctagaat   agataacatt   ctgtcgaaaa   tggaagcgct    420
gaaccttcaa   gcttacattc   ctcctcatct   ggccttcaat   tgtggggaac   aactagcatc    480
ccaacaccag   actaactcca   cccagatgaa   accagttgtc   gcttaccagt   caatgaatgt    540
tgagctaacg   ttccttgaaa   ctcgaatgat   cccagccttg   ctgcgtatca   tccctccgct    600
attccgccgc   ttgctccaac   catgtttccg   ccttttttcga   acatcctgcc   tttttttagcc   660 tcaggtctcg   gttagcctct   aggcaaattc   tggtcttcat   acctatatca   acttttcatc    720
agatagcctt   tgggttcaaa   aagaactaa    agcaggatgc   ctgatatata   aatcccagat    780
gatctgcttt   tgaaactatt   ttcagtatct   tgattcgttt   acttacaaac   aactattgtt    840
gattttatct   ggagaataat   cgaacaaa                                             868
```

<210> SEQ ID NO 88
<211> LENGTH: 979
<212> TYPE: DNA
<213> ORGANISM: Artificial Sequence
<220> FEATURE:
<223> OTHER INFORMATION: Promotor

<400> SEQUENCE: 88

```
attactgttt   tgggcaatcc   tgttgataag   acgcattcta   gagttgtttc   atgaaagggt     60
tacgggtgtt   gattggtttg   agatatgcca   gaggacagat   caatctgtgg   tttgctaaac    120
tggaagtctg   gtaaggactc   tagcatacca   agtaagatta   cgtaacacct   gggcatgact    180
ttctaagtta   gcaagtcacc   aagagggtcc   tatttaacgt   ttggcggtat   ctgaaacaca    240
agacttgcct   atcccatagt   acatcatatt   acctgtcaag   ctatgctacc   ccacagaaat    300
accccaaaag   ttgaagtgaa   aaatgaaaa   ttactggtaa   cttcaccca   taacaaactt     360 aataatttct   gtagccaatg   aaagtaaacc   ccattcaatg   ttccgagatt   tagtatactt    420
gcccctataa   gaaacgaagg   atttcagctt   ccttacccca   tgaacagaaa   tcttccattt    480 acccccccact  ggagagatcc   gcccaaacga   acagataata   gaaaaagaa   attcggacaa     540 atagaacact   ttctcagcca   attaaagtca   ttccatgcac   tccctttagc   tgccgttcca    600
```

```
tcccttttgtt gagcaacacc atcgttagcc agtacgaaag aggaaactta accgatacct    660
tggagaaatc taaggcgcga atgagtttag cctagatatc cttagtgaag ggttgttccg    720
atacttctcc acattcagtc atagatgggc agctttgtta tcatgaagag acggaaacgg    780
gcattaaggg ttaaccgcca aattatataa agacaacatg tccccagttt aaagtttttc    840
tttcctattc ttgtatcctg agtgaccgtt gtgtttaata taacaagttc gttttaactt    900
aagaccaaaa ccagttacaa caaattataa cccctctaaa cactaaagtt cactcttatc    960
aaactatcaa acatcaaaa                                                 979
```

<210> SEQ ID NO 89
<211> LENGTH: 960
<212> TYPE: DNA
<213> ORGANISM: Artificial Sequence
<220> FEATURE:
<223> OTHER INFORMATION: Promotor

<400> SEQUENCE: 89

```
attactgttt tgggcaatcc tgttgataag acgcattcta gagttgtttc atgaaagggt     60
tacgggtgtt gattggtttg agatatgcca gaggacagat caatctgtgg tttgctaaac    120
tggaagtctg gtaaggactc tagcaagtcc gttactcaaa aagtcatacc aagtaagatt    180
acgtaacacc tgggcatgac tttctaagtt agcaagtcac caagagggtc ctatttatag    240
tacatcatat tacctgtcaa gctatgctac cccacagaaa taccccaaaa gttgaagtga    300
aaaaatgaaa attactggta acttcacccc ataacaaact taataatttc tgtagccaat    360
gaaagtaaac cccattcaat gttccgagat ttagtatact tgcccctata agaaacgaag    420
gatttcagct tccttacccc atgaacagaa atcttccatt tacccccac tggagagatc    480 cgcccaaacg aacagataat agaaaaaaga aattcggaca aatagaacac tttctcagcc    540
aattaaagtc attccatgca ctcccttttag ctgccgttcc atccctttgt tgagcaacac    600
catcgttagc cagtacgaaa gaggaaactt aaccgatacc ttggagaaat ctaaggcgcg    660
aatgagttta gcctagatat ccttagtgaa gggttgttcc gatacttctc cacattcagt    720
catagatggg cagctttgtt atcatgaaga cacggaaacg ggcattaagg gttaaccgcc    780
aaattatata aagacaacat gtccccagtt taaagttttt ctttcctatt cttgtatcct    840
gagtgaccgt tgtgtttaat ataacaagtt cgttttaact taagaccaaa accagttaca    900
acaaattata accctctaa acactaaagt tcactcttat caaactatca acatcaaaa    960
```

<210> SEQ ID NO 90
<211> LENGTH: 962
<212> TYPE: DNA
<213> ORGANISM: Artificial Sequence
<220> FEATURE:
<223> OTHER INFORMATION: Promotor

<400> SEQUENCE: 90

```
attactgttt tgggcaatcc tgttgataag acgcattcta gagttgtttc atgaaagggt     60
tacgggtgtt gattggtttg agatatgcca gaggacagat caatctgtgg tttgctaaac    120
tggaagtctg gtaaggactc tagcaagtcc gttactcaaa aagtcatacc aagtaagatt    180
acgtaacacc tgggcatgac tttctaagtt agcaagtcac caagagggtc ctatttaacg    240
tttggcggta tctgaaacac aagacttgcc tatcccatag tacatcatat tacctgtcaa    300
gctatgctac cccacagaaa taccccaaaa gttgaagtga aaaaatgaaa attactggta    360
acttcacccc ataacaaact taataatgag atttagtata cttgccccta taagaaacga    420
```

```
aggatttcag cttccttacc ccatgaacag aaatcttcca tttaccccc  actggagaga    480 tccgcccaaa cgaacagata atagaaaaaa gaaattcgga caaatagaac actttctcag    540
ccaattaaag tcattccatg cactcccttt agctgccgtt ccatccctt  gttgagcaac    600 accatcgtta gccagtacga aagaggaaac ttaaccgata ccttggagaa atctaaggcg    660
cgaatgagtt tagcctagat atccttagtg aagggttgtt ccgatacttc tccacattca    720
gtcatagatg ggcagctttg ttatcatgaa gagacgaaaa cgggcattaa gggttaaccg    780
ccaaattata taaagacaac atgtccccag tttaaagttt ttctttccta ttcttgtatc    840
ctgagtgacc gttgtgttta ataacaagtt cgttttaa   cttaagacca aaaccagtta    900
caacaaatta taaccctctc aaacactaaa gttcactctt atcaaactat caaacatcaa    960
aa                                                                   962

<210> SEQ ID NO 91
<211> LENGTH: 950
<212> TYPE: DNA
<213> ORGANISM: Artificial Sequence
<220> FEATURE:
<223> OTHER INFORMATION: Promotor

<400> SEQUENCE: 91
attactgttt tgggcaatcc tgttgataag acgcattcta gagttgtttc atgaaagggt     60
tacgggtgtt gattggtttg agatatgcca gaggacagat caatctgtgg tttgctaaac    120
tggaagtctg gtaaggactc tagcaagtcc gttactcaaa aagtcatacc aagtaagatt    180
acgtaacacc tgggcatgac tttctaagtt agcaagtcac caagagggtc ctatttaacg    240
tttggcggta tctgaaacac aagacttgcc tatcccatag tacatcatat tacctgtcaa    300
gctatgctac cccacagaaa taccccaaaa gttgaagtga aaaaatgaaa attactggta    360
acttcacccc ataacaaact taataatttc tgtagccaat gaaagtaaac cccattcaat    420
gttccgagat ttagtatact tgcccctata agaaacgaag gattgagatc cgcccaaacg    480
aacagataat agaaaaaaga aattcggaca aatagaacac tttctcagcc aattaaagtc    540
attccatgca ctccctttag ctgccgttcc atcccttgt  tgagcaacac catcgttagc    600
cagtacgaaa gaggaaactt aaccgatacc ttggagaaat ctaaggcgcg aatgagttta    660
gcctagatat ccttagtgaa gggttgttcc gatacttctc acattcagt  catagatggg    720 cagctttgtt atcatgaaga gacggaaacg gcattaagg  gttaaccgcc aaattatata    780
aagacaacat gtccccagtt taaagttttt ctttcctatt cttgtatcct gagtgaccgt    840
tgtgtttaat ataacaagtt cgttttaact taagaccaaa accagttaca acaaattata    900 accctctaa  acactaaagt tcactcttat caaactatca acatcaaaa               950

<210> SEQ ID NO 92
<211> LENGTH: 944
<212> TYPE: DNA
<213> ORGANISM: Artificial Sequence
<220> FEATURE:
<223> OTHER INFORMATION: Promotor

<400> SEQUENCE: 92
attactgttt tgggcaatcc tgttgataag acgcattcta gagttgtttc atgaaagggt     60
tacgggtgtt gattggtttg agatatgcca gaggacagat caatctgtgg tttgctaaac    120
tggaagtctg gtaaggactc tagcaagtcc gttactcaaa aagtcatacc aagtaagatt    180
```

-continued

```
acgtaacacc tgggcatgac tttctaagtt agcaagtcac caagagggtc ctatttaacg    240
tttggcggta tctgaaacac aagacttgcc tatcccatag tacatcatat tacctgtcaa    300
gctatgctac cccacagaaa taccccaaaa gttgaagtga aaaaatgaaa attactggta    360
acttcacccc ataacaaact taataatttc tgtagccaat gaaagtaaac cccattcaat    420
gttccgagat ttagtatact tgcccctata agaaacgaag gatttcagct tccttacccc    480
atgaacagaa atcttccatt tacccccac tggagagatc cgcccaaacg aacagataat     540
tgcactccct ttagctgccg ttccatccct ttgttgagca acaccatcgt tagccagtac    600
gaaagaggaa acttaaccga taccttggag aaatctaagg cgcgaatgag tttagcctag    660
atatccttag tgaagggttg ttccgatact tctccacatt cagtcataga tgggcagctt    720
tgttatcatg aagagacgga aacgggcatt aagggttaac cgccaaatta tataaagaca    780
acatgtcccc agtttaaagt ttttctttcc tattcttgta tcctgagtga ccgttgtgtt    840
taatataaca agttcgtttt aacttaagac caaaaccagt tacaacaat tataacccct     900 ctaaacacta aagttcactc ttatcaaact atcaaacatc aaaa                     944
```

<210> SEQ ID NO 93
<211> LENGTH: 956
<212> TYPE: DNA
<213> ORGANISM: Artificial Sequence
<220> FEATURE:
<223> OTHER INFORMATION: Promotor

<400> SEQUENCE: 93

```
attactgttt tgggcaatcc tgttgataag acgcattcta gagttgtttc atgaaagggt    60
tacgggtgtt gattggtttg agatatgcca gaggacagat caatctgtgg tttgctaaac    120
tggaagtctg gtaaggactc tagcaagtcc gttactcaaa aagtcatacc aagtaagatt    180
acgtaacacc tgggcatgac tttctaagtt agcaagtcac caagagggtc ctatttaacg    240
tttggcggta tctgaaacac aagacttgcc tatcccatag tacatcatat tacctgtcaa    300
gctatgctac cccacagaaa taccccaaaa gttgaagtga aaaaatgaaa attactggta    360
acttcacccc ataacaaact taataatttc tgtagccaat gaaagtaaac cccattcaat    420
gttccgagat ttagtatact tgcccctata agaaacgaag gatttcagct tccttacccc    480
atgaacagaa atcttccatt tacccccac tggagagatc cgcccaaacg aacagataat     540 agaaaaaga aattcggaca aatagaacac tttctcagcc aattaaagtc attccatgca     600 ctcccttag ctgcaagagg aaacttaacc gataccttgg agaaatctaa ggcgcgaatg     660
agtttagcct agatatcctt agtgaagggt tgttccgata cttctccaca ttcagtcata    720
gatgggcagc tttgttatca tgaagagacg gaaacgggca ttaagggtta accgccaaat    780
tatataaaga caacatgtcc ccagtttaaa gttttctttt cctattcttg tatcctgagt    840
gaccgttgtg tttaatataa caagttcgtt ttaacttaag accaaaacca gttacaacaa    900
attataaccc ctctaaacac taaagttcac tcttatcaaa ctatcaaaca tcaaaa       956
```

<210> SEQ ID NO 94
<211> LENGTH: 974
<212> TYPE: DNA
<213> ORGANISM: Artificial Sequence
<220> FEATURE:
<223> OTHER INFORMATION: Promotor

<400> SEQUENCE: 94

```
attactgttt tgggcaatcc tgttgataag acgcattcta gagttgtttc atgaaagggt    60
```

```
tacgggtgtt gattggtttg agatatgcca gaggacagat caatctgtgg tttgctaaac    120
tggaagtctg gtaaggactc tagcaagtcc gttactcaaa aagtcatacc aagtaagatt    180
acgtaacacc tgggcatgac tttctaagtt agcaagtcac caagagggtc ctatttaacg    240
tttggcggta tctgaaacac aagacttgcc tatcccatag tacatcatat tacctgtcaa    300
gctatgctac cccacagaaa taccccaaaa gttgaagtga aaaaatgaaa attactggta    360
acttcacccc ataacaaact taataatttc tgtagccaat gaaagtaaac cccattcaat    420
gttccgagat ttagtatact tgcccctata agaaacgaag gatttcagct tccttacccc    480
atgaacagaa tcttccatt taccccccac tggagagatc cgcccaaacg aacagataat    540 agaaaaaga aattcggaca aatagaacac tttctcagcc aattaaagtc attccatgca    600
ctccctttag ctgccgttcc atcccttgt tgagcaacac catcgttagc cagtacgaaa    660
gaggaaactt aaccgatacc ttggagaaag atatccttag tgaagggttg ttccgatact    720
tctccacatt cagtcataga tgggcagctt tgttatcatg aagagacgga aacgggcatt    780
aagggttaac cgccaaatta tataagaca acatgtcccc agtttaaagt ttttctttcc    840
tattcttgta tcctgagtga ccgttgtgtt taatataaca agttcgtttt aacttaagac    900
caaaaccagt tacaacaaat tataaccccct ctaaacacta aagttcactc ttatcaaact    960
atcaaacatc aaaa                                                      974

<210> SEQ ID NO 95
<211> LENGTH: 950
<212> TYPE: DNA
<213> ORGANISM: Artificial Sequence
<220> FEATURE:
<223> OTHER INFORMATION: Promotor

<400> SEQUENCE: 95
attactgttt tgggcaatcc tgttgataag acgcattcta gagttgtttc atgaaagggt     60
tacgggtgtt gattggtttg agatatgcca gaggacagat caatctgtgg tttgctaaac    120
tggaagtctg gtaaggactc tagcaagtcc gttactcaaa aagtcatacc aagtaagatt    180
acgtaacacc tgggcatgac tttctaagtt agcaagtcac caagagggtc ctatttaacg    240
tttggcggta tctgaaacac aagacttgcc tatcccatag tacatcatat tacctgtcaa    300
gctatgctac cccacagaaa taccccaaaa gttgaagtga aaaaatgaaa attactggta    360
acttcacccc ataacaaact taataatttc tgtagccaat gaaagtaaac cccattcaat    420
gttccgagat ttagtatact tgcccctata agaaacgaag gatttcagct tccttacccc    480
atgaacagaa tcttccatt taccccccac tggagagatc cgcccaaacg aacagataat    540 agaaaaaga aattcggaca aatagaacac tttctcagcc aattaaagtc attccatgca    600
ctccctttag ctgccgttcc atcccttgt tgagcaacac catcgttagc cagtacgaaa    660
gaggaaactt aaccgatacc ttggagaaat ctaaggcgcg aatgagttta gcctagatat    720
ccttagtgaa gggttgttca gacggaaacg ggcattaagg gttaaccgcc aaattatata    780
aagacaacat gtccccagtt taagttttt ctttcctatt cttgtatcct gagtgaccgt    840
tgtgtttaat ataacaagtt cgttttaact taagaccaaa accagttaca acaaattata    900
acccctctaa acactaaagt tcactcttat caaactatca aacatcaaaa                950

<210> SEQ ID NO 96
<211> LENGTH: 692
<212> TYPE: DNA
```

<213> ORGANISM: Artificial Sequence
<220> FEATURE:
<223> OTHER INFORMATION: Promotor

<400> SEQUENCE: 96

```
agtgtgtaat catatatata ataaatgagg aataataatt gaatagagat ttaacgagtc      60
gaagtttctg aaatatacgc acagtttata tttatgattt tgatatctaa ctacagtctt     120
ctccatatat ttaactataa ataataaagt atataactct tatgaaactg tttcaccaca     180
ttttttttcta cgtaatcgaa ctccgaatgc ggttctcctg taaccttaat tgtagcatag    240
atcacttaaa taaactcatg gcctgacatc tgtacacgtt cttattggtc ttttagcaat     300
cttgaagtct ttctattgtt ccggtcggca ttacctaata aattcgaatc gagattgcta     360
gtacctgata tcatatgaag taatcatcac atgcaagttc catgataccc tctactaatg     420
gaattgaaca aagtttaagc ttctcgcacg agaccgaatc catactatgc accoctcaaa     480
gttgggatta gtcaggaaag ctgagcaatt aacttccctc gattggcctg gacttttcgc     540
ttagcctgcc gcaatcggta agtttcatta tcccagcggg gtgatagcct ctgttgctca     600
tcaggccaaa atcatatata agctgtagac ccagcacttc aattacttga aattcaccat     660
aacacttgct ctagtcaaga cttacaatta aa                                   692
```

<210> SEQ ID NO 97
<211> LENGTH: 970
<212> TYPE: DNA
<213> ORGANISM: Artificial Sequence
<220> FEATURE:
<223> OTHER INFORMATION: Promotor

<400> SEQUENCE: 97

```
ctaaatgctg tttctcttag catagtcaat gattagtttt tcactcattt gtacaacaat      60
cggtttggta tctgcaatga cactagagat aattctggag gttagcttgc atacataagc     120
cggttctgtt ccttgataat aattccaatc aaggtctagt ttgcgaagat aatctctgga     180
tagaccagct cttctcttctt cgtttaggat tttatcgcta tgcaacaccg aaatattcct     240
gtaaacccat tgatctagtg gttgatgcaa tcctatcccg tgatacttag agcagctctc     300
ttttagagcc caatactgtg ttagaatttc aaattgtcta tcttctgtgt gtcgaggaag     360
ttcacgttca agaaagttcg tttcgtctgg gtgaaaaata tcagaaaagg atcgtaaaag     420
ctgtattggg tcctcttgaa actgtttgat tgtttgtata tcagccaaat cgattcctaa     480
ttgcttaatc gaaggttttt cagactcact tcccagtttt tgtgcatctt ttcttcgaaa     540
gacaattcct actacagatt catcgtctgc catattatat tccaattgtt ttatagatgg     600
cttgccacac ggtgccacag ttatctcagg ttcaaacagg gtgtccatct catagtttaa     660
ggacagaatt gttcttagca acaagcctcc tagtaaggcc atcctctgat catgtctatt     720
ctttctcgct aggattctgt tacgctgttt caacgacaat tgacgtaaac acagttccat     780
taaataatca tcttctaact cgttgccgac tttgaccact acaagaatat ttctttctcc     840
ttctgtcaac tgcttccaat gttgaaagac atcgtccatt cttcaacgaa gaagtttatt     900
agaacagtat tacctaatct gagaagttca aggcgacgtg tactgatcca tatggtccca     960
tcatcactgc                                                            970
```

<210> SEQ ID NO 98
<211> LENGTH: 1001
<212> TYPE: DNA
<213> ORGANISM: Artificial Sequence

```
<220> FEATURE:
<223> OTHER INFORMATION: Promotor

<400> SEQUENCE: 98
aactgccact tatgcgaaac ttcctagata agttcaaagc tgtccacgtg tatacagaaa      60
agaatgcgcc agagacattc tacagggagg tacttacagt aaacgactgc gcgattgcca     120
acaaactatg taggtaacat gtggaaaatt gtctccacac tagataggcc aaagagaacg     180
catcatcgtt cgcttttagt atccaataag atttcattta cattcttttt ttaaatgatc     240
ttgcccttag atagacatcg atttgggctc ctttctgaga acatgtgtgg ggcaatggta     300
accattagga ttcttcatga gataatcttg atggtaatcg tcagcatcca agtaactagt     360
taacttttcc acttgagtaa caatcttatg gtgcggaaac cacttcttct gtgcttctgc     420
cagcgattgc tccgttatct ctttctcctt ctcatcgagg taaaagacag cagatctgta     480
ttgacttcca atatcattac cttggcgatc tttctgagtt gggtcgtgga ctaggaaaaa     540
gaaatctatc aactcgttaa atgaagtgac gtctggattg tatgagattt gcagaacctc     600
agcatggtgg gtcattccca ggcaaatctg agtgtaagtt ggattggcca catttccatt     660
ggcaaagccg acttgtgtat caacaattct gtctttaaaa tgcattttgt agatgtgctc     720
taatccccaa aaacagcctc cagcgactgt cactactttg tcctgaggag attttctgat     780
gttcgacgaa acaagactgc tattgacggg catatgagaa gaactacgtt tgaaaaaatt     840
tcggaaagag cccatgaatg caaaaccgct tgccttgctt gaactgggag caagcaagaa     900
tatatatcct ttcattccgt ttcgtttaat caaatgatat ttgaaatttt gggagctgta     960
ctgaaatgtg attggttcat ttgatatgaa attgatgtga a                       1001

<210> SEQ ID NO 99
<211> LENGTH: 1001
<212> TYPE: DNA
<213> ORGANISM: Artificial Sequence
<220> FEATURE:
<223> OTHER INFORMATION: Promotor

<400> SEQUENCE: 99
atccgcgagg attccatcat caattggatg cgaaatgaag atgaagagtc aataggtaaa      60
tcttcaatcc aaggttatta gtcctagaat atagcagtct atgatgcttt gcgactggag     120
ttgtcactag tcagggagat tgtataaatt aaacatataa aaacaatctt gcatgataga     180
ttacaatgga caagctccat aaccgtttca attacacgat tgtaactagt tcaatctggt     240
aataattaag tacctcttat aattagaatg aaatagcagc atgaaaatga ttggggccat     300
ttgatcatcg tatcattaat ccttgtccct catcctagtc tttcgatgag atgtactcca     360
ctatcacttt ccactatgtc tgatatttca ccaacttgta atgcaaatgc agctctttca     420
aatgatggat gcattgtctt tctcccaaaa aggcccaaat ccccgttccg ggcatgtgag     480
gagcaatcac tttcagtagc agccagttga cctaaagtgg cagaaccatc aagaatctgt     540
ttttggaatc ctctaagctt ttcaattgct tcttccttag ttcttgtaat ctgaggctcc     600
ttccaggagc tcggtttcct agagttcttg tgtttcacca gaagatgagc acaccgaact     660
tgttctgggt catgaaggcg tttccttgatg tactcgccca gtgcttctaa gttagttcca     720 gaaggggggct cccaggaaga ttcttgtgtt tccttgttat agaaatactc agattgatga     780 gttttttgata ttttaattgt ccaattcctc ggtaatccgt taaatgtatt tgtcatgcta     840
cgttaattta gcatcacaag atctctcact aattgaattc ttaagccacc agcctcgaat     900
```

```
tctagattcg aaaattacta atgtcaagaa tactcttaac cagaccattt gctctaagaa    960
atcttctctt cttcacgcat tcctcaaagc aaataagaac a                      1001
```

<210> SEQ ID NO 100
<211> LENGTH: 1001
<212> TYPE: DNA
<213> ORGANISM: Artificial Sequence
<220> FEATURE:
<223> OTHER INFORMATION: Promotor

<400> SEQUENCE: 100

```
tgtctccaca ctaacttatt tgataaatga ttaattcaat aaaaccttgt tttgaggtat     60
tatttaggta cgtcagatgg tacggttcat cgatggattt ccttcacaat ggacctttat    120
tcttcttttc aattttgctt acatagtaac agaattcata gctgacatgt cgcttttctt    180
gatggaaggc atgtcagagt tcatggccga catgtcgctc ttcttcatag aaggcatgtc    240
agagttcatg gccgacatgt cgctcttctt cacagaagac atgtcagttt ttttcatgga    300
aggcatgtca gagttcatgg ccgacatgtg agaagaactt cgtttgaaaa agcgtcggaa    360
aaaggtcatg aaacaaaaag tcactgcctt tcttgatcat gggaagcaaa tgcatttaga    420
tattttcgtt tcgttcgtac tacatgctat ttgaaacttg gaagctgttc caaaaggtca    480
ttggttcact tgatgtgaaa ttgatgtgaa atagtaaaga cttttactcc ttttgcagac    540
cttgattgca gaaaagtgat ctgatcccat aaacttcaat cgcgacttcg tttcaaaaat    600
taggtaatct ggagtgagaa ttctcgtttt tatgttctga gcgttctttc ttcttgacgg    660
gtggataaag agaagacctg aattacagag aagagctaaa attccaagag caattattat    720 tatctttta aaccgcagtt cccctgaca tggtaataga ggtattcaca aatttggcgc     780
cttgtcagtt cttcttgaat taccatttac ggactcccaa ctcctcatcc ggtgctaagc    840
ctcaataaaa aaagaaagac taagttttgc tcaaaccttt ctagttgcca cctgccttgt    900
agtccgaagc aaagtggctg aatatcactt cgcgcaatgc tttccagttg ccaccggctg    960
agaatgaggt tcaactctgt ttaaacagta attgtttcga a                      1001
```

<210> SEQ ID NO 101
<211> LENGTH: 1001
<212> TYPE: DNA
<213> ORGANISM: Artificial Sequence
<220> FEATURE:
<223> OTHER INFORMATION: Promotor

<400> SEQUENCE: 101

```
tgtctccaca ctaacttatt tgataaatga ttaattcaat aaaaccttgt tttgaggtat     60
tatttaggta cgtcagatgg tacggttcat cgatggattt ccttcacaat ggacctttat    120
tcttcttttc aattttgctt acatagtaac agaattcata gctgacatgt cgcttttctt    180
gatggaaggc atgtcagagt tcatggccga catgtcgctc ttcttcatag aaggcatgtc    240
agagttcatg gccgacatgt cgctcttctt cacagaagac atgtcagttt ttttcatgga    300
aggcatgtca gagttcatgg ccgacatgtg agaagaactt cgtttgaaaa agcgtcggaa    360
aaaggtcatg aaacaaaaag tcactgcctt tcttgatcat gggaagcaaa tgcatttaga    420
tattttcgtt tcgttcgtac tacatgctat ttgaaacttg gaagctgttc caaaaggtca    480
ttggttcact tgatgtgaaa ttgatgtgaa atagtaaaga cttttactcc ttttgcagac    540
cttgattgca gaaaagtgat ctgatcccat aaacttcaat cgcgacttcg tttcaaaaat    600
taggtaatct ggagtgagaa ttctcgtttt tatgttctga gcgttctttc ttcttgacgg    660
```

```
gtggataaag agaagacctg aattacagag aagagctaaa attccaagag caattattat      720
tatcttttta aaccgcagtt cccctgaca tggtaataga ggtattcaca aatttggcgc       780
cttgtcagtt cttcttgaat taccatttac ggactcccaa ctcctcatcc ggtgctaagc      840
ctcaataaaa aaagaaagac taagttttgc tcaaaccttt ctagttgcca cctgccttgt      900
agtccgaagc aaagtggctg aatatcactt cgcgcaatgc tttccagttg ccaccggctg      960
agaatgaggt tcaactctgt ttaaacagta attgtttcga a                         1001
```

<210> SEQ ID NO 102
<211> LENGTH: 1000
<212> TYPE: DNA
<213> ORGANISM: Artificial Sequence
<220> FEATURE:
<223> OTHER INFORMATION: Promotor

<400> SEQUENCE: 102

```
actttctttt actgcttatt tcattcgtat agccaataga tttcccatat tttttccaga       60
gtacgtagat ggtggattag gtaattgttg gcatttctag ttgctagtga acttagctct      120
ggattattgt agtaggtgaa aaataccaag ggcgatggaa atttcaaagg ccgatctggg      180
gatgtgtggg gtaaagactt tggatggaat ccaggggcaa agacaagggc tagacttcac      240
tatattggtg gtaaaagtga atctactaga agtttgagtc aacgacgata tggagtaacc      300
aagtgaagac gatatcttta gttcgttatg gccaccttaa aagaagccca ctcagtccat      360
gtgagttctg aaacttttaa agacagttaa cccaaggttc acaattgtgt gaccttatgt      420
caactgtact agaaggccaa agattattgg acgattgggt tatctatttc cttgataagc      480
atgtgctcca atcaatacac ccacctgtca ggggatacac agtgcggagc tccgtttttct    540 cccagaaatt cggttggagc tcttttctta aacttcgaaa gtcccccgac agagaagtgc      600
cgttagccaa tagtgtccct gcattctggt tcctccccac tgcagcgtca gctggaaagg      660
gctctattct aagctattct aaagcaatcc aaaggtgggg gtcggatcaa tgcgcgatct      720
ttcgtcgcca gtgtcggggc ccggcacggg ggccgtaacc ggcttttctc taggttgaca      780
ccatgggata tcccctgatt gggcaaatcc cacataagta tggcttgcgg cttactaatc      840
gcgtaagtcg cgcattctct ttttcctgat ccttaatatc aatcctccgg caccatcatc      900
gtagtttgcg agattccata aacttttttgg cccctaact tttttttttgt tgccatcctt     960 tacttccatc taaaaaaacc gacacagaat ctgccaaaca                           1000
```

<210> SEQ ID NO 103
<211> LENGTH: 1000
<212> TYPE: DNA
<213> ORGANISM: Artificial Sequence
<220> FEATURE:
<223> OTHER INFORMATION: Promotor

<400> SEQUENCE: 103

```
aggaaccctt aaaagtggag gtatccgtac ttaaagagaa tccattacaa gaaaatgcca       60
caacattcat gttttggtca ttccttggaa caaaaaattg ataactatcg ttaataaaac      120
cgttgagaga gtacttaatt ctctgttcgt aatgaatcaa atcaagctca acagaaaatc      180
tccaaaagct gtagccttgc tcctgatgaa gcttgattac aggaaattca ccagttgaaa      240
tgacatccga tagcagatgt tccttcaagt cgtttcggtg agcgggtcca atatgatacc      300
taattgttgg gttcttcgaa taatcactct catcgtcttt tgtcaccacc aaaatagttg      360
```

```
ccctgtaatt attggactta ttttcaaaag cggagaccaa acgaagaagt ggaccggtag        420
aaactttcaa ttttgggtct cctaagtgtt cagtaactgg aacttttggt tgtccatgac        480
taactgtagt ttcccaggct tgttgatact ccgataaagg taatgaattg aaccagttgg        540
aaagtatcga gtctgacatt gatggcacga tgaaagaaac tgaattaagc gagcaatact        600 aaagaagta gaagtagctg aacgtgaata aactacaact ctggaataac aaaggatggc         660
tctgagaagc gcgacaaatg aatcactgaa accatactcc tacaacatcg tgttgcaaat        720
cctcactatt tgtctccctc tccaattcgc agaacctatg cgaaagatgg aaaacttaaa        780
gactaaatca caggttataa attcttttg catcagctta tagaaagatc tgtataatcg         840 aaagaaaaa aaaaaaggg taaacactgg tattaccaaa aaaacatcct aagactaata         900
tacaccgacg agttcgctac acttctcgaa ctgttaataa aaaggttggt aggtagcctt        960
agttattctc gtctgttaac catcccataa caatatcgaa                              1000

<210> SEQ ID NO 104
<211> LENGTH: 1000
<212> TYPE: DNA
<213> ORGANISM: Artificial Sequence
<220> FEATURE:
<223> OTHER INFORMATION: Promotor

<400> SEQUENCE: 104
ccgaagggtg tagggtcgtc atatctactt cctgggggat gcctcaaatt tggctgcctt         60
tcattagggt taaaaatagg gtggttcaat gagggataca ttccatgtcc ttctgtttgt        120
agatcgctag caaaaggcga tagtgaaggg tgagcccctc caggaggcaa cctatcaccc        180
tctccaattg gtggaggccc tgatggtggg cggaaattcg aagctacagg atcatccagt        240
aactgatatt cgtctgtaaa ttgtggggga gcttctccta gtggtggcga tattggatt        300 gtttctctta agcggctaaa actactctct ccagtctggg tttgttcagc tggctttgga        360
tcttccgttg acttcggaat tggctcgctt gtgatcagac tggcattgat tatcctagtc        420
tctatgatat cacccaacag tactaggagt atactgttgt tatcaagttt tgtaacaata        480
ccttttgttc cgccaacatc aatttcccga ctctccaatg gcttcgagct gtgccatttt        540
gctacgtatt cctccagctt gtccataatt atttcaaaga taattttatc gggaaaagca        600
attgatacgg agttcttaga cggggaaact ttcaggttaa aggggatgag acccttcga        660 gcgtgatcgc cctcttctcc cgcctagaaa aatccagaag gagtgtgtgt gatgcttggg        720
ggttggttgc taatcaggta gtcgcaaccc aaatcagccg gcaacaagct agaatttaca        780
tctaaagctt tcaaataacc ctctaacgat tcaattaatc gttttccca ttggtacaca         840 ccgagcctta tagtcttatc tgaatctaca aaaataccaa ggaagagagt agtgcttcaa        900
ccaacaaaaa gcctacctgt gtccattctt tatctcctac aagtataata taaataccag        960
agacccacaa aatcagtaat cgattcacaa ttggcctatt                              1000

<210> SEQ ID NO 105
<211> LENGTH: 1000
<212> TYPE: DNA
<213> ORGANISM: Artificial Sequence
<220> FEATURE:
<223> OTHER INFORMATION: Promotor

<400> SEQUENCE: 105
ttatggtaga atcatcaatt ggaatgaccc tatcgttgct atacagactc gtagccccat         60
ttcttgtttg ttggttttcg tcgtcaattg cctccaaaat tgaagagatg gcacttcgtc        120
```

```
gcgtgggttc ctgggaaata ttttgaagtg gaacatcgtt gaaataaggc agtatatcat      180
gctgattctc agcattggag tcagtagctt caagtgaatc tatactgtat gagtcggaag      240
aggatttccg gctcgttttt gtcttcattt tgttattaga aggaatgata acgttgggaa      300
accggaggtt ggagattttg tatatataaa actttcttgg agcttattaa taaatgcggg      360
atgcagtaaa cttgcatata tctattgtaa cacttttgca atagctgcat gccttgactc      420
atcattcagt atcgtgtgaa aaccaatgat acatccgtac attcaaacta caaccttcct      480
cattagtaat tcttttgaa tttttcggaa cccgaagctc cgcctatccc cccaactaac       540
acatcttcca atttgggtgg gagaacacct agcaacatca cgatcattgc gcgaacgttc      600
gcactgtatt ttttctccc aaacacccaa cttctaggcc aaatatccac ttctcggggt       660
tctattcacc catttaattg ttggccttaa aagtcaattg agttccaatc atagtcccta      720
gttgattgct tgtagcaaat gccacaacag taggcattta cgtcctcaca gtctcttccc      780
ttgtccctca ttgataccte tttattctcc cccaccacca tacactacct tcctcgcacc      840
cctgtcatca aaccgcaat ataatcgatg cgcggtttct tgcctaatcc atcgtccaac       900
agagaggtcg ctctccttat atatatagtt gatccccctt tttttctacc cttgcaattt      960
ttttttggga ccaaagaaaa gaaacaagac tgatacaaat                            1000

<210> SEQ ID NO 106
<211> LENGTH: 1000
<212> TYPE: DNA
<213> ORGANISM: Artificial Sequence
<220> FEATURE:
<223> OTHER INFORMATION: Promotor

<400> SEQUENCE: 106
tgaagttatt cctctacaaa tcgaccgaat atttctatac gtgtaataac ttcttcgtat       60
tagctgcaac gatgcctaaa tatacatttc ccaaaaacaa cgacgcttcg tagaaattat      120
aaagtttcac ttgggatctc gaagacaact tgcttaccag tcagcttacc gtagacagcc      180
tggaaagagt caagcttgta gtcaatgttg gaagagtcct tggagtcaag caaaactttg      240
gtgatttggt caccaccgac caagtatctg attctcttac cgataatctc ggttgggaaa      300
accaagtcct ccaaaatctt ctcgtgaacg accttgacgg ttctagatct aggtctcttc      360
tggacaacct ttggtcctct tggaatcttt ggggtgatct ttctctcagc caagaaaacg      420
acatggcggt cagggaactt cttctccaac tctctggtca acttgatttg taccttgtgg      480 aaaagcagtca acagaggaac tggtacaaag attacgatgg cagtcttcc gctctcagtc      540 tcaatctcct tgatggagtt gaattgcaaa ggtctcaagt cagcctttaa gtctggggag      600
ttagcttcca agtcaacaaa tgattgggcg acttgcagct ccaactcagt gggctcttcg      660
ttcaggattt tggctgatga catcttgtga tactgctgtt accgtgtgag tttcgacaga      720
attgaaaaaa gattgttaag gctctggagg aaaaactgga ttcgcgcaca acagtcccaa      780
gagaagagta gtaacaaaaa aaattacagt catgtgatgt aggggatgtg gttagggtcg      840
aagcccagta cggtgttggg atgctaagag gttaatatct aatgcacaat acgcttatgt      900
aagttcatgc ttgaaatagc ctattgatga atgtaaggga aattagaccg tcctttgtgg      960
gtacttattc acgtcttgcc tctagcatct tagacaacta                            1000

<210> SEQ ID NO 107
<211> LENGTH: 927
<212> TYPE: DNA
```

```
<213> ORGANISM: Artificial Sequence
<220> FEATURE:
<223> OTHER INFORMATION: Promotor

<400> SEQUENCE: 107
atggttaaaa caattattgc tccttcaatc ctgtcggcag atttttcaaa cttgggatgt      60
gaatgtcaca agatgtttaa gctacgggct gactgggtcc acattgacgt catggacggc     120
catttcgtcc ctaatttgac catgggtcct ccaattatct cgtcccttag aaaagctgtt     180
ccgaggggag agaaagatgg acagacgaca cacttctttg actgccatat gatggtggcc     240
aatcccgaac aatgggtccc agaggttgca aaggcaggtg gtgatcagta cacttttcac     300
tacgaagcaa ctaaggatcc agtgaagtta gtggaactta tcaagagcca tggactgaaa     360
gctgcatgtg ctatcaagcc cggaacatca gtcgatgtct tgtaccctct agcagacaag     420
cttgacatgg ctctggtaat gacagttgag ccagggtttg gtggacagaa gtttatggct     480
gatatgatgc ccaaagttga agcattgcgg gccaaatttc caaacttaga tattcaggtc     540
gatggtggtc ttggaaagga gaccattgga gtagcagcta tgctggggc aaacgtaatt     600
gttgctggat cttctgtttt tggtgctaaa gacccgtg aggttatccg atatcttcgt     660
gatacggtag aaaatgctca gaaaaagct aagccaaac cgaaacccaa tttatgactg     720
aatagtatat taagtaggat ttgatatacg tctttagagg tgattgaaag accgaatgag     780
tttttgctgg gcggaatgcg attccttact gcgcgaacaa acgttccgtc tagtgggttt     840
tccatccacc aattaatctg ccccagatct caaaccatat ttccaatttt actacctttc     900
cttcatatca cctagctatt cgaaaaa                                        927

<210> SEQ ID NO 108
<211> LENGTH: 1001
<212> TYPE: DNA
<213> ORGANISM: Artificial Sequence
<220> FEATURE:
<223> OTHER INFORMATION: Promotor

<400> SEQUENCE: 108
agcgatggac agactgcctc acaacagttc gtcaaacagg gaaagacgc cttgagagtc      60
tactggttga tgcttatcta catgattatc atgatggccg cattcaactt tagttctcac     120
tcctcccaag atctttaccc tactcttcta acagttcaat atgaatttgg taaagacaga     180
tctacagtta ctaacgtcgt ggcaaatctt ggagccattg tcggaggtat tttctggggt     240
catatgtcca acttcattgg tcgacgtctt gcagttttgc tctgttgtat agtaggtgga     300
gctttcattt acccttgggc atttataaat ggttcaggga tcaatgctgg tgctttcttc     360
ttacaatttg ctgtccaagg tggatgggt gtatgtccag ttcatcttgc tgagatgtct     420
ccgccccatt tccgagcttt tgttacagga accacctacc agctaggaaa cctggcatca     480
tctggatcat ctactatcct ggccgatatt ggagaaagat tccccattta cgacgagaat     540
ggagtgcgga agagggtgt ttatgactat gccaaagtaa tggctatatt tatgggagct     600
gtgtttgctt tcctgtttat tgtgatgttg ctgggtccag aaagaagagg agcctccaat     660
cttgatgatc tccaggatta cattgacgat tgggagcaaa aagatctgga caacaaaaaa     720
ggaattgaaa ctgagttcat cgaagatgtt cagttaatgg aggctgtctc taatgaggac     780
ctttctgaga aaggcaatga gaaagtagag gcttttgaag gaataagta agattagggt     840
acttcttaga aattactaat actacacctc tacattcgtt atcttatcag gcttgtcgcg     900
atgggctaaa ctatagccta tgagtggggg gtcgtagtta agaaatata tactatatgc     960
```

```
gaagatggga aagtaaaact agttgaatac tgtgtgagat c                 1001
```

<210> SEQ ID NO 109
<211> LENGTH: 1000
<212> TYPE: DNA
<213> ORGANISM: Artificial Sequence
<220> FEATURE:
<223> OTHER INFORMATION: Promotor

<400> SEQUENCE: 109

```
gattccactg ctcagagtct tttcatcaag ctctaagaaa agtccgggga tggaggagcc   60
agcgcaacag aaaactatgt cgggactaaa accaacttcc tctaaaacac gctcacactg  120
gtcatatttg gagatatctg ctgccacgta agaaattgtg ttgcccttct cggtcccgtg  180
aatatcaata gcgtccttta ctacctgctt tagtaaggat tctgttctag ccacaatcac  240
aacggaacat cctttccat acaaaagttt agcaaactcg gctccaacac cctgggatgc   300
acccgtaata attgcctttt tgttggtgac atcaaaatta tcaaacattc cagttccctc  360
tacactttgt atgagaatga tagctgaaat tgtgcaccag atgttagaag ataaggtcgt  420
gtcatgaact aatatcatga attccgaggg tggctcaaca actattcacg tgacttggac  480
gttggaagtt gaggtggttg gtggatgttg cacggagtat catttgtaag catgaaatca  540
gtctaaaaaa cttgcagaat agcagagcgg ttcggaaatt cattcaaaac cacctcctca  600
gattggatct gccctactct gtttagctct gggagatttt ctcggtcgtg ttctttcgct  660
ggtctaccca cgctatagga atcgctgtga acgctacctt cttcccaact tctcggtgac  720
tattataagc cattcccact ttgttttcaa gcaccaacaa cccacccca ccttatctac    780
tccatcttgg gtgtccccgc gcctgttgca aagtccgaac catagaaccc ccgacctttg  840
tcccactaac cctcagacac ccctcggaag tcagggagaa accactccga agtacattaa  900
tcatccctcg tattctcgac ggtgcccatt ttctttataa aaagggagac acaggttgct  960
tcactaactc tagacttgta ttctacatcc actctacaca                       1000
```

<210> SEQ ID NO 110
<211> LENGTH: 1000
<212> TYPE: DNA
<213> ORGANISM: Artificial Sequence
<220> FEATURE:
<223> OTHER INFORMATION: Promotor

<400> SEQUENCE: 110

```
aataaaaaaa cgttatagaa agaaattgga ctacgatatg ctccaatcca aattgtcaaa   60
attgaccacc gaaaagaac aattggaatt tgacaagagg aacaactcac tagattctca   120
aacggagcgt cacctagagt cagtttccaa gtcaattaca gaaagtttgg aaacagaaga  180
ggagtatcta caattgaatt ccaaacttaa agtcgagctg tccgaattca tgtcgctaag  240
gctttcttac ttggaccca tttttgaaag tttcattaaa gttcagtcaa aaattttcat   300
ggacatttat gacacattaa agagcggact accttatgtt gattctctat ccaaagagga  360
ttatcagtcc aagatcttgg actctagaat agataacatt ctgtcgaaaa tggaagcgct  420
gaaccttcaa gcttacattg atgattagag caatgatata aacaacaatt gagtgacagg  480
tctactttgt tctcaaaagg ccataaccat ctgtttgcat ctcttatcac cacaccatcc  540
tcctcatctg gccttcaatt gtggggaaca actagcatcc caacaccaga ctaactccac  600
ccagatgaaa ccagttgtcg cttaccagtc aatgaatgtt gagctaacgt tccttgaaac  660
```

```
tcgaatgatc ccagccttgc tgcgtatcat ccctccgcta ttccgccgct tgctccaacc    720
atgtttccgc cttttcgaa caagttcaaa tacctatctt tggcaggact tttcctcctg    780 cctttttag cctcaggtct cggttagcct ctaggcaaat tctggtcttc atacctatat    840 caactttca tcagatagcc tttgggttca aaaagaact aaagcaggat gcctgatata    900
taaatcccag atgatctgct tttgaaacta ttttcagtat cttgattcgt ttacttacaa    960
acaactattg ttgattttat ctggagaata atcgaacaaa                        1000

<210> SEQ ID NO 111
<211> LENGTH: 1000
<212> TYPE: DNA
<213> ORGANISM: Artificial Sequence
<220> FEATURE:
<223> OTHER INFORMATION: Promotor

<400> SEQUENCE: 111
attactgttt tgggcaatcc tgttgataag acgcattcta gagttgtttc atgaaagggt     60
tacgggtgtt gattggtttg agatatgcca gaggacagat caatctgtgg tttgctaaac   120
tggaagtctg gtaaggactc tagcaagtcc gttactcaaa aagtcatacc aagtaagatt   180
acgtaacacc tggcatgac tttctaagtt agcaagtcac caagagggtc ctatttaacg   240
tttggcggta tctgaaacac aagacttgcc tatcccatag tacatcatat tacctgtcaa   300
gctatgctac cccacagaaa taccccaaaa gttgaagtga aaaatgaaa attactggta   360 acttcacccc ataacaaact taataatttc tgtagccaat gaaagtaaac cccattcaat   420
gttccgagat ttagtatact tgcccctata agaaacgaag gatttcagct tccttaccc   480 atgaacagaa atcttccatt tacccccac tggagagatc cgcccaaacg aacagataat   540 agaaaaaga aattcggaca aatagaacac tttctcagcc aattaaagtc attccatgca   600 ctcccttag ctgccgttcc atcccttgt tgagcaacac catcgttagc cagtacgaaa   660
gaggaaactt aaccgatacc ttggagaaat ctaaggcgcg aatgagttta gcctagatat   720
ccttagtgaa gggttgttcc gatacttctc cacattcagt catagatggg cagctttgtt   780
atcatgaaga gacggaaacg ggcattaagg gttaaccgcc aaattatata agacaaacat   840
gtccccagtt taaagttttt cttctctat cttgtatcct gagtgaccgt tgtgtttaat   900
ataacaagtt cgttttaact taagaccaaa accagttaca acaaattata acccctctaa   960
acactaaagt tcactcttat caaactatca aacatcaaa                        1000

<210> SEQ ID NO 112
<211> LENGTH: 1001
<212> TYPE: DNA
<213> ORGANISM: Artificial Sequence
<220> FEATURE:
<223> OTHER INFORMATION: Promotor

<400> SEQUENCE: 112
cagagatcgt gttttgatta agattgctgc tacctgggag ggaatacaag cagccctgga     60
gttggagcag gtctacgata tacactgcaa cttgacacta atttttctt tgttcaagc   120 tgttgcgtgt gctgaagcgc aggtaacact tatctctcct tttgttggac gtattcttga   180
ctggtacaag gcaaaaacag gtaagcaata tgaaggtgct gctgaccctg gagttatttc   240
tgttgttcgt atattcaagt atttcaaggc atacggatac aaaactatag tcatgggagc   300
ttctttccga aatgtcagcg aaataaaagc tctagctgga tgcgattatc taacaattgc   360
accaactttg ttggatcaat tacaaagctc cacagatgct gtccctaaag tccttgaccc   420
```

```
tgcaacctca gcggctgagg agcaggagcc ttttgtgtcg tttgtatcca acgaaactgc      480
tttccgtttt gaactcaacg aggatcaaat ggccacagaa aagttgtctg aggggttcg       540 aaagttttca gctgactgca ataccctgtt tgatcttttg agagaaaaag taaaagtcgc      600
tcaagaggag gtgaataata tctccaatgg cgtgccatca cttttccgtc gtgttttatc      660
caagttgtaa gccattgggc caaacgtttc tggatcttga agctaaccaa acctgatagg      720
gcaatgctca ggacagctaa acttagtttg aagtttcccc caggttttct tcggaagatg      780
ttttcaccca caatcacccc cactctaagt atgtttgcaa taccaactcc gcgcttatta      840
cccccattat caggatttgc tctcccgaac ctcccgcaaa ctgcacctat accgatcgcg      900
gcgaactgtg ctccacacac ttgcccaatc ttataaaagt tcttcctccg ccacctgggt      960
tgcgctcttt cttttactct aattgaaatt ttatttctac a                        1001

<210> SEQ ID NO 113
<211> LENGTH: 1001
<212> TYPE: DNA
<213> ORGANISM: Artificial Sequence
<220> FEATURE:
<223> OTHER INFORMATION: Promotor

<400> SEQUENCE: 113
gatatcgatc tacacttaat agtagatgac gaggcatctc tccataggt accatatctg       60 gtgtttcttg taatttaaga atctgttggt ctatgaatgt agatttgtca tgaacaatga      120
tatatgggtc aggaggacaa gatggttttct ctgagttggg ttgttgaggt gcctggcaag     180
acttcggagc gttgatatcc ccaagacttg tagtgaccga tagttgaagc gtgtgtttgc      240
aggaacggca catcaatgca actttcgtaa ctttggaatt gagagttgat gcactgatga      300
cgatacccga aattttgacg attttaccaa tatgacttga agacaagtct ctcattgaaa      360
ccttattatc gttactaagc aaaacgagct gacaagaagg gaaggtggtc ggtatttcct      420
cgttgttcaa atatatgatt ctcctggcaa tatctgtgat ggcctgttca aaaagtggaa      480
tcatttctgc aggatcatct accaactttt tattgagctc ctcattgaat acgattaagt      540
ggtcattttg aatcgtcagt aagtacttgt ttacaagtaa attctgtctg agttgttctc      600
tgtagatgta ctgattttcc atacgaaact ccaaaatgaa cgaacggaat gccttaatga      660
cctcactgaa ctggtcatcg ttctgttctc cgggaaggac acttgtgtta aagactgatg      720
ctctatcaaa ggacattgca acaaagtata acggttgtg agcgggaaaa agatgtgtag      780
gtaattgtcg tagatgagac tgattcagta gaaaacgcgt cctgcactat ttttttcttt      840
cttcattaca tttcctaatc gggacaaaat gaatctaaag acgtggttat gtagtacacg      900
catcgatagg ctatccccat accaaaacac tattttaccc catccttgac aggttataaa      960
tatgcgatag tatgagtatc ttcaaattca gctgaaatat c                         1001

<210> SEQ ID NO 114
<211> LENGTH: 1425
<212> TYPE: DNA
<213> ORGANISM: Artificial Sequence
<220> FEATURE:
<223> OTHER INFORMATION: Promotor

<400> SEQUENCE: 114
cgtttcgaat aattagttgt tttttgatct tctcaagttg tcgttaaaag tcgttaaaat       60
caaaagcttg tcaattggaa ccagtcgcaa ttatgaaagt aagctaataa tgatgataaa      120
```

| | |
|---|---|
| aaaaaggttt aagacagggc agcttccttc tgtttatata ttgctgtcaa gtaggggtta | 180 |
| gaacagttaa attttgatca tgaacgttag gctatcagca gtattcccac cagaatcttg | 240 |
| gaagcataca atgtggagac aatgcataat catccaaaaa gcgggtgttt ccccatttgc | 300 |
| gtttcggcac aggtgcaccg gggttcagaa gcgatagaga gactgcgcta agcattaatg | 360 |
| agattatttt tgagcattcg tcaatcaata ccaaacaaga caaacggtat gccgactttt | 420 |
| ggaagtttct ttttgaccaa ctggccgtta gcatttcaac gaaccaaact tagttcatct | 480 |
| tggatgagat cacgcttttg tcatattagg ttccaagaca gcgtttaaac tgtcagtttt | 540 |
| gggccatttg gggaacatga aactatttga ccccacactc agaaagccct catctggagt | 600 |
| gatgttcggg tgtaatgcgg agcttgttgc attcggaaat aaacaaacat gaacctcgcc | 660 |
| agggggggcca ggatagacag gctaataaag tcatggtgtt agtagcctaa tagaaggaat | 720 |
| tggaatgagc gagctccaat caagcccaat aactgggctg ttttttcgat ggcaaaagtg | 780 |
| ggtgttgagg agaagaggag tggaggtcct gcgtttgcaa cggtctgctg ctagtgtatc | 840 |
| ccctcctgtt gcgtttggca cttatgtgtg agaatggacc tgtggatgtc ggatggcaaa | 900 |
| aaggtttcat tcaaccttc gtctttggat gttagatctt ttttgtagaa atgtcttggt | 960 |
| gtcctcgtcc aatcaggtag ccatctctga atatctggc tccgttgcaa ctccgaacga | 1020 |
| cctgctggca acgtaaaatt ctccggggta aacttaaat gtggagtaat ggaaccagaa | 1080 |
| acgtctcttc ccttctctct ccttccaccg cccgttaccg tccctaggaa attttactct | 1140 |
| gctggagagc ttcttctacg gccccttgc agcaatgctc ttcccagcat tacgttgcgg | 1200 |
| gtaaaacgga ggtcgtgtac ccgacctagc agcccaggga tggaaaagtc ccggccgtcg | 1260 |
| ctggcaataa tagcgggcgg acgcatgtca tgagattatt ggaaaccacc agaatcgaat | 1320 |
| ataaaaggcg aacacctttc ccaatttttgg tttctcctga cccaaagact ttaaatttaa | 1380 |
| tttatttgtc cctatttcaa tcaattgaac aactatcaaa acaca | 1425 |

<210> SEQ ID NO 115
<211> LENGTH: 1631
<212> TYPE: DNA
<213> ORGANISM: Artificial Sequence
<220> FEATURE:
<223> OTHER INFORMATION: Promotor

<400> SEQUENCE: 115

| | |
|---|---|
| cgtttcgaat aattagttgt tttttgatct tctcaagttg tcgttaaaag tcgttaaaat | 60 |
| caaaagcttg tcaattggaa ccagtcgcaa ttatgaaagt aagctaataa tgatgataaa | 120 |
| aaaaaggttt aagacagggc agcttccttc tgtttatata ttgctgtcaa gtaggggtta | 180 |
| gaacagttaa attttgatca tgaacgttag gctatcagca gtattcccac cagaatcttg | 240 |
| gaagcataca atgtggagac aatgcataat catccaaaaa gcgggtgttt ccccatttgc | 300 |
| gtttcggcac aggtgcaccg gggttcagaa gcgatagaga gactgcgcta agcattaatg | 360 |
| agattatttt tgagcattcg tcaatcaata ccaaacaaga caaacggtat gccgactttt | 420 |
| ggaagtttct ttttgaccaa ctggccgtta gcatttcaac gaaccaaact tagttcatct | 480 |
| tggatgagat cacgcttttg tcatattagg ttccaagaca gcgtttaaac tgtcagtttt | 540 |
| gggccatttg gggaacatga aactatttga ccccacactc agaaagccct catctggagt | 600 |
| gatgttcggg tgtaatgcgg agcttgttgc attcggaaat aaacaaacat gaacctcgcc | 660 |
| agggggggcca ggatagacag gctaataaag tcatggtgtt agtagcctaa tagaaggaat | 720 |
| tggaatgagc gagctccaat caagcccaat aactgggctg ttttttcgat ggcaaaagtg | 780 |

```
ggtgttgagg agaagaggag tggaggtcct gcgtttgcaa cggtctgctg ctagtgtatc    840
ccctcctgtt gcgtttggca cttatgtgtg agaatggacc tgtggatgtc ggatggcaaa    900
aaggtttcat tcaacctttc gtctttggat gttagatcta gtgtgtaatc atatatataa    960
taaatgagga ataataattg aatagagatt taacgagtcg aagtttctga aatatacgca   1020
cagtttatat ttatgatttt gatatctaac tacagtcttc tccatatatt taactataaa   1080
taataaagta tataactctt atgaaactgt tcaccacat tttttctac gtaatcgaac    1140 tccgaatgcg gttctcctgt aaccttaatt gtagcataga tcacttaaat aaactcatgg   1200
cctgacatct gtacacgttc ttattggtct tttagcaatc ttgaagtctt tctattgttc   1260
cggtcggcat tacctaataa attcgaatcg agattgctag tacctgatat catatgaagt   1320
aatcatcaca tgcaagttcc atgataccct ctactaatgg aattgaacaa agtttaagct   1380
tctcgcacga gaccgaatcc atactatgca cccctcaaag ttgggattag tcaggaaagc   1440
tgagcaatta acttccctcg attggcctgg acttttcgct tagcctgccg caatcggtaa   1500
gtttcattat cccagcgggg tgatagcctc tgttgctcat caggccaaaa tcatatataa   1560
gctgtagacc cagcacttca attacttgaa attcaccata acacttgctc tagtcaagac   1620
ttacaattaa a                                                        1631

<210> SEQ ID NO 116
<211> LENGTH: 1178
<212> TYPE: DNA
<213> ORGANISM: Artificial Sequence
<220> FEATURE:
<223> OTHER INFORMATION: Promotor

<400> SEQUENCE: 116
tgtgttttga tagttgttca attgattgaa atagggacaa ataaattaaa tttaaagtct     60
ttgggtcagg agaaaccaaa attgggaaag gtgttcgcct tttatattcg attctggtgg    120
tttccaataa tctcatgaca tgcgtccgcc cgctattatt gccagcgacg gccgggactt    180
ttccatccct gggctgctag gtcgggtaca cgacctccgt tttacccgca acgtaatgct    240
gggaagagca ttgctgcaag ggggccgtag aagaagctct ccagcagagt aaaatttcct    300
agggacggta acgggcggtg gaaggagaga gaagggaaga gacgtttctg gttccattac    360
tccacattta agttttaccc cggagaattt tacgttgcca gcaggtcgtt cggagttgca    420
acggagccag atatttcaga gatggctacc tgattggacg aggacaccaa gacatttcta    480
caaaaaagtg tgtaatcata tatataataa atgaggaata ataattgaat agagatttaa    540
cgagtcgaag tttctgaaat atacgcacag tttatattta tgattttgat atctaactac    600
agtcttctcc atatatttaa ctataaataa taaagtatat aactcttatg aaactgtttc    660
accacatttt tttctacgta atcgaactcc gaatgcggtt ctcctgtaac cttaattgta    720
gcatagatca cttaaataaa ctcatggcct gacatctgta cacgttctta ttggtctttt    780
agcaatcttg aagtctttct attgttccgg tcggcattac ctaataaatt cgaatcgaga    840
ttgctagtac ctgatatcat atgaagtaat catcacatgc aagttccatg ataccctcta    900
ctaatggaat tgaacaaagt ttaagcttct cgcacgagac cgaatccata ctatgcaccc    960
ctcaaagttg ggattagtca ggaaagctga gcaattaact tccctcgatt ggcctggact   1020
tttcgcttag cctgccgcaa tcggtaagtt tcattatccc agcggggtga tagcctctgt   1080
tgctcatcag gccaaaatca tatataagct gtagacccag cacttcaatt acttgaaatt   1140
```
caccataaca cttgctctag tcaagactta caattaaa    1178

<210> SEQ ID NO 117
<211> LENGTH: 1486
<212> TYPE: DNA
<213> ORGANISM: Artificial Sequence
<220> FEATURE:
<223> OTHER INFORMATION: Promotor

<400> SEQUENCE: 117
tgtgttttga tagttgttca attgattgaa atagggacaa ataaattaaa tttaaagtct    60
ttgggtcagg agaaaccaaa attgggaaag gtgttcgcct tttatattcg attctggtgg    120
tttccaataa tctcatgaca tgcgtccgcc cgctattatt gccagcgacg gccgggactt    180
ttccatccct gggctgctag gtcgggtaca cgacctccgt tttacccgca acgtaatgct    240
gggaagagca ttgctgcaag ggggccgtag aagaagctct ccagcagagt aaaatttcct    300
agggacggta acgggcggtg gaaggagaga gaagggaaga gacgtttctg gttccattac    360
tccacattta agttttaccc cggagaattt tacgttgcca gcaggtcgtt cggagttgca    420
acggagccag atatttcaga gatggctacc tgattggacg aggacaccaa gacatttcta    480
caaaaaggta tttgacaggt tggggagcaa ataagtgatg atgtcccatg aaagtagaaa    540
atggctagta gaaggcaaaa atttgaaatt cttagagtca aatagttaga ctccaagttc    600
taatccacat ttggtcagtt tcatagcatc cagagctttt gccactggtg aacatatcta    660
cccattgcga tgcaacaagt cactgaaagc ctaaaacgga gattcccta tcttacagcc    720
tcgttcaaaa aaactgctac cgtttatctg ctatggccga tgtgaggatg cgctcatgcc    780
caagagtcca actttatcaa aaacttgacc cgtcatacag gctctagatc aagaagcaaa    840
cttaatctca gcatctggtt acgtaactct ggcaaccagt aacacgctta aggtttggaa    900
caacactaaa ctaccttgcg gtactaccat tgacactaca catccttaat tccaatcctg    960
tctggcctcc ttcaccttt aaccatcttg cccattccaa ctcgtgtcag attgcgtatc    1020
aagtgaaaaa aaaaaattt aaatctttaa cccaatcagg taataactgt cgcctctttt    1080
atctgccgca ctgcatgagg tgtcccctta gtgggaaaga gtactgagcc aaccctggag    1140
gacagcaagg gaaaaatacc tacaacttgc ttcataatgg tcgtaaaaac aatccttgtc    1200
ggatataagt gttgtagact gtcccttatc ctctgcgatg ttcttcctct caaagtttgc    1260
gatttctctc tatcagaatt gccatcaaga gactcaggac taatttcgca gtcccacacg    1320
cactcgtaca tgattggctg aaatttccct aaagaatttc tttttcacga aaatttttt    1380
tttacacaag atttttcagca gatataaaat ggagagcagg acctccgctg tgactcttct    1440
tttttttctt ttattctcac tacatacatt ttagttattc gccaac    1486

<210> SEQ ID NO 118
<211> LENGTH: 1001
<212> TYPE: DNA
<213> ORGANISM: Artificial Sequence
<220> FEATURE:
<223> OTHER INFORMATION: Promotor

<400> SEQUENCE: 118
atttatgaaa ttaatcaatt accttatcaa ggtagaattt gggtgaattt gtatgtttaa    60
ataccggcta agagaatagg ctacgtaccc cacagactgg aagtcgcatc cgaaccgaaa    120
tggaaaaggc gtgtaagggt tgcatggtac gaataggga agaagagaac tgggaagtga    180
tcattgatag tgtgagtggc gggaaatatt aggtgtgagt ttgaaaggcc tacaataggg    240

-continued

```
atgcaaaaat cctgctcata gggtcactgg ggagtattta ttttctgttt tcaggtttcc      300
caccaatgta aatgttcttc ttagaataga agaaagcttt ctgtttgcag ataacattt       360 ttgtccagta aaagatatca ttttagtttg agttcatgtg atcacattta gatcacatta     420
aaagcaaaag tgacggtacg tcttctataa ctgtttaaat ggttgaggtt tgaagtcctg     480
gtaaaagtca agtcacaatg ccaacttttt attgagctcc tcattgaata cgattaagtg     540
gtcattttga atcgtcagta agtacttgtt tacaagtaaa ttctgtctga gttgttctct    600
gtagatgtac tgattttcca tacgaaactc caaaatgaac gaacggaatg ccttaatgac     660
ctcactgaac tggtcatcgt tctgttctcc gggaaggaca cttgtgttaa agactgatgc     720
tctatcaaag gacattgcaa caaagtataa acggttgtga gcgggaaaaa gatgtgtagg     780
taattgtcgt agatgagact gattcagtag aaaacgcgtc ctgcactatt ttttttcttt     840
cttcattaca tttcctaatc gggacaaaat gaatctaaag acgtggttat gtagtacacg     900
catcgatagg ctatccccat accaaaacac tattttaccc catccttgac aggttataaa    960
tatgcgatag tatgagtatc ttcaaattca gctgaaatat c                        1001
```

<210> SEQ ID NO 119
<211> LENGTH: 1116
<212> TYPE: DNA
<213> ORGANISM: Artificial Sequence
<220> FEATURE:
<223> OTHER INFORMATION: Promotor

<400> SEQUENCE: 119

```
tgtttaagtg ggtgatgttg gaggtatttg aggtaaaata ggtttatagt ttgataacta      60
gcggagaaaa gaaggagagt ctcatctgga ggagaaataa acttacttaa atagtttttc    120
ggccatttaa ctgggttacg acatcattac gtgtaggtca gcacactgaa tagaattaga    180
ctaagtataa gcacagggag ttgggggtag ccctcgaaaa tcaggacatc tggggtaaat     240 tttcctaaa atgcgcacca actgcagtac aatatggcgt ttgggaggag caacatcccg     300
acaagattgg gatttctgta gcctttgcca taaactggac aggagtttcc acacccgttt    360
cagccggtcc cttttattgg ttcttcggaa ggctagagta acggcccaat gtgaagagag    420
gaacattgtt tcgttacgtt ccgaaaccta gaatggtgtt ttgggaaggg actactaaga    480
tgatgctgtg tagaagtttg agccgtagag tcccacttag agaacatcat cgaactattt    540
aattagaagc tggttccgca cccaagcaat gatataaaca acaattgagt gacaggtcta    600
ctttgttctc aaaaggccat aaccatcgt ttgcatctct tatcaccaca ccatcctcct    660
catctggcct tcaattgtgg ggaacaacta gcatcccaac accagactaa ctccacccag    720
atgaaaccag ttgtcgctta ccagtcaatg aatgttgagc taacgttcct tgaaactcga    780
atgatcccag ccttgctgcg tatcatccct ccgctattcc gccgcttgct ccaaccatgt    840
ttccgccttt ttcgaacaag ttcaaatacc tatctttggc aggactttc ctcctgcctt    900 ttttagcctc aggtctcggt tagcctctag gcaaattctg gtcttcatac ctatatcaac   960
ttttcatcag atagcctttg ggttcaaaaa agaactaaag caggatgcct gatatataaa    1020
tcccagatga tctgcttttg aaactatttt cagtatcttg attcgtttac ttacaaacaa    1080
ctattgttga ttttatctgg agaataatcg aacaaa                                 1116
```

<210> SEQ ID NO 120
<211> LENGTH: 1064
<212> TYPE: DNA

<213> ORGANISM: Artificial Sequence
<220> FEATURE:
<223> OTHER INFORMATION: Promotor

<400> SEQUENCE: 120

```
tgtttaagtg ggtgatgttg gaggtatttg aggtaaaata ggtttatagt ttgataacta      60
gcggagaaaa gaaggagagt ctcatctgga ggagaaataa acttacttaa atagttttc     120
ggccatttaa ctgggttacg acatcattac gtgtaggtca gcacactgaa tagaattaga    180
ctaagtataa gcacagggag ttgggggtag ccctcgaaaa tcaggacatc tggggtaaat    240
tttccctaaa atgcgcacca actgcagtac aatatggcgt ttgggaggag caacatcccg    300
acaagattgg gatttctgta gcctttgcca taaactggac aggagtttcc acaccgttt    360
cagccggtcc cttttattgg ttcttcggaa ggctagagta acggcccaat gtgaagagag    420
gaacattgtt tcgttacgtt ccgaaaccta gaatggtgtt ttgggaaggg actactaaga   480
tgatgctgtg tagaagtttg agccgtagag tcccacttag agaacatcat cgaactattt    540
aattagaagc tggttccgca cccataatcg aactccgaat gcggttctcc tgtaaccttta  600
attgtagcat agatcactta aataaactca tggcctgaca tctgtacacg ttcttattgg   660
tcttttagca atcttgaagt ctttctattg ttccggtcgg cattacctaa taaattcgaa    720
tcgagattgc tagtacctga tatcatatga agtaatcatc acatgcaagt tccatgatac    780
cctctactaa tggaattgaa caaagtttaa gcttctcgca cgagaccgaa tccatactat    840
gcaccctca aagttgggat tagtcaggaa agctgagcaa ttaacttccc tcgattggcc    900
tggactttc gcttagcctg ccgcaatcgg taagtttcat tatcccagcg gggtgatagc    960
ctctgttgct catcaggcca aaatcatata aagctgtag acccagcact tcaattactt   1020
gaaattcacc ataacacttg ctctagtcaa gacttacaat taaa                   1064
```

<210> SEQ ID NO 121
<211> LENGTH: 1251
<212> TYPE: DNA
<213> ORGANISM: Artificial Sequence
<220> FEATURE:
<223> OTHER INFORMATION: Promotor

<400> SEQUENCE: 121

```
ttttgatgtt tgatagtttg ataagagtga actttagtgt ttagaggggt tataatttgt     60
tgtaactggt tttggtctta agttaaaacg aacttgttat attaaacaca acggtcactc    120
aggatacaag aataggaaag aaaaacttta aactggggac atgttgtctt tatataattt    180
ggcggttaac ccttaatgcc cgtttccgtc tcttcatgat aacaaagctg cccatctatg   240
actgaatgtg gagaagtatc ggaacaaccc ttcactaagg atatctaggc taaactcatt    300
cgcgccttag atttctccaa ggtatcggtt aagtttcctc tttcgtactg gctaacgatg   360
gtgttgctca acaaagggat ggaacggcag ctaaagggag tgcatggaat gactttaatt   420
ggctgagaaa gtgttctatt tgtccgaatt tcttttttct attatctgtt cgtttgggcg    480
gatctctcca gtgggggta aatggaagat ttctgttcat ggggtaagga agctgaaatc    540
cttcgtttct tataggggca agtatactaa atctcggaac attgaatggg gtttactttc   600
attggctaca gaaattatta agtttgttat ggggtgaagt taccagtaat tttcattttt    660
tcacttcaac ttttggggta tttctgtggg gtagcataga gcaatgatat aaacaacaat    720
tgagtgacag gtctactttg ttctcaaaag gccataacca tctgtttgca tctcttatca   780
ccacaccatc ctcctcatct ggccttcaat tgtggggaac aactagcatc ccaacaccag    840
```

```
actaactcca cccagatgaa accagttgtc gcttaccagt caatgaatgt tgagctaacg      900
ttccttgaaa ctcgaatgat cccagccttg ctgcgtatca tccctccgct attccgccgc      960
ttgctccaac catgtttccg ccttttttcga acaagttcaa atacctatct ttggcaggac    1020
ttttcctcct gccttttttta gcctcaggtc tcggttagcc tctaggcaaa ttctggtctt    1080
catacctata tcaactttttc atcagatagc ctttgggttc aaaaaagaac taaagcagga    1140
tgcctgatat ataaatccca gatgatctgc ttttgaaact attttcagta tcttgattcg    1200
tttacttaca aacaactatt gttgattttta tctggagaat aatcgaacaa a            1251
```

<210> SEQ ID NO 122
<211> LENGTH: 956
<212> TYPE: DNA
<213> ORGANISM: Artificial Sequence
<220> FEATURE:
<223> OTHER INFORMATION: Promotor

<400> SEQUENCE: 122

```
tgtttaagtg ggtgatgttg gaggtatttg aggtaaaata ggtttatagt ttgataacta       60
gcggagaaaa gaaggagagt ctcatctgga ggagaaataa acttacttaa atagttttc      120 ggccatttaa ctgggttacg acatcattac gtgtaggtca gcacactgaa tagaattaga      180
ctaagtataa gcacagggag ttggggtag ccctcgaaaa tcaggacatc tggggtaaat      240
tttccctaaa atgcgcacca actgcagtac aatatggcgt ttgggaggag caacatcccg      300
acaagattgg gatttctgta gcctttgcca taaactggac aggagttttcc acaccccgttt    360 cagccggtcc ctttttattgg ttcttcggaa ggctagagta acggcccaat gtgaagagag      420
gaacattgtt tcgttacgtt ccgaaaccta aatggtgtt ttgggaaggg actactaaga      480
tgatgctgtg tagaagtttg agccgtagag tcccacttag agaacatcat cgaactattt      540
aattagaagc tggttccgca cccaccaaaa agagaaaaaa gagggaatcc ctgttctttc      600
caatggaaat gacgtaactt taacttgaaa ataccccca ccagaagggt tcaaactcaa      660
caaggattgc gtaattccta caagtagctt agagctgggg gagagacaac tgaaggcagc      720
ttaacgataa cgcggggggaa ttggtgcacg actcgaaagg aggtatctta gtcttgtaac      780
ctcttttttc cagaggctat tcaagattca taggcgatat cgatgtggag aagggtgaac      840
aatataaaag gctggagaga tgtcaatgaa gcagctggat agattttcaaa ttttctagat      900 ttcagagtaa tcgcacaaaa cgaaggaatc ccaccaagca aaaaaaaaa tctaag          956
```

<210> SEQ ID NO 123
<211> LENGTH: 1009
<212> TYPE: DNA
<213> ORGANISM: Artificial Sequence
<220> FEATURE:
<223> OTHER INFORMATION: Promotor

<400> SEQUENCE: 123

```
tgtgaatatc aagaattgta tgaacaagca aagttggagc tttgagcgat gtatttatat       60
gagtagtgaa atcctgattg cgatcaggta aggctctaaa aatcgatgat ggtcccgaat      120
tctttgatag gctaaggact tcctcatcgg gcagttcgaa ggaagaaggg gcatgagccc      180
tgcgaaacca tatgaggaag ggagatagaa gcagaagatt atccttcggg agcaagtctt      240
tccagcccgc atcttgtgat tggatgatag ttttaactaa ggaaagagtg cgacatccgt      300
tgtgtagtaa tcatgcatac gtctattatt ctctctagtt acccaactct gttatctcac      360
```

```
taattcttat tttccgaatgc aacaagctcc gcattacacc cgaacatcac tccagatgag      420
ggctttctga gtgtggggtc aaatagtttc atgttcccca aatggcccaa aactgacagt      480
ttaaacgctg tcttggaacc taatatgaca aaagcgtgat ctcatccaag atgaactaag      540
tttggttcgt tgaaatgcta acggccagtt ggtcaaaaag aaacttccaa aagtcggcat      600
accgtttgtc ttgtttggta ttgattgacg aatgctcaaa ataatctca ttaatgctta       660 gcgcagtctc tctatcgctt ctgaaccccg gtgcacctgt gccgaaacgc aaatggggaa      720
acaccgcctt tttggatgat tatgcattgt ctccacattg tatgcttcca agattctggt      780
gggaatactg ctgatagcct aacgttcatg atcaaaattt aactgttcta acccctactt      840
gacagcaata tataaacaga aggaagctgc cctgtcttaa acctttttt ttatcatcat       900 tattagctta ctttcataat tgcgactggt tccaattgac aagcttttga ttttaacgac      960
ttttaacgac aacttgagaa gatcaaaaaa caactaatta ttcgaaacg               1009
```

<210> SEQ ID NO 124
<211> LENGTH: 1000
<212> TYPE: DNA
<213> ORGANISM: Artificial Sequence
<220> FEATURE:
<223> OTHER INFORMATION: Promotor

<400> SEQUENCE: 124

```
ttttctcagt tgatttgttt gtggggattt agtaagtcgt aaacttcgtt aaaaaagatc       60
aatgtagtca atacagttga tccgaaatag aaggaagagg tttgcaatgt gtaagaacaa      120
tgtagttaaa agcccgtttt aagacaatat tctttgatgc tgatcagaaa aggacaataa      180
gggattttgg ttgcttcttt tataccaata atcgtctcct catcgcttaa ttttctcccc      240
atctcaaccg gtgaagggta ggacgcttct gtaatctgtt cacataaaag gggttttcac      300
tccgagacaa aaatttatgc gacaaaaata gcctatcttg gaaggtgatg tcttatcaac      360
ttgcattgtt tgcaaggaga agcaaggaca actcaacatg ggtaaaaatt caaaaccaac      420
caattggaaa ctcccaactg tccactaggt agctgacagc tgtcactttt gctgttcgtt      480
gtcttgtctc tttcgcttaa taatcgaact ccgaatgcgg ttctcctgta accttaattg      540
tagcatagat cacttaaata aactcatggc ctgacatctg tacacgttct tattggtctt      600
ttagcaatct tgaagtcttt ctattgttcc ggtcggcatt acctaataaa ttcgaatcga      660
gattgctagt acctgatatc atatgaagta atcatcacat gcaagttcca tgatacccttc     720 tactaatgga attgaacaaa gtttaagctt ctcgcacgag accgaatcca tactatgcac      780
ccctcaaagt tgggattagt caggaaagct gagcaattaa cttccctcga ttggcctgga     840
cttttcgctt agcctgccgc aatcggtaag tttcattatc ccagcggggt gatagcctct      900
gttgctcatc aggccaaaat catatataag ctgtagaccc agcacttcaa ttacttgaaa      960
ttcaccataa cacttgctct agtcaagact tacaattaaa                          1000
```

<210> SEQ ID NO 125
<211> LENGTH: 758
<212> TYPE: DNA
<213> ORGANISM: Artificial Sequence
<220> FEATURE:
<223> OTHER INFORMATION: Promotor

<400> SEQUENCE: 125

```
tgtgaatatc aagaattgta tgaacaagca aagttggagc tttgagcgat gtatttatat       60
gagtagtgaa atcctgattg cgatcaggta aggctctaaa aatcgatgat ggtcccgaat      120
```

```
tctttgatag gctaaggact tcctcatcgg gcagttcgaa ggaagaaggg gcatgagccc    180
tgcgaaacca tatgaggaag ggagatagaa gcagaagatt atccttcggg agcaagtctt    240
tccagcccgc atcttgtgat tggatgatag ttttaactaa ggaaagagtg cgacatccgt    300
tgtgtagtaa tcatgcatac gtctattatt ctctctagtt acccaactct gttatctcac    360
taattcccaa aaagagaaaa aagagggaat ccctgttctt tccaatggaa atgacgtaac    420
tttaacttga aaataccccc aaccagaagg gttcaaactc aacaaggatt gcgtaattcc    480
tacaagtagc ttagagctgg gggagagaca actgaaggca gcttaacgat aacgcggggg    540
gattggtgca cgactcgaaa ggaggtatct tagtcttgta acctcttttt tccagaggct    600
attcaagatt cataggcgat atcgatgtgg agaagggtga acaatataaa aggctggaga    660
gatgtcaatg aagcagctgg atagatttca aattttctag atttcagagt aatcgcacaa    720
aacgaaggaa tcccaccaag caaaaaaaaa aatctaag                             758
```

<210> SEQ ID NO 126
<211> LENGTH: 2000
<212> TYPE: DNA
<213> ORGANISM: Artificial Sequence
<220> FEATURE:
<223> OTHER INFORMATION: Promotor
<400> SEQUENCE: 126

```
ttttgatgtt tgatagtttg ataagagtga actttagtgt ttagaggggt tataatttgt     60
tgtaactggt tttggtctta agttaaaacg aacttgttat attaaacaca acggtcactc    120
aggatacaag aataggaaag aaaaacttta aactggggac atgttgtctt tatataattt    180
ggcggttaac ccttaatgcc cgtttccgtc tcttcatgat aacaaagctg cccatctatg    240
actgaatgtg gagaagtatc ggaacaaccc ttcactaagg atatctaggc taaactcatt    300
cgcgccttag atttctccaa ggtatcggtt aagtttcctc tttcgtactg gctaacgatg    360
gtgttgctca acaaagggat ggaacggcag ctaaagggag tgcatggaat gactttaatt    420
ggctgagaaa gtgttctatt tgtccgaatt tcttttttct attatctgtt cgtttgggcg    480
gatctctcca gtgggggta aatggaagat ttctgttcat ggggtaagga agctgaaatc    540
cttcgtttct tataggggca agtatactaa atctcggaac attgaatggg gtttactttc    600
attggctaca gaaattatta agtttgttat ggggtgaagt taccagtaat tttcattttt    660
tcacttcaac ttttggggta tttctgtggg gtagcatagc ttgacaggta atatgatgta    720
ctatgggata ggcaagtctt gtgtttcaga taccgccaaa cgttaaatag gaccctcttg    780
gtgacttgct aacttagaaa gtcatgccca ggtgttacgt aatcttactt ggtatgactt    840
tttgagtaac ggacttgcta gagtccttac cagacttcca gttagcaaa ccacagattg    900 atctgtcctc tggcatatct caaaccaatc aacacccgta acccttcat gaaacaactc    960 tagaatgcgt cttatcaaca ggattgccca aaacagtaat aataaaaaaa cgttatagaa   1020
agaaattgga ctacgatatg ctccaatcca aattgtcaaa attgaccacc gaaaagaac    1080 aattggaatt tgacaagagg aacaactcac tagattctca aacggagcgt cacctagagt   1140
cagtttccaa gtcaattaca gaaagtttgg aaacagaaga ggagtatcta caattgaatt   1200
ccaaacttaa agtcgagctg tccgaattca tgtcgctaag gctttcttac ttggaccca    1260 tttttgaaag tttcattaaa gttcagtcaa aaatttcat ggacatttat gacacattaa    1320
agagcggact accttatgtt gattctctat ccaaagagga ttatcagtcc aagatcttgg   1380
```

```
actctagaat agataacatt ctgtcgaaaa tggaagcgct gaaccttcaa gcttacattg    1440
atgattagag caatgatata aacaacaatt gagtgacagg tctactttgt tctcaaaagg    1500
ccataaccat ctgtttgcat ctcttatcac cacaccatcc tcctcatctg gccttcaatt    1560
gtggggaaca actagcatcc caacaccaga ctaactccac ccagatgaaa ccagttgtcg    1620
cttaccagtc aatgaatgtt gagctaacgt tccttgaaac tcgaatgatc ccagccttgc    1680
tgcgtatcat ccctccgcta ttccgccgct tgctccaacc atgtttccgc cttttttcgaa   1740 caagttcaaa tacctatctt tggcaggact tttcctcctg cctttttag cctcaggtct     1800 cggttagcct ctaggcaaat tctggtcttc atacctatat caacttttca tcagatagcc    1860
tttgggttca aaaagaact aaagcaggat gcctgatata taaatcccag atgatctgct     1920
tttgaaacta ttttcagtat cttgattcgt ttacttacaa caactattg ttgattttat     1980 ctggagaata atcgaacaaa                                                2000
```

<210> SEQ ID NO 127
<211> LENGTH: 1818
<212> TYPE: DNA
<213> ORGANISM: Artificial Sequence
<220> FEATURE:
<223> OTHER INFORMATION: Promotor

<400> SEQUENCE: 127

```
ttttgatgtt tgatagtttg ataagagtga actttagtgt ttagaggggt tataatttgt      60
tgtaactggt tttggtctta agttaaaacg aacttgttat attaaacaca acggtcactc     120
aggatacaag aataggaaag aaaaacttta aactggggac atgttgtctt tatataattt     180
ggcggttaac ccttaatgcc cgtttccgtc tgaacaaccc ttcactaagg atatctaggc    240
taaactcatt cgcgccttag atttctccaa ggtatcggtt aagtttcctc tttcgtactg     300
gctaacgatg gtgttgctca acaaagggat ggaacggcag ctaaagggag tgcatggaat    360
gactttaatt ggctgagaaa gtgttctatt tgtccgaatt tctttttct attatctgtt     420 cgtttgggcg gatctctcca gtggggggta aatggaagat ttctgttcat ggggtaagga    480
agctgaaatc cttcgtttct tatagggggca agtatactaa atctcggaac attgaatggg   540
gtttactttc attggctaca gaaattatta agtttgttat ggggtgaagt taccagtaat    600 tttcatttttt tcacttcaac ttttgggta tttctgtggg gtagcatagc ttgacaggta    660
atatgatgta ctatgggata ggcaagtctt gtgtttcaga taccgccaaa cgttaaatag    720
gaccctcttg gtgacttgct aacttagaaa gtcatgccca ggtgttacgt aatcttactt    780
ggtatgactt tttgagtaac ggacttgcta gagtccttac cagacttcca gtttagcaaa    840
ccacagattg atctgtcctc tggcatatct caaaccaatc aacaccgta acccttcat      900 gaaacaactc tagaatgcgt cttatcaaca ggattgccca aacagtaat aataaaaaaa     960 cgttatagaa agaaattgga ctacgatatg ctccaatcca aattgtcaaa attgaccacc   1020 gaaaagaac aattggaatt tgacaagagg aacaactcac tagattctca aacgagcgt     1080 cacctagagt cagttttccaa gtcaattaca gaaagtttgg aaacagaaga ggagtatcta   1140
caattgaatt ccaaacttaa agtcgagctg tccgaattca tgtcgctaag gctttcttac    1200
ttggacccca ttttttgaaag tttcattaaa gttcagtcaa aaattttcat ggacatttat    1260
gacacattaa agagcggact accttatgtt gattctctat ccaaagagga ttatcagtcc   1320
aagatcttgg actctagaat agataacatt ctgtcgaaaa tggaagcgct gaaccttcaa   1380
gcttacattc ctcctcatct ggccttcaat tgtggggaac aactagcatc ccaacaccag    1440
```

```
actaactcca cccagatgaa accagttgtc gcttaccagt caatgaatgt tgagctaacg    1500
ttccttgaaa ctcgaatgat cccagccttg ctgcgtatca tccctccgct attccgccgc    1560
ttgctccaac catgtttccg ccttttttcga acatcctgcc ttttttagcc tcaggtctcg    1620
gttagcctct aggcaaattc tggtcttcat acctatatca acttttcatc agatagcctt    1680
tgggttcaaa aagaactaa agcaggatgc ctgatatata aatcccagat gatctgcttt    1740
tgaaactatt ttcagtatct tgattcgttt acttacaaac aactattgtt gattttatct    1800
ggagaataat cgaacaaa                                                  1818
```

<210> SEQ ID NO 128
<211> LENGTH: 1828
<212> TYPE: DNA
<213> ORGANISM: Artificial Sequence
<220> FEATURE:
<223> OTHER INFORMATION: Promotor

<400> SEQUENCE: 128

```
ttttgatgtt tgatagtttg ataagagtga actttagtgt ttagaggggt tataatttgt     60
tgtaactggt tttggtctta agttaaaacg aacttgttat attaaacaca acggtcactc    120
aggatacaag aataggaaag aaaaacttta aactgggac atgttgtctt tatataattt    180
ggcggttaac ccttaatgcc cgtttccgtc tcttcatgat aacaaagctg cccatctatg    240
actgaatgtg gagaagtatc ggaacaaccc ttcactaagg atatctaggc taaactcatt    300
cgcgccttag atttctccaa ggtatcggtt aagtttcctc tttcgtactg gctaacgatg    360
gtgttgctca acaaagggat ggaacggcag ctaaagggag tgcatggaat gactttaatt    420
ggctgagaaa gtgttctatt tgtccgaatt tcttttttct attatctgtt cgtttgggcg    480
gatctctcca gtgggggta aatggaagat ttctgttcat ggggtaagga agctgaaatc    540
cttcgtttct tagggggca agtatactaa atctcggaac attgaatggg gtttactttc    600
attggctaca gaaattatta agtttgttat ggggtgaagt taccagtaat tttcattttt    660
tcacttcaac ttttggggta tttctgtggg gtagcatagc ttgacaggta atatgatgta    720
ctataaatag gaccctcttg gtgacttgct aacttagaaa gtcatgccca ggtgttacgt    780
aatcttactt ggtatgactt tttgagtaac ggacttgcta gagtccttac cagacttcca    840
gtttagcaaa ccagagattg atctgtcctc tggcatatct caaaccaatc aacacccgta    900 acccttttcat gaaacaactc tagaatgcgt cttatcaaca ggattgccca aaacagtaat    960
aataaaaaaa cgttatagaa agaaattgga ctacgatatg ctccaatcca aattgtcaaa   1020
attgaccacc gaaaagaac aattggaatt tgacaagagg aacaactcac tagattctca   1080
aacggagcgt cacctagagt cagtttccaa gtcaattaca gaaagtttgg aaacagaaga   1140
ggagtatcta caattgaatt ccaaacttaa agtcgagctg tccgaattca tgtcgctaag   1200
gctttcttac ttggacccca ttttttgaaag tttcattaaa gttcagtcaa aaattttcat   1260
ggacatttat gacacattaa agagcggact accttatgtt gattctctat ccaaagagga   1320
ttatcagtcc aagatcttgg actctagaat agataacatt ctgtcgaaaa tggaagcgct   1380
gaaccttcaa gcttacattc ctcctcatct ggccttcaat tgtggggaac aactagcatc   1440
ccaacaccag actaactcca cccagatgaa accagttgtc gcttaccagt caatgaatgt   1500
tgagctaacg ttccttgaaa ctcgaatgat cccagccttg ctgcgtatca tccctccgct   1560
attccgccgc ttgctccaac catgtttccg ccttttttcga acatcctgcc ttttttagcc   1620
```

```
tcaggtctcg gttagcctct aggcaaattc tggtcttcat acctatatca acttttcatc    1680
agatagcctt tggggttcaaa aaagaactaa agcaggatgc ctgatatata aatcccagat   1740
gatctgcttt tgaaactatt ttcagtatct tgattcgttt acttacaaac aactattgtt   1800
gattttatct ggagaataat cgaacaaa                                      1828
```

<210> SEQ ID NO 129
<211> LENGTH: 1927
<212> TYPE: DNA
<213> ORGANISM: Artificial Sequence
<220> FEATURE:
<223> OTHER INFORMATION: Promotor

<400> SEQUENCE: 129

```
ttttgatgtt tgatagtttg ataagagtga actttagtgt ttagaggggt tataaatttgt     60 tgtaactggt tttggtctta agttaaaacg aacttgttat attaaacaca acggtcactc    120
aggatacaag aataggaaag aaaaacttta aactggggac atgttgtctt tatataattt    180
ggcggttaac ccttaatgcc cgtttccgtc tcttcatgat aacaaagctg cccatctatg    240
actgaatgtg gagaagtatc ggaacaaccc ttcactaagg atatctaggc taaactcatt    300
cgcgccttag atttctccaa ggtatcggtt aagtttcctc ttgcagctaa agggagtgca    360
tggaatgact ttaattggct gagaaagtgt tctatttgtc cgaatttctt ttttctatta    420
tctgttcgtt tgggcggatc tctccagtgg ggggtaaatg gaagatttct gttcatgggg    480
taaggaagct gaaatccttc gtttcttata ggggcaagta tactaaatct cggaacattg    540 aatgggggttt actttcattg gctacagaaa ttattaagtt tgttatgggg tgaagttacc    600
agtaattttc atttttttcac ttcaacttttt ggggtatttc tgtggggtag catagcttga    660
caggtaatat gatgtactat gggataggca agtcttgtgt ttcagatacc gccaaacgtt    720
aaataggacc ctcttggtga cttgctaact tagaaagtca tgcccaggtg ttacgtaatc    780
ttacttggta tgacttttttg agtaacggac ttgctagagt ccttaccaga cttccagttt    840
agcaaaccac agattgatct gtcctctggc atatctcaaa ccaatcaaca cccgtaaccc    900
tttcatgaaa caactctaga atgcgtctta tcaacaggat tgcccaaaac agtaataata    960
aaaaaacgtt atagaaagaa attggactac gatatgctcc aatccaaatt gtcaaaattg   1020
accaccgaaa agaacaatt ggaatttgac aagaggaaca actcactaga ttctcaaacg    1080
gagcgtcacc tagagtcagt ttccaagtca attacagaaa gtttggaaac agaagaggag   1140
tatctacaat tgaattccaa acttaaagtc gagctgtccg aattcatgtc gctaaggctt   1200
tcttacttgg accccatttt tgaaagtttc attaaagttc agtcaaaaat tttcatggac   1260
atttatgaca cattaaagag cggactacct tatgttgatt ctctatccaa agaggattat   1320
cagtccaaga tcttggactc tagaatagat aacattctgt cgaaaatgga agcgctgaac   1380
cttcaagctt acattgatga ttagagcaat gatataaaca acaattgagt gacaggtcta   1440
ctttgttctc aaaaggccat aaccatctgt ttgcatctct tatcaccaca ccatcctcct   1500
catctggcct tcaattgtgg ggaacaacta gcatcccaac accagactaa ctccacccag   1560
atgaaaccag ttgtcgctta ccagtcaatg aatgttgagc taacgttcct tgaaactcga   1620
atgatcccag ccttgctgcg tatcatccct ccgctattcc gccgcttgct ccaaccatgt   1680
ttccgccttt ttcgaacaag ttcaaatacc tatctttggc aggactttttc ctcctgcctt   1740 tgcaaattct ggtcttcata cctatatcaa ctttttcatca gatagccttt ggggttcaaaa    1800 aagaactaaa gcaggatgcc tgatatataa atcccagatg atctgctttt gaaactattt   1860
```

```
tcagtatctt gattcgttta cttacaaaca actattgttg attttatctg gagaataatc   1920
gaacaaa                                                             1927

<210> SEQ ID NO 130
<211> LENGTH: 1921
<212> TYPE: DNA
<213> ORGANISM: Artificial Sequence
<220> FEATURE:
<223> OTHER INFORMATION: Promotor

<400> SEQUENCE: 130
ttttgatgtt tgatagtttg ataagagtga actttagtgt ttagaggggt tataatttgt     60
tgtaactggt tttggtctta agttaaaacg aacttgttat attaaacaca acggtcactc    120
aggatacaag aataggaaag aaaaacttta aactggggac atgttgtctt tatataattt    180
ggcggttaac ccttaatgcc cgtttccgtc tgaacaaccc ttcactaagg atatctaggc    240
taaactcatt cgcgccttag atttctccaa ggtatcggtt aagttcctc tttcgtactg     300 gctaacgatg gtgttgctca acaaagggat ggaacggcag ctaaagggag tgcatggaat    360
gactttaatt ggctgagaaa gtgttctatt tgtccgaatt tcttttttct attatctgtt    420
cgtttgggcg gatctctcca gtgggggta aatggaagat ttctgttcat ggggtaagga     480
agctgaaatc cttcgtttct tataggggca agtatactaa atctcggaac attgaatggg    540
gtttactttc attggctaca gaaattatta agtttgttat ggggtgaagt taccagtaat    600
tttcattttt tcacttcaac tttgggta tttctgtggg gtagcatagc ttgacaggta      660
atatgatgta ctatgggata ggcaagtctt gtgtttcaga taccgccaaa cgttaaatag    720
gaccctcttg gtgacttgct aacttagaaa gtcatgccca ggtgttacgt aatcttactt    780
ggtatgactt tttgagtaac ggacttgcta gagtccttac cagacttcca gtttagcaaa    840
ccacagattg atctgtcctc tggcatatct caaaccaatc aacacccgta acccttcat     900 gaaacaactc tagaatgcgt cttatcaaca ggattgccca aaacagtaat aataaaaaaa    960
cgttatagaa agaaattgga ctacgatatg ctccaatcca aattgtcaaa attgaccacc   1020 gaaaagaac aattggaatt tgacaagagg aacaactcac tagattctca aacggagcgt    1080
cacctagagt cagtttccaa gtcaattaca gaaagtttgg aaacagaaga ggagtatcta   1140
caattgaatt ccaaacttaa agtcgagctg tccgaattca tgtcgctaag ctttcttac    1200 ttggaccca tttttgaaag tttcattaaa gttcagtcaa aattttcat ggacatttat     1260 gacacattaa agagcggact acctttatgtt gattctctat ccaaagagga ttatcagtcc   1320
aagatcttgg actctagaat agataacatt ctgtcgaaaa tggaagcgct gaaccttcaa   1380
gcttacattg atgattagag caatgatata acaacaatt gagtgacagg tctactttgt    1440
tctcaaaagg ccataaccat ctgtttgcat ctcttatcac cacaccatcc tcctcatctg   1500
gccttcaatt gtggggaaca actagcatcc caacaccaga ctaactccac ccagatgaaa   1560
ccagttgtcg cttaccagtc aatgaatgtt gagctaacgt tccttgaaac tcgaatgatc   1620
ccagccttgc tgcgtatcat ccctccgcta ttccgccgct tgctccaacc atgtttccgc   1680 cttttttcgaa caagttcaaa tacctatctt tggcaggact tttcctcctg cctttgcaaa   1740
ttctggtctt catacctata tcaacttttc atcagatagc ctttgggttc aaaaaagaac   1800
taaagcagga tgcctgatat ataaatccca gatgatctgc ttttgaaact attttcagta    1860
tcttgattcg tttacttaca aacaactatt gttgatttta tctggagaat aatcgaacaa   1920
```

| | |
|---|---|
| a | 1921 |

<210> SEQ ID NO 131
<211> LENGTH: 1824
<212> TYPE: DNA
<213> ORGANISM: Artificial Sequence
<220> FEATURE:
<223> OTHER INFORMATION: Promotor

<400> SEQUENCE: 131

| | | | | | |
|---|---|---|---|---|---|
| ttttgatgtt | tgatagtttg | ataagagtga | actttagtgt | ttagaggggt | tataatttgt | 60 |
| tgtaactggt | tttggtctta | agttaaaacg | aacttgttat | attaaacaca | acggtcactc | 120 |
| aggatacaag | aataggaaag | aaaaacttta | aactggggac | atgttgtctt | tatataattt | 180 |
| ggcggttaac | ccttaatgcc | cgtttccgtc | tcttcatgat | aacaaagctg | cccatctatg | 240 |
| actgaatgtg | gagaagtatc | ggaacaaccc | ttcactaagg | atatctaggc | taaactcatt | 300 |
| cgcgccttag | atttctccaa | ggtatcggtt | aagtttcctc | ttgcagctaa | agggagtgca | 360 |
| tggaatgact | ttaattggct | gagaaagtgt | tctatttgtc | cgaatttctt | ttttctatta | 420 |
| tctgttcgtt | tgggcggatc | tctccagtgg | ggggtaaatg | gaagatttct | gttcatgggg | 480 |
| taaggaagct | gaaatccttc | gtttcttata | ggggcaagta | tactaaatct | cggaacattg | 540 |
| aatgggcttt | actttcattg | gctacagaaa | ttattaagtt | tgttatgggg | tgaagttacc | 600 |
| agtaattttc | attttttcac | ttcaactttt | ggggtatttc | tgtggggtag | catagcttga | 660 |
| caggtaatat | gatgtactat | gggataggca | agtcttgtgt | ttcagatacc | gccaaacgtt | 720 |
| aaataggacc | ctcttggtga | cttgctaact | tagaaagtca | tgcccaggtg | ttacgtaatc | 780 |
| ttacttggta | tgactttttg | agtaacggac | ttgctagagt | ccttaccaga | cttccagttt | 840 |
| agcaaaccac | agattgatct | gtcctctggc | atatctcaaa | ccaatcaaca | cccgtaaccc | 900 |
| tttcatgaaa | caactctaga | atgcgtctta | tcaacaggat | tgcccaaaac | agtaataata | 960 |
| aaaaaacgtt | atagaaagaa | attggactac | gatatgctcc | aatccaaatt | gtcaaaattg | 1020 |
| accaccgaaa | agaacaatt | ggaatttgac | aagaggaaca | actcactaga | ttctcaaacg | 1080 |
| gagcgtcacc | tagagtcagt | ttccaagtca | attacagaaa | gtttggaaac | agaagaggag | 1140 |
| tatctacaat | tgaattccaa | acttaaagtc | gagctgtccg | aattcatgtc | gctaaggctt | 1200 |
| tcttacttgg | accccatttt | tgaaagtttc | attaaagttc | agtcaaaaat | tttcatggac | 1260 |
| atttatgaca | cattaaagag | cggactacct | tatgttgatt | ctctatccaa | agaggattat | 1320 |
| cagtccaaga | tcttggactc | tagaatagat | aacattctgt | cgaaaatgga | agcgctgaac | 1380 |
| cttcaagctt | acattcctcc | tcatctggcc | ttcaattgtg | gggaacaact | agcatcccaa | 1440 |
| caccagacta | actccaccca | gatgaaacca | gttgtcgctt | accagtcaat | gaatgttgag | 1500 |
| ctaacgttcc | ttgaaactcg | aatgatccca | gccttgctgc | gtatcatccc | tccgctattc | 1560 |
| cgccgcttgc | tccaaccatg | tttccgcctt | tttcgaacat | cctgcctttt | ttagcctcag | 1620 |
| gtctcggtta | gcctctaggc | aaattctggt | cttcatacct | atatcaactt | ttcatcagat | 1680 |
| agcctttggg | ttcaaaaaag | aactaaagca | ggatgcctga | tatataaatc | ccagatgatc | 1740 |
| tgcttttgaa | actattttca | gtatcttgat | tcgtttactt | acaaacaact | attgttgatt | 1800 |
| ttatctggag | aataatcgaa | caaa | | | | 1824 |

<210> SEQ ID NO 132
<211> LENGTH: 1915
<212> TYPE: DNA
<213> ORGANISM: Artificial Sequence
<220> FEATURE:
<223> OTHER INFORMATION: Promotor

<400> SEQUENCE: 132

```
ttttgatgtt tgatagtttg ataagagtga actttagtgt ttagaggggt tataatttgt    60
tgtaactggt tttggtctta agttaaaacg aacttgttat attaaacaca acggtcactc   120
aggatacaag aataggaaag aaaaacttta aactggggac atgttgtctt tatataattt   180
ggcggttaac ccttaatgcc cgtttccgtc tcttcatgat aacaaagctg cccatctatg   240
actgaatgtg gagaagtatc ggaacaaccc ttcactaagg atatctaggc taaactcatt   300
cgcgccttag atttctccaa ggtatcggtt aagtttcctc tttcgtactg gctaacgatg   360
gtgttgctca acaaagggat ggaacggcag ctaagggag tgcaattatc tgttcgtttg    420
ggcggatctc tccagtgggg ggtaaatgga agatttctgt tcatgggta aggaagctga    480
aatccttcgt ttcttatagg ggcaagtata ctaaatctcg gaacattgaa tggggtttac   540
tttcattggc tacagaaatt attaagtttg ttatggggtg aagttaccag taattttcat   600
ttttcactt caacttttgg ggtatttctg tggggtagca tagcttgaca ggtaatatga    660
tgtactatgg gataggcaag tcttgtgttt cagataccgc caaacgttaa ataggaccct   720
cttggtgact tgctaactta gaaagtcatg cccaggtgtt acgtaatctt acttggtatg   780
acttttgag taacggactt gctagagtcc ttaccagact tccagtttag caaaccacag   840
attgatctgt cctctggcat atctcaaacc aatcaacacc cgtaacccct tcatgaaaca   900
actctagaat gcgtcttatc aacaggattg cccaaaacag taataataaa aaaacgttat   960
agaaagaaat tggactacga tatgctccaa tccaaattgt caaaattgac caccgaaaaa  1020
gaacaattgg aatttgacaa gaggaacaac tcactagatt ctcaaacgga gcgtcaccta  1080
gagtcagttt ccaagtcaat tacagaaagt ttggaaacag aagaggagta tctacaattg  1140
aattccaaac ttaaagtcga gctgtccgaa ttcatgtcgc taaggcttc ttacttggac   1200
cccatttttg aaagtttcat taaagttcag tcaaaaattt tcatggacat ttatgacaca  1260
ttaaagagcg gactaccta tgttgattct ctatccaaag aggattatca gtccaagatc   1320
ttggactcta gaatagataa cattctgtcg aaaatggaag cgctgaacct tcaagcttac  1380
attgatgatt agagcaatga tataaacaac aattgagtga caggtctact ttgttctcaa  1440
aaggccataa ccatctgttt gcatctctta tcaccacacc atcctcctca tctgccttc   1500
aattgtgggg aacaactagc atcccaacac cagactaact ccacccagat gaaaccagtt  1560
gtcgcttacc agtcaatgaa tgttgagcta acgttccttg aaactcgaat gatcccagcc  1620
ttgctgcgta tcatccctcc gctattccgc cgcttgctcc aaccatgttt ccgccttttt  1680
cgaacaagtt caaatcccta tctttggcag gactttccct cctgcctttg caaattctgg  1740
tcttcatacc tatatcaact tttcatcaga tagcctttgg gttcaaaaaa gaactaaagc  1800
aggatgcctg atatataaat cccagatgat ctgcttttga aactattttc agtatcttga  1860
ttcgtttact tacaaacaac tattgttgat tttatctgga gaataatcga acaaa        1915
```

<210> SEQ ID NO 133
<211> LENGTH: 1927
<212> TYPE: DNA
<213> ORGANISM: Artificial Sequence
<220> FEATURE:
<223> OTHER INFORMATION: Promotor

<400> SEQUENCE: 133

```
ttttgatgtt tgatagtttg ataagagtga actttagtgt ttagaggggt tataatttgt      60
tgtaactggt tttggtctta agttaaaacg aacttgttat attaaacaca acggtcactc     120
aggatacaag aataggaaag aaaaacttta aactggggac atgttgtctt tatataattt     180
ggcggttaac ccttaatgcc cgtttccgtc tcttcatgat aacaaagctg cccatctatg     240
actgaatgtg gagaagtatc ggaacaaccc ttcactaagg atatctaggc taaactcatt     300
cgcgccttag atttctccaa ggtatcggtt aagtttcctc ttgcagctaa agggagtgca     360
tggaatgact ttaattggct gagaaagtgt tctatttgtc cgaatttctt ttttctatta     420
tctgttcgtt tgggcggatc tctccagtgg ggggtaaatg gaagatttct gttcatgggg     480
taaggaagct gaaatccttc gtttcttata ggggcaagta tactaaatct cggaacattg     540
aatgggtttt actttcattg gctacagaaa ttattaagtt tgttatgggg tgaagttacc     600
agtaattttc attttttcac ttcaactttt ggggtatttc tgtggggtag catagcttga     660
caggtaatat gatgtactat gggataggca agtcttgtgt ttcagatacc gccaaacgtt     720
aaataggacc ctcttggtga cttgctaact tagaaagtca tgcccaggtg ttacgtaatc     780
ttacttggta tgacttttg  agtaacggac ttgctagagt ccttaccaga cttccagttt     840
```

```
agcaaaccac agattgatct gtcctctggc atatctcaaa ccaatcaaca cccgtaaccc     900
tttcatgaaa caactctaga atgcgtctta tcaacaggat tgcccaaaac agtaataata     960
aaaaaacgtt atagaaagaa attggactac gatatgctcc aatccaaatt gtcaaaattg    1020
accaccgaaa aagaacaatt ggaatttgac aagaggaaca actcactaga ttctcaaacg    1080
gagcgtcacc tagagtcagt ttccaagtca attacagaaa gtttggaaac agaagaggag    1140
tatctacaat tgaattccaa acttaaagtc gagctgtccg aattcatgtc gctaaggctt    1200
tcttacttgg accccatttt tgaaagtttc attaaagttc agtcaaaaat tttcatggac    1260
atttatgaca cattaaagag cggactacct tatgttgatt ctctatccaa agaggattat    1320
cagtccaaga tcttggactc tagaatagat aacattctgt cgaaaatgga agcgctgaac    1380
cttcaagctt acattgatga ttagagcaat gatataaaca acaattgagt gacaggtcta    1440
ctttgttctc aaaaggccat aaccatctgt ttgcatctct tatcaccaca ccatcctcct    1500
catctggcct tcaattgtgg ggaacaacta gcatcccaac accagactaa ctccacccag    1560
atgaaaccag ttgtcgctta ccagtcaatg aatgttgagc taacgttcct tgaaactcga    1620
atgatcccag ccttgctgcg tatcatccct ccgctattcc gccgcttgct ccaaccatgt    1680
ttccgccttt ttcgaacaag ttcaaatacc tatctttggc aggactttc  ctcctgcctt    1740 ttttagcctc aggtctcggt tagcctctag gcaaattctg gtcttcatac cggttcaaaa    1800
aagaactaaa gcaggatgcc tgatatataa atcccagatg atctgctttt gaaactattt    1860
tcagtatctt gattcgttta cttacaaaca actattgttg attttatctg gagaataatc    1920
gaacaaa                                                              1927
```

<210> SEQ ID NO 134
<211> LENGTH: 1357
<212> TYPE: DNA
<213> ORGANISM: Artificial Sequence
<220> FEATURE:
<223> OTHER INFORMATION: Promotor

<400> SEQUENCE: 134

```
ttttgatgtt tgatagtttg ataagagtga actttagtgt ttagaggggt tataatttgt      60
tgtaactggt tttggtctta agttaaaacg aacttgttat attaaacaca acggtcactc     120
```

```
aggatacaag aataggaaag aaaaacttta aactggggac atgttgtctt tatataattt    180
ggcggttaac ccttaatgcc cgtttccgtc tcttcatgat aacaaagctg cccatctatg    240
actgaatgtg gagaagtatc ggaacaaccc ttcactaagg atatctaggc taaactcatt    300
cgcgccttag atttctccaa ggtatcggtt aagtttcctc tttcgtactg gctaacgatg    360
gtgttgctca acaaagggat ggaacgaata aaaaaacgtt atagaaagaa attggactac    420
gatatgctcc aatccaaatt gtcaaaattg accaccgaaa agaacaatt  ggaatttgac    480 aagaggaaca actcactaga ttctcaaacg gagcgtcacc tagagtcagt tccaagtca    540 attacagaaa gtttggaaac agaagaggag tatctacaat tgaattccaa acttaaagtc    600
gagctgtccg aattcatgtc gctaaggctt tcttacttgg accccatttt tgaaagtttc    660
attaaagttc agtcaaaaat tttcatggac atttatgaca cattaaagag cggactacct    720
tatgttgatt ctctatccaa agaggattat cagtccaaga tcttggactc tagaatagat    780
aacattctgt cgaaaatgga agcgctgaac cttcaagctt acattgatga ttagagcaat    840
gatataaaca acaattgagt gacaggtcta ctttgttctc aaaaggccat aaccatctgt    900
ttgcatctct tatcaccaca ccatcctcct catctggcct tcaattgtgg ggaacaacta    960
gcatcccaac accagactaa ctccacccag atgaaaccag ttgtcgctta ccagtcaatg   1020
aatgttgagc taacgttcct tgaaactcga atgatcccag ccttgctgcg tatcatccct   1080
ccgctattcc gccgcttgct ccaaccatgt ttccgccttt ttcgaacaag ttcaaatacc   1140
tatctttggc aggacttttc ctcctgcctt tgcaaattct ggtcttcata cctatatcaa   1200
cttttcatca gatagccttt gggttcaaaa agaactaaa  gcaggatgcc tgatatataa   1260
atcccagatg atctgctttt gaaactattt tcagtatctt gattcgttta cttacaaaca   1320
actattgttg attttatctg gagaataatc gaacaaa                            1357

<210> SEQ ID NO 135
<211> LENGTH: 1232
<212> TYPE: DNA
<213> ORGANISM: Artificial Sequence
<220> FEATURE:
<223> OTHER INFORMATION: Promotor

<400> SEQUENCE: 135
ttttgatgtt tgatagtttg ataagagtga actttagtgt ttagaggggt tataatttgt     60
tgtaactggt tttggtctta agttaaaacg aacttgttat attaaacaca acggtcactc    120
aggatacaag aataggaaag aaaaacttta aactggggac atgttgtctt tatataattt    180
ggcggttaac ccttaatgcc cgtttccgtc tcttcatgat aacaaagctg cccatctatg    240
actgaatgtg gagaagtatc gaataaaaaa acgttataga agaaattgg  actacgatat    300 gctccaatcc aaattgtcaa aattgaccac cgaaaagaa  caattggaat tgacaagag    360 gaacaactca ctagattctc aaacggagcg tcacctagag tcagtttcca agtcaattac    420
agaaagtttg gaaacagaag aggagtatct acaattgaat tccaaactta aagtcgagct    480
gtccgaattc atgtcgctaa ggcttcttcta cttggacccc attttgaaa gtttcattaa    540 agttcagtca aaaattttca tggcattta  tgacacatta aagagcggac taccttatgt    600
tgattctcta tccaaagagg attatcagtc caagatcttg gactctagaa tagataacat    660
tctgtcgaaa atggaagcgc tgaaccttca agcttacatt gatgattaga gcaatgatat    720
aaacaacaat tgagtgacag gtctactttg ttctcaaaag gccataacca tctgtttgca    780
```

```
tctcttatca ccacaccatc ctcctcatct ggccttcaat tgtggggaac aactagcatc    840
ccaacaccag actaactcca cccagatgaa accagttgtc gcttaccagt caatgaatgt    900
tgagctaacg ttccttgaaa ctcgaatgat cccagccttg ctgcgtatca tccctccgct    960
attccgccgc ttgctccaac catgtttccg ccttttttcga acaagttcaa ataccatatct   1020 ttggcaggac ttttcctcct gcctttgcaa attctggtct tcatacctat atcaactttt   1080
catcagatag cctttgggtt caaaaaagaa ctaaagcagg atgcctgata tataaatccc   1140
agatgatctg cttttgaaac tattttcagt atcttgattc gtttacttac aaacaactat   1200
tgttgatttt atctggagaa taatcgaaca aa                                  1232

<210> SEQ ID NO 136
<211> LENGTH: 1013
<212> TYPE: DNA
<213> ORGANISM: Artificial Sequence
<220> FEATURE:
<223> OTHER INFORMATION: Promotor

<400> SEQUENCE: 136
ttttactacg atagacacaa gaagaagcag gaggggagg atctggatat ttataagagt      60
ctcccataga taaagatcta acatccaaag acgaaaggtt gaatgaaacc ttttttgccat   120 ccgacatcca caggtccatt ctcacacata agtgccaaac gcaacaggag gggatacact   180
agcagcagac cgttgcaaac gcaggacctc cactcctctt ctcctcaaca cccacttttg   240
ccatcgaaaa accagcccag ttattgggct tgattggagc tcgctcattc caattccttc   300
tattaggcta ctaacaccat gactttatta gcctgtctat cctggccccc ctggcgaggt   360
tcatgtttgt ttatttccga atgcaacaag ctccgcatta cacccgaaca tcactccaga   420
tgagggcttt ctgagtgtgg ggtcaaatag tttcatgttc cccaaatggc ccaaaactga   480
cagtttaaac gctgtcttgg aacctaatat gacaaaagcg tgatctcatc caagatgaac   540
taagtttggt tcgttgaaat gctaacggcc agttggtcaa aaagaaactt ccaaaagtcg   600
gcataccgtt tgtcttgttt ggtattgatt gacgaatgct caaaaataat ctcattaatg   660
cttagcgcag tctctctatc gcttctgaac cccggtgcac ctgtgccgaa acgcaaatgg   720 ggaaacacccc gcttttggaa tgattatgca ttgtctccac attgtatgct tccaagattc   780
tggtgggaat actgctgata gcctaacgtt catgatcaaa atttaactgt tctaaccct    840 acttgacagc aatatataaa cagaaggaag ctgccctgtc ttaaaccttt tttttatca    900 tcattattag cttactttca taattgcgac tggttccaat tgacaagctt ttgattttaa    960 cgactttta a cgacaacttg agaagatcaa aaaacaacta attattcgaa acg           1013

<210> SEQ ID NO 137
<211> LENGTH: 784
<212> TYPE: DNA
<213> ORGANISM: Artificial Sequence
<220> FEATURE:
<223> OTHER INFORMATION: Promotor

<400> SEQUENCE: 137
ttttactacg atagacacaa gaagaagcag gaggggagg atctggatat ttataagagt      60
ctcccataga taattaggct actaacacca tgactttatt agcctgtcta tcctggcccc    120
cctggcgagg ttcatgtttg tttatttccg aatgcaacaa gctccgcatt acacccgaac    180
atcactccag atgagggctt tctgagtgtg gggtcaaata gtttcatgtt ccccaaatgg    240
cccaaaactg acagtttaaa cgctgtcttg gaacctaata tgacaaaagc gtgatctcat    300
```

```
ccaagatgaa ctaagtttgg ttcgttgaaa tgctaacggc cagttggtca aaaagaaact      360
tccaaaagtc ggcataccgt ttgtcttgtt tggtattgat tgacgaatgc tcaaaaataa      420
tctcattaat gcttagcgca gtctctctat cgcttctgaa ccccggtgca cctgtgccga      480
aacgcaaatg gggaaacacc cgcttttggg atgattatgc attgtctcca cattgtatgc      540
ttccaagatt ctggtgggaa tactgctgat agcctaacgt tcatgatcaa aatttaactg      600
ttctaacccc tacttgacag caatatataa acagaaggaa gctgccctgt cttaaacctt      660
tttttttatc atcattatta gcttactttc ataattgcga ctggttccaa ttgacaagct      720
tttgatttta acgacttta acgacaactt gagaagatca aaaacaact aattattcga       780 aacg                                                                  784

<210> SEQ ID NO 138
<211> LENGTH: 716
<212> TYPE: DNA
<213> ORGANISM: Artificial Sequence
<220> FEATURE:
<223> OTHER INFORMATION: Promotor

<400> SEQUENCE: 138
ttttactacg atagacacaa gaagaagcag gaggggagg atctggatat ttataagagt       60
ctcccataga taattatttc cgaatgcaac aagctccgca ttacacccga acatcactcc     120
agatgagggc tttctgagtg tggggtcaaa tagtttcatg ttccccaaat ggcccaaaac     180
tgacagttta aacgctgtct tggaacctaa tatgacaaaa gcgtgatctc atccaagatg     240
aactaagttt ggttcgttga atgctaacg gccagttggt caaaagaaa cttccaaaag      300 tcggcatacc gtttgtcttg tttggtattg attgacgaat gctcaaaaat aatctcatta     360
atgcttagcg cagtctctct atcgcttctg aaccccggtg cacctgtgcc gaaacgcaaa     420
tggggaaaca cccgcttttt ggatgattat gcattgtctc cacattgtat gcttccaaga     480
ttctggtggg aatactgctg atagcctaac gttcatgatc aaaatttaac tgttctaacc     540
cctacttgac agcaatatat aaacagaagg aagctgccct gtcttaaacc ttttttttta    600
tcatcattat tagcttactt tcataattgc gactggttcc aattgacaag cttttgattt     660
taacgacttt taacgacaac ttgagaagat caaaaaacaa ctaattattc gaaacg          716

<210> SEQ ID NO 139
<211> LENGTH: 628
<212> TYPE: DNA
<213> ORGANISM: Artificial Sequence
<220> FEATURE:
<223> OTHER INFORMATION: Promotor

<400> SEQUENCE: 139
atttattgat tatttgttta tgggtgagtc tagaaaagga cgcactcgtc ttgtatttat       60
agatgaaaag agtaaagca atgatataaa caacaattga gtgacaggtc tactttgttc      120
tcaaaaggcc ataaccatct gtttgcatct cttatcacca caccatcctc ctcatctggc     180
cttcaattgt ggggaacaac tagcatccca acaccagact aactccaccc agatgaaacc     240
agttgtcgct taccagtcaa tgaatgttga gctaacgttc ttgaaactc gaatgatccc      300 agccttgctg cgtatcatcc ctccgctatt ccgccgcttg ctccaaccat gtttccgcct     360
ttttcgaaca agttcaaata cctatctttg gcaggacttt tcctcctgcc tttttagcc      420 tcaggtctcg gttagcctct aggcaaattc tggtcttcat acctatatca acttttcatc     480
```

| | |
|---|---|
| agatagcctt tgggttcaaa aaagaactaa agcaggatgc ctgatatata aatcccagat | 540 |
| gatctgcttt tgaaactatt ttcagtatct tgattcgttt acttacaaac aactattgtt | 600 |
| gattttatct ggagaataat cgaacaaa | 628 |

<210> SEQ ID NO 140
<211> LENGTH: 1076
<212> TYPE: DNA
<213> ORGANISM: Artificial Sequence
<220> FEATURE:
<223> OTHER INFORMATION: Promotor

<400> SEQUENCE: 140

| | |
|---|---|
| atttattgat tatttgttta tgggtgagtc tagaaaagga cgcactcgtc ttgtatttat | 60 |
| agatgaaaag agttaaaata aaaaaacgtt atagaaagaa attggactac gatatgctcc | 120 |
| aatccaaatt gtcaaaattg accaccgaaa aagaacaatt ggaatttgac aagaggaaca | 180 |
| actcactaga ttctcaaacg gagcgtcacc tagagtcagt ttccaagtca attacagaaa | 240 |
| gtttggaaac agaagaggag tatctacaat tgaattccaa acttaaagtc gagctgtccg | 300 |
| aattcatgtc gctaaggctt tcttacttgg accccatttt tgaaagtttc attaaagttc | 360 |
| agtcaaaaat tttcatggac atttatgaca cattaaagag cggactacct tatgttgatt | 420 |
| ctctatccaa agaggattat cagtccaaga tcttggactc tagaatagat aacattctgt | 480 |
| cgaaaatgga agcgctgaac cttcaagctt acattgatga ttagagcaat gatataaaca | 540 |
| acaattgagt gacaggtcta ctttgttctc aaaaggccat aaccatctgt ttgcatctct | 600 |
| tatcaccaca ccatcctcct catctggcct tcaattgtgg ggaacaacta gcatcccaac | 660 |
| accagactaa ctccacccag atgaaaccag ttgtcgctta ccagtcaatg aatgttgagc | 720 |
| taacgttcct tgaaactcga atgatcccag ccttgctgcg tatcatccct ccgctattcc | 780 |
| gccgcttgct ccaaccatgt ttccgccttt ttcgaacaag ttcaaatacc tatctttggc | 840 |
| aggacttttc ctcctgcctt ttttagcctc aggtctcggt tagcctctag gcaaattctg | 900 |
| gtcttcatac ctatatcaac ttttcatcag atagcctttg ggttcaaaaa agaactaaag | 960 |
| caggatgcct gatatataaa tcccagatga tctgcttttg aaactatttt cagtatcttg | 1020 |
| attcgtttac ttacaaacaa ctattgttga ttttatctgg agaataatcg aacaaa | 1076 |

<210> SEQ ID NO 141
<211> LENGTH: 780
<212> TYPE: DNA
<213> ORGANISM: Artificial Sequence
<220> FEATURE:
<223> OTHER INFORMATION: Promotor

<400> SEQUENCE: 141

| | |
|---|---|
| tgttgtagtt ttaatatagt ttgagtatga gatggaactc agaacgaagg aattatcacc | 60 |
| agtttatata ttctgaggaa actatgctac cccacagaaa taccccaaaa gttgaagtga | 120 |
| aaaaatgaaa attactggta acttcacccc ataacaaact taataatttc tgtagccaat | 180 |
| gaaagtaaac cccattcaat gttccgagat ttagtatact tgcccctata agaaacgaag | 240 |
| gatttcagct tccttacccc atgaacagaa atcttccatt tacccccac tggagagatc | 300 |
| cgcccaaacg aacagataat agaaaaaaga aattcggaca aatagaacac tttctcagcc | 360 |
| aattaaagtc attccatgca ctcccttag ctgccgttcc atccctttgt tgagcaacac | 420 |
| catcgttagc cagtacgaaa gaggaaactt aaccgatacc ttggagaaat ctaaggcgcg | 480 |
| aatgagttta gcctagatat ccttagtgaa gggttgttcc gatacttctc cacattcagt | 540 |

```
catagatggg cagctttgtt atcatgaaga gacggaaacg ggcattaagg gttaaccgcc      600
aaattatata aagacaacat gtccccagtt taaagttttt ctttcctatt cttgtatcct      660
gagtgaccgt tgtgtttaat ataacaagtt cgttttaact taagaccaaa accagttaca      720
acaaattata acccctctaa acactaaagt tcactcttat caaactatca aacatcaaaa      780
```

<210> SEQ ID NO 142
<211> LENGTH: 1081
<212> TYPE: DNA
<213> ORGANISM: Artificial Sequence
<220> FEATURE:
<223> OTHER INFORMATION: Promotor

<400> SEQUENCE: 142

```
tgttgtagtt ttaatatagt ttgagtatga gatggaactc agaacgaagg aattatcacc       60
agtttatata ttctgaggaa aattactgtt ttgggcaatc ctgttgataa gacgcattct      120
agagttgttt catgaaaggg ttacgggtgt tgattggttt gagatatgcc agaggacaga      180
tcaatctgtg gtttgctaaa ctggaagtct ggtaaggact ctagcaagtc cgttactcaa      240
aaagtcatac caagtaagat tacgtaacac ctgggcatga ctttctaagt tagcaagtca      300
ccaagagggt cctatttaac gtttggcggt atctgaaaca caagacttgc ctatcccata      360
gtacatcata ttacctgtca agctatgcta ccccacagaa ataccccaaa agttgaagtg      420
aaaaaatgaa aattactggt aacttcaccc cataacaaac ttaataattt ctgtagccaa      480
tgaaagtaaa ccccattcaa tgttccgaga tttagtatac ttgcccctat aagaaacgaa      540
ggatttcagc ttccttaccc catgaacaga atcttccat ttaccccca ctggagagat      600 ccgcccaaac gaacagataa tagaaaaaag aaattcggac aaatagaaca ctttctcagc      660
caattaaagt cattccatgc actcccttta gctgccgttc catcccttg ttgagcaaca      720 ccatcgttag ccagtacgaa agaggaaact taaccgatac cttggagaaa tctaaggcgc      780
gaatgagttt agcctagata tccttagtga agggttgttc cgatacttct ccacattcag      840
tcatagatgg gcagctttgt tatcatgaag gacggaaac gggcattaag ggttaaccgc      900
caaattatat aaagacaaca tgtccccagt ttaaagtttt ctttcctat tcttgtatcc      960 tgagtgaccg ttgtgtttaa tataacaagt tcgttttaac ttaagaccaa accagttac     1020 aacaaattat aacccctcta acactaaag ttcactctta tcaaactatc aaacatcaaa     1080
a                                                                    1081
```

<210> SEQ ID NO 143
<211> LENGTH: 564
<212> TYPE: DNA
<213> ORGANISM: Artificial Sequence
<220> FEATURE:
<223> OTHER INFORMATION: Promotor

<400> SEQUENCE: 143

```
tttgatttgt ttaggtaact tgaactggat gtattagttt ggtgacaagc ggatgtggga       60
tatcagtgtg tttatatata cgtgatttct ggagtgtcaa aacagtagtg ataaaaggct      120
atgaaggagg ttgtctaggg gctcgcggag gaaagtgatt caaacagacc tgccaaaaag      180
agaaaaaaga gggaatccct gttctttcca atggaaatga cgtaacttta acttgaaaaa      240 tacccccaacc agaagggttc aaactcaaca aggattgcgt aattcctaca agtagcttag      300
agctggggga gagacaactg aaggcagctt aacgataacg cggggggatt ggtgcacgac      360
```

```
tcgaaaggag gtatcttagt cttgtaacct ctttttttcca gaggctattc aagattcata    420
ggcgatatcg atgtggagaa gggtgaacaa tataaaaggc tggagagatg tcaatgaagc    480
agctggatag atttcaaatt ttctagattt cagagtaatc gcacaaaacg aaggaatccc    540
accaagcaaa aaaaaaaatc taag                                           564

<210> SEQ ID NO 144
<211> LENGTH: 478
<212> TYPE: DNA
<213> ORGANISM: Artificial Sequence
<220> FEATURE:
<223> OTHER INFORMATION: Promotor

<400> SEQUENCE: 144
tttgatttgt ttaggtaact tgaactggat gtattagttt ggtgacaagc ggatgtggga     60
tatcagtgtg tttatatata cgtgatccaa aagagaaaa aagagggaat ccctgttctt    120
tccaatggaa atgacgtaac tttaacttga aaaatacccc aaccagaagg gttcaaactc    180
aacaaggatt gcgtaattcc tacaagtagc ttagagctgg gggagagaca actgaaggca    240
gcttaacgat aacgcggggg gattggtgca cgactcgaaa ggaggtatct tagtcttgta    300
acctcttttt tccagaggct attcaagatt cataggcgat atcgatgtgg agaagggtga    360
acaatataaa aggctggaga gatgtcaatg aagcagctgg atagatttca aattttctag    420
atttcagagt aatcgcacaa aacgaaggaa tcccaccaag caaaaaaaaa aatctaag     478

<210> SEQ ID NO 145
<211> LENGTH: 566
<212> TYPE: DNA
<213> ORGANISM: Artificial Sequence
<220> FEATURE:
<223> OTHER INFORMATION: Promotor

<400> SEQUENCE: 145
tttgatttgt ttaggtaact tgaactggat gtattagttt ggtgacaagc ggatgtggga     60
tatcagtgtg tttatatata cgtgatttct ggagtgtcaa acagtagtg ataaaaggct    120 atgaaggagg ttgtctaggg gctcgcggag gaaagtgatt caaacagacc tgccaaaaag    180
agaaaaaaga gggaatccct gttctttcca atggaaatga cgtaacttta acttgaaaaa    240
taccccaacc agaagggttc aaactcaaca aggattgcgt aattcctaca gtagcttag    300 agctggggga gagacaactg aaggcagctt aacgataacg cggggggatt ggtgcacgac    360
tcgaaaggag gtatcttagt cttgtaacct ctttttttcca gaggctattc aagattcata    420
ggcgatatcg atgtggagaa gggtgaacaa tataaaaggc tggagagatg tcaatgaagc    480
agctggatag atttcaaatt ttctagattt cagagtaatc gcacaaaacg aaggaatccc    540
accaagacaa aaaaaaaaat tctaag                                        566

<210> SEQ ID NO 146
<211> LENGTH: 457
<212> TYPE: DNA
<213> ORGANISM: Artificial Sequence
<220> FEATURE:
<223> OTHER INFORMATION: Promotor

<400> SEQUENCE: 146
ttttctttac ctggatataa ataaaaaaaa ggaaacacaa tctctgtttc aagaaattag     60 ggatttagt ctgcttatat acttcgcgct agaattagtg agataacaga ttgggtaac    120 tagagagaat aatagacgta tgcatgatta ctacacaacg gatgtcgcac tctttcctta    180
```

```
gttaaaacta tcatccaatc acaagatgcg ggctggaaag acttgctccc gaaggataat    240
cttctgcttc tatctcccctt cctcatatgg tttcgcaggg ctcatgcccc ttcttccttc    300
gaactgcccg atgaggaagt ccttagccta tcaaagaatt cgggaccatc atcgattttt    360
agagccttac ctgatcgcaa tcaggatttc actactcata taaatacatc gctcaaagct    420
ccaactttgc ttgttcatac aattcttgat attcaca                             457
```

```
<210> SEQ ID NO 147
<211> LENGTH: 644
<212> TYPE: DNA
<213> ORGANISM: Artificial Sequence
<220> FEATURE:
<223> OTHER INFORMATION: Promotor

<400> SEQUENCE: 147
gttttatcga tagtagttga gcaataaaaa aaaggagaaa aagcaggtag gagggaactc    60
gtctatatat accagttgat tgggtgcgga accagcttct aattaaatag ttcgatgatg    120
ttctctaagt gggactctac ggctcaaact tctacacagc atcatcttag tagtcccttc    180
ccaaaacacc attctaggtt tcggaacgta acgaaacaat gttcctctct tcacattggg    240
ccgttactct agccttccga agaaccaata aaagggaccg gctgaaacgg gtgtggaaac    300
tcctgtccag tttatggcaa aggctacaga aatcccaatc ttgtcgggat gttgctcctc    360
ccaaacgcca tattgtactg cagttggtgc gcattttagg gaaaatttac cccagatgtc    420
ctgattttcg agggctaccc ccaactccct gtgcttatac ttagtctaat tctattcagt    480
gtgctgacct acacgtaatg atgtcgtaac ccagttaaat ggccgaaaaa ctatttaagt    540
aagtttattt ctcctccaga tgagactctc cttctttct ccgctagtta tcaaactata    600
aacctatttt acctcaaata cctccaacat cacccactta aaca                    644
```

```
<210> SEQ ID NO 148
<211> LENGTH: 591
<212> TYPE: DNA
<213> ORGANISM: Artificial Sequence
<220> FEATURE:
<223> OTHER INFORMATION: Promotor

<400> SEQUENCE: 148
ttttctttac ctggatataa ataaaaaaaa ggaaacacaa tctctgtttc aagaaattag    60 ggatttagt ctgcttatat acttcgcgct acattgtgac ttgactttta ccaggacttc    120
aaacctcaac catttaaaca gttatagaag acgtaccgtc acttttgctt ttaatgtgat    180
ctaaatgtga tcacatgaac tcaaactaaa atgatatctt ttactggaca aaaatgttat    240
cctgcaaaca gaaagctttc ttctattcta agaagaacat ttacattggt gggaaacctg    300
aaaacagaaa ataaatactc cccagtgacc ctatgagcag gatttttgca tccctattgt    360 aggccttca aactcacacc taatatttcc cgccactcac actatcaatg atcacttccc    420
agttctcttc ttcccctatt cgtaccatgc aacccttaca cgccttttcc atttcggttc    480
ggatgcgact tccagtctgt ggggtacgta gcctattctc ttagccggta tttaaacata    540
caaattcacc caaattctac cttgataagg taattgatta atttcataaa t            591
```

```
<210> SEQ ID NO 149
<211> LENGTH: 795
<212> TYPE: DNA
<213> ORGANISM: Artificial Sequence
<220> FEATURE:
```

<223> OTHER INFORMATION: Promotor

<400> SEQUENCE: 149

```
ttttctttac ctggatataa ataaaaaaaa ggaaacacaa tctctgtttc aagaaattag      60
ggattttagt ctgcttatat acttcgcgct aaaattaatc cataagataa ggcaaatgtg    120
cttaagtaat tgaaaacagt gttgtgatta tataagcatg gtatttgaat agaactactg    180
gggttaactt atctagtagg atggaagttg agggagatca agatgcttaa agaaaaggat    240
tggccaatat gaaagccata attagcaata cttatttaat cagataattg tggggcattg    300
tgacttgact tttaccagga cttcaaacct caaccattta aacagttata gaagacgtac    360
cgtcactttt gcttttaatg tgatctaaat gtgatcacat gaactcaaac taaaatgata    420
tcttttactg gacaaaaatg ttatcctgca aacagaaagc tttcttctat tctaagaaga    480
acatttacat tggtgggaaa cctgaaaaca gaaataaat actccccagt gaccctatga     540
gcaggatttt tgcatcccta ttgtaggcct ttcaaactca cacctaatat ttcccgccac    600
tcacactatc aatgatcact tcccagttct cttcttcccc tattcgtacc atgcaaccct    660
tacacgcctt ttccatttcg gttcggatgc gacttccagt ctgtggggta cgtagcctat    720
tctcttagcc ggtatttaaa catacaaatt caccccaaatt ctaccttgat aaggtaattg    780
attaatttca taaat                                                      795
```

<210> SEQ ID NO 150
<211> LENGTH: 1080
<212> TYPE: DNA
<213> ORGANISM: Artificial Sequence
<220> FEATURE:
<223> OTHER INFORMATION: Promotor

<400> SEQUENCE: 150

```
gttttatcga tagtagttga gcaataaaaa aaaggagaaa aagcaggtag gagggaactc      60
gtctatatat accagttgat atatcgatct acacttaata gtagatgacg aggcatctct    120
ccaataggta ccatatctgg tgtttcttgt aatttaagaa tctgttggtc tatgaatgta    180
gatttgtcat gaacaatgat atatgggtca ggaggacaag atggtttctc tgagttgggt    240
tgttgaggtg cctggcaaga cttcggagcg ttgatatccc caagacttgt agtgaccgat    300
agttgaagcg tgtgtttgca ggaacggcac atcaatgcaa ctttcgtaac tttggaattg    360
agagttgatg cactgatgac gatacccgaa attttgacga ttttaccaat atgacttgaa    420
gacaagtctc tcattgaaac cttattatcg ttactaagca aaacgagctg acaagaaggg    480
aaggtggtcg gtatttcctc gttgttcaaa tatatgattc tcctggcaat atctgtgatg    540
gcctgttcaa aaagtggaat catttctgca ggatcatcta ccaactttt attgagctcc    600
tcattgaata cgattaagtg gtcatttga atcgtcagta agtacttgtt tacaagtaaa   660
ttctgtctga gttgttctct gtagatgtac tgattttcca tacgaaactc caaaatgaac    720
gaacggaatg ccttaatgac ctcactgaac tggtcatcgt tctgttctcc gggaaggaca    780
cttgtgttaa agactgatgc tctatcaaag gacattgcaa caaagtataa acggttgtga    840
gcgggaaaaa gatgtgtagg taattgtcgt agatgagact gattcagtag aaaacgcgtc    900
ctgcactatt ttttctttc ttcattacat ttcctaatcg ggacaaaatg aatctaaaga    960
cgtggttatg tagtacacgc atcgataggc tatccccata ccaaaacact attttacccc   1020
atccttgaca ggttataaat atgcgatagt atgagtatct tcaaattcag ctgaaatatc   1080
```

<210> SEQ ID NO 151
<211> LENGTH: 580
<212> TYPE: DNA
<213> ORGANISM: Artificial Sequence
<220> FEATURE:
<223> OTHER INFORMATION: Promotor

<400> SEQUENCE: 151

```
gttttatcga tagtagttga gcaataaaaa aaaggagaaa aagcaggtag gagggaactc      60
gtctatatat accagttgat ccaactttt attgagctcc tcattgaata cgattaagtg     120
gtcattttga atcgtcagta agtacttgtt tacaagtaaa ttctgtctga gttgttctct    180
gtagatgtac tgattttcca tacgaaactc caaaatgaac gaacgaatg ccttaatgac     240
ctcactgaac tggtcatcgt tctgttctcc gggaaggaca cttgtgttaa agactgatgc    300
tctatcaaag acattgcaa caaagtataa acggttgtga gcgggaaaaa gatgtgtagg     360
taattgtcgt agatgagact gattcagtag aaaacgcgtc ctgcactatt tttttctttc    420
ttcattacat ttcctaatcg ggacaaaatg aatctaaaga cgtggttatg tagtacacgc    480
atcgataggc tatccccata ccaaaacact attttacccc atccttgaca ggttataaat    540
atgcgatagt atgagtatct tcaaattcag ctgaaatatc                          580
```

<210> SEQ ID NO 152
<211> LENGTH: 765
<212> TYPE: DNA
<213> ORGANISM: Artificial Sequence
<220> FEATURE:
<223> OTHER INFORMATION: Promotor

<400> SEQUENCE: 152

```
ttttactacg atagacacaa gaagaagcag gaggggagg atctggatat ttataagagt      60
ctcccataga taaagtgtgt aatcatatat ataataaatg aggaataata attgaataga    120
gatttaacga gtcgaagttt ctgaaatata cgcacagttt atatttatga ttttgatatc    180
taactacagt cttctccata tatttaacta taaataataa agtatataac tcttatgaaa    240
ctgtttcacc acatttttt ctacgtaatc gaactccgaa tgcggttctc ctgtaacctt     300
aattgtagca tagatcactt aaataaactc atggcctgac atctgtacac gttcttattg    360
gtcttttagc aatcttgaag tctttctatt gttccggtcg gcattaccta ataaattcga    420
atcgagattg ctagtacctg atatcatatg aagtaatcat cacatgcaag ttccatgata    480
ccctctacta atggaattga acaaagttta agcttctcgc acgagaccga atccatacta    540
tgcacccctc aaagttggga ttagtcagga aagctgagca attaacttcc ctcgattggc    600
ctggactttt cgcttagcct gccgcaatcg gtaagtttca ttatcccagc ggggtgatag    660
cctctgttgc tcatcaggcc aaaatcatat ataagctgta gacccagcac ttcaattact    720
tgaaattcac cataacactt gctctagtca agacttacaa ttaaa                    765
```

<210> SEQ ID NO 153
<211> LENGTH: 573
<212> TYPE: DNA
<213> ORGANISM: Artificial Sequence
<220> FEATURE:
<223> OTHER INFORMATION: Promotor

<400> SEQUENCE: 153

```
ttttactacg atagacacaa gaagaagcag gaggggagg atctggatat ttataagagt      60
ctcccataga taataatcga actccgaatg cggttctcct gtaaccttaa ttgtagcata    120
```

```
gatcacttaa ataaactcat ggcctgacat ctgtacacgt tcttattggt cttttagcaa    180
tcttgaagtc tttctattgt tccggtcggc attacctaat aaattcgaat cgagattgct    240
agtacctgat atcatatgaa gtaatcatca catgcaagtt ccatgatacc ctctactaat    300
ggaattgaac aaagtttaag cttctcgcac gagaccgaat ccatactatg cacccctcaa    360
agttgggatt agtcaggaaa gctgagcaat taacttccct cgattggcct ggacttttcg    420
cttagcctgc cgcaatcggt aagtttcatt atcccagcgg ggtgatagcc tctgttgctc    480
atcaggccaa aatcatatat aagctgtaga cccagcactt caattacttg aaattcacca    540
taacacttgc tctagtcaag acttacaatt aaa                                 573

<210> SEQ ID NO 154
<211> LENGTH: 562
<212> TYPE: DNA
<213> ORGANISM: Artificial Sequence
<220> FEATURE:
<223> OTHER INFORMATION: Promotor

<400> SEQUENCE: 154
atttattgat tatttgttta tgggtgagtc tagaaaagga cgcactcgtc ttgtatttat     60
agatgaaaag agttaatttt tgtagaaatg tcttggtgtc ctcgtccaat caggtagcca    120
tctctgaaat atctggctcc gttgcaactc cgaacgacct gctggcaacg taaaattctc    180
cggggtaaaa cttaaatgtg gagtaatgga accagaaacg tctcttccct tctctctcct    240
tccaccgccc gttaccgtcc ctaggaaatt ttactctgct ggagagcttc ttctacggcc    300
cccttgcagc aatgctcttc ccagcattac gttgcgggta aaacggaggt cgtgtacccg    360
acctagcagc ccagggatgg aaaagtcccg gccgtcgctg gcaataatag cgggcggacg    420
catgtcatga gattattgga aaccaccaga atcgaatata aaaggcgaac acctttccca    480
attttggttt ctcctgaccc aaagacttta aatttaattt atttgtccct atttcaatca    540
attgaacaac tatcaaaaca ca                                             562

<210> SEQ ID NO 155
<211> LENGTH: 505
<212> TYPE: DNA
<213> ORGANISM: Artificial Sequence
<220> FEATURE:
<223> OTHER INFORMATION: Promotor

<400> SEQUENCE: 155
tgttgtagtt ttaatatagt ttgagtatga gatggaactc agaacgaagg aattatcacc     60
agtttatata ttctgaggaa ataactgtc gcctctttta tctgccgcac tgcatgaggt    120 gtcccttag tgggaaagag tactgagcca accctggagg acagcaaggg aaaaatacct    180
acaacttgct tcataatggt cgtaaaaaca atccttgtcg gatataagtg ttgtagactg    240
tcccttatcc tctgcgatgt tcttcctctc aaagtttgcg atttctctct atcgaattg    300 ccatcaagag actcaggact aatttcgcag tcccacacgc actcgtacat gattggctga    360
aatttcccta agaatttct ttttcacgaa atttttttt ttacacaaga ttttcagcag    420
atataaaatg gagagcagga cctccgctgt gactcttctt ttttttcttt tattctcact    480
acatacattt tagttattcg ccaac                                          505

<210> SEQ ID NO 156
<211> LENGTH: 586
<212> TYPE: DNA
<213> ORGANISM: Artificial Sequence
```

```
<220> FEATURE:
<223> OTHER INFORMATION: Promotor

<400> SEQUENCE: 156
tttgatttgt ttaggtaact tgaactggat gtattagttt ggtgacaagc ggatgtggga      60
tatcagtgtg tttatatata cgtgatatag cgagactttt ttgatttcgc aacgggagtg    120
cctgttccat tcgattgcaa ttctcacccc ttctgcccag tcctgccaat tgcccatgaa    180
tctgctaatt tcgttgattc cacccccct ttccaactcc acaaattgtc caatctcgtt     240
ttccatttgg gagaatctgc atgtcgacta cataaagcga ccggtgtccg aaaagatctg    300
tgtagttttc aacattttgt gctcccccg ctgtttgaaa acggggtga gcgctctccg      360 gggtgcgaat tcgtgcccaa ttcctttcac cctgcctatt gtagacgtca acccgcatct    420
ggtgcgaata tagcgcaccc ccaatgatca caccaacaat tggtccaccc ctccccaatc    480
tctaatattc acaattcacc tcactataaa taccctgtc ctgctcccaa attcttttt      540 ccttcttcca tcagctacta gcttttatct tatttacttt acgaaa                    586

<210> SEQ ID NO 157
<211> LENGTH: 800
<212> TYPE: DNA
<213> ORGANISM: Artificial Sequence
<220> FEATURE:
<223> OTHER INFORMATION: Promotor

<400> SEQUENCE: 157
ttttactacg atagacacaa gaagaagcag gaggggagg atctggatat ttataagagt       60
ctcccataga taacgatttg gcactttttt taggctacta acaccatgac tttattagcc    120
tgtctatcct ggccccctg gcgaggttca tgtttgttta tttccgaatg caacaagctc     180
cgcattacac ccgaacatca ctccagatga gggctttctg agtgtggggt caaatagttt    240
catgttcccc aaatggccca aaactgcacg tttaaacgct gtcttggaac ctaatatgac    300
aaaagcgtga tctcatccaa gatgaactaa gtttggttcg ttgaaatgct aacggccagt    360
tggtcaaaaa gaaacttcca aaagtcggca taccgtttgt cttgtttggt attgattgac    420
gaatgctcaa aaataatctc attaatgctt agcgcagtct ctctatcgct tctgaaccc     480 ggtgcacctg tgccgaaacg caaatgggga acacccgct ttttggatga ttatgcattg    540
tctccacatt gtatgcttcc aagattctgg tgggaatact gctgatagcc taacgttcat    600
gatcaaaatt taactgttct aaccctact tgacagcaat atataaacag aaggaagctg    660
ccctgtctta aacctttttt tttatcatca ttattagctt actttcataa ttgcgactgg    720
ttccaattga caagcttttg attttaacga cttttaacga caacttgaga agatcaaaaa   780
acaactaatt attcgaaacg                                                800

<210> SEQ ID NO 158
<211> LENGTH: 816
<212> TYPE: DNA
<213> ORGANISM: Artificial Sequence
<220> FEATURE:
<223> OTHER INFORMATION: Promotor

<400> SEQUENCE: 158
ttttactacg atagacacaa gaagaagcag gaggggagg atctggatat ttataagagt       60
ctcccataga taacgatttg gcacttttg ccatcagtgc caacattagg ctactaacac     120
catgacttta ttagcctgtc tatcctggcc cccctggcga ggttcatgtt tgtttatttc    180
```

```
cgaatgcaac aagctccgca ttacacccga acatcactcc agatgagggc tttctgagtg      240
tggggtcaaa tagtttcatg ttccccaaat ggcccaaaac tgacagttta aacgctgtct      300
tggaacctaa tatgacaaaa gcgtgatctc atccaagatg aactaagttt ggttcgttga      360
aatgctaacg gccagttggt caaaagaaa cttccaaaag tcggcatacc gtttgtcttg       420
tttggtattg attgacgaat gctcaaaaat aatctcatta atgcttagcg cagtctctct      480
atcgcttctg aaccccggtg cacctgtgcc gaaacgcaaa tggggaaaca cccgcttttt      540
ggatgattat gcattgtctc cacattgtat gcttccaaga ttctggtggg aatactgctg      600
atagcctaac gttcatgatc aaaatttaac tgttctaacc cctacttgac agcaatatat      660
aaacagaagg aagctgccct gtcttaaacc tttttttta tcatcattat tagcttactt       720
tcataattgc gactggttcc aattgacaag cttttgattt taacgacttt taacgacaac      780
ttgagaagat caaaaaacaa ctaattattc gaaacg                                816
```

<210> SEQ ID NO 159
<211> LENGTH: 498
<212> TYPE: DNA
<213> ORGANISM: Artificial Sequence
<220> FEATURE:
<223> OTHER INFORMATION: Promotor

<400> SEQUENCE: 159

```
tttgatttgt ttaggtaact tgaactggat gtattagttt ggtgacaagc ggatgtggga       60
tatcagtgtg tttatatata cgtgatgggg ggaggactct cgtttcccaa aagagaaaa      120 aagagggaat ccctgttctt tccaatggaa atgacgtaac tttaacttga aaaatacccc      180
aaccagaagg gttcaaactc aacaaggatt gcgtaattcc tacaagtagc ttagagctgg      240
gggagagaca actgaaggca gcttaacgat aacgcggggg gattggtgca cgactcgaaa      300
ggaggtatct tagtcttgta acctcttttt tccagaggct attcaagatt cataggcgat      360
atcgatgtgg agaagggtga acaatataaa aggctggaga gatgtcaatg aagcagctgg      420
atagatttca aattttctag atttcagagt aatcgcacaa aacgaaggaa tcccaccaag      480
caaaaaaaaa aatctaag                                                    498
```

<210> SEQ ID NO 160
<211> LENGTH: 518
<212> TYPE: DNA
<213> ORGANISM: Artificial Sequence
<220> FEATURE:
<223> OTHER INFORMATION: Promotor

<400> SEQUENCE: 160

```
tttgatttgt ttaggtaact tgaactggat gtattagttt ggtgacaagc ggatgtggga       60
tatcagtgtg tttatatata cgtgatgggg ggaggactct cgtttcctat gataccttat      120
ggaatgccaa aaagagaaaa aagagggaat ccctgttctt tccaatggaa atgacgtaac      180
tttaacttga aaaatacccc aaccagaagg gttcaaactc aacaaggatt gcgtaattcc      240
tacaagtagc ttagagctgg gggagagaca actgaaggca gcttaacgat aacgcggggg      300
gattggtgca cgactcgaaa ggaggtatct tagtcttgta acctcttttt tccagaggct      360
attcaagatt cataggcgat atcgatgtgg agaagggtga acaatataaa aggctggaga      420
gatgtcaatg aagcagctgg atagatttca aattttctag atttcagagt aatcgcacaa      480
aacgaaggaa tcccaccaag caaaaaaaaa aatctaag                              518
```

```
<210> SEQ ID NO 161
<211> LENGTH: 477
<212> TYPE: DNA
<213> ORGANISM: Artificial Sequence
<220> FEATURE:
<223> OTHER INFORMATION: Promotor

<400> SEQUENCE: 161
ttttctttac ctggatataa ataaaaaaaa ggaaacacaa tctctgtttc aagaaattag     60
ggattttagt ctgcttatat acttcgcgct accccgcgac ccgagcaact agaattagtg    120
agataacaga gttgggtaac tagagagaat aatagacgta tgcatgatta ctacacaacg    180
gatgtcgcac tctttcctta gttaaaacta tcatccaatc acaagatgcg ggctggaaag    240
acttgctccc gaaggataat cttctgcttc tatctccctt cctcatatgg tttcgcaggg    300
ctcatgcccc ttcttccttc gaactgcccg atgaggaagt ccttagccta tcaaagaatt    360
cgggaccatc atcgattttt agagccttac ctgatcgcaa tcaggatttc actactcata    420
taaatacatc gctcaaagct ccaactttgc ttgttcatac aattcttgat attcaca      477

<210> SEQ ID NO 162
<211> LENGTH: 497
<212> TYPE: DNA
<213> ORGANISM: Artificial Sequence
<220> FEATURE:
<223> OTHER INFORMATION: Promotor

<400> SEQUENCE: 162
ttttctttac ctggatataa ataaaaaaaa ggaaacacaa tctctgtttc aagaaattag     60
ggattttagt ctgcttatat acttcgcgct accccgcgac ccgagcaact actagcctta    120
caaacgcttt ggaattagtg agataacaga gttgggtaac tagagagaat aatagacgta    180
tgcatgatta ctacacaacg gatgtcgcac tctttcctta gttaaaacta tcatccaatc    240
acaagatgcg ggctggaaag acttgctccc gaaggataat cttctgcttc tatctccctt    300
cctcatatgg tttcgcaggg ctcatgcccc ttcttccttc gaactgcccg atgaggaagt    360
ccttagccta tcaaagaatt cgggaccatc atcgattttt agagccttac ctgatcgcaa    420
tcaggatttc actactcata taaatacatc gctcaaagct ccaactttgc ttgttcatac    480
aattcttgat attcaca                                                   497

<210> SEQ ID NO 163
<211> LENGTH: 791
<212> TYPE: DNA
<213> ORGANISM: Artificial Sequence
<220> FEATURE:
<223> OTHER INFORMATION: Promotor

<400> SEQUENCE: 163
gttttatcga tagtagttga gcaataaaaa aaggagaaa aagcaggtag gagggaactc      60
gtctatatat accagttgat ttaggctact aacaccatga ctttattagc ctgtctatcc    120 tggccccct ggcgaggttc atgtttgttt atttccgaat gcaacaagct ccgcattaca     180
cccgaacatc actccagatg agggctttct gagtgtgggg tcaaatagtt tcatgttccc    240
caaatggccc aaaactgaca gtttaaacgc tgtcttggaa cctaatatga caaaagcgtg    300
atctcatcca agatgaacta agtttggttc gttgaaatgc taacggccag ttggtcaaaa    360
agaaacttcc aaaagtcggc ataccgtttg tcttgtttgg tattgattga cgaatgctca    420 aaataatct cattaatgct tagcgcagtc tctctatcgc ttctgaaccc cggtgcacct    480
```

```
gtgccgaaac gcaaatgggg aaacacccgc tttttggatg attatgcatt gtctccacat    540
tgtatgcttc caagattctg gtgggaatac tgctgatagc ctaacgttca tgatcaaaat    600
ttaactgttc taacccctac ttgacagcaa tatataaaca gaaggaagct gccctgtctt    660 aaacctttt ttttatcatc attattagct tactttcata attgcgactg gttccaattg    720
acaagctttt gattttaacg acttttaacg acaacttgag aagatcaaaa aacaactaat    780
tattcgaaac g                                                        791

<210> SEQ ID NO 164
<211> LENGTH: 811
<212> TYPE: DNA
<213> ORGANISM: Artificial Sequence
<220> FEATURE:
<223> OTHER INFORMATION: Promotor

<400> SEQUENCE: 164
gttttatcga tagtagttga gcaataaaaa aaaggagaaa aagcaggtag gagggaactc     60
gtctatatat accagttgat ggctcacctt gttagcagca ttaggctact aacaccatga    120
ctttattagc ctgtctatcc tggcccccct ggcgaggttc atgtttgttt atttccgaat    180
gcaacaagct ccgcattaca cccgaacatc actccagatg agggctttct gagtgtgggg    240
tcaaatagtt tcatgttccc caaatggccc aaaactgaca gtttaaacgc tgtcttggaa    300
cctaatatga caaaagcgtg atctcatcca agatgaacta agtttggttc gttgaaatgc    360
taacggccag ttggtcaaaa agaaacttcc aaaagtcggc ataccgtttg tcttgtttgg    420
tattgattga cgaatgctca aaaataatct cattaatgct tagcgcagtc tctctatcgc    480
ttctgaaccc cggtgcacct gtgccgaaac gcaaatgggg aaacacccgc tttttggatg    540
attatgcatt gtctccacat tgtatgcttc caagattctg gtgggaatac tgctgatagc    600
ctaacgttca tgatcaaaat ttaactgttc taaccccta ttgacagcaa tatataaaca    660
gaaggaagct gccctgtctt aaacctttt ttttatcatc attattagct tactttcata    720
attgcgactg gttccaattg acaagctttt gattttaacg acttttaacg acaacttgag    780
aagatcaaaa aacaactaat tattcgaaac g                                  811

<210> SEQ ID NO 165
<211> LENGTH: 832
<212> TYPE: DNA
<213> ORGANISM: Artificial Sequence
<220> FEATURE:
<223> OTHER INFORMATION: Promotor

<400> SEQUENCE: 165
gttttatcga tagtagttga gcaataaaaa aaaggagaaa aagcaggtag gagggaactc     60
gtctatatat accagttgat ggctcacctt gttagcagca acgccactca tttggccaca    120
attaggctac taacaccatg actttattag cctgtctatc ctggcccccc tggcgaggtt    180
catgtttgtt tatttccgaa tgcaacaagc tccgcattac acccgaacat cactccagat    240
gagggctttc tgagtgtggg gtcaaatagt tcatgttcc caaatggcc caaaactgac    300 agtttaaacg ctgtcttgga acctaatatg acaaaagcgt gatctcatcc aagatgaact    360
aagtttggtt cgttgaaatg ctaacggcca gttggtcaaa agaaacttc caaaagtcgg    420 cataccgttt gtcttgtttg gtattgattg acgaatgctc aaaaataatc tcattaatgc    480
ttagcgcagt ctctctatcg cttctgaacc ccggtgcacc tgtgccgaaa cgcaaatggg    540
gaaacacccg cttttttggat gattatgcat tgtctccaca ttgtatgctt ccaagattct    600
```

| | |
|---|---|
| ggtgggaata ctgctgatag cctaacgttc atgatcaaaa tttaactgtt ctaacccta | 660 |
| cttgacagca atatataaac agaaggaagc tgccctgtct taaacctttt tttttatcat | 720 |
| cattattagc ttactttcat aattgcgact ggttccaatt gacaagcttt tgattttaac | 780 |
| gacttttaac gacaacttga gaagatcaaa aaacaactaa ttattcgaaa cg | 832 |

<210> SEQ ID NO 166
<211> LENGTH: 335
<212> TYPE: DNA
<213> ORGANISM: Artificial Sequence
<220> FEATURE:
<223> OTHER INFORMATION: Promotor

<400> SEQUENCE: 166

| | |
|---|---|
| tctgcttaga aaataactcg gagcgtactg aatatagcaa gcataatggg gccttttat | 60 |
| ttgcgctaaa aagaggaaa ataagttgtt attttatatt gtttaaattt tcaaacgtgc | 120 |
| tagggttttc cagattgggg gagaacattg agtctttccc cgtcttgatt ggagctaccg | 180 |
| cagcagggag taaagagccg gggtgggggt ggggcctata gctccgccca cgggttgctg | 240 |
| ttttcaaaca ggtccgctcc tagggaatat aagctctggc ttgggcgcac tgcattgtag | 300 |
| ttctctcttg tttctctgct gattgtttgt tcacc | 335 |

<210> SEQ ID NO 167
<211> LENGTH: 309
<212> TYPE: DNA
<213> ORGANISM: Artificial Sequence
<220> FEATURE:
<223> OTHER INFORMATION: Promotor

<400> SEQUENCE: 167

| | |
|---|---|
| agcgaaagta acctttcaca gcctaacggc cgaaaacact tccaactgct gagaaaacac | 60 |
| agtccactag aagctgagaa gagtggtatt tataggcgtg gacctcgaat gacgtatgga | 120 |
| cacacgttgt ctgattggat aataagtgct ctgcatatgc aaataagggg aattcaagta | 180 |
| gtgctttctg attggctagt ccataatcaa tcagccaatc aggtggcaat taaggacctt | 240 |
| ccatcagact ataaataggc ctggaagcgc tcgctccctt acgcttttct taaggctttt | 300 |
| gaagaaatc | 309 |

<210> SEQ ID NO 168
<211> LENGTH: 316
<212> TYPE: DNA
<213> ORGANISM: Artificial Sequence
<220> FEATURE:
<223> OTHER INFORMATION: Promotor

<400> SEQUENCE: 168

| | |
|---|---|
| actgatgacc taaagcaact ggaggttaca aaggaaaaca gagccaaccc ccttgacttt | 60 |
| tatagtcaag ctacggcgcg aaaaaggaaa tgcgtcattg gttaacattc tgagttcatt | 120 |
| ttaaccaatg gaaacgcggt ttgggaattt ttgcattctt attgggtaaa aacagactca | 180 |
| gccttttctc tgagtgacca ctaacaagac acatagcact ttactttatt tgcatacaaa | 240 |
| gctctagata aagcatacac aaccattccc ttagttgggc ttatccgtgg gtgtttgatt | 300 |
| cgcctggttc ttcgat | 316 |

<210> SEQ ID NO 169
<211> LENGTH: 322
<212> TYPE: DNA

<213> ORGANISM: Artificial Sequence
<220> FEATURE:
<223> OTHER INFORMATION: Promotor

<400> SEQUENCE: 169

```
aattaaaaca caaggcgacc tagcgagcag gaaaacaaac tggaagccga tggacctgag      60
ccttttataa ccgccttatg taaattagga ctcaaaatac ttttcatttc cattggctca     120
tacatgaaac ttgcgttttc agtacaagcc tcttgtaaca gactaaattt cagatttcat     180
tggactcctc cggggccaaa ctaagaccaa tgaaaagctg gctcctgacc ccaccsctag     240
gaaaccttat aaaggcctta gagacgttac agcctagttt tgtaagtaaa gtccacaagg     300
gttgattttt tattgtgaag ac                                              322
```

<210> SEQ ID NO 170
<211> LENGTH: 292
<212> TYPE: DNA
<213> ORGANISM: Artificial Sequence
<220> FEATURE:
<223> OTHER INFORMATION: Promotor

<400> SEQUENCE: 170

```
ggtgaagact aaacacacta ctgtaacttg gtagatggaa agtacaagag cttgactta      60 tagttttcgc tgggcgccaa aaagaacccg tgtgattggc tggcttcttc ttgtcagtta    120
ggccaatggg aagagttgtg cccaggcgta tttcgattgg gcaagacttc aaatgacgtc    180
accgaaatag tactcaatca aaagtgtgct tttctaagcc tcatttgaat aaatactttt    240
aaaagggaag gcacgactgc cttgctgttg tagttcttct ttctgtgtca gt            292
```

<210> SEQ ID NO 171
<211> LENGTH: 311
<212> TYPE: DNA
<213> ORGANISM: Artificial Sequence
<220> FEATURE:
<223> OTHER INFORMATION: Promotor

<400> SEQUENCE: 171

```
gataacgata tagtaaaaac agcaaaaaac caccaaagtc ctccgcttca aaaggtatgg     60
ctgcttttat agtcggttcc tggatagtaa agcaactat ttgattggtt acaagatggc    120
tcagagatgt agccaataga aaatctgtgt ctcaaaacct catttgcata attccgccca    180
cgaagccacc gcttttttctt cttccaatta gctaagtatc attcgaaatc cctcattagc   240
ataaacgccc tataagtagg agaagtccaa ttccaaccca cactgagctt ccggtgttta    300
gagattctaa g                                                         311
```

<210> SEQ ID NO 172
<211> LENGTH: 331
<212> TYPE: DNA
<213> ORGANISM: Artificial Sequence
<220> FEATURE:
<223> OTHER INFORMATION: Promotor

<400> SEQUENCE: 172

```
agtgaaaatg acagggaaag agaggaaggc aatggaaagt ttggcgaaac tgtcttttga     60
agggcaacca gaagatactt atactggtgg atgggagagg aaagggtgaa gtgtgattgg    120
ttaacattag ctctctggct gcagccaata acagaggccc cataatacac cgtcatttgc    180
ataatggtgt cactagctgg ttttcaaatc atagccgact atccctgaat cacttatttg    240
catagacggt ctataaaagc ccggcaagta gaaagcttcc acactttgc ctgttttccg     300
```

```
tctgtgtgtt tttccgtttc agcatctcaa c                                  331
```

<210> SEQ ID NO 173
<211> LENGTH: 273
<212> TYPE: DNA
<213> ORGANISM: Artificial Sequence
<220> FEATURE:
<223> OTHER INFORMATION: Promotor

<400> SEQUENCE: 173

```
actagaaact taactgtgcc tattgttatt aaaaagacac actggcaata tttatagata    60
atgcagggcg cgaaaaagga gcaattccat tggttacaca gaaacaccaa cggcaccgtg   120
gttttgaaaa actcctcctt tgattggaca gttagtagat gacgttttct gactcaggct   180
aagtatagcc acaagtttgt ttaaaaaggg accagttcgc tcaactccaa acaactattt   240
cttttgtttc tcgtataggt ttctatcttc gct                                273
```

<210> SEQ ID NO 174
<211> LENGTH: 331
<212> TYPE: DNA
<213> ORGANISM: Artificial Sequence
<220> FEATURE:
<223> OTHER INFORMATION: Promotor

<400> SEQUENCE: 174

```
agcgaaaatg acagagaaag agaggaaggc agtagaaagt ttggtgaaat tgtctcttga    60
gtggcaacga agatactt atactggtag atgggagtgg aaagggtgaa gtgtgattgg    120
ttaacattag ctctctggct gcagccaata acagaggccc cataatacac cgtcatttgc   180
ataatggtgt cactagctgg ttttcaaatc atagccgact atccctgagt cacttatttg   240
catagacggt ctataaaagc ccggcaagta gaaggctacc cacttttgc ctgtttcccg   300
tttgtctgtt tttcccttc agcatctcaa c                                   331
```

<210> SEQ ID NO 175
<211> LENGTH: 302
<212> TYPE: DNA
<213> ORGANISM: Artificial Sequence
<220> FEATURE:
<223> OTHER INFORMATION: Promotor

<400> SEQUENCE: 175

```
gttgacacac caagtccagg aactccaacg atgaggctat gggcaatttg cctttataa    60
gctgttattc aaatgcggct taaaaaatca cacttctgat tgggtaatgt ttcagtgacg   120
tcataaccaa agccttgctc aatttaaata acatagtggc acagatgctt cccattggtc   180
taaatgaaaa gaagaaacca gccaatcgcc agggcttttt tcgagccgag cgaaaactat   240
aagtgccaag ctattgcagc tttcaagtct acttagttat taggtagtgt ttactttcca   300
tc                                                                  302
```

<210> SEQ ID NO 176
<211> LENGTH: 293
<212> TYPE: DNA
<213> ORGANISM: Artificial Sequence
<220> FEATURE:
<223> OTHER INFORMATION: Promotor

<400> SEQUENCE: 176

```
ggcgaagaac aaaaggaaat caggaaagca gaaacagaaa atacgagaat gcactcggcg    60
```

```
ccgactgctt ttaaaacaaa cttgtgacta tgcttatcgt gattaaaaac gtcattcact    120
tagtgtccaa tcaaagcaaa tacttttcaa aaccacggtg ccattgggtt aggtggaaaa    180
gatgcatgta gccaatgaaa tcgcttcatt ttcgcgcctt gtgttgacta taaacagcac    240
cagtgtctct tttagttgct cgctgattga ttttttagcag ctaccaatct att           293
```

<210> SEQ ID NO 177
<211> LENGTH: 301
<212> TYPE: DNA
<213> ORGANISM: Artificial Sequence
<220> FEATURE:
<223> OTHER INFORMATION: Promotor

<400> SEQUENCE: 177

```
ggcgggaagg aaacaaaaat tagctatcca gtaaggctga gaactgcagg agcttggccc     60
ttatagtttt ctctgggctc gaaaaagacc ccttgcgatt ggctgactta ctcttttcac   120
gtagaccaat gggaagcgtt tgtgccaacg cgtatttcga ttggacaaga ggttttggtg   180
acgtcattag aatagcaccc aataagaagt gggagttttt gagcctcatt tgaataacag   240
catataaaaa gggaaccgcc ggccggctcc tcgtctgagt tccagtaccc ggagtgtcaa   300
t                                                                    301
```

<210> SEQ ID NO 178
<211> LENGTH: 294
<212> TYPE: DNA
<213> ORGANISM: Artificial Sequence
<220> FEATURE:
<223> OTHER INFORMATION: Promotor

<400> SEQUENCE: 178

```
ggtaaacaaa gacaaagatc agagttggaa atgaaaccga ggttgagaga gacgcctgct    60
ctccctgcta tttaaacaaa gctgtggttg ttcttgtaag ggagtctgca aacgtcatgc   120
acttactgtc caatcaaatc aagaatattt cagaagcacg ttaccattgg ttcaggtgaa   180
gcagtatgtg cagccaatga tgtccctctg ttttcgcgcc gggagatgct tataagtttg   240
ctgctgtggc tctttcgctt taggctgaac agttcctgtc tactgattct gacc          294
```

<210> SEQ ID NO 179
<211> LENGTH: 283
<212> TYPE: DNA
<213> ORGANISM: Artificial Sequence
<220> FEATURE:
<223> OTHER INFORMATION: Promotor

<400> SEQUENCE: 179

```
tatgtaagtt atgtaaacag tgaaaagcaa cattcagatg tagattatgc ttggtcacaa    60
aagagttttg tcctattggt caaaataagc ttgcttttac gtccagtaga aaataagact   120
ttaggtaccc tcatttgcaa agtcttattg ttgtccaatc acaagtgagg aatttaacgg   180
cctcatttgc atttcaagac tataaatgaa acactctagt tcatatcagc tttctttttc   240
tcgttgtaat actgtagtat agtttagctt tggtctgaaa acg                       283
```

<210> SEQ ID NO 180
<211> LENGTH: 1163
<212> TYPE: DNA
<213> ORGANISM: Artificial Sequence
<220> FEATURE:
<223> OTHER INFORMATION: Promotor

<400> SEQUENCE: 180

```
ggtaaacaaa gacaaagatc agagttggaa atgaaaccga ggttgagaga gacgcctgct      60
ctccctgcta tttaaataaa gctgtggttg ttcttgtaag ggagtctgca aacgtcatgc     120
actagccgtc caatcaaagc atgcatctta tctagggaaa gacaagcaga gtattgttta     180
caggcagcct atgcaaatga agtaggactc gtctttgttt ctgattggct aaggggaacc     240
atcagaagct ctatattcaa attagacgaa ataagggtt tagaaaaatc ctcgttgaca      300
tcgccgcaac aaaggcagtc ttttatttt  taaacgttaa aattatttt  tccagtagta     360 tccctgcatt ctgtcccta  ggcacaaatg cctgatataa attatagctt tatatagttt     420
ggttcgcgtt ttgaagtcta tgaagtatcc agagggaaga taacagaaat tattcagcta     480
atgattctag aatccctatt tattgtacag tccgttttaa gcagtcagat ttttgtcttc     540
tcaagaatca aaggaactgc tgctttgcag caccagagca attttaatga tcccgggaca     600 tagttttga  aaatcattct agtgctttt  tttttaaaag acgcattctt aattaggttt     660
tgaggctaag gctatcatga aactcatgaa ttcattaaaa aaatggacaa aatccagtgt     720
gtttgtccgt gtcttttaga ccacatttga ctctgagagg aacatgctgc ctttgcttcc     780
ttcctgcaac tacaatataa agaatagtac agagctcagt ttgggtaacc aagttcaacc     840
agtagtcctt taaactgctc aggcgttgtc aaaatctcaa tagtctctaa ttagttggta     900
agcaaaatta caactaaag  tacttaattg caacaatgta tctaatggag taacagggaa     960
caatgaatca tacgtcaaat aatataagac attttcattg gctacacatt ttaaaattga    1020
tgtctgttat ccaattacca atcacttccg catacatcat tcatggcgcg gcgtttgaag    1080
attcccacca atcagggaga ccttgttgtt ataaatagga acccacacac ttttttttctt   1140 aggtttctcc ttttactcca ata                                             1163

<210> SEQ ID NO 181
<211> LENGTH: 1463
<212> TYPE: DNA
<213> ORGANISM: Artificial Sequence
<220> FEATURE:
<223> OTHER INFORMATION: Promotor

<400> SEQUENCE: 181
agaggacact tgtagcagta caagactgag tgtagcagtg caagactgag tacttggaac      60
gcggctctgg atgcctaccg agctagtatt tatagtctac aaaaactaat gattgggtga     120
aacgactgct cacctgtgac gtttaagact ctgattggtt gaagaactgc cattgcattt     180
tccctaagtt agtcttcagc cgcccttgtg tgtgtgtgtg tgtgtgtgcg tgtgtgtttt     240
aaataaaatg aaataagatt gtggtgactg tcaatctctc cagcacctct gccggccaac     300
acatagaaag tttgctttgc tgctactaaa gaatcgagaa caaacttgat gtctcgagta     360
ttgaaatgct taatgaaatt ctgcgttttg cctcggtagg ccagattcta cgttttgatt     420
ggtttactgt gttttcctca gtagccacta aaaagcaga  tcttgaatcc cttatttgca     480
tgcccggtct ccctttggtc tgtagctaca attaaaacaa tggggagaaa catggcatta     540
agatagtaca gaaatctgag tcacgttatt ttgcatattt atccactaaa cagctgaatc     600
tgtttagatg ctttgagttc ttgcactcaa acatttccaa gtattcttgg ccagaaatca     660
cccttccaac ttttgttttt ataagacact attaccggtc ataatgatta tattattttg     720
tattttcttt aaaagaaact agacaagttt ttttttttccc cctcctagct atttggact    780 tgtcgggatg agaattcatg tcatggcctt gctttcccga ccaataatgg gtgctttgtc     840
```

```
agaactgtag tgaacagttc aaccacatct tattagcgct attggttcga aatgttaaat    900
cactatagca agaagcttct taaatcccta aaaaactata ccttaactaa aatataaagt    960
gacgttacat agctcttcag tacagaagct cgtctacaag gtctacagcc tggttttctg   1020
atcctctaac catggaagta ttgatctaca agctatctct aacacctcaa cagccaaact   1080
gcttgggttc tgattggcta atttagacac ccttcaccat ttcagctact ttttgataga   1140
catctacggt cttgtggtgt ccctgctgtg cttgaaattc ccaccttaag cagccagcca   1200
gaaaggtctg ggagggcctc tgcgcgcagc gaggcagtgt gattataggt ccctagagtc   1260
ctggacttca gaactagtta ggagcaaaga tcttgcaaac gcgtcgggga ccgtgggggc   1320
ggggcttcca gggtctaagg ggcgggcttt agcgtgcacc aatcacagcg cggccctgct   1380
ctataaatac gccgcgcgga ggccttgtct ctttacttct tttcttcgcc ttggcattac   1440
ttgtgctatc atctgcacca acc                                          1463

<210> SEQ ID NO 182
<211> LENGTH: 44
<212> TYPE: DNA
<213> ORGANISM: Artificial Sequence
<220> FEATURE:
<223> OTHER INFORMATION: Primer

<400> SEQUENCE: 182
gcccacatgt atttaaattg ccagtgtatg tgcacttata gagg                      44

<210> SEQ ID NO 183
<211> LENGTH: 59
<212> TYPE: DNA
<213> ORGANISM: Artificial Sequence
<220> FEATURE:
<223> OTHER INFORMATION: Primer

<400> SEQUENCE: 183
caacagaggt cggcgcgcca ctgggtgcta ggaccttctc gcagaatggt ataaatatc       59

<210> SEQ ID NO 184
<211> LENGTH: 59
<212> TYPE: DNA
<213> ORGANISM: Artificial Sequence
<220> FEATURE:
<223> OTHER INFORMATION: Primer

<400> SEQUENCE: 184
ctgcgagaag gtcctagcac ccagtggcgc gccgacctct gttgcctctt tgttggacg       59

<210> SEQ ID NO 185
<211> LENGTH: 59
<212> TYPE: DNA
<213> ORGANISM: Artificial Sequence
<220> FEATURE:
<223> OTHER INFORMATION: Primer

<400> SEQUENCE: 185
cctttgctag ccatcagtcc cagtgagctc ttaagctgga agagccaatc tcttgaaag       59

<210> SEQ ID NO 186
<211> LENGTH: 59
<212> TYPE: DNA
<213> ORGANISM: Artificial Sequence
<220> FEATURE:
<223> OTHER INFORMATION: Primer

<400> SEQUENCE: 186
```

```
ggctcttcca gcttaagagc tcactgggac tgatggctag caaaggagaa gaacttttc        59

<210> SEQ ID NO 187
<211> LENGTH: 39
<212> TYPE: DNA
<213> ORGANISM: Artificial Sequence
<220> FEATURE:
<223> OTHER INFORMATION: Primer

<400> SEQUENCE: 187
gatcgcggcc gcttacttgt acaattcatc catgccatg                              39

<210> SEQ ID NO 188
<211> LENGTH: 33
<212> TYPE: DNA
<213> ORGANISM: Artificial Sequence
<220> FEATURE:
<223> OTHER INFORMATION: Primer

<400> SEQUENCE: 188
agttctggac tgataggctc ggtttctccc gtg                                    33

<210> SEQ ID NO 189
<211> LENGTH: 33
<212> TYPE: DNA
<213> ORGANISM: Artificial Sequence
<220> FEATURE:
<223> OTHER INFORMATION: Primer

<400> SEQUENCE: 189
cacgggagaa accgagccta tcagtccaga act                                    33

<210> SEQ ID NO 190
<211> LENGTH: 24
<212> TYPE: DNA
<213> ORGANISM: Artificial Sequence
<220> FEATURE:
<223> OTHER INFORMATION: Primer

<400> SEQUENCE: 190
ctagataccc gtgaactttg tctc                                              24

<210> SEQ ID NO 191
<211> LENGTH: 24
<212> TYPE: DNA
<213> ORGANISM: Artificial Sequence
<220> FEATURE:
<223> OTHER INFORMATION: Primer

<400> SEQUENCE: 191
ttccgtatgt agcatcacct tcac                                              24

<210> SEQ ID NO 192
<211> LENGTH: 43
<212> TYPE: DNA
<213> ORGANISM: Artificial Sequence
<220> FEATURE:
<223> OTHER INFORMATION: Primer

<400> SEQUENCE: 192
ggtcggcgcg ccactgggtg ctatggtttc taagggtgag gaa                         43

<210> SEQ ID NO 193
<211> LENGTH: 60
<212> TYPE: DNA
```

```
<213> ORGANISM: Artificial Sequence
<220> FEATURE:
<223> OTHER INFORMATION: Primer

<400> SEQUENCE: 193
ttataccatt ctgcgagaag gtccctgca gggcacaaac gaaggtctca cttaatcttc      60

<210> SEQ ID NO 194
<211> LENGTH: 60
<212> TYPE: DNA
<213> ORGANISM: Artificial Sequence
<220> FEATURE:
<223> OTHER INFORMATION: Primer

<400> SEQUENCE: 194
gacccctagg ccgtacgaca gtcagttagt agatatttat accattctgc gagaaggtcc      60

<210> SEQ ID NO 195
<211> LENGTH: 38
<212> TYPE: DNA
<213> ORGANISM: Artificial Sequence
<220> FEATURE:
<223> OTHER INFORMATION: Primer

<400> SEQUENCE: 195
accattcaaa acccaataca gttgttgcat cacagctc                              38

<210> SEQ ID NO 196
<211> LENGTH: 37
<212> TYPE: DNA
<213> ORGANISM: Artificial Sequence
<220> FEATURE:
<223> OTHER INFORMATION: Primer

<400> SEQUENCE: 196
gtaggaagtt cgacagatta cttggtgaga aaggtgg                               37

<210> SEQ ID NO 197
<211> LENGTH: 37
<212> TYPE: DNA
<213> ORGANISM: Artificial Sequence
<220> FEATURE:
<223> OTHER INFORMATION: Primer

<400> SEQUENCE: 197
ccacctttct caccaagtaa tctgtcgaac ttcctac                               37

<210> SEQ ID NO 198
<211> LENGTH: 60
<212> TYPE: DNA
<213> ORGANISM: Artificial Sequence
<220> FEATURE:
<223> OTHER INFORMATION: Primer

<400> SEQUENCE: 198
gcaacagagg tcggcgcgcc actgggtgct atgacggttc atgacatcat cgctacttac      60

<210> SEQ ID NO 199
<211> LENGTH: 55
<212> TYPE: DNA
<213> ORGANISM: Artificial Sequence
<220> FEATURE:
<223> OTHER INFORMATION: Primer

<400> SEQUENCE: 199
acttgcggcc gcttaataca tttcaatgtt tgcaccatcg aacaaagaca tagtc           55
```

<210> SEQ ID NO 200
<211> LENGTH: 60
<212> TYPE: DNA
<213> ORGANISM: Artificial Sequence
<220> FEATURE:
<223> OTHER INFORMATION: Primer

<400> SEQUENCE: 200
catgaaccgt catagcaccc agtggcgcgc cgacctctgt tgcctctttg ttggacgaac    60

<210> SEQ ID NO 201
<211> LENGTH: 60
<212> TYPE: DNA
<213> ORGANISM: Artificial Sequence
<220> FEATURE:
<223> OTHER INFORMATION: Primer

<400> SEQUENCE: 201
atcaagtgcc atcagtccca gtgagctctt aagctggaag agccaatctc ttgaaagtac    60

<210> SEQ ID NO 202
<211> LENGTH: 60
<212> TYPE: DNA
<213> ORGANISM: Artificial Sequence
<220> FEATURE:
<223> OTHER INFORMATION: Primer

<400> SEQUENCE: 202
agagctcact gggactgatg gcacttgata aactagattt gtacgtgatt atcaccttag    60

<210> SEQ ID NO 203
<211> LENGTH: 52
<212> TYPE: DNA
<213> ORGANISM: Artificial Sequence
<220> FEATURE:
<223> OTHER INFORMATION: Primer

<400> SEQUENCE: 203
taatgcggcc gcttaccaaa catcctcctg ataacgattt tgaactttcc ag            52

<210> SEQ ID NO 204
<211> LENGTH: 60
<212> TYPE: DNA
<213> ORGANISM: Artificial Sequence
<220> FEATURE:
<223> OTHER INFORMATION: Primer

<400> SEQUENCE: 204
aagtagcgat gatgtcatga accgtcattt ttgatgtttg atagtttgat aagagtgaac    60

<210> SEQ ID NO 205
<211> LENGTH: 60
<212> TYPE: DNA
<213> ORGANISM: Artificial Sequence
<220> FEATURE:
<223> OTHER INFORMATION: Primer

<400> SEQUENCE: 205
acgtacaaat ctagtttatc aagtgccatt ttgttcgatt attctccaga taaaatcaac    60

<210> SEQ ID NO 206
<211> LENGTH: 60
<212> TYPE: DNA
<213> ORGANISM: Artificial Sequence
<220> FEATURE:

<223> OTHER INFORMATION: Primer

<400> SEQUENCE: 206
taagtagcga tgatgtcatg aaccgtcatt tgttcgatt attctccaga taaaatcaac    60

<210> SEQ ID NO 207
<211> LENGTH: 60
<212> TYPE: DNA
<213> ORGANISM: Artificial Sequence
<220> FEATURE:
<223> OTHER INFORMATION: Primer

<400> SEQUENCE: 207
cgtacaaatc tagtttatca agtgccattt tgatgtttg atagtttgat aagagtgaac    60

<210> SEQ ID NO 208
<211> LENGTH: 60
<212> TYPE: DNA
<213> ORGANISM: Artificial Sequence
<220> FEATURE:
<223> OTHER INFORMATION: Primer

<400> SEQUENCE: 208
aagtagcgat gatgtcatga accgtcatcg tttcgaataa ttagttgttt tttgatcttc    60

<210> SEQ ID NO 209
<211> LENGTH: 60
<212> TYPE: DNA
<213> ORGANISM: Artificial Sequence
<220> FEATURE:
<223> OTHER INFORMATION: Primer

<400> SEQUENCE: 209
atcacgtaca aatctagttt atcaagtgcc attgtgtttt gatagttgtt caattgattg    60

<210> SEQ ID NO 210
<211> LENGTH: 60
<212> TYPE: DNA
<213> ORGANISM: Artificial Sequence
<220> FEATURE:
<223> OTHER INFORMATION: Primer

<400> SEQUENCE: 210
gtagcgatga tgtcatgaac cgtcattgtg ttttgatagt tgttcaattg attgaaatag    60

<210> SEQ ID NO 211
<211> LENGTH: 60
<212> TYPE: DNA
<213> ORGANISM: Artificial Sequence
<220> FEATURE:
<223> OTHER INFORMATION: Primer

<400> SEQUENCE: 211
cgtacaaatc tagtttatca agtgccatcg tttcgaataa ttagttgttt tttgatcttc    60

<210> SEQ ID NO 212
<211> LENGTH: 60
<212> TYPE: DNA
<213> ORGANISM: Artificial Sequence
<220> FEATURE:
<223> OTHER INFORMATION: Primer

<400> SEQUENCE: 212
cacgtacaaa tctagtttat caagtgccat tttaattgta agtcttgact agagcaagtg    60

```
<210> SEQ ID NO 213
<211> LENGTH: 60
<212> TYPE: DNA
<213> ORGANISM: Artificial Sequence
<220> FEATURE:
<223> OTHER INFORMATION: Primer

<400> SEQUENCE: 213
gtaagtagcg atgatgtcat gaaccgtcat tttaattgta agtcttgact agagcaagtg    60

<210> SEQ ID NO 214
<211> LENGTH: 60
<212> TYPE: DNA
<213> ORGANISM: Artificial Sequence
<220> FEATURE:
<223> OTHER INFORMATION: Primer

<400> SEQUENCE: 214
acgtacaaat ctagtttatc aagtgccatg ttggcgaata actaaaatgt atgtagtgag    60

<210> SEQ ID NO 215
<211> LENGTH: 60
<212> TYPE: DNA
<213> ORGANISM: Artificial Sequence
<220> FEATURE:
<223> OTHER INFORMATION: Primer

<400> SEQUENCE: 215
taagtagcga tgatgtcatg aaccgtcatg ttggcgaata actaaaatgt atgtagtgag    60

<210> SEQ ID NO 216
<211> LENGTH: 24
<212> TYPE: DNA
<213> ORGANISM: Artificial Sequence
<220> FEATURE:
<223> OTHER INFORMATION: Primer

<400> SEQUENCE: 216
agccttaaaa ccgaaacaac cgtc                                           24

<210> SEQ ID NO 217
<211> LENGTH: 24
<212> TYPE: DNA
<213> ORGANISM: Artificial Sequence
<220> FEATURE:
<223> OTHER INFORMATION: Primer

<400> SEQUENCE: 217
acgggacagt tgttggcgt aatc                                            24

<210> SEQ ID NO 218
<211> LENGTH: 60
<212> TYPE: DNA
<213> ORGANISM: Artificial Sequence
<220> FEATURE:
<223> OTHER INFORMATION: Primer

<400> SEQUENCE: 218
caacagaggt cggcgcgcca ctgggtgcta tgagattccc atctattttc accgctgtct    60

<210> SEQ ID NO 219
<211> LENGTH: 43
<212> TYPE: DNA
<213> ORGANISM: Artificial Sequence
<220> FEATURE:
<223> OTHER INFORMATION: Primer
```

```
<400> SEQUENCE: 219
taatgcggcc gcttatgggg tcacgatacc ggaacaagtt ctc                  43

<210> SEQ ID NO 220
<211> LENGTH: 60
<212> TYPE: DNA
<213> ORGANISM: Artificial Sequence
<220> FEATURE:
<223> OTHER INFORMATION: Primer

<400> SEQUENCE: 220
atagatggga atctcatagc acccagtggc gcgccgacct ctgttgcctc tttgttggac    60

<210> SEQ ID NO 221
<211> LENGTH: 60
<212> TYPE: DNA
<213> ORGANISM: Artificial Sequence
<220> FEATURE:
<223> OTHER INFORMATION: Primer

<400> SEQUENCE: 221
attgaattgc atcagtccca gtgagctctt aagctggaag agccaatctc ttgaaagtac    60

<210> SEQ ID NO 222
<211> LENGTH: 60
<212> TYPE: DNA
<213> ORGANISM: Artificial Sequence
<220> FEATURE:
<223> OTHER INFORMATION: Primer

<400> SEQUENCE: 222
agcttaagag ctcactggga ctgatgcaat tcaattggga catcaagaca gttgcatcca    60

<210> SEQ ID NO 223
<211> LENGTH: 43
<212> TYPE: DNA
<213> ORGANISM: Artificial Sequence
<220> FEATURE:
<223> OTHER INFORMATION: Primer

<400> SEQUENCE: 223
ttttgcggcc gcttacaatt cgtcgtgagc atcagcttca gac                  43

<210> SEQ ID NO 224
<211> LENGTH: 60
<212> TYPE: DNA
<213> ORGANISM: Artificial Sequence
<220> FEATURE:
<223> OTHER INFORMATION: Primer

<400> SEQUENCE: 224
cagcggtgaa aatagatggg aatctcattt ttgatgtttg atagtttgat aagagtgaac    60

<210> SEQ ID NO 225
<211> LENGTH: 60
<212> TYPE: DNA
<213> ORGANISM: Artificial Sequence
<220> FEATURE:
<223> OTHER INFORMATION: Primer

<400> SEQUENCE: 225
actgtcttga tgtcccaatt gaattgcatt ttgttcgatt attctccaga taaaatcaac    60

<210> SEQ ID NO 226
<211> LENGTH: 60
```

```
<212> TYPE: DNA
<213> ORGANISM: Artificial Sequence
<220> FEATURE:
<223> OTHER INFORMATION: Primer

<400> SEQUENCE: 226
acagcggtga aaatagatgg gaatctcatt ttgttcgatt attctccaga taaaatcaac    60

<210> SEQ ID NO 227
<211> LENGTH: 60
<212> TYPE: DNA
<213> ORGANISM: Artificial Sequence
<220> FEATURE:
<223> OTHER INFORMATION: Primer

<400> SEQUENCE: 227
ctgtcttgat gtcccaattg aattgcattt ttgatgtttg atagtttgat aagagtgaac    60

<210> SEQ ID NO 228
<211> LENGTH: 60
<212> TYPE: DNA
<213> ORGANISM: Artificial Sequence
<220> FEATURE:
<223> OTHER INFORMATION: Primer

<400> SEQUENCE: 228
cagcggtgaa aatagatggg aatctcatcg tttcgaataa ttagttgttt tttgatcttc    60

<210> SEQ ID NO 229
<211> LENGTH: 60
<212> TYPE: DNA
<213> ORGANISM: Artificial Sequence
<220> FEATURE:
<223> OTHER INFORMATION: Primer

<400> SEQUENCE: 229
gtcttgatgt cccaattgaa ttgcattgtg ttttgatagt tgttcaattg attgaaatag    60

<210> SEQ ID NO 230
<211> LENGTH: 60
<212> TYPE: DNA
<213> ORGANISM: Artificial Sequence
<220> FEATURE:
<223> OTHER INFORMATION: Primer

<400> SEQUENCE: 230
gcggtgaaaa tagatgggaa tctcattgtg ttttgatagt tgttcaattg attgaaatag    60

<210> SEQ ID NO 231
<211> LENGTH: 60
<212> TYPE: DNA
<213> ORGANISM: Artificial Sequence
<220> FEATURE:
<223> OTHER INFORMATION: Primer

<400> SEQUENCE: 231
ctgtcttgat gtcccaattg aattgcatcg tttcgaataa ttagttgttt tttgatcttc    60

<210> SEQ ID NO 232
<211> LENGTH: 60
<212> TYPE: DNA
<213> ORGANISM: Artificial Sequence
<220> FEATURE:
<223> OTHER INFORMATION: Primer

<400> SEQUENCE: 232
```

-continued

```
aactgtcttg atgtcccaat tgaattgcat tttaattgta agtcttgact agagcaagtg    60

<210> SEQ ID NO 233
<211> LENGTH: 60
<212> TYPE: DNA
<213> ORGANISM: Artificial Sequence
<220> FEATURE:
<223> OTHER INFORMATION: Primer

<400> SEQUENCE: 233
gacagcggtg aaaatagatg ggaatctcat tttaattgta agtcttgact agagcaagtg    60

<210> SEQ ID NO 234
<211> LENGTH: 60
<212> TYPE: DNA
<213> ORGANISM: Artificial Sequence
<220> FEATURE:
<223> OTHER INFORMATION: Primer

<400> SEQUENCE: 234
gcggtgaaaa tagatgggaa tctcattgtt gtagttttaa tatagtttga gtatgagatg    60

<210> SEQ ID NO 235
<211> LENGTH: 60
<212> TYPE: DNA
<213> ORGANISM: Artificial Sequence
<220> FEATURE:
<223> OTHER INFORMATION: Primer

<400> SEQUENCE: 235
actgtcttga tgtcccaatt gaattgcatt ttgatttgtt taggtaactt gaactggatg    60

<210> SEQ ID NO 236
<211> LENGTH: 60
<212> TYPE: DNA
<213> ORGANISM: Artificial Sequence
<220> FEATURE:
<223> OTHER INFORMATION: Primer

<400> SEQUENCE: 236
acagcggtga aaatagatgg gaatctcatt ttgatttgtt taggtaactt gaactggatg    60

<210> SEQ ID NO 237
<211> LENGTH: 60
<212> TYPE: DNA
<213> ORGANISM: Artificial Sequence
<220> FEATURE:
<223> OTHER INFORMATION: Primer

<400> SEQUENCE: 237
gtcttgatgt cccaattgaa ttgcattgtt gtagttttaa tatagtttga gtatgagatg    60

<210> SEQ ID NO 238
<211> LENGTH: 60
<212> TYPE: DNA
<213> ORGANISM: Artificial Sequence
<220> FEATURE:
<223> OTHER INFORMATION: Primer

<400> SEQUENCE: 238
gacagcggtg aaaatagatg ggaatctcat ttttactacg atagacacaa gaagaagcag    60

<210> SEQ ID NO 239
<211> LENGTH: 60
<212> TYPE: DNA
<213> ORGANISM: Artificial Sequence
```

<220> FEATURE:
<223> OTHER INFORMATION: Primer

<400> SEQUENCE: 239
tgtcttgatg tcccaattga attgcatatt tattgattat ttgtttatgg gtgagtctag    60

<210> SEQ ID NO 240
<211> LENGTH: 60
<212> TYPE: DNA
<213> ORGANISM: Artificial Sequence
<220> FEATURE:
<223> OTHER INFORMATION: Primer

<400> SEQUENCE: 240
agcggtgaaa atagatggga atctcatatt tattgattat ttgtttatgg gtgagtctag    60

<210> SEQ ID NO 241
<211> LENGTH: 60
<212> TYPE: DNA
<213> ORGANISM: Artificial Sequence
<220> FEATURE:
<223> OTHER INFORMATION: Primer

<400> SEQUENCE: 241
aactgtcttg atgtcccaat tgaattgcat ttttactacg atagacacaa gaagaagcag    60

<210> SEQ ID NO 242
<211> LENGTH: 24
<212> TYPE: DNA
<213> ORGANISM: Artificial Sequence
<220> FEATURE:
<223> OTHER INFORMATION: Primer

<400> SEQUENCE: 242
aaggtcagag taaccgataa ctgc                                           24

<210> SEQ ID NO 243
<211> LENGTH: 24
<212> TYPE: DNA
<213> ORGANISM: Artificial Sequence
<220> FEATURE:
<223> OTHER INFORMATION: Primer

<400> SEQUENCE: 243
agtagcctca gtcaacttca caac                                           24

<210> SEQ ID NO 244
<211> LENGTH: 27
<212> TYPE: DNA
<213> ORGANISM: Artificial Sequence
<220> FEATURE:
<223> OTHER INFORMATION: Primer

<400> SEQUENCE: 244
gttggtattg tgaaatagac gcagatc                                        27

<210> SEQ ID NO 245
<211> LENGTH: 42
<212> TYPE: DNA
<213> ORGANISM: Artificial Sequence
<220> FEATURE:
<223> OTHER INFORMATION: Primer

<400> SEQUENCE: 245
cgtttcgaat aattagttgt ttttgatct tctcaagttg tc                        42

<210> SEQ ID NO 246
<211> LENGTH: 36
<212> TYPE: DNA
<213> ORGANISM: Artificial Sequence
<220> FEATURE:
<223> OTHER INFORMATION: Primer

<400> SEQUENCE: 246
gaattagtga gataacagag ttgggtaact agagag                        36

<210> SEQ ID NO 247
<211> LENGTH: 36
<212> TYPE: DNA
<213> ORGANISM: Artificial Sequence
<220> FEATURE:
<223> OTHER INFORMATION: Primer

<400> SEQUENCE: 247
tgtgaatatc aagaattgta tgaacaagca aagttg                        36

<210> SEQ ID NO 248
<211> LENGTH: 37
<212> TYPE: DNA
<213> ORGANISM: Artificial Sequence
<220> FEATURE:
<223> OTHER INFORMATION: Primer

<400> SEQUENCE: 248
ttttgatgtt tgatagtttg ataagagtga actttag                       37

<210> SEQ ID NO 249
<211> LENGTH: 36
<212> TYPE: DNA
<213> ORGANISM: Artificial Sequence
<220> FEATURE:
<223> OTHER INFORMATION: Primer

<400> SEQUENCE: 249
tttgttcgat tattctccag ataaaatcaa caatag                        36

<210> SEQ ID NO 250
<211> LENGTH: 37
<212> TYPE: DNA
<213> ORGANISM: Artificial Sequence
<220> FEATURE:
<223> OTHER INFORMATION: Primer

<400> SEQUENCE: 250
ttttgatgtt tgatagtttg ataagagtga actttag                       37

<210> SEQ ID NO 251
<211> LENGTH: 33
<212> TYPE: DNA
<213> ORGANISM: Artificial Sequence
<220> FEATURE:
<223> OTHER INFORMATION: Primer

<400> SEQUENCE: 251
aatgatattt gagggtgtta gttacttcgt ctc                           33

<210> SEQ ID NO 252
<211> LENGTH: 34
<212> TYPE: DNA
<213> ORGANISM: Artificial Sequence
<220> FEATURE:
<223> OTHER INFORMATION: Primer

```
<400> SEQUENCE: 252
agcaatgata taaacaacaa ttgagtgaca ggtc                              34

<210> SEQ ID NO 253
<211> LENGTH: 36
<212> TYPE: DNA
<213> ORGANISM: Artificial Sequence
<220> FEATURE:
<223> OTHER INFORMATION: Primer

<400> SEQUENCE: 253
tttgttcgat tattctccag ataaaatcaa caatag                            36

<210> SEQ ID NO 254
<211> LENGTH: 31
<212> TYPE: DNA
<213> ORGANISM: Artificial Sequence
<220> FEATURE:
<223> OTHER INFORMATION: Primer

<400> SEQUENCE: 254
ttctctattg aacggcttga aatttggaaa c                                 31

<210> SEQ ID NO 255
<211> LENGTH: 36
<212> TYPE: DNA
<213> ORGANISM: Artificial Sequence
<220> FEATURE:
<223> OTHER INFORMATION: Primer

<400> SEQUENCE: 255
tgtgtaaaaa atatgttcaa ttgatatgtg gggaac                            36

<210> SEQ ID NO 256
<211> LENGTH: 40
<212> TYPE: DNA
<213> ORGANISM: Artificial Sequence
<220> FEATURE:
<223> OTHER INFORMATION: Primer

<400> SEQUENCE: 256
aaattaatcc ataagataag gcaaatgtgc ttaagtaatt                        40

<210> SEQ ID NO 257
<211> LENGTH: 45
<212> TYPE: DNA
<213> ORGANISM: Artificial Sequence
<220> FEATURE:
<223> OTHER INFORMATION: Primer

<400> SEQUENCE: 257
atttatgaaa ttaatcaatt accttatcaa ggtagaattt gggtg                  45

<210> SEQ ID NO 258
<211> LENGTH: 38
<212> TYPE: DNA
<213> ORGANISM: Artificial Sequence
<220> FEATURE:
<223> OTHER INFORMATION: Primer

<400> SEQUENCE: 258
tttcgtaaag taaataagat aaaagctagt agctgatg                          38

<210> SEQ ID NO 259
```

```
<211> LENGTH: 25
<212> TYPE: DNA
<213> ORGANISM: Artificial Sequence
<220> FEATURE:
<223> OTHER INFORMATION: Primer

<400> SEQUENCE: 259
cgcagcgttt tctgacggta ctaga                                   25

<210> SEQ ID NO 260
<211> LENGTH: 29
<212> TYPE: DNA
<213> ORGANISM: Artificial Sequence
<220> FEATURE:
<223> OTHER INFORMATION: Primer

<400> SEQUENCE: 260
tagaaagatg gaatgaacgc tacagcgag                               29

<210> SEQ ID NO 261
<211> LENGTH: 30
<212> TYPE: DNA
<213> ORGANISM: Artificial Sequence
<220> FEATURE:
<223> OTHER INFORMATION: Primer

<400> SEQUENCE: 261
atcttcattg atgaaacgtt gtgatcggtg                              30

<210> SEQ ID NO 262
<211> LENGTH: 30
<212> TYPE: DNA
<213> ORGANISM: Artificial Sequence
<220> FEATURE:
<223> OTHER INFORMATION: Primer

<400> SEQUENCE: 262
tgtttaagtg ggtgatgttg gaggtatttg                              30

<210> SEQ ID NO 263
<211> LENGTH: 30
<212> TYPE: DNA
<213> ORGANISM: Artificial Sequence
<220> FEATURE:
<223> OTHER INFORMATION: Primer

<400> SEQUENCE: 263
tgggtgcgga accagcttct aattaaatag                              30

<210> SEQ ID NO 264
<211> LENGTH: 39
<212> TYPE: DNA
<213> ORGANISM: Artificial Sequence
<220> FEATURE:
<223> OTHER INFORMATION: Primer

<400> SEQUENCE: 264
ttaaagtgta taaattcctt tgtttcctgt tataaaaga                    39

<210> SEQ ID NO 265
<211> LENGTH: 24
<212> TYPE: DNA
<213> ORGANISM: Artificial Sequence
<220> FEATURE:
<223> OTHER INFORMATION: Primer

<400> SEQUENCE: 265
```
tgtcatctgc tgatgctgtg aggg                                             24

<210> SEQ ID NO 266
<211> LENGTH: 25
<212> TYPE: DNA
<213> ORGANISM: Artificial Sequence
<220> FEATURE:
<223> OTHER INFORMATION: Primer

<400> SEQUENCE: 266
tgctcaaacg agtggagagg gaaat                                            25

<210> SEQ ID NO 267
<211> LENGTH: 39
<212> TYPE: DNA
<213> ORGANISM: Artificial Sequence
<220> FEATURE:
<223> OTHER INFORMATION: Primer

<400> SEQUENCE: 267
gctaatgtaa gataacgtaa gaagagagga atgaaatag                             39

<210> SEQ ID NO 268
<211> LENGTH: 34
<212> TYPE: DNA
<213> ORGANISM: Artificial Sequence
<220> FEATURE:
<223> OTHER INFORMATION: Primer

<400> SEQUENCE: 268
taacaggcac ctgaagatag gtaaaaaaaa attg                                  34

<210> SEQ ID NO 269
<211> LENGTH: 30
<212> TYPE: DNA
<213> ORGANISM: Artificial Sequence
<220> FEATURE:
<223> OTHER INFORMATION: Primer

<400> SEQUENCE: 269
gacctctgat tcgttctgaa agctcaattg                                       30

<210> SEQ ID NO 270
<211> LENGTH: 32
<212> TYPE: DNA
<213> ORGANISM: Artificial Sequence
<220> FEATURE:
<223> OTHER INFORMATION: Primer

<400> SEQUENCE: 270
tacgattagt tagatggttg ggttgagaat ag                                    32

<210> SEQ ID NO 271
<211> LENGTH: 24
<212> TYPE: DNA
<213> ORGANISM: Artificial Sequence
<220> FEATURE:
<223> OTHER INFORMATION: Primer

<400> SEQUENCE: 271
tccaaaccaa acggtctagc aaaa                                             24

<210> SEQ ID NO 272
<211> LENGTH: 31
<212> TYPE: DNA

<210> SEQ ID NO 273
<211> LENGTH: 38
<212> TYPE: DNA
<213> ORGANISM: Artificial Sequence
<220> FEATURE:
<223> OTHER INFORMATION: Primer

<400> SEQUENCE: 272
tcttctcata aaaaggtca atctgctagt t    31

<210> SEQ ID NO 273
<211> LENGTH: 38
<212> TYPE: DNA
<213> ORGANISM: Artificial Sequence
<220> FEATURE:
<223> OTHER INFORMATION: Primer

<400> SEQUENCE: 273
tgtgttttga tagttgttca attgattgaa atagggac    38

<210> SEQ ID NO 274
<211> LENGTH: 33
<212> TYPE: DNA
<213> ORGANISM: Artificial Sequence
<220> FEATURE:
<223> OTHER INFORMATION: Primer

<400> SEQUENCE: 274
tgtttgtttg tgtaattgaa agttgttact gac    33

<210> SEQ ID NO 275
<211> LENGTH: 31
<212> TYPE: DNA
<213> ORGANISM: Artificial Sequence
<220> FEATURE:
<223> OTHER INFORMATION: Primer

<400> SEQUENCE: 275
tatcaatacc ttgggttatt agtagtgtcc g    31

<210> SEQ ID NO 276
<211> LENGTH: 35
<212> TYPE: DNA
<213> ORGANISM: Artificial Sequence
<220> FEATURE:
<223> OTHER INFORMATION: Primer

<400> SEQUENCE: 276
tttatcaatt ggttggagtt gaattattcc ggaag    35

<210> SEQ ID NO 277
<211> LENGTH: 24
<212> TYPE: DNA
<213> ORGANISM: Artificial Sequence
<220> FEATURE:
<223> OTHER INFORMATION: Primer

<400> SEQUENCE: 277
ttgagtggac tcggcgcaaa agtg    24

<210> SEQ ID NO 278
<211> LENGTH: 38
<212> TYPE: DNA
<213> ORGANISM: Artificial Sequence
<220> FEATURE:
<223> OTHER INFORMATION: Primer

<400> SEQUENCE: 278
ctgtaattcg atttgagtct aacaagcaaa caaaatac    38

<210> SEQ ID NO 279
<211> LENGTH: 36
<212> TYPE: DNA
<213> ORGANISM: Artificial Sequence
<220> FEATURE:
<223> OTHER INFORMATION: Primer

<400> SEQUENCE: 279
ctaccttctg aatgtatcaa aagtactcaa ttgaag					36

<210> SEQ ID NO 280
<211> LENGTH: 31
<212> TYPE: DNA
<213> ORGANISM: Artificial Sequence
<220> FEATURE:
<223> OTHER INFORMATION: Primer

<400> SEQUENCE: 280
gaattccgag ggtggctcaa caactattca c					31

<210> SEQ ID NO 281
<211> LENGTH: 36
<212> TYPE: DNA
<213> ORGANISM: Artificial Sequence
<220> FEATURE:
<223> OTHER INFORMATION: Primer

<400> SEQUENCE: 281
tgtgtagagt ggatgtagaa tacaagtcta gagtta					36

<210> SEQ ID NO 282
<211> LENGTH: 35
<212> TYPE: DNA
<213> ORGANISM: Artificial Sequence
<220> FEATURE:
<223> OTHER INFORMATION: Primer

<400> SEQUENCE: 282
cttagatttt ttttttgct tggtgggatt ccttc					35

<210> SEQ ID NO 283
<211> LENGTH: 37
<212> TYPE: DNA
<213> ORGANISM: Artificial Sequence
<220> FEATURE:
<223> OTHER INFORMATION: Primer

<400> SEQUENCE: 283
ttctggagtg tcaaaacagt agtgataaaa ggctatg					37

<210> SEQ ID NO 284
<211> LENGTH: 29
<212> TYPE: DNA
<213> ORGANISM: Artificial Sequence
<220> FEATURE:
<223> OTHER INFORMATION: Primer

<400> SEQUENCE: 284
ggtcgaacca atcaaggagg aagggacag					29

<210> SEQ ID NO 285
<211> LENGTH: 41
<212> TYPE: DNA
<213> ORGANISM: Artificial Sequence
<220> FEATURE:

```
<223> OTHER INFORMATION: Primer

<400> SEQUENCE: 285
gttaatttag gtcaaaggta agtagatgat tccgctctct g                          41

<210> SEQ ID NO 286
<211> LENGTH: 34
<212> TYPE: DNA
<213> ORGANISM: Artificial Sequence
<220> FEATURE:
<223> OTHER INFORMATION: Primer

<400> SEQUENCE: 286
ctgaaaaaaa ctacgtttgg aaaaacgtgg gaag                                  34

<210> SEQ ID NO 287
<211> LENGTH: 26
<212> TYPE: DNA
<213> ORGANISM: Artificial Sequence
<220> FEATURE:
<223> OTHER INFORMATION: Primer

<400> SEQUENCE: 287
ttttagtgca gttgcgccgt gatttc                                           26

<210> SEQ ID NO 288
<211> LENGTH: 37
<212> TYPE: DNA
<213> ORGANISM: Artificial Sequence
<220> FEATURE:
<223> OTHER INFORMATION: Primer

<400> SEQUENCE: 288
agttaatttt caagcagttg agagaaaaaa atgcgag                               37

<210> SEQ ID NO 289
<211> LENGTH: 36
<212> TYPE: DNA
<213> ORGANISM: Artificial Sequence
<220> FEATURE:
<223> OTHER INFORMATION: Primer

<400> SEQUENCE: 289
cttgtagtct tattgggggg tataaagttt gaacag                                36

<210> SEQ ID NO 290
<211> LENGTH: 31
<212> TYPE: DNA
<213> ORGANISM: Artificial Sequence
<220> FEATURE:
<223> OTHER INFORMATION: Primer

<400> SEQUENCE: 290
ggcactggat gatgttcaaa tcttattctc g                                     31

<210> SEQ ID NO 291
<211> LENGTH: 43
<212> TYPE: DNA
<213> ORGANISM: Artificial Sequence
<220> FEATURE:
<223> OTHER INFORMATION: Primer

<400> SEQUENCE: 291
ttttgtgtag atgttaaata gggaagaaac acagaaaata aag                        43
```

```
<210> SEQ ID NO 292
<211> LENGTH: 49
<212> TYPE: DNA
<213> ORGANISM: Artificial Sequence
<220> FEATURE:
<223> OTHER INFORMATION: Primer

<400> SEQUENCE: 292
agtcagctag ccatgtttct gcttctagaa gaatgtgatg tgatgagtg            49

<210> SEQ ID NO 293
<211> LENGTH: 42
<212> TYPE: DNA
<213> ORGANISM: Artificial Sequence
<220> FEATURE:
<223> OTHER INFORMATION: Primer

<400> SEQUENCE: 293
gactagctag ccattgtgtg actttgaagg gagaaggaag ag                   42

<210> SEQ ID NO 294
<211> LENGTH: 50
<212> TYPE: DNA
<213> ORGANISM: Artificial Sequence
<220> FEATURE:
<223> OTHER INFORMATION: Primer

<400> SEQUENCE: 294
agtcagctag ccatgttgtc aattaaagag gtgatatatt cagaagaaag           50

<210> SEQ ID NO 295
<211> LENGTH: 41
<212> TYPE: DNA
<213> ORGANISM: Artificial Sequence
<220> FEATURE:
<223> OTHER INFORMATION: Primer

<400> SEQUENCE: 295
gactagctag ccattacggt tggatgaaac ttaacagcca g                    41

<210> SEQ ID NO 296
<211> LENGTH: 58
<212> TYPE: DNA
<213> ORGANISM: Artificial Sequence
<220> FEATURE:
<223> OTHER INFORMATION: Primer

<400> SEQUENCE: 296
agtcagctag ccattgttac tcttacaaag aacaagtttt tgttagcaa ttttttc    58

<210> SEQ ID NO 297
<211> LENGTH: 55
<212> TYPE: DNA
<213> ORGANISM: Artificial Sequence
<220> FEATURE:
<223> OTHER INFORMATION: Primer

<400> SEQUENCE: 297
gactagctag ccatctttga ttgttgtagt taacctggaa gcttttttta acttg     55

<210> SEQ ID NO 298
<211> LENGTH: 48
<212> TYPE: DNA
<213> ORGANISM: Artificial Sequence
<220> FEATURE:
<223> OTHER INFORMATION: Primer
```

<400> SEQUENCE: 298
agtcagctag ccattgctta cttttgtttc caaaaaacca cccctttc         48

<210> SEQ ID NO 299
<211> LENGTH: 41
<212> TYPE: DNA
<213> ORGANISM: Artificial Sequence
<220> FEATURE:
<223> OTHER INFORMATION: Primer

<400> SEQUENCE: 299
gactagctag ccatgttcct gtccctgaaa tgtgccaaaa g         41

<210> SEQ ID NO 300
<211> LENGTH: 58
<212> TYPE: DNA
<213> ORGANISM: Artificial Sequence
<220> FEATURE:
<223> OTHER INFORMATION: Primer

<400> SEQUENCE: 300
agtcagctag ccattgtaaa tgataattga taacttgttt agaagtttgt atgaggag         58

<210> SEQ ID NO 301
<211> LENGTH: 48
<212> TYPE: DNA
<213> ORGANISM: Artificial Sequence
<220> FEATURE:
<223> OTHER INFORMATION: Primer

<400> SEQUENCE: 301
gactagctag ccattgttta agtttgtgtg caggtatcta gagatgac         48

<210> SEQ ID NO 302
<211> LENGTH: 47
<212> TYPE: DNA
<213> ORGANISM: Artificial Sequence
<220> FEATURE:
<223> OTHER INFORMATION: Primer

<400> SEQUENCE: 302
agtcagctag ccattttgaa aagaactaca acgaccactg aacgttg         47

<210> SEQ ID NO 303
<211> LENGTH: 58
<212> TYPE: DNA
<213> ORGANISM: Artificial Sequence
<220> FEATURE:
<223> OTHER INFORMATION: Primer

<400> SEQUENCE: 303
gactagctag ccatcataaa ttcttttttc tgttcgaaac ggattgtaac aaaggtag         58

<210> SEQ ID NO 304
<211> LENGTH: 60
<212> TYPE: DNA
<213> ORGANISM: Artificial Sequence
<220> FEATURE:
<223> OTHER INFORMATION: Primer

<400> SEQUENCE: 304
agtcagctag ccattttta ttggtgcttt tttgaggttt tttttttgag tttctctaac         60

<210> SEQ ID NO 305
<211> LENGTH: 44

```
<212> TYPE: DNA
<213> ORGANISM: Artificial Sequence
<220> FEATURE:
<223> OTHER INFORMATION: Primer

<400> SEQUENCE: 305
gactagctag ccatcttggt ggttgtattg gaagtgagga agag                    44

<210> SEQ ID NO 306
<211> LENGTH: 46
<212> TYPE: DNA
<213> ORGANISM: Artificial Sequence
<220> FEATURE:
<223> OTHER INFORMATION: Primer

<400> SEQUENCE: 306
agtcagctag ccattgttta agtgggtgat gttggaggta tttgag                  46

<210> SEQ ID NO 307
<211> LENGTH: 54
<212> TYPE: DNA
<213> ORGANISM: Artificial Sequence
<220> FEATURE:
<223> OTHER INFORMATION: Primer

<400> SEQUENCE: 307
gactagctag ccattagatg gttatcttga atggtatttg taaggattga tctc         54

<210> SEQ ID NO 308
<211> LENGTH: 35
<212> TYPE: DNA
<213> ORGANISM: Artificial Sequence
<220> FEATURE:
<223> OTHER INFORMATION: Primer

<400> SEQUENCE: 308
gaaaaggttt actatcccga tttaggcgaa aagag                              35

<210> SEQ ID NO 309
<211> LENGTH: 48
<212> TYPE: DNA
<213> ORGANISM: Artificial Sequence
<220> FEATURE:
<223> OTHER INFORMATION: Primer

<400> SEQUENCE: 309
tatagtagat atatctgtgg tatagtgtga aaaagtagaa gaagagtc                48

<210> SEQ ID NO 310
<211> LENGTH: 60
<212> TYPE: DNA
<213> ORGANISM: Artificial Sequence
<220> FEATURE:
<223> OTHER INFORMATION: Primer

<400> SEQUENCE: 310
ttgataactt cctcacccett agaaaccatt ttgatttgtt taggtaactt gaactggatg  60

<210> SEQ ID NO 311
<211> LENGTH: 60
<212> TYPE: DNA
<213> ORGANISM: Artificial Sequence
<220> FEATURE:
<223> OTHER INFORMATION: Primer

<400> SEQUENCE: 311
```
aaagttcttc tcctttgcta gccattgttg tagttttaat atagtttgag tatgagatgg    60

<210> SEQ ID NO 312
<211> LENGTH: 60
<212> TYPE: DNA
<213> ORGANISM: Artificial Sequence
<220> FEATURE:
<223> OTHER INFORMATION: Primer

<400> SEQUENCE: 312
acttcctcac ccttagaaac catgttttat cgatagtagt tgagcaataa aaaaaggag    60

<210> SEQ ID NO 313
<211> LENGTH: 60
<212> TYPE: DNA
<213> ORGANISM: Artificial Sequence
<220> FEATURE:
<223> OTHER INFORMATION: Primer

<400> SEQUENCE: 313
gttcttctcc tttgctagcc attttctttt acctggatat aaataaaaaa aaggaaacac    60

<210> SEQ ID NO 314
<211> LENGTH: 60
<212> TYPE: DNA
<213> ORGANISM: Artificial Sequence
<220> FEATURE:
<223> OTHER INFORMATION: Primer

<400> SEQUENCE: 314
cttcctcacc cttagaaacc atatttattg attatttgtt tatgggtgag tctagaaaag    60

<210> SEQ ID NO 315
<211> LENGTH: 60
<212> TYPE: DNA
<213> ORGANISM: Artificial Sequence
<220> FEATURE:
<223> OTHER INFORMATION: Primer

<400> SEQUENCE: 315
gaaaagttct tctcctttgc tagccatttt tactacgata gacacaagaa gaagcaggag    60

<210> SEQ ID NO 316
<211> LENGTH: 58
<212> TYPE: DNA
<213> ORGANISM: Artificial Sequence
<220> FEATURE:
<223> OTHER INFORMATION: Primer

<400> SEQUENCE: 316
cttgataact tcctcaccct tagaaaccat tgatccagc tgtaaaggga gaaggatg      58

<210> SEQ ID NO 317
<211> LENGTH: 60
<212> TYPE: DNA
<213> ORGANISM: Artificial Sequence
<220> FEATURE:
<223> OTHER INFORMATION: Primer

<400> SEQUENCE: 317
aagttcttct cctttgctag ccatggttca acttctttat ggactattta gcaaaaacac    60

<210> SEQ ID NO 318
<211> LENGTH: 60
<212> TYPE: DNA
<213> ORGANISM: Artificial Sequence

```
<220> FEATURE:
<223> OTHER INFORMATION: Primer

<400> SEQUENCE: 318
tgataacttc ctcaccctta gaaaccattg caagaggtag cggtatgatt tgcaaagctg      60

<210> SEQ ID NO 319
<211> LENGTH: 60
<212> TYPE: DNA
<213> ORGANISM: Artificial Sequence
<220> FEATURE:
<223> OTHER INFORMATION: Primer

<400> SEQUENCE: 319
gtgaaaagtt cttctccttt gctagccatg agttatagct caattgttga tctggaagag      60

<210> SEQ ID NO 320
<211> LENGTH: 60
<212> TYPE: DNA
<213> ORGANISM: Artificial Sequence
<220> FEATURE:
<223> OTHER INFORMATION: Primer

<400> SEQUENCE: 320
cttgataact tcctcaccct tagaaaccat ggaggggggag gatctggata tttataagag      60

<210> SEQ ID NO 321
<211> LENGTH: 60
<212> TYPE: DNA
<213> ORGANISM: Artificial Sequence
<220> FEATURE:
<223> OTHER INFORMATION: Primer

<400> SEQUENCE: 321
gaaaagttct tctcctttgc tagccatatt tattgattat ttgtttatgg gtgagtctag      60

<210> SEQ ID NO 322
<211> LENGTH: 84
<212> TYPE: DNA
<213> ORGANISM: Artificial Sequence
<220> FEATURE:
<223> OTHER INFORMATION: Primer

<400> SEQUENCE: 322
cttgataact tcctcaccct tagaaaccat ttttactacg atagacacaa gaagtaagag      60
tctcccatag ataacgattt ggca                                             84

<210> SEQ ID NO 323
<211> LENGTH: 60
<212> TYPE: DNA
<213> ORGANISM: Artificial Sequence
<220> FEATURE:
<223> OTHER INFORMATION: Primer

<400> SEQUENCE: 323
gaaaagttct tctcctttgc tagccatatt tattgattat ttgtttatgg gtgagtctag      60

<210> SEQ ID NO 324
<211> LENGTH: 100
<212> TYPE: DNA
<213> ORGANISM: Artificial Sequence
<220> FEATURE:
<223> OTHER INFORMATION: Primer

<400> SEQUENCE: 324
```

-continued cttgataact tcctcaccct tagaaaccat ttttactacg atagacacaa gaagaagcag    60
gagggggagg atctggattt ggcactttt gccatcagtg    100

<210> SEQ ID NO 325
<211> LENGTH: 60
<212> TYPE: DNA
<213> ORGANISM: Artificial Sequence
<220> FEATURE:
<223> OTHER INFORMATION: Primer

<400> SEQUENCE: 325
gaaaagttct tctcctttgc tagccatatt tattgattat ttgtttatgg gtgagtctag    60

<210> SEQ ID NO 326
<211> LENGTH: 127
<212> TYPE: DNA
<213> ORGANISM: Artificial Sequence
<220> FEATURE:
<223> OTHER INFORMATION: Primer

<400> SEQUENCE: 326
cttgataact tcctcaccct tagaaaccat ttttactacg atagacacaa gaagaagcag    60
gagggggagg atctggatat ttataagagt ctcccataga taaacagtat ttcgcactgc    120
gacactc    127

<210> SEQ ID NO 327
<211> LENGTH: 60
<212> TYPE: DNA
<213> ORGANISM: Artificial Sequence
<220> FEATURE:
<223> OTHER INFORMATION: Primer

<400> SEQUENCE: 327
gaaaagttct tctcctttgc tagccatatt tattgattat ttgtttatgg gtgagtctag    60

<210> SEQ ID NO 328
<211> LENGTH: 158
<212> TYPE: DNA
<213> ORGANISM: Artificial Sequence
<220> FEATURE:
<223> OTHER INFORMATION: Primer

<400> SEQUENCE: 328
cttgataact tcctcaccct tagaaaccat ttttactacg atagacacaa gaagaagcag    60
gagggggagg atctggatat ttataagagt ctcccataga taacgatttg gcacttttg    120 ccatcacccg actgaaatgg gatgcaagtt tattatga    158

<210> SEQ ID NO 329
<211> LENGTH: 60
<212> TYPE: DNA
<213> ORGANISM: Artificial Sequence
<220> FEATURE:
<223> OTHER INFORMATION: Primer

<400> SEQUENCE: 329
gaaaagttct tctcctttgc tagccatatt tattgattat ttgtttatgg gtgagtctag    60

<210> SEQ ID NO 330
<211> LENGTH: 158
<212> TYPE: DNA
<213> ORGANISM: Artificial Sequence
<220> FEATURE:
<223> OTHER INFORMATION: Primer

<400> SEQUENCE: 330
cttgataact tcctcaccct tagaaaccat ttttactacg atagacacaa gaagaagcag    60 gaggggagg atctggatat ttataagagt ctcccataga taacgatttg gcactttttg    120
ccatcacccg actgaaatgg gatgcaagtt tattatga                           158

<210> SEQ ID NO 331
<211> LENGTH: 47
<212> TYPE: DNA
<213> ORGANISM: Artificial Sequence
<220> FEATURE:
<223> OTHER INFORMATION: Primer

<400> SEQUENCE: 331
gtatttcgca ctgcgtatta tgagttctgg tagcatagaa atgggac                 47

<210> SEQ ID NO 332
<211> LENGTH: 37
<212> TYPE: DNA
<213> ORGANISM: Artificial Sequence
<220> FEATURE:
<223> OTHER INFORMATION: Primer

<400> SEQUENCE: 332
ccagaactca taatacgcag tgcgaaatac tgttggc                            37

<210> SEQ ID NO 333
<211> LENGTH: 60
<212> TYPE: DNA
<213> ORGANISM: Artificial Sequence
<220> FEATURE:
<223> OTHER INFORMATION: Primer

<400> SEQUENCE: 333
gaaaagttct tctcctttgc tagccatatt tattgattat ttgtttatgg gtgagtctag    60

<210> SEQ ID NO 334
<211> LENGTH: 158
<212> TYPE: DNA
<213> ORGANISM: Artificial Sequence
<220> FEATURE:
<223> OTHER INFORMATION: Primer

<400> SEQUENCE: 334
cttgataact tcctcaccct tagaaaccat ttttactacg atagacacaa gaagaagcag    60 gaggggagg atctggatat ttataagagt ctcccataga taacgatttg gcactttttg    120
ccatcacccg actgaaatgg gatgcaagtt tattatga                           158

<210> SEQ ID NO 335
<211> LENGTH: 51
<212> TYPE: DNA
<213> ORGANISM: Artificial Sequence
<220> FEATURE:
<223> OTHER INFORMATION: Primer

<400> SEQUENCE: 335
actgaaatgg gatgcaatgg gacatgttct tacagtttca aatttacgca c            51

<210> SEQ ID NO 336
<211> LENGTH: 50
<212> TYPE: DNA
<213> ORGANISM: Artificial Sequence
<220> FEATURE:

<223> OTHER INFORMATION: Primer

<400> SEQUENCE: 336
tttgaaactg taagaacatg tcccattgca tcccatttca gtcgggagtg               50

<210> SEQ ID NO 337
<211> LENGTH: 60
<212> TYPE: DNA
<213> ORGANISM: Artificial Sequence
<220> FEATURE:
<223> OTHER INFORMATION: Primer

<400> SEQUENCE: 337
gaaaagttct tctcctttgc tagccatatt tattgattat ttgtttatgg gtgagtctag    60

<210> SEQ ID NO 338
<211> LENGTH: 158
<212> TYPE: DNA
<213> ORGANISM: Artificial Sequence
<220> FEATURE:
<223> OTHER INFORMATION: Primer

<400> SEQUENCE: 338
cttgataact tcctcaccct tagaaaccat ttttactacg atagacacaa gaagaagcag    60 gaggggagg atctggatat ttataagagt ctcccataga taacgatttg cacttttg     120 ccatcacccg actgaaatgg gatgcaagtt tattatga                          158

<210> SEQ ID NO 339
<211> LENGTH: 57
<212> TYPE: DNA
<213> ORGANISM: Artificial Sequence
<220> FEATURE:
<223> OTHER INFORMATION: Primer

<400> SEQUENCE: 339
gatgcaagtt tattatgagt tctggtagca aatttacgca cgctctgcct ctaggag       57

<210> SEQ ID NO 340
<211> LENGTH: 60
<212> TYPE: DNA
<213> ORGANISM: Artificial Sequence
<220> FEATURE:
<223> OTHER INFORMATION: Primer

<400> SEQUENCE: 340
tagaggcaga gcgtgcgtaa atttgctacc agaactcata taaacttgc atcccatttc    60

<210> SEQ ID NO 341
<211> LENGTH: 60
<212> TYPE: DNA
<213> ORGANISM: Artificial Sequence
<220> FEATURE:
<223> OTHER INFORMATION: Primer

<400> SEQUENCE: 341
gaaaagttct tctcctttgc tagccatatt tattgattat ttgtttatgg gtgagtctag    60

<210> SEQ ID NO 342
<211> LENGTH: 158
<212> TYPE: DNA
<213> ORGANISM: Artificial Sequence
<220> FEATURE:
<223> OTHER INFORMATION: Primer

<400> SEQUENCE: 342

```
cttgataact tcctcaccct tagaaaccat ttttactacg atagacacaa gaagaagcag    60 gaggggagg atctggatat ttataagagt ctcccataga taacgatttg gcactttttg    120
ccatcacccg actgaaatgg gatgcaagtt tattatga                            158
```

<210> SEQ ID NO 343
<211> LENGTH: 44
<212> TYPE: DNA
<213> ORGANISM: Artificial Sequence
<220> FEATURE:
<223> OTHER INFORMATION: Primer

<400> SEQUENCE: 343

```
gacatgttct tacaggagta cggctcagtt catcgcgtac cgtg                     44
```

<210> SEQ ID NO 344
<211> LENGTH: 48
<212> TYPE: DNA
<213> ORGANISM: Artificial Sequence
<220> FEATURE:
<223> OTHER INFORMATION: Primer

<400> SEQUENCE: 344

```
aactgagccg tactcctgta agaacatgtc ccatttctat gctaccag                 48
```

<210> SEQ ID NO 345
<211> LENGTH: 60
<212> TYPE: DNA
<213> ORGANISM: Artificial Sequence
<220> FEATURE:
<223> OTHER INFORMATION: Primer

<400> SEQUENCE: 345

```
gaaaagttct tctcctttgc tagccatatt tattgattat ttgtttatgg gtgagtctag    60
```

<210> SEQ ID NO 346
<211> LENGTH: 158
<212> TYPE: DNA
<213> ORGANISM: Artificial Sequence
<220> FEATURE:
<223> OTHER INFORMATION: Primer

<400> SEQUENCE: 346

```
cttgataact tcctcaccct tagaaaccat ttttactacg atagacacaa gaagaagcag    60 gaggggagg atctggatat ttataagagt ctcccataga taacgatttg gcactttttg    120
ccatcacccg actgaaatgg gatgcaagtt tattatga                            158
```

<210> SEQ ID NO 347
<211> LENGTH: 179
<212> TYPE: DNA
<213> ORGANISM: Artificial Sequence
<220> FEATURE:
<223> OTHER INFORMATION: Primer

<400> SEQUENCE: 347

```
gtgaaaagtt cttctccttt gctagccata tttattgatt atttgtttat gggtgagtct    60
agaaaaggac gcactcgtct tgtatttata gatgaaaaga gttaaggtgg acaatgcagt    120
gccaaaccgt aatgttgata cgacacggtg cagagcgtgc gtaaatttga aactgtaag    179
```

<210> SEQ ID NO 348
<211> LENGTH: 158
<212> TYPE: DNA

```
<213> ORGANISM: Artificial Sequence
<220> FEATURE:
<223> OTHER INFORMATION: Primer

<400> SEQUENCE: 348
cttgataact tcctcaccct tagaaaccat ttttactacg atagacacaa gaagaagcag      60 gaggggagg atctggatat ttataagagt ctcccataga taacgatttg gcacttttg      120 ccatcacccg actgaaatgg gatgcaagtt tattatga                            158

<210> SEQ ID NO 349
<211> LENGTH: 42
<212> TYPE: DNA
<213> ORGANISM: Artificial Sequence
<220> FEATURE:
<223> OTHER INFORMATION: Primer

<400> SEQUENCE: 349
tacggctcag ttcatttggc actgcattgt ccaccttaac tc                        42

<210> SEQ ID NO 350
<211> LENGTH: 43
<212> TYPE: DNA
<213> ORGANISM: Artificial Sequence
<220> FEATURE:
<223> OTHER INFORMATION: Primer

<400> SEQUENCE: 350
acaatgcagt gccaaatgaa ctgagccgta ctcctagagg cag                       43

<210> SEQ ID NO 351
<211> LENGTH: 60
<212> TYPE: DNA
<213> ORGANISM: Artificial Sequence
<220> FEATURE:
<223> OTHER INFORMATION: Primer

<400> SEQUENCE: 351
gaaaagttct tctcctttgc tagccatatt tattgattat ttgtttatgg gtgagtctag     60

<210> SEQ ID NO 352
<211> LENGTH: 158
<212> TYPE: DNA
<213> ORGANISM: Artificial Sequence
<220> FEATURE:
<223> OTHER INFORMATION: Primer

<400> SEQUENCE: 352
cttgataact tcctcaccct tagaaaccat ttttactacg atagacacaa gaagaagcag     60 gaggggagg atctggatat ttataagagt ctcccataga taacgatttg gcacttttg     120 ccatcacccg actgaaatgg gatgcaagtt tattatga                           158

<210> SEQ ID NO 353
<211> LENGTH: 58
<212> TYPE: DNA
<213> ORGANISM: Artificial Sequence
<220> FEATURE:
<223> OTHER INFORMATION: Primer

<400> SEQUENCE: 353
tgtcgtatca acattctctt ttcatctata aatacaagac gagtgcgtcc ttttctag       58

<210> SEQ ID NO 354
<211> LENGTH: 55
```

```
<212> TYPE: DNA
<213> ORGANISM: Artificial Sequence
<220> FEATURE:
<223> OTHER INFORMATION: Primer

<400> SEQUENCE: 354
gtcttgtatt tatagatgaa aagagaatgt tgatacgaca cggtacgcga tgaac         55

<210> SEQ ID NO 355
<211> LENGTH: 60
<212> TYPE: DNA
<213> ORGANISM: Artificial Sequence
<220> FEATURE:
<223> OTHER INFORMATION: Primer

<400> SEQUENCE: 355
gaaaagttct ctcctttgc tagccatatt tattgattat ttgtttatgg gtgagtctag     60

<210> SEQ ID NO 356
<211> LENGTH: 158
<212> TYPE: DNA
<213> ORGANISM: Artificial Sequence
<220> FEATURE:
<223> OTHER INFORMATION: Primer

<400> SEQUENCE: 356
cttgataact tcctcaccct tagaaaccat ttttactacg atagacacaa gaagaagcag    60 gaggggagg atctggatat ttataagagt ctcccataga taacgatttg gcactttttg   120
ccatcacccg actgaaatgg gatgcaagtt tattatga                          158

<210> SEQ ID NO 357
<211> LENGTH: 60
<212> TYPE: DNA
<213> ORGANISM: Artificial Sequence
<220> FEATURE:
<223> OTHER INFORMATION: Primer

<400> SEQUENCE: 357
gaaaagttct ctcctttgc tagccatatt tattgattat ttgtttatgg gtgagtctag     60

<210> SEQ ID NO 358
<211> LENGTH: 158
<212> TYPE: DNA
<213> ORGANISM: Artificial Sequence
<220> FEATURE:
<223> OTHER INFORMATION: Primer

<400> SEQUENCE: 358
cttgataact tcctcaccct tagaaaccat ttttactacg atagacacaa gaagaagcag    60 gaggggagg atctggatat ttataagagt ctcccataga taacgatttg gcactttttg   120
ccatcacccg actgaaatgg gatgcaagtt tattatga                          158

<210> SEQ ID NO 359
<211> LENGTH: 94
<212> TYPE: DNA
<213> ORGANISM: Artificial Sequence
<220> FEATURE:
<223> OTHER INFORMATION: Primer

<400> SEQUENCE: 359
agtgaaaagt tcttctccctt tgctagccat atttattgat tatttgttta tgggtattta   60
tagatgaaaa gagttaaggt ggacaatgca gtgc                                94
```

<210> SEQ ID NO 360
<211> LENGTH: 158
<212> TYPE: DNA
<213> ORGANISM: Artificial Sequence
<220> FEATURE:
<223> OTHER INFORMATION: Primer

<400> SEQUENCE: 360
cttgataact tcctcaccct tagaaaccat ttttactacg atagacacaa gaagaagcag    60
gagggggagg atctggatat ttataagagt ctcccataga taacgatttg gcacttttg    120 ccatcacccg actgaaatgg gatgcaagtt tattatga                            158

<210> SEQ ID NO 361
<211> LENGTH: 63
<212> TYPE: DNA
<213> ORGANISM: Artificial Sequence
<220> FEATURE:
<223> OTHER INFORMATION: Primer

<400> SEQUENCE: 361
agtgaaaagt tcttctcctt tgctagccat ctagaaaagg acgcactcgt cttgtattta    60
tag                                                                   63

<210> SEQ ID NO 362
<211> LENGTH: 55
<212> TYPE: DNA
<213> ORGANISM: Artificial Sequence
<220> FEATURE:
<223> OTHER INFORMATION: Primer

<400> SEQUENCE: 362
agtgaaaagt tcttctcctt tgctagccat taaggtggac aatgcagtgc caaac         55

<210> SEQ ID NO 363
<211> LENGTH: 60
<212> TYPE: DNA
<213> ORGANISM: Artificial Sequence
<220> FEATURE:
<223> OTHER INFORMATION: Primer

<400> SEQUENCE: 363
cttgataact tcctcaccct tagaaaccat ttttactacg atagacacaa gaagaagcag    60

<210> SEQ ID NO 364
<211> LENGTH: 59
<212> TYPE: DNA
<213> ORGANISM: Artificial Sequence
<220> FEATURE:
<223> OTHER INFORMATION: Primer

<400> SEQUENCE: 364
agtgaaaagt tcttctcctt tgctagccat gaggcagagc gtgcgtaaat ttgaaactg     59

<210> SEQ ID NO 365
<211> LENGTH: 60
<212> TYPE: DNA
<213> ORGANISM: Artificial Sequence
<220> FEATURE:
<223> OTHER INFORMATION: Primer

<400> SEQUENCE: 365
cttgataact tcctcaccct tagaaaccat ttttactacg atagacacaa gaagaagcag    60

```
<210> SEQ ID NO 366
<211> LENGTH: 57
<212> TYPE: DNA
<213> ORGANISM: Artificial Sequence
<220> FEATURE:
<223> OTHER INFORMATION: Primer

<400> SEQUENCE: 366
agtgaaaagt tcttctcctt tgctagccat ttgcatccca tttcagtcgg gagtgtc        57

<210> SEQ ID NO 367
<211> LENGTH: 60
<212> TYPE: DNA
<213> ORGANISM: Artificial Sequence
<220> FEATURE:
<223> OTHER INFORMATION: Primer

<400> SEQUENCE: 367
cttgataact tcctcaccct tagaaaccat ttttactacg atagacacaa gaagaagcag     60

<210> SEQ ID NO 368
<211> LENGTH: 106
<212> TYPE: DNA
<213> ORGANISM: Artificial Sequence
<220> FEATURE:
<223> OTHER INFORMATION: Primer

<400> SEQUENCE: 368
agtgaaaagt tcttctcctt tgctagccat ttatctatgg gagactctta taaatatcca    60
gatcctcccc ctcctgcttc ttcttgtgtc tatcgtagta aaaatg                  106

<210> SEQ ID NO 369
<211> LENGTH: 60
<212> TYPE: DNA
<213> ORGANISM: Artificial Sequence
<220> FEATURE:
<223> OTHER INFORMATION: Primer

<400> SEQUENCE: 369
cttgataact tcctcaccct tagaaaccat ttttactacg atagacacaa gaagaagcag     60

<210> SEQ ID NO 370
<211> LENGTH: 56
<212> TYPE: DNA
<213> ORGANISM: Artificial Sequence
<220> FEATURE:
<223> OTHER INFORMATION: Primer

<400> SEQUENCE: 370
cttgataact tcctcaccct tagaaaccat cgatttggca ctttttgcca tcagtg         56

<210> SEQ ID NO 371
<211> LENGTH: 60
<212> TYPE: DNA
<213> ORGANISM: Artificial Sequence
<220> FEATURE:
<223> OTHER INFORMATION: Primer

<400> SEQUENCE: 371
gaaaagttct tctcctttgc tagccatatt tattgattat tgtttatgg gtgagtctag     60

<210> SEQ ID NO 372
<211> LENGTH: 60
<212> TYPE: DNA
<213> ORGANISM: Artificial Sequence
<220> FEATURE:
```

<223> OTHER INFORMATION: Primer

<400> SEQUENCE: 372
tgataacttc ctcaccctta gaaaccatgt ttattatgag ttctggtagc atagaaatgg    60

<210> SEQ ID NO 373
<211> LENGTH: 60
<212> TYPE: DNA
<213> ORGANISM: Artificial Sequence
<220> FEATURE:
<223> OTHER INFORMATION: Primer

<400> SEQUENCE: 373
gaaaagttct tctcctttgc tagccatatt tattgattat ttgtttatgg gtgagtctag    60

<210> SEQ ID NO 374
<211> LENGTH: 52
<212> TYPE: DNA
<213> ORGANISM: Artificial Sequence
<220> FEATURE:
<223> OTHER INFORMATION: Primer

<400> SEQUENCE: 374
cttgataact tcctcaccct tagaaaccat taggagtacg gctcagttca tc            52

<210> SEQ ID NO 375
<211> LENGTH: 60
<212> TYPE: DNA
<213> ORGANISM: Artificial Sequence
<220> FEATURE:
<223> OTHER INFORMATION: Primer

<400> SEQUENCE: 375
gaaaagttct tctcctttgc tagccatatt tattgattat ttgtttatgg gtgagtctag    60

<210> SEQ ID NO 376
<211> LENGTH: 108
<212> TYPE: DNA
<213> ORGANISM: Artificial Sequence
<220> FEATURE:
<223> OTHER INFORMATION: Primer

<400> SEQUENCE: 376
cttgataact tcctcaccct tagaaaccat actcttttca tctataaata caagacgagt    60
gcgtcctttt ctagactcac ccataaacaa ataatcaata aatatggc               108

<210> SEQ ID NO 377
<211> LENGTH: 60
<212> TYPE: DNA
<213> ORGANISM: Artificial Sequence
<220> FEATURE:
<223> OTHER INFORMATION: Primer

<400> SEQUENCE: 377
gaaaagttct tctcctttgc tagccatatt tattgattat ttgtttatgg gtgagtctag    60

<210> SEQ ID NO 378
<211> LENGTH: 55
<212> TYPE: DNA
<213> ORGANISM: Artificial Sequence
<220> FEATURE:
<223> OTHER INFORMATION: Primer

<400> SEQUENCE: 378
gtcacctgca ggaataaaaa aacgttatag aaagaaattg gactacgata tgctc          55

<210> SEQ ID NO 379
<211> LENGTH: 60
<212> TYPE: DNA
<213> ORGANISM: Artificial Sequence
<220> FEATURE:
<223> OTHER INFORMATION: Primer

<400> SEQUENCE: 379
tctcaaacgg agcgtcacct ttggaaacag aagaggagta tctacaattg aattccaaac    60

<210> SEQ ID NO 380
<211> LENGTH: 60
<212> TYPE: DNA
<213> ORGANISM: Artificial Sequence
<220> FEATURE:
<223> OTHER INFORMATION: Primer

<400> SEQUENCE: 380
aattcaattg tagatactcc tcttctgttt ccaaaggtga cgctccgttt gagaatctag    60

<210> SEQ ID NO 381
<211> LENGTH: 61
<212> TYPE: DNA
<213> ORGANISM: Artificial Sequence
<220> FEATURE:
<223> OTHER INFORMATION: Primer

<400> SEQUENCE: 381
cctttgctag ccattttgtt cgattattct ccagataaaa tcaacaatag ttgtttgtaa    60
g                                                                   61

<210> SEQ ID NO 382
<211> LENGTH: 55
<212> TYPE: DNA
<213> ORGANISM: Artificial Sequence
<220> FEATURE:
<223> OTHER INFORMATION: Primer

<400> SEQUENCE: 382
gtcacctgca ggaataaaaa aacgttatag aaagaaattg gactacgata tgctc         55

<210> SEQ ID NO 383
<211> LENGTH: 60
<212> TYPE: DNA
<213> ORGANISM: Artificial Sequence
<220> FEATURE:
<223> OTHER INFORMATION: Primer

<400> SEQUENCE: 383
cgaaaatgga agcgctgaac cttcaagctt acattcctcc tcatctggcc ttcaattgtg    60

<210> SEQ ID NO 384
<211> LENGTH: 60
<212> TYPE: DNA
<213> ORGANISM: Artificial Sequence
<220> FEATURE:
<223> OTHER INFORMATION: Primer

<400> SEQUENCE: 384
ttgttcccca caattgaagg ccagatgagg aggaatgtaa gcttgaaggt tcagcgcttc    60

<210> SEQ ID NO 385
<211> LENGTH: 61
<212> TYPE: DNA

```
<213> ORGANISM: Artificial Sequence
<220> FEATURE:
<223> OTHER INFORMATION: Primer

<400> SEQUENCE: 385
cctttgctag ccattttgtt cgattattct ccagataaaa tcaacaatag ttgtttgtaa    60
g                                                                    61

<210> SEQ ID NO 386
<211> LENGTH: 55
<212> TYPE: DNA
<213> ORGANISM: Artificial Sequence
<220> FEATURE:
<223> OTHER INFORMATION: Primer

<400> SEQUENCE: 386
gtcacctgca ggaataaaaa aacgttatag aaagaaattg gactacgata tgctc         55

<210> SEQ ID NO 387
<211> LENGTH: 60
<212> TYPE: DNA
<213> ORGANISM: Artificial Sequence
<220> FEATURE:
<223> OTHER INFORMATION: Primer

<400> SEQUENCE: 387
actaactcca cccagatgaa accagttgtc taacgttcct tgaaactcga atgatcccag    60

<210> SEQ ID NO 388
<211> LENGTH: 60
<212> TYPE: DNA
<213> ORGANISM: Artificial Sequence
<220> FEATURE:
<223> OTHER INFORMATION: Primer

<400> SEQUENCE: 388
gctgggatca ttcgagtttc aaggaacgtt agacaactgg tttcatctgg gtggagttag    60

<210> SEQ ID NO 389
<211> LENGTH: 61
<212> TYPE: DNA
<213> ORGANISM: Artificial Sequence
<220> FEATURE:
<223> OTHER INFORMATION: Primer

<400> SEQUENCE: 389
cctttgctag ccattttgtt cgattattct ccagataaaa tcaacaatag ttgtttgtaa    60
g                                                                    61

<210> SEQ ID NO 390
<211> LENGTH: 55
<212> TYPE: DNA
<213> ORGANISM: Artificial Sequence
<220> FEATURE:
<223> OTHER INFORMATION: Primer

<400> SEQUENCE: 390
gtcacctgca ggaataaaaa aacgttatag aaagaaattg gactacgata tgctc         55

<210> SEQ ID NO 391
<211> LENGTH: 58
<212> TYPE: DNA
<213> ORGANISM: Artificial Sequence
<220> FEATURE:
<223> OTHER INFORMATION: Primer
```

```
<400> SEQUENCE: 391
cagtcaatga atgttgagct aacgttcctt gaaactcctc cgctattccg ccgcttgc      58

<210> SEQ ID NO 392
<211> LENGTH: 60
<212> TYPE: DNA
<213> ORGANISM: Artificial Sequence
<220> FEATURE:
<223> OTHER INFORMATION: Primer

<400> SEQUENCE: 392
tggagcaagc ggcggaatag cggaggagtt tcaaggaacg ttagctcaac attcattgac   60

<210> SEQ ID NO 393
<211> LENGTH: 61
<212> TYPE: DNA
<213> ORGANISM: Artificial Sequence
<220> FEATURE:
<223> OTHER INFORMATION: Primer

<400> SEQUENCE: 393
cctttgctag ccattttgtt cgattattct ccagataaaa tcaacaatag ttgtttgtaa   60
g                                                                    61

<210> SEQ ID NO 394
<211> LENGTH: 55
<212> TYPE: DNA
<213> ORGANISM: Artificial Sequence
<220> FEATURE:
<223> OTHER INFORMATION: Primer

<400> SEQUENCE: 394
gtcacctgca ggaataaaaa aacgttatag aaagaaattg gactacgata tgctc         55

<210> SEQ ID NO 395
<211> LENGTH: 60
<212> TYPE: DNA
<213> ORGANISM: Artificial Sequence
<220> FEATURE:
<223> OTHER INFORMATION: Primer

<400> SEQUENCE: 395
cttgctccaa ccatgtttcc gccttttcg aacatcctgc cttttttagc ctcaggtctc    60

<210> SEQ ID NO 396
<211> LENGTH: 60
<212> TYPE: DNA
<213> ORGANISM: Artificial Sequence
<220> FEATURE:
<223> OTHER INFORMATION: Primer

<400> SEQUENCE: 396
gctaaccgag acctgaggct aaaaaaggca ggatgttcga aaaaggcgga aacatggttg   60

<210> SEQ ID NO 397
<211> LENGTH: 61
<212> TYPE: DNA
<213> ORGANISM: Artificial Sequence
<220> FEATURE:
<223> OTHER INFORMATION: Primer

<400> SEQUENCE: 397
cctttgctag ccattttgtt cgattattct ccagataaaa tcaacaatag ttgtttgtaa   60
```

```
g                                                              61
```

<210> SEQ ID NO 398
<211> LENGTH: 55
<212> TYPE: DNA
<213> ORGANISM: Artificial Sequence
<220> FEATURE:
<223> OTHER INFORMATION: Primer

<400> SEQUENCE: 398

```
gtcacctgca ggaataaaaa aacgttatag aaagaaattg gactacgata tgctc        55
```

<210> SEQ ID NO 399
<211> LENGTH: 60
<212> TYPE: DNA
<213> ORGANISM: Artificial Sequence
<220> FEATURE:
<223> OTHER INFORMATION: Primer

<400> SEQUENCE: 399

```
ggactttttcc tcctgccttt gcaaattctg gtcttcatac ctatatcaac ttttcatcag    60
```

<210> SEQ ID NO 400
<211> LENGTH: 60
<212> TYPE: DNA
<213> ORGANISM: Artificial Sequence
<220> FEATURE:
<223> OTHER INFORMATION: Primer

<400> SEQUENCE: 400

```
aagttgatat aggtatgaag accagaattt gcaaaggcag gaggaaaagt cctgccaaag    60
```

<210> SEQ ID NO 401
<211> LENGTH: 61
<212> TYPE: DNA
<213> ORGANISM: Artificial Sequence
<220> FEATURE:
<223> OTHER INFORMATION: Primer

<400> SEQUENCE: 401

```
cctttgctag ccatttttgtt cgattattct ccagataaaa tcaacaatag ttgtttgtaa    60
g                                                                    61
```

<210> SEQ ID NO 402
<211> LENGTH: 55
<212> TYPE: DNA
<213> ORGANISM: Artificial Sequence
<220> FEATURE:
<223> OTHER INFORMATION: Primer

<400> SEQUENCE: 402

```
gtcacctgca ggaataaaaa aacgttatag aaagaaattg gactacgata tgctc        55
```

<210> SEQ ID NO 403
<211> LENGTH: 60
<212> TYPE: DNA
<213> ORGANISM: Artificial Sequence
<220> FEATURE:
<223> OTHER INFORMATION: Primer

<400> SEQUENCE: 403

```
aattctggtc ttcataccgg ttcaaaaaag aactaaagca ggatgcctga tatataaatc    60
```

<210> SEQ ID NO 404
<211> LENGTH: 60

```
<212> TYPE: DNA
<213> ORGANISM: Artificial Sequence
<220> FEATURE:
<223> OTHER INFORMATION: Primer

<400> SEQUENCE: 404
catcctgctt tagttctttt ttgaaccggt atgaagacca gaatttgcct agaggctaac    60

<210> SEQ ID NO 405
<211> LENGTH: 61
<212> TYPE: DNA
<213> ORGANISM: Artificial Sequence
<220> FEATURE:
<223> OTHER INFORMATION: Primer

<400> SEQUENCE: 405
cctttgctag ccattttgtt cgattattct ccagataaaa tcaacaatag ttgtttgtaa    60
g                                                                    61

<210> SEQ ID NO 406
<211> LENGTH: 55
<212> TYPE: DNA
<213> ORGANISM: Artificial Sequence
<220> FEATURE:
<223> OTHER INFORMATION: Primer

<400> SEQUENCE: 406
gtcacctgca ggaataaaaa aacgttatag aaagaaattg gactacgata tgctc          55

<210> SEQ ID NO 407
<211> LENGTH: 67
<212> TYPE: DNA
<213> ORGANISM: Artificial Sequence
<220> FEATURE:
<223> OTHER INFORMATION: Primer

<400> SEQUENCE: 407
cctttgctag ccattttgtt cgatgtaagt aaacgaatca agatactgaa aatagtttca    60
aaagcag                                                               67

<210> SEQ ID NO 408
<211> LENGTH: 55
<212> TYPE: DNA
<213> ORGANISM: Artificial Sequence
<220> FEATURE:
<223> OTHER INFORMATION: Primer

<400> SEQUENCE: 408
gtcacctgca ggaataaaaa aacgttatag aaagaaattg gactacgata tgctc          55

<210> SEQ ID NO 409
<211> LENGTH: 61
<212> TYPE: DNA
<213> ORGANISM: Artificial Sequence
<220> FEATURE:
<223> OTHER INFORMATION: Primer

<400> SEQUENCE: 409
cctttgctag ccattttgtt cgattattct ccagataaaa tcaacaatag ttgtttgtaa    60
g                                                                    61

<210> SEQ ID NO 410
<211> LENGTH: 44
<212> TYPE: DNA
```

```
<213> ORGANISM: Artificial Sequence
<220> FEATURE:
<223> OTHER INFORMATION: Primer

<400> SEQUENCE: 410
gtcacctgca ggattactgt tttgggcaat cctgttgata agac                44

<210> SEQ ID NO 411
<211> LENGTH: 60
<212> TYPE: DNA
<213> ORGANISM: Artificial Sequence
<220> FEATURE:
<223> OTHER INFORMATION: Primer

<400> SEQUENCE: 411
aactggaagt ctggtaagga ctctagcata ccaagtaaga ttacgtaaca cctgggcatg    60

<210> SEQ ID NO 412
<211> LENGTH: 60
<212> TYPE: DNA
<213> ORGANISM: Artificial Sequence
<220> FEATURE:
<223> OTHER INFORMATION: Primer

<400> SEQUENCE: 412
gttacgtaat cttacttggt atgctagagt ccttaccaga cttccagttt agcaaaccac    60

<210> SEQ ID NO 413
<211> LENGTH: 60
<212> TYPE: DNA
<213> ORGANISM: Artificial Sequence
<220> FEATURE:
<223> OTHER INFORMATION: Primer

<400> SEQUENCE: 413
cctttgctag ccatttttga tgtttgatag tttgataaga gtgaacttta gtgtttagag    60

<210> SEQ ID NO 414
<211> LENGTH: 60
<212> TYPE: DNA
<213> ORGANISM: Artificial Sequence
<220> FEATURE:
<223> OTHER INFORMATION: Primer

<400> SEQUENCE: 414
cctttgctag ccatttttga tgtttgatag tttgataaga gtgaacttta gtgtttagag    60

<210> SEQ ID NO 415
<211> LENGTH: 60
<212> TYPE: DNA
<213> ORGANISM: Artificial Sequence
<220> FEATURE:
<223> OTHER INFORMATION: Primer

<400> SEQUENCE: 415
gtcaccaaga gggtcctatt tatagtacat catattacct gtcaagctat gctaccccac    60

<210> SEQ ID NO 416
<211> LENGTH: 60
<212> TYPE: DNA
<213> ORGANISM: Artificial Sequence
<220> FEATURE:
<223> OTHER INFORMATION: Primer

<400> SEQUENCE: 416
gcatagcttg acaggtaata tgatgtacta taaataggac cctcttggtg acttgctaac    60
```

<210> SEQ ID NO 417
<211> LENGTH: 60
<212> TYPE: DNA
<213> ORGANISM: Artificial Sequence
<220> FEATURE:
<223> OTHER INFORMATION: Primer

<400> SEQUENCE: 417
cctttgctag ccatttttga tgtttgatag tttgataaga gtgaacttta gtgtttagag      60

<210> SEQ ID NO 418
<211> LENGTH: 60
<212> TYPE: DNA
<213> ORGANISM: Artificial Sequence
<220> FEATURE:
<223> OTHER INFORMATION: Primer

<400> SEQUENCE: 418
cctttgctag ccatttttga tgtttgatag tttgataaga gtgaacttta gtgtttagag      60

<210> SEQ ID NO 419
<211> LENGTH: 60
<212> TYPE: DNA
<213> ORGANISM: Artificial Sequence
<220> FEATURE:
<223> OTHER INFORMATION: Primer

<400> SEQUENCE: 419
ataacaaact taataatgag atttagtata cttgcccta taagaaacga aggatttcag      60

<210> SEQ ID NO 420
<211> LENGTH: 60
<212> TYPE: DNA
<213> ORGANISM: Artificial Sequence
<220> FEATURE:
<223> OTHER INFORMATION: Primer

<400> SEQUENCE: 420
ggcaagtata ctaaatctca ttattaagtt tgttatgggg tgaagttacc agtaattttc      60

<210> SEQ ID NO 421
<211> LENGTH: 60
<212> TYPE: DNA
<213> ORGANISM: Artificial Sequence
<220> FEATURE:
<223> OTHER INFORMATION: Primer

<400> SEQUENCE: 421
cctttgctag ccatttttga tgtttgatag tttgataaga gtgaacttta gtgtttagag      60

<210> SEQ ID NO 422
<211> LENGTH: 60
<212> TYPE: DNA
<213> ORGANISM: Artificial Sequence
<220> FEATURE:
<223> OTHER INFORMATION: Primer

<400> SEQUENCE: 422
cctttgctag ccatttttga tgtttgatag tttgataaga gtgaacttta gtgtttagag      60

<210> SEQ ID NO 423
<211> LENGTH: 60
<212> TYPE: DNA
<213> ORGANISM: Artificial Sequence
<220> FEATURE:

<223> OTHER INFORMATION: Primer

<400> SEQUENCE: 423
ctataagaaa cgaaggattg agatccgccc aaacgaacag ataatagaaa aagaaattc        60

<210> SEQ ID NO 424
<211> LENGTH: 60
<212> TYPE: DNA
<213> ORGANISM: Artificial Sequence
<220> FEATURE:
<223> OTHER INFORMATION: Primer

<400> SEQUENCE: 424
ctgttcgttt gggcggatct caatccttcg tttcttatag ggcaagtat actaaatctc        60

<210> SEQ ID NO 425
<211> LENGTH: 60
<212> TYPE: DNA
<213> ORGANISM: Artificial Sequence
<220> FEATURE:
<223> OTHER INFORMATION: Primer

<400> SEQUENCE: 425
cctttgctag ccattttga tgtttgatag tttgataaga gtgaacttta gtgtttagag        60

<210> SEQ ID NO 426
<211> LENGTH: 60
<212> TYPE: DNA
<213> ORGANISM: Artificial Sequence
<220> FEATURE:
<223> OTHER INFORMATION: Primer

<400> SEQUENCE: 426
cctttgctag ccattttga tgtttgatag tttgataaga gtgaacttta gtgtttagag        60

<210> SEQ ID NO 427
<211> LENGTH: 60
<212> TYPE: DNA
<213> ORGANISM: Artificial Sequence
<220> FEATURE:
<223> OTHER INFORMATION: Primer

<400> SEQUENCE: 427
cactggagag atccgcccaa acgaacagat aattgcactc cctttagctg ccgttccatc        60

<210> SEQ ID NO 428
<211> LENGTH: 60
<212> TYPE: DNA
<213> ORGANISM: Artificial Sequence
<220> FEATURE:
<223> OTHER INFORMATION: Primer

<400> SEQUENCE: 428
aaagggatgg aacggcagct aaagggagtg caattatctg ttcgtttggg cggatctctc        60

<210> SEQ ID NO 429
<211> LENGTH: 60
<212> TYPE: DNA
<213> ORGANISM: Artificial Sequence
<220> FEATURE:
<223> OTHER INFORMATION: Primer

<400> SEQUENCE: 429
cctttgctag ccattttga tgtttgatag tttgataaga gtgaacttta gtgtttagag        60

```
<210> SEQ ID NO 430
<211> LENGTH: 60
<212> TYPE: DNA
<213> ORGANISM: Artificial Sequence
<220> FEATURE:
<223> OTHER INFORMATION: Primer

<400> SEQUENCE: 430
cctttgctag ccatttttga tgtttgatag tttgataaga gtgaacttta gtgtttagag    60

<210> SEQ ID NO 431
<211> LENGTH: 60
<212> TYPE: DNA
<213> ORGANISM: Artificial Sequence
<220> FEATURE:
<223> OTHER INFORMATION: Primer

<400> SEQUENCE: 431
ttccatgcac tccctttagc tgcaagagga aacttaaccg ataccttgga gaaatctaag    60

<210> SEQ ID NO 432
<211> LENGTH: 60
<212> TYPE: DNA
<213> ORGANISM: Artificial Sequence
<220> FEATURE:
<223> OTHER INFORMATION: Primer

<400> SEQUENCE: 432
gatttctcca aggtatcggt taagtttcct cttgcagcta aagggagtgc atggaatgac    60

<210> SEQ ID NO 433
<211> LENGTH: 60
<212> TYPE: DNA
<213> ORGANISM: Artificial Sequence
<220> FEATURE:
<223> OTHER INFORMATION: Primer

<400> SEQUENCE: 433
cctttgctag ccatttttga tgtttgatag tttgataaga gtgaacttta gtgtttagag    60

<210> SEQ ID NO 434
<211> LENGTH: 60
<212> TYPE: DNA
<213> ORGANISM: Artificial Sequence
<220> FEATURE:
<223> OTHER INFORMATION: Primer

<400> SEQUENCE: 434
cctttgctag ccatttttga tgtttgatag tttgataaga gtgaacttta gtgtttagag    60

<210> SEQ ID NO 435
<211> LENGTH: 60
<212> TYPE: DNA
<213> ORGANISM: Artificial Sequence
<220> FEATURE:
<223> OTHER INFORMATION: Primer

<400> SEQUENCE: 435
ggaaacttaa ccgatacctt ggagaaagat atccttagtg aagggttgtt ccgatacttc    60

<210> SEQ ID NO 436
<211> LENGTH: 60
<212> TYPE: DNA
<213> ORGANISM: Artificial Sequence
<220> FEATURE:
<223> OTHER INFORMATION: Primer
```

<400> SEQUENCE: 436
aacaaccctt cactaaggat atctttctcc aaggtatcgg ttaagtttcc tctttcgtac    60

<210> SEQ ID NO 437
<211> LENGTH: 60
<212> TYPE: DNA
<213> ORGANISM: Artificial Sequence
<220> FEATURE:
<223> OTHER INFORMATION: Primer

<400> SEQUENCE: 437
cctttgctag ccattttga tgtttgatag tttgataaga gtgaacttta gtgtttagag    60

<210> SEQ ID NO 438
<211> LENGTH: 60
<212> TYPE: DNA
<213> ORGANISM: Artificial Sequence
<220> FEATURE:
<223> OTHER INFORMATION: Primer

<400> SEQUENCE: 438
cctttgctag ccattttga tgtttgatag tttgataaga gtgaacttta gtgtttagag    60

<210> SEQ ID NO 439
<211> LENGTH: 60
<212> TYPE: DNA
<213> ORGANISM: Artificial Sequence
<220> FEATURE:
<223> OTHER INFORMATION: Primer

<400> SEQUENCE: 439
tttagcctag atatccttag tgaagggttg ttcagacgga aacgggcatt aagggttaac    60

<210> SEQ ID NO 440
<211> LENGTH: 60
<212> TYPE: DNA
<213> ORGANISM: Artificial Sequence
<220> FEATURE:
<223> OTHER INFORMATION: Primer

<400> SEQUENCE: 440
aacccttaat gcccgtttcc gtctgaacaa cccttcacta aggatatcta ggctaaactc    60

<210> SEQ ID NO 441
<211> LENGTH: 60
<212> TYPE: DNA
<213> ORGANISM: Artificial Sequence
<220> FEATURE:
<223> OTHER INFORMATION: Primer

<400> SEQUENCE: 441
cctttgctag ccattttga tgtttgatag tttgataaga gtgaacttta gtgtttagag    60

<210> SEQ ID NO 442
<211> LENGTH: 60
<212> TYPE: DNA
<213> ORGANISM: Artificial Sequence
<220> FEATURE:
<223> OTHER INFORMATION: Primer

<400> SEQUENCE: 442
cctttgctag ccattttga tgtttgatag tttgataaga gtgaacttta gtgtttagag    60

<210> SEQ ID NO 443
<211> LENGTH: 60

<212> TYPE: DNA
<213> ORGANISM: Artificial Sequence
<220> FEATURE:
<223> OTHER INFORMATION: Primer

<400> SEQUENCE: 443
cctttgctag ccattttga tgtttgatag tttgataaga gtgaacttta gtgtttagag    60

<210> SEQ ID NO 444
<211> LENGTH: 32
<212> TYPE: DNA
<213> ORGANISM: Artificial Sequence
<220> FEATURE:
<223> OTHER INFORMATION: Primer

<400> SEQUENCE: 444
cgtttcgaat aattagttgt tttttgatct tc    32

<210> SEQ ID NO 445
<211> LENGTH: 50
<212> TYPE: DNA
<213> ORGANISM: Artificial Sequence
<220> FEATURE:
<223> OTHER INFORMATION: Primer

<400> SEQUENCE: 445
aagacatttc tacaaaaaag atctaacatc caaagacgaa aggttgaatg    50

<210> SEQ ID NO 446
<211> LENGTH: 50
<212> TYPE: DNA
<213> ORGANISM: Artificial Sequence
<220> FEATURE:
<223> OTHER INFORMATION: Primer

<400> SEQUENCE: 446
cgtctttgga tgttagatct tttttgtaga aatgtcttgg tgtcctcgtc    50

<210> SEQ ID NO 447
<211> LENGTH: 34
<212> TYPE: DNA
<213> ORGANISM: Artificial Sequence
<220> FEATURE:
<223> OTHER INFORMATION: Primer

<400> SEQUENCE: 447
tgtgttttga tagttgttca attgattgaa atag    34

<210> SEQ ID NO 448
<211> LENGTH: 32
<212> TYPE: DNA
<213> ORGANISM: Artificial Sequence
<220> FEATURE:
<223> OTHER INFORMATION: Primer

<400> SEQUENCE: 448
cgtttcgaat aattagttgt tttttgatct tc    32

<210> SEQ ID NO 449
<211> LENGTH: 60
<212> TYPE: DNA
<213> ORGANISM: Artificial Sequence
<220> FEATURE:
<223> OTHER INFORMATION: Primer

<400> SEQUENCE: 449
ttcctcattt attatatata tgattacaca ctagatctaa catccaaaga cgaaaggttg    60

<210> SEQ ID NO 450
<211> LENGTH: 60
<212> TYPE: DNA
<213> ORGANISM: Artificial Sequence
<220> FEATURE:
<223> OTHER INFORMATION: Primer

<400> SEQUENCE: 450
gtctttggat gttagatcta gtgtgtaatc atatatataa taaatgagga ataataattg    60

<210> SEQ ID NO 451
<211> LENGTH: 60
<212> TYPE: DNA
<213> ORGANISM: Artificial Sequence
<220> FEATURE:
<223> OTHER INFORMATION: Primer

<400> SEQUENCE: 451
agtgaaaagt tcttctcctt tgctagccat tttaattgta agtcttgact agagcaagtg    60

<210> SEQ ID NO 452
<211> LENGTH: 34
<212> TYPE: DNA
<213> ORGANISM: Artificial Sequence
<220> FEATURE:
<223> OTHER INFORMATION: Primer

<400> SEQUENCE: 452
tgtgttttga tagttgttca attgattgaa atag    34

<210> SEQ ID NO 453
<211> LENGTH: 60
<212> TYPE: DNA
<213> ORGANISM: Artificial Sequence
<220> FEATURE:
<223> OTHER INFORMATION: Primer

<400> SEQUENCE: 453
cctcatttat tatatatatg attacacact tttttgtaga aatgtcttgg tgtcctcgtc    60

<210> SEQ ID NO 454
<211> LENGTH: 60
<212> TYPE: DNA
<213> ORGANISM: Artificial Sequence
<220> FEATURE:
<223> OTHER INFORMATION: Primer

<400> SEQUENCE: 454
caagacattt ctacaaaaaa gtgtgtaatc atatatataa taaatgagga ataataattg    60

<210> SEQ ID NO 455
<211> LENGTH: 60
<212> TYPE: DNA
<213> ORGANISM: Artificial Sequence
<220> FEATURE:
<223> OTHER INFORMATION: Primer

<400> SEQUENCE: 455
agtgaaaagt tcttctcctt tgctagccat tttaattgta agtcttgact agagcaagtg    60

<210> SEQ ID NO 456
<211> LENGTH: 34
<212> TYPE: DNA
<213> ORGANISM: Artificial Sequence -continued
<220> FEATURE:
<223> OTHER INFORMATION: Primer

<400> SEQUENCE: 456
tgtgttttga tagttgttca attgattgaa atag                                34

<210> SEQ ID NO 457
<211> LENGTH: 60
<212> TYPE: DNA
<213> ORGANISM: Artificial Sequence
<220> FEATURE:
<223> OTHER INFORMATION: Primer

<400> SEQUENCE: 457
acttatttgc tccccaacct gtcaaatacc tttttgtaga aatgtcttgg tgtcctcgtc     60

<210> SEQ ID NO 458
<211> LENGTH: 60
<212> TYPE: DNA
<213> ORGANISM: Artificial Sequence
<220> FEATURE:
<223> OTHER INFORMATION: Primer

<400> SEQUENCE: 458
ggacgaggac accaagacat ttctacaaaa aggtatttga caggttgggg agcaaataag     60

<210> SEQ ID NO 459
<211> LENGTH: 60
<212> TYPE: DNA
<213> ORGANISM: Artificial Sequence
<220> FEATURE:
<223> OTHER INFORMATION: Primer

<400> SEQUENCE: 459
cagtgaaaag ttcttctcct ttgctagcca tgttggcgaa taactaaaat gtatgtagtg     60

<210> SEQ ID NO 460
<211> LENGTH: 41
<212> TYPE: DNA
<213> ORGANISM: Artificial Sequence
<220> FEATURE:
<223> OTHER INFORMATION: Primer

<400> SEQUENCE: 460
agtgtgtaat catatatata ataaatgagg aataataatt g                        41

<210> SEQ ID NO 461
<211> LENGTH: 35
<212> TYPE: DNA
<213> ORGANISM: Artificial Sequence
<220> FEATURE:
<223> OTHER INFORMATION: Primer

<400> SEQUENCE: 461
tttaattgta agtcttgact agagcaagtg ttatg                               35

<210> SEQ ID NO 462
<211> LENGTH: 42
<212> TYPE: DNA
<213> ORGANISM: Artificial Sequence
<220> FEATURE:
<223> OTHER INFORMATION: Primer

<400> SEQUENCE: 462
ctaaatgctg tttctcttag catagtcaat gattagtttt tc                       42

```
<210> SEQ ID NO 463
<211> LENGTH: 28
<212> TYPE: DNA
<213> ORGANISM: Artificial Sequence
<220> FEATURE:
<223> OTHER INFORMATION: Primer

<400> SEQUENCE: 463
gcagtgatga tgggaccata tggatcag                                  28

<210> SEQ ID NO 464
<211> LENGTH: 35
<212> TYPE: DNA
<213> ORGANISM: Artificial Sequence
<220> FEATURE:
<223> OTHER INFORMATION: Primer

<400> SEQUENCE: 464
aactgccact tatgcgaaac ttcctagata agttc                          35

<210> SEQ ID NO 465
<211> LENGTH: 44
<212> TYPE: DNA
<213> ORGANISM: Artificial Sequence
<220> FEATURE:
<223> OTHER INFORMATION: Primer

<400> SEQUENCE: 465
ttcacatcaa tttcatatca aatgaaccaa tcacatttca gtac                44

<210> SEQ ID NO 466
<211> LENGTH: 30
<212> TYPE: DNA
<213> ORGANISM: Artificial Sequence
<220> FEATURE:
<223> OTHER INFORMATION: Primer

<400> SEQUENCE: 466
atccgcgagg attccatcat caattggatg                                30

<210> SEQ ID NO 467
<211> LENGTH: 31
<212> TYPE: DNA
<213> ORGANISM: Artificial Sequence
<220> FEATURE:
<223> OTHER INFORMATION: Primer

<400> SEQUENCE: 467
tgttcttatt tgctttgagg aatgcgtgaa g                              31

<210> SEQ ID NO 468
<211> LENGTH: 46
<212> TYPE: DNA
<213> ORGANISM: Artificial Sequence
<220> FEATURE:
<223> OTHER INFORMATION: Primer

<400> SEQUENCE: 468
tgtctccaca ctaacttatt tgataaatga ttaattcaat aaaacc              46

<210> SEQ ID NO 469
<211> LENGTH: 36
<212> TYPE: DNA
<213> ORGANISM: Artificial Sequence
<220> FEATURE:
<223> OTHER INFORMATION: Primer
```

-continued

```
<400> SEQUENCE: 469
ttcgaaacaa ttactgttta aacagagttg aacctc                                36

<210> SEQ ID NO 470
<211> LENGTH: 28
<212> TYPE: DNA
<213> ORGANISM: Artificial Sequence
<220> FEATURE:
<223> OTHER INFORMATION: Primer

<400> SEQUENCE: 470
tttggtgcac tggattgata ttgagtcc                                         28

<210> SEQ ID NO 471
<211> LENGTH: 37
<212> TYPE: DNA
<213> ORGANISM: Artificial Sequence
<220> FEATURE:
<223> OTHER INFORMATION: Primer

<400> SEQUENCE: 471
ggtgataata attgctgttg aatcattgct aaattgg                               37

<210> SEQ ID NO 472
<211> LENGTH: 39
<212> TYPE: DNA
<213> ORGANISM: Artificial Sequence
<220> FEATURE:
<223> OTHER INFORMATION: Primer

<400> SEQUENCE: 472
actttctttt actgcttatt tcattcgtat agccaatag                             39

<210> SEQ ID NO 473
<211> LENGTH: 34
<212> TYPE: DNA
<213> ORGANISM: Artificial Sequence
<220> FEATURE:
<223> OTHER INFORMATION: Primer

<400> SEQUENCE: 473
tgtttggcag attctgtgtc ggttttttta gatg                                  34

<210> SEQ ID NO 474
<211> LENGTH: 30
<212> TYPE: DNA
<213> ORGANISM: Artificial Sequence
<220> FEATURE:
<223> OTHER INFORMATION: Primer

<400> SEQUENCE: 474
aggaaccctt aaaagtggag gtatccgtac                                       30

<210> SEQ ID NO 475
<211> LENGTH: 33
<212> TYPE: DNA
<213> ORGANISM: Artificial Sequence
<220> FEATURE:
<223> OTHER INFORMATION: Primer

<400> SEQUENCE: 475
ttcgatattg ttatgggatg gttaacagac gag                                   33

<210> SEQ ID NO 476
```

```
<211> LENGTH: 31
<212> TYPE: DNA
<213> ORGANISM: Artificial Sequence
<220> FEATURE:
<223> OTHER INFORMATION: Primer

<400> SEQUENCE: 476
ccgaagggtg tagggtcgtc atatctactt c                            31

<210> SEQ ID NO 477
<211> LENGTH: 35
<212> TYPE: DNA
<213> ORGANISM: Artificial Sequence
<220> FEATURE:
<223> OTHER INFORMATION: Primer

<400> SEQUENCE: 477
aataggccaa ttgtgaatcg attactgatt ttgtg                        35

<210> SEQ ID NO 478
<211> LENGTH: 35
<212> TYPE: DNA
<213> ORGANISM: Artificial Sequence
<220> FEATURE:
<223> OTHER INFORMATION: Primer

<400> SEQUENCE: 478
ttatggtaga atcatcaatt ggaatgaccc tatcg                        35

<210> SEQ ID NO 479
<211> LENGTH: 32
<212> TYPE: DNA
<213> ORGANISM: Artificial Sequence
<220> FEATURE:
<223> OTHER INFORMATION: Primer

<400> SEQUENCE: 479
atttgtatca gtcttgtttc ttttctttgg tc                           32

<210> SEQ ID NO 480
<211> LENGTH: 43
<212> TYPE: DNA
<213> ORGANISM: Artificial Sequence
<220> FEATURE:
<223> OTHER INFORMATION: Primer

<400> SEQUENCE: 480
tgaagttatt cctctacaaa tcgaccgaat atttctatac gtg               43

<210> SEQ ID NO 481
<211> LENGTH: 31
<212> TYPE: DNA
<213> ORGANISM: Artificial Sequence
<220> FEATURE:
<223> OTHER INFORMATION: Primer

<400> SEQUENCE: 481
tagttgtcta agatgctaga ggcaagacgt g                            31

<210> SEQ ID NO 482
<211> LENGTH: 35
<212> TYPE: DNA
<213> ORGANISM: Artificial Sequence
<220> FEATURE:
<223> OTHER INFORMATION: Primer

<400> SEQUENCE: 482
```
atggttaaaa caattattgc tccttcaatc ctgtc       35

<210> SEQ ID NO 483
<211> LENGTH: 36
<212> TYPE: DNA
<213> ORGANISM: Artificial Sequence
<220> FEATURE:
<223> OTHER INFORMATION: Primer

<400> SEQUENCE: 483
tttttcgaat agctaggtga tatgaaggaa aggtag       36

<210> SEQ ID NO 484
<211> LENGTH: 25
<212> TYPE: DNA
<213> ORGANISM: Artificial Sequence
<220> FEATURE:
<223> OTHER INFORMATION: Primer

<400> SEQUENCE: 484
agcgatggac agactgcctc acaac       25

<210> SEQ ID NO 485
<211> LENGTH: 41
<212> TYPE: DNA
<213> ORGANISM: Artificial Sequence
<220> FEATURE:
<223> OTHER INFORMATION: Primer

<400> SEQUENCE: 485
gatctcacac agtattcaac tagttttact ttcccatctt c       41

<210> SEQ ID NO 486
<211> LENGTH: 31
<212> TYPE: DNA
<213> ORGANISM: Artificial Sequence
<220> FEATURE:
<223> OTHER INFORMATION: Primer

<400> SEQUENCE: 486
gattccactg ctcagagtct tttcatcaag c       31

<210> SEQ ID NO 487
<211> LENGTH: 36
<212> TYPE: DNA
<213> ORGANISM: Artificial Sequence
<220> FEATURE:
<223> OTHER INFORMATION: Primer

<400> SEQUENCE: 487
tgtgtagagt ggatgtagaa tacaagtcta gagtta       36

<210> SEQ ID NO 488
<211> LENGTH: 43
<212> TYPE: DNA
<213> ORGANISM: Artificial Sequence
<220> FEATURE:
<223> OTHER INFORMATION: Primer

<400> SEQUENCE: 488
aataaaaaaa cgttatagaa agaaattgga ctacgatatg ctc       43

<210> SEQ ID NO 489
<211> LENGTH: 36
<212> TYPE: DNA

```
<213> ORGANISM: Artificial Sequence
<220> FEATURE:
<223> OTHER INFORMATION: Primer

<400> SEQUENCE: 489
tttgttcgat tattctccag ataaaatcaa caatag                              36

<210> SEQ ID NO 490
<211> LENGTH: 32
<212> TYPE: DNA
<213> ORGANISM: Artificial Sequence
<220> FEATURE:
<223> OTHER INFORMATION: Primer

<400> SEQUENCE: 490
attactgttt tgggcaatcc tgttgataag ac                                  32

<210> SEQ ID NO 491
<211> LENGTH: 37
<212> TYPE: DNA
<213> ORGANISM: Artificial Sequence
<220> FEATURE:
<223> OTHER INFORMATION: Primer

<400> SEQUENCE: 491
ttttgatgtt tgatagtttg ataagagtga actttag                             37

<210> SEQ ID NO 492
<211> LENGTH: 33
<212> TYPE: DNA
<213> ORGANISM: Artificial Sequence
<220> FEATURE:
<223> OTHER INFORMATION: Primer

<400> SEQUENCE: 492
cagagatcgt gttttgatta agattgctgc tac                                 33

<210> SEQ ID NO 493
<211> LENGTH: 43
<212> TYPE: DNA
<213> ORGANISM: Artificial Sequence
<220> FEATURE:
<223> OTHER INFORMATION: Primer

<400> SEQUENCE: 493
tgtagaaata aaatttcaat tagagtaaaa gaaagagcgc aac                      43

<210> SEQ ID NO 494
<211> LENGTH: 38
<212> TYPE: DNA
<213> ORGANISM: Artificial Sequence
<220> FEATURE:
<223> OTHER INFORMATION: Primer

<400> SEQUENCE: 494
gatatcgatc tacacttaat agtagatgac gaggcatc                            38

<210> SEQ ID NO 495
<211> LENGTH: 49
<212> TYPE: DNA
<213> ORGANISM: Artificial Sequence
<220> FEATURE:
<223> OTHER INFORMATION: Primer

<400> SEQUENCE: 495
gatatttcag ctgaatttga agatactcat actatcgcat atttataac                49
```

<210> SEQ ID NO 496
<211> LENGTH: 11
<212> TYPE: DNA
<213> ORGANISM: Artificial Sequence
<220> FEATURE:
<223> OTHER INFORMATION: BsaI
<220> FEATURE:
<221> NAME/KEY: misc_feature
<222> LOCATION: 7..11
<223> OTHER INFORMATION: /function="N is any nucleotid"

<400> SEQUENCE: 496
ggtctcnnnn n                11

<210> SEQ ID NO 497
<211> LENGTH: 11
<212> TYPE: DNA
<213> ORGANISM: Artificial Sequence
<220> FEATURE:
<223> OTHER INFORMATION: BsaI
<220> FEATURE:
<221> NAME/KEY: misc_feature
<222> LOCATION: 1..5
<223> OTHER INFORMATION: /function="N is any nucleotid"

<400> SEQUENCE: 497
nnnnngagac c                11

<210> SEQ ID NO 498
<211> LENGTH: 11
<212> TYPE: DNA
<213> ORGANISM: Artificial Sequence
<220> FEATURE:
<223> OTHER INFORMATION: BmrI
<220> FEATURE:
<221> NAME/KEY: misc_feature
<222> LOCATION: 7..11
<223> OTHER INFORMATION: N is any nucleotide

<400> SEQUENCE: 498
actgggnnnn n                11

<210> SEQ ID NO 499
<211> LENGTH: 11
<212> TYPE: DNA
<213> ORGANISM: Artificial Sequence
<220> FEATURE:
<223> OTHER INFORMATION: BmrI
<220> FEATURE:
<221> NAME/KEY: misc_feature
<222> LOCATION: 1..5
<223> OTHER INFORMATION: N is any nucleotide

<400> SEQUENCE: 499
nnnnncccag t                11

<210> SEQ ID NO 500
<211> LENGTH: 10
<212> TYPE: DNA
<213> ORGANISM: Artificial Sequence
<220> FEATURE:
<223> OTHER INFORMATION: MlyI
<220> FEATURE:
<221> NAME/KEY: misc_feature
<222> LOCATION: 6..10
<223> OTHER INFORMATION: N is any nucleotide

<400> SEQUENCE: 500 gagtcnnnnn                                                          10

<210> SEQ ID NO 501
<211> LENGTH: 10
<212> TYPE: DNA
<213> ORGANISM: Artificial Sequence
<220> FEATURE:
<223> OTHER INFORMATION: MlyI
<220> FEATURE:
<221> NAME/KEY: misc_feature
<222> LOCATION: 1..5
<223> OTHER INFORMATION: N is any nucleotide

<400> SEQUENCE: 501 nnnnngactc                                                          10

<210> SEQ ID NO 502
<211> LENGTH: 23
<212> TYPE: DNA
<213> ORGANISM: Artificial Sequence
<220> FEATURE:
<223> OTHER INFORMATION: Gene 2 CDS
<220> FEATURE:
<221> NAME/KEY: misc_feature
<222> LOCATION: 1..6
<223> OTHER INFORMATION: N is any nucleotide
<220> FEATURE:
<221> NAME/KEY: misc_feature
<222> LOCATION: 20..23
<223> OTHER INFORMATION: N is any nucleotide

<400> SEQUENCE: 502
nnnnnncata gcacccagtn nnn                                           23

<210> SEQ ID NO 503
<211> LENGTH: 23
<212> TYPE: DNA
<213> ORGANISM: Artificial Sequence
<220> FEATURE:
<223> OTHER INFORMATION: Gene 2 CDS
<220> FEATURE:
<221> NAME/KEY: misc_feature
<222> LOCATION: 1..4
<223> OTHER INFORMATION: N is any nucleotide
<220> FEATURE:
<221> NAME/KEY: misc_feature
<222> LOCATION: 18..23
<223> OTHER INFORMATION: N is any nucleotide

<400> SEQUENCE: 503
nnnnactggg tgctatgnnn nnn                                           23

<210> SEQ ID NO 504
<211> LENGTH: 23
<212> TYPE: DNA
<213> ORGANISM: Artificial Sequence
<220> FEATURE:
<223> OTHER INFORMATION: Gene 1 CDS
<220> FEATURE:
<221> NAME/KEY: misc_feature
<222> LOCATION: 1..4
<223> OTHER INFORMATION: N is any nucleotide
<220> FEATURE:
<221> NAME/KEY: misc_feature
<222> LOCATION: 18..23
<223> OTHER INFORMATION: N is any nucleotide

<400> SEQUENCE: 504
nnnnactggg actgatgnnn nnn                                           23

```
<210> SEQ ID NO 505
<211> LENGTH: 23
<212> TYPE: DNA
<213> ORGANISM: Artificial Sequence
<220> FEATURE:
<223> OTHER INFORMATION: Gene 2 CDS
<220> FEATURE:
<221> NAME/KEY: misc_feature
<222> LOCATION: 1..6
<223> OTHER INFORMATION: N is any nucleotide
<220> FEATURE:
<221> NAME/KEY: misc_feature
<222> LOCATION: 20..23
<223> OTHER INFORMATION: N is any nucleotide

<400> SEQUENCE: 505
nnnnnncatc agtcccagtn nnn                                           23

<210> SEQ ID NO 506
<211> LENGTH: 15
<212> TYPE: DNA
<213> ORGANISM: Artificial Sequence
<220> FEATURE:
<223> OTHER INFORMATION: Promotor
<220> FEATURE:
<221> NAME/KEY: misc_feature
<222> LOCATION: 1..14
<223> OTHER INFORMATION: N is any nucleotide

<400> SEQUENCE: 506
nnnnnnnnnn nnnna                                                    15

<210> SEQ ID NO 507
<211> LENGTH: 32
<212> TYPE: DNA
<213> ORGANISM: Artificial Sequence
<220> FEATURE:
<223> OTHER INFORMATION: Promotor
<220> FEATURE:
<221> NAME/KEY: misc_feature
<222> LOCATION: 1..6
<223> OTHER INFORMATION: N is any nucleotide
<220> FEATURE:
<221> NAME/KEY: misc_feature
<222> LOCATION: 10..23
<223> OTHER INFORMATION: N is any nucleotide
<220> FEATURE:
<221> NAME/KEY: misc_feature
<222> LOCATION: 27..32
<223> OTHER INFORMATION: N is any nucleotide

<400> SEQUENCE: 507
nnnnnncatn nnnnnnnnnn nnnatgnnnn nn                                 32
```

UNITED STATES PATENT AND TRADEMARK OFFICE
CERTIFICATE OF CORRECTION

PATENT NO. : 9,822,357 B2  
APPLICATION NO. : 14/325111  
DATED : November 21, 2017  
INVENTOR(S) : Thomas Vogl et al.

Page 1 of 1

It is certified that error appears in the above-identified patent and that said Letters Patent is hereby corrected as shown below:

The Assignee is corrected to add a second party and should read as follows:

(73) Assignee: TECHNISCHE UNIVERSITAT GRAZ, Graz (AT) and
              ACIB GmbH, Graz (AT)

Signed and Sealed this  
Thirtieth Day of January, 2018

Joseph Matal  
*Performing the Functions and Duties of the*  
*Under Secretary of Commerce for Intellectual Property and*  
*Director of the United States Patent and Trademark Office*